(12) United States Patent
Foley et al.

(10) Patent No.: US 10,428,029 B2
(45) Date of Patent: *Oct. 1, 2019

(54) ISOXAZOLE CARBOXAMIDE COMPOUNDS

(71) Applicant: EPIZYME, INC., Cambridge, MA (US)

(72) Inventors: Megan Alene Cloonan Foley, Somerville, MA (US); Kevin Wayne Kuntz, Woburn, MA (US); James Edward John Mills, Kent (GB); Lorna Helen Mitchell, Cambridge, MA (US); Michael John Munchhof, Salem, CT (US); Darren Martin Harvey, Acton, MA (US)

(73) Assignee: EPIZYME, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/510,593

(22) PCT Filed: Sep. 9, 2015

(86) PCT No.: PCT/US2015/049213
§ 371 (c)(1),
(2) Date: Mar. 10, 2017

(87) PCT Pub. No.: WO2016/040498
PCT Pub. Date: Mar. 17, 2016

(65) Prior Publication Data
US 2017/0190676 A1     Jul. 6, 2017

Related U.S. Application Data

(60) Provisional application No. 62/048,759, filed on Sep. 10, 2014, provisional application No. 62/146,794, filed on Apr. 13, 2015.

(51) Int. Cl.
*C07D 261/18*   (2006.01)
*C07D 413/14*   (2006.01)
*C07D 413/12*   (2006.01)

(52) U.S. Cl.
CPC ......... *C07D 261/18* (2013.01); *C07D 413/12* (2013.01); *C07D 413/14* (2013.01)

(58) Field of Classification Search
None
See application file for complete search history.

(56) References Cited

U.S. PATENT DOCUMENTS

| 3,065,225 A | 10/1962 | Gardner et al. |
| 2004/0147517 A1 | 7/2004 | Jelley et al. |
| 2017/0253601 A1* | 9/2017 | Foley .................. C07D 413/12 |

FOREIGN PATENT DOCUMENTS

| WO | WO 02/080928 A1 | 10/2002 |
| WO | WO 02/100352 A2 | 12/2002 |
| WO | WO 2007/052123 A2 | 5/2007 |
| WO | WO 2008/040149 A1 | 4/2008 |
| WO | WO 2008/135826 A2 | 11/2008 |
| WO | WO 2008/137834 A2 | 11/2008 |
| WO | WO 2016/040502 A1 | 3/2016 |
| WO | WO 2016/040504 A1 | 3/2016 |
| WO | WO 2016/040505 A1 | 3/2016 |
| WO | WO 2016/040508 A1 | 3/2016 |
| WO | WO 2016/040511 A1 | 3/2016 |
| WO | WO 2016/040515 A1 | 3/2016 |

OTHER PUBLICATIONS

Mazurov, A.A., et al., "Discovery of (2S,3R)-N-[2-(Pyridin-3-ylmethyl)-1-azabicyclo[2.2.2]oct-3-yl]benzo[b]furan-2-carboxamide (TC-5619), a Selective α7 Nicotinic Acetylcholine Receptor Agonist, for the Treatment of Cognitive Disorders," *J Med Chem* 55:9793-9809, ACS Publications, United States (2012).
Jamal, S., et al., "Computational analysis and predictive modeling of small molecule modulators of microRNA," Journal of Cheminformatics 4:16, SpringerOpen, United Kingdom (2012).
Lepage, F., et al., "New N-aryl isoxazolecarboxamides and N-isoxazolylbenzamides as anticonvulsant agents," Eur J Med Chem 27:581-593, Elsevier, Netherlands (1992).
Supplementary European Search Report for EP Application No. 15 83 9331, Germany, dated Jan. 26, 2018, 9 pages.
Abu-Farha, M. et al., "Proteomic analyses of the SMYD family interactomes identify HSP90 as a novel target for SMYD2," *J. Mol. Cell Biol.* 3:301-308, Oxford University Press, United States (2011).
Bingham, A.L. et al., "Over one hundred solvates of sulfathiazole," *Chem. Commun.* 7:603-604, Royal Society of Chemistry, United Kingdom (2001).
Caira, M.R. et al., "Preparation and Crystal Characterization of a Polymorph, a Monohydrate, and an Ethyl Acetate Solvate of the Antifungal Fluconazole," *J. Pharm. Sci.* 93:601-611, Wiley-Liss, Inc. and American Pharmaceutical Association, United States (2004).

(Continued)

*Primary Examiner* — Kamal A Saeed
(74) *Attorney, Agent, or Firm* — Sterne, Kessler, Goldstein & Fox P.L.L.C.

(57) ABSTRACT

The present disclosure provides substituted isoxazole carboxamide compounds having Formula (I) and the pharmaceutically acceptable salts and solvates thereof, wherein $R^1$, $R^2$, A, X, and Z are defined as set forth in the specification. The present disclosure is also directed to the use of compounds of Formula I to treat a disorder responsive to the blockade of SMYD proteins such as SMYD3 or SMYD2. Compounds of the present disclosure are especially useful for treating cancer.

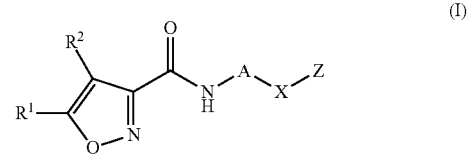

(I)

10 Claims, No Drawings
Specification includes a Sequence Listing.

(56) References Cited

OTHER PUBLICATIONS

Cho, H.-S. et al., "RB1 Methylation by SMYD2 Enhances Cell Cycle Progression through an Increase of RB1 Phosphorylation," *Neoplasia* 14:476-486, Neoplasia Press, Inc., United States (2012).
Fujii, T. et al., "Smyd3 Is Required for the Development of Cardiac and Skeletal Muscle in Zebrafish," *PLoS One* 6:e23491, Public Library of Science, United States (2011).
GenBank, "*Homo sapiens* mitogen-activated protein kinase kinase kinase 2 (MAP3K2), mRNA," Accession No. NM_006609.3, accessed at https://www.ncbi.nlm.nih.gov/nuccore/NM_006609.3, Mar. 27, 2011.
GenBank, "N-lysine methyltransferase SMYD2 [*Homo sapiens*]," Accession No. NP_064582.2, accessed at https://www.ncbi.nlm.nih.gov/protein/NP_064582.2, Jun. 25, 2017.
GenPept, "Histone-lysine N-methyltransferase SMYD3 isoform 1 [*Homo sapiens*]," Sequence NP_001161212.1, accessed at https://www.ncbi.nlm.nih.gov/protein/267844824/, Jun. 26, 2017.
Hamamoto, R. et al., "Enhanced SMYD3 expression is essential for the growth of breast cancer cells," *Cancer Sci.* 97:113-118, Japanese Cancer Association, Wiley Publishing, United Kingdom (2006).
Hamamoto, R. et al., "SMYD3 encodes a histone methyltransferase involved in the proliferation of cancer cells," *Nat. Cell Biol.* 6:731-740, Nature Publishing Group, Macmillan Magazines Ltd., United Kingdom (2004).
Hu, L. et al., "Identification of Smyd4 as a Potential Tumor Suppressor Gene Involved in Breast Cancer Development," *Cancer Res.* 69:4067-4072, American Association for Cancer Research, United States (2009).
International Preliminary Report on Patentability for International Patent Application No. PCT/US2015/049213, The International Bureau of WIPO, Switzerland, dated Mar. 14, 2017.
International Search Report for International Patent Application No. PCT/US2015/049213, U.S. Patent and Trademark Office, Alexandria, Virginia, dated Feb. 9, 2016.
Komatsu, S. et al., "Overexpression of SMYD2 contributes to malignant outcome in gastric cancer," *Br. J. Cancer* 112:357-364, Nature Publishing Group, United Kingdom (2015).
Komatsu, S. et al., "Overexpression of SMYD2 relates to tumor cell proliferation and malignant outcome of esophageal squamous cell carcinoma," *Carcinogenesis* 30:1139-1146, Oxford University Press, United Kingdom (2009).
Liu, C. et al., "SMYD3 as an Oncogenic Driver in Prostate Cancer by Stimulation of Androgen Receptor Transcription," *J. Nat. Cancer Inst.* 105:1719-1728, Oxford University Press, United States (2013).
Mazur, P.K. et al., "SMYD3 links lysine methylation of MAP3K2 to Ras-driven cancer," *Nature* 510: 283-287, Nature Publishing Group, United Kingdom (2014).
Moss, G.P., "Basic Terminology of Stereochemistry," *Pure Appl. Chem.* 68:2193-2222, IUPAC, Blackwell Scientific Publications, United Kingdom (1996).
De Almeida Nagata, D.E. et al., "Epigenetic control of Foxp3 by SMYD3 H3K4 histone methyltransferase controls iTreg development and regulates pathogenic T cell responses during pulmonary viral infection," *Mucosal Immunol.* 8:1131-1143, Nature Publishing Group, United States (2015).
Nguyen, H. et al., "LLY-507, a Cell-active, Potent, and Selective Inhibitor of Protein-lysine Methyltransferase SMYD2," *J. Biol. Chem.* 290:13641-13653, American Society for Biochemistry and Molecular Biology, Inc., United States (2015).
Peserico, A. et al., "A SMYD3 Small-Molecule Inhibitor Impairing Cancer Cell Growth," *J. Cell. Physiol.* 230:2447-2460, Wiley Periodicals, Inc., United States (2015).
Proserpio, V. et al., "The methyltransferase SMYD3 mediates the recruitment of transcriptional cofactors at the myostatin and c-Met genes and regulates skeletal muscle atrophy," *Genes Dev.* 27:1299-1312, Cold Spring Harbor Laboratory Press, United States (2013).
PubChem-16677096 Create Date: Aug. 17, 2007.
PubChem-60068551 Create Date: Aug. 20, 2012.
PubChem-61574221 Create Date: Oct. 19, 2012.
PubChem-61803752 Create Date: Oct. 22, 2012.
PubChem-66770059 Create Date: Nov. 30, 2012.
Sakamoto, L.H. et al., "SMYD2 Is highly expressed in pediatric acute lymphoblastic leukemia and constitutes a bad prognostic factor," *Leuk. Res.* 38:496-502, Pergamon Press, United Kingdom (2014).
UniProtKB/Swiss-Prot, "SMYD3_HUMAN," accession No. Q9H7B4.4, accessed at https://www.ncbi.nlm.nih.gov/protein/Q9H7B4, accessed on Jun. 7, 2017.
Van Aller, G.S. et al., "Smyd3 regulates cancer cell phenotypes and catalyzes histone H4 lysine 5 methylation," *Epigenetics* 7:340-343, Landes Bioscience, United States (2012).
Van Tonder, E.C. et al., "Preparation and Physicochemical Characterization of 5 Niclosamide Solvates and 1 Hemisolvate," *AAPS PharmSciTech* 5:E12, American Association of Pharmaceutical Scientists, United States (2004).
Wuts, P.G.M. and Greene, T.W., Greene's Protective Groups in Organic Synthesis, 4th Ed., John Wiley & Sons, Inc., United States (2007).
Xu, G. et al., "The Histone Methyltransferase Smyd2 is a Negative Regulator of Macrophage Activation by Suppressing Interleukin 6 (IL-6) and Tumor Necrosis Factor α (TNF-α) Production," *J. Biol. Chem.* 290:5414-5423, American Society for Biochemistry and Molecular Biology, United States (2015).

\* cited by examiner

ISOXAZOLE CARBOXAMIDE COMPOUNDS

BACKGROUND OF THE INVENTION

Field of the Invention

The present disclosure provides substituted isoxazole carboxamides as SMYD protein inhibitors, such as SMYD3 and SMYD2 inhibitors, and therapeutic methods of treating conditions and diseases wherein inhibition of SMYD proteins such as SMYD3 and SMYD2 provides a benefit.

Background

Epigenetic regulation of gene expression is an important biological determinant of protein production and cellular differentiation and plays a significant pathogenic role in a number of human diseases. Epigenetic regulation involves heritable modification of genetic material without changing its nucleotide sequence. Typically, epigenetic regulation is mediated by selective and reversible modification (e.g., methylation) of DNA and proteins (e.g., histones) that control the conformational transition between transcriptionally active and inactive states of chromatin. These covalent modifications can be controlled by enzymes such as methyltransferases (e.g., SMYD proteins such as SMYD3 and SMYD2), many of which are associated with genetic alterations that can cause human disease, such as proliferative disorders. Thus, there is a need for the development of small molecules that are capable of inhibiting the activity of SMYD proteins such as SMYD3 and SMYD2.

BRIEF SUMMARY OF THE INVENTION

In one aspect, the present disclosure provides substituted isoxazole carboxamide compounds represented by Formulae I-XVII below, and the pharmaceutically acceptable salts and solvates thereof, collectively referred to herein as "Compounds of the Disclosure."

In another aspect, the present disclosure provides a Compound of the Disclosure and one or more pharmaceutically acceptable carriers.

In another aspect, the present disclosure provides a method of inhibiting SMYD proteins, such as SMYD3 or SMYD2, or both, in a mammal, comprising administering to the mammal an effective amount of at least one Compound of the Disclosure.

In another aspect, the present disclosure provides methods for treating a disease, disorder, or condition, e.g., cancer, responsive to inhibition of SMYD proteins, such as SMYD3 or SMYD2, or both, comprising administering a therapeutically effective amount of a Compound of the Disclosure.

In another aspect, the present disclosure provides the use of Compounds of the Disclosure as inhibitors of SMYD3.

In another aspect, the present disclosure provides the use of Compounds of the Disclosure as inhibitors of SMYD2.

In another aspect, the present disclosure provides the use of Compounds of the Disclosure as inhibitors of SMYD proteins.

In another aspect, the present disclosure provides a pharmaceutical composition for treating a disease, disorder, or condition responsive to inhibition of SMYD proteins, such as SMYD3 or SMYD2, or both, wherein the pharmaceutical composition comprises a therapeutically effective amount of a Compound of the Disclosure in a mixture with one or more pharmaceutically acceptable carriers.

In another aspect, the present disclosure provides Compounds of the Disclosure for use in treating cancer in a mammal, e.g., breast, cervical, colon, kidney, liver, head and neck, skin, pancreatic, ovary, esophageal, lung, and prostate cancer.

In another aspect, the present disclosure provides a Compound of the Disclosure for use in the manufacture of a medicament for treating cancer in a mammal.

In another aspect, the present disclosure provides kit comprising a Compound of the Disclosure.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

DETAILED DESCRIPTION OF THE INVENTION

One aspect of the present disclosure is based on the use of Compounds of the Disclosure as inhibitors of SMYD proteins. In view of this property, the Compounds of the Disclosure are useful for treating diseases, disorders, or conditions, e.g., cancer, responsive to inhibition of SMYD proteins.

One aspect of the present disclosure is based on the use of Compounds of the Disclosure as inhibitors of SMYD3. In view of this property, the Compounds of the Disclosure are useful for treating diseases, disorders, or conditions, e.g., cancer, responsive to inhibition of SMYD3.

One aspect of the present disclosure is based on the use of Compounds of the Disclosure as inhibitors of SMYD2. In view of this property, the Compounds of the Disclosure are useful for treating diseases, disorders, or conditions, e.g., cancer, responsive to inhibition of SMYD2.

In one embodiment, Compounds of the Disclosure are compounds having Formula I:

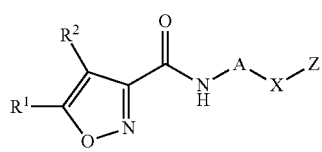

and the pharmaceutically acceptable salts or solvates, e.g., hydrates, thereof wherein:

$R^1$ is selected from the group consisting of hydrogen, $C_{1-6}$ alkyl, $C_{1-4}$ alkenyl, $C_{1-4}$ haloalkyl, $C_{3-6}$ cycloalkyl, and hydroxyalkyl;

$R^2$ is selected from the group consisting of hydrogen, halo, and carboxamido;

A is selected from the group consisting of $C_{1-10}$ alkylenyl, (cycloalkylenyl)alkyl, optionally substituted $C_{3-12}$ cycloalkylenyl, optionally substituted $C_{6-14}$ arylenyl, optionally substituted 5- to 14-membered heteroarylenyl, optionally substituted 4- to 14-membered heterocyclenyl, and —C(H)$R^3R^4$;

with the provisos:

a) when $R^1$ is ethyl, n-propyl, isopropyl, isobutyl, or cyclopropyl; and $R^2$ is hydrogen, then A is not optionally substituted, optionally bridged piperidinenyl;

b) when $R^1$ is ethyl or cyclopropyl; $R^2$ is hydrogen; and X is —N($R^7$)S(=O)$_2$—, —N($R^7$)C(=O)—, or —N($R^7$)C(=O)C($R^8$)(H)—, then A is not optionally substituted 1,4-cyclohexylenyl;

c) when $R^1$ is ethyl or cyclopropyl; $R^2$ is hydrogen; X is absent; and Z is amino, alkylamino, dialkylamino, or heterocycloamino, then A is not optionally substituted 1,4-cyclohexylenyl; and d) when $R^1$ is hydrogen, $C_{1-6}$ alkyl, or $C_{3-6}$ cycloalkyl; and $R^2$ is hydrogen, then A is not optionally substituted pyrrolidinenyl;

$R^3$ is selected from the group consisting of hydrogen, $C_{1-6}$ alkyl, (hydroxy)(aryl)alkyl, (amino)alkyl, (alkylamino)alkyl, (dialkylamino)alkyl, hydroxyalkyl, alkoxyalkyl, aryloxyalkyl, optionally substituted $C_{3-12}$ cycloalkyl, optionally substituted 4- to 14-membered heterocyclo, optionally substituted $C_{6-14}$ aryl, aralkyl, alkoxycarbonyl, and —C(=O)N($R^5$)($R^6$);

$R^4$ is selected from the group consisting of $C_{1-6}$ alkyl, hydroxyalkyl, optionally substituted $C_{3-12}$ cycloalkyl, optionally substituted $C_{6-14}$ aryl, optionally substituted 5- to 14-membered heteroaryl, optionally substituted 4- to 14-membered heterocyclo, and (heteroaryl)alkyl;

$R^5$ is selected from the from the group consisting of hydrogen and $C_{1-4}$ alkyl;

$R^6$ is selected from the group consisting of hydrogen, optionally substituted $C_{1-6}$ alkyl, fluoroalkyl, hydroxyalkyl, (amino)alkyl, (alkylamino)alkyl, (dialkylamino)alkyl, (cycloalkylamino)alkyl, (heterocyclo)alkyl, (cycloalkyl)alkyl, (amino)(carboxamido)alkyl, (amino)(hydroxy)alkyl, (amino)(aryl)alkyl, (amino)(heteroaryl)alkyl, (hydroxy)(aryl)alkyl, (aralkylamino)alkyl, (hydroxyalkylamino)alkyl, alkoxyalkyl, optionally substituted $C_{6-14}$ aryl, optionally substituted 4- to 14-membered heterocyclo, optionally substituted 5- to 14-membered heteroaryl optionally substituted $C_{3-12}$ cycloalkyl, aralkyl, and (heteroaryl)alkyl;

X is selected from the group consisting of —S(=O)$_2$—, —S(=O)$_2$N($R^7$)—, —N($R^7$)S(=O)$_2$—, —S(=O)$_2$C($R^8$)(H)—, —C(=O)—, —C(=O)N($R^7$)—, —N($R^7$)C(=O)—, —C(=O)O—, —OC(=O)—, —C(=O)C($R^8$)(H)N($R^7$)—, —N($R^7$)C(=O)C($R^8$)(H)—, —C($R^8$)(H)C(=O)N($R^7$)—, —C($R^8$)(H)N($R^7$)C(=O)—, and —C(=O)C($R^8$)(H)—; or X is absent, i.e., Z forms a bond with A;

Z is selected from the group consisting of hydrogen, optionally substituted $C_{1-6}$ alkyl, fluoroalkyl, hydroxyalkyl, amino, alkylamino, dialkylamino, heterocycloamino, (amino)alkyl, (alkylamino)alkyl, (dialkylamino)alkyl, (cycloalkylamino)alkyl, (heterocyclo)alkyl, (cycloalkyl)alkyl, (amino)(hydroxy)alkyl, (amino)(aryl)alkyl, (amino)(heteroaryl)alkyl (hydroxy)(aryl)alkyl, (aralkylamino)alkyl, (hydroxyalkylamino)alkyl, alkoxyalkyl, optionally substituted $C_{6-14}$ aryl, optionally substituted 4- to 14-membered heterocyclo, optionally substituted 5- to 14-membered heteroaryl optionally substituted $C_{3-12}$ cycloalkyl, aralkyl, and (heteroaryl)alkyl;

wherein —X—Z is attached to any available carbon or nitrogen atom of A, $R^3$, $R^4$, or $R^6$; e.g., when $R^4$ is $C_{1-6}$ alkyl, e.g., ethyl, a hydrogen atom of that ethyl group is replaced with —X—Z to give —CH$_2$CH$_2$—X—Z or

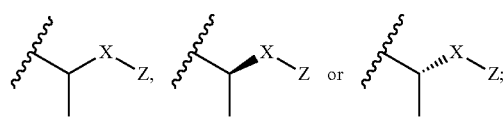

or when $R^4$ is optionally substituted $C_{3-12}$ cycloalkyl, e.g., cyclohexyl, a hydrogen atom of the cyclohexyl group is replaced with —X—Z to give:

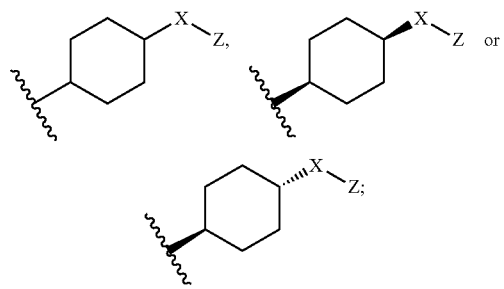

or when $R^4$ is optionally substituted 4- to 14-membered heterocyclo, e.g., piperidinyl, the hydrogen atom attached to the piperidinyl nitrogen atom is replaced with —X—Z to give:

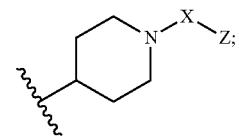

or when $R^4$ is optionally substituted $C_{6-14}$ aryl, e.g., phenyl, a hydrogen atom on that phenyl group is replaced with —X—Z to give:

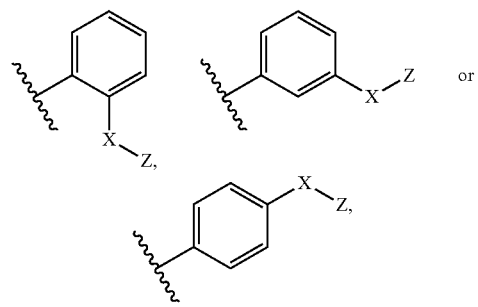

$R^7$ is selected from the group consisting of hydrogen and $C_{1-4}$ alkyl; and $R^8$ is selected from the group consisting of hydrogen, $C_{1-4}$ alkyl, hydroxy, amino, alkylamino, dialkylamino, cycloalkylamino, (amino)alkyl, (alkylamino)alkyl, (dialkylamino)alkyl, and hydroxyalkyl.

In another embodiment, Compounds of the Disclosure are compounds having Formula I, and the pharmaceutically acceptable salts or solvates, e.g., hydrates, thereof, wherein A is $C_{1-10}$ alkylenyl.

In another embodiment, Compounds of the Disclosure are compounds having Formula II:

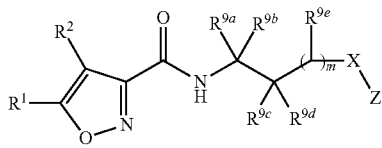

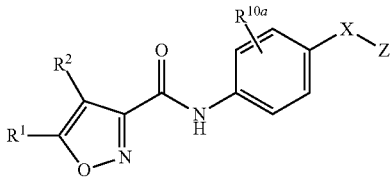

and the pharmaceutically acceptable salts or solvates, e.g., hydrates, thereof, wherein:

$R^{9a}$ and $R^{9b}$ are independently selected from the group consisting of hydrogen and $C_{1-4}$ alkyl;

$R^{9c}$ and $R^{9d}$ are independently selected from the group consisting of hydrogen and $C_{1-4}$ alkyl; or $R^{9c}$ and $R^{9d}$ taken together with the carbon atom to which they are attached form a 3- to 6-membered cycloalkyl;

$R^{9e}$ is selected from the group consisting of hydrogen and $C_{1-4}$ alkyl;

m is 0 or 1;

X is selected from the group consisting of —N(R$^7$)C (=O)—, —N(R$^7$)C(=O)C(R$^8$)(H)—, and —N(R$^7$)S(=O)$_2$—;

$R^8$ is selected from the group consisting of $C_{1-4}$ alkyl, amino, alkylamino, and dialkylamino; and Z is selected from the group consisting of $C_{1-6}$ alkyl, (amino)alkyl, (alkylamino)alkyl, (dialkylamino)alkyl, optionally substituted 4- to 14-membered heterocyclo, and optionally substituted $C_{3-12}$ cycloalkyl, and $R^1$, $R^2$, and $R^7$ are as defined above in connection with Formula I.

In another embodiment, Compounds of the Disclosure are compounds having Formula I, and the pharmaceutically acceptable salts or solvates, e.g., hydrates, thereof, wherein A is optionally substituted $C_{6-14}$ arylenyl.

In another embodiment, Compounds of the Disclosure are compounds having Formula III:

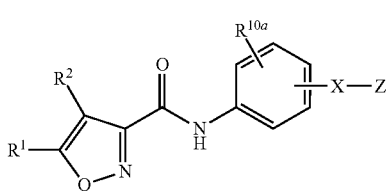

and the pharmaceutically acceptable salts or solvates, e.g., hydrates, thereof, wherein:

$R^{10a}$ is selected from the group consisting of hydrogen, halo, $C_{1-6}$ alkyl, alkoxy, hydroxyalkyl, and alkoxycarbonyl;

X is selected from the group consisting of —C(=O)N (R$^7$)—, —N(R$^7$)C(=O)—, —C(=O)C(R$^8$)(H)N(R$^7$)—, —C(R$^8$)(H)C(=O)N(R$^7$)— and —S(=O)$_2$N(R$^7$)—; or X is absent;

$R^8$ is selected from the group consisting of $C_{1-4}$ alkyl, amino, alkylamino, and dialkylamino; and Z is selected from the group consisting of hydrogen, amino, alkylamino, dialkylamino, (amino)alkyl, (alkylamino)alkyl, (dialkylamino)alkyl, (amino)(heteroaryl)alkyl, heteroalkyl, (amino)(hydroxy)alkyl, (heterocyclo)alkyl, optionally substituted $C_{3-12}$ cycloalkyl, and optionally substituted 4- to 14-membered heterocyclo, and $R^1$, $R^2$, and $R^7$ are as defined above in connection with Formula I.

In another embodiment, Compounds of the Disclosure are compounds having Formula IV:

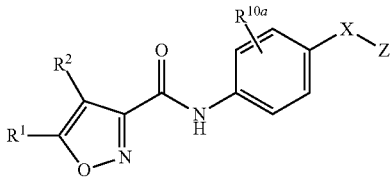

and the pharmaceutically acceptable salts or solvates, e.g., hydrates, thereof, wherein:

$R^{10a}$ is selected from the group consisting of hydrogen, halo, $C_{1-6}$ alkyl, alkoxy, hydroxyalkyl, and alkoxycarbonyl;

X is selected from the group consisting of —C(=O)N (R$^7$)—, —N(R$^7$)C(=O)—, —C(=O)C(R$^8$)(H)N(R$^7$)—, —C(R$^8$)(H)C(=O)N(R$^7$)— and —S(=O)$_2$N(R$^7$)—; or X is absent;

$R^8$ is selected from the group consisting of $C_{1-4}$ alkyl, amino, alkylamino, and dialkylamino; and Z is selected from the group consisting of hydrogen, amino, alkylamino, dialkylamino, (amino)alkyl, (alkylamino)alkyl, (dialkylamino)alkyl, (amino)(heteroaryl)alkyl, heteroalkyl, (amino)(hydroxy)alkyl, (heterocyclo)alkyl, optionally substituted $C_{3-12}$ cycloalkyl, and optionally substituted 4- to 14-membered heterocyclo, and $R^1$, $R^2$, and $R^7$ are as defined above in connection with Formula I.

In another embodiment, Compounds of the Disclosure are compounds having Formula I, and the pharmaceutically acceptable salts or solvates, e.g., hydrates, thereof, wherein A is optionally substituted $C_{3-12}$ cycloalkylenyl.

In another embodiment, Compounds of the Disclosure are compounds having Formula V:

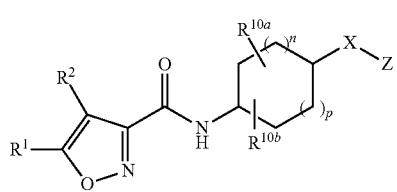

and the pharmaceutically acceptable salts or solvates, e.g., hydrates, thereof, wherein:

$R^{10a}$ and $R^{10b}$ are independently selected from the group consisting of hydrogen and $C_{1-4}$ alkyl;

X is selected from the group consisting of —S(=O)$_2$—, —S(=O)$_2$N(R$^7$)—, —N(R$^7$)C(=O)—, —C(=O)N(R$^7$)—, —N(R$^7$)S(=O)—, and —OC(=O)—; or X is absent;

Z is selected from the group consisting of amino, alkylamino, dialkylamino, heterocycloamino, (amino)alkyl, (alkylamino)alkyl, (dialkylamino)alkyl, and (hydroxyalkylamino)alkyl; n is 0 or 1; and p is 0 or 1, and $R^1$, $R^2$, and $R^7$ are as defined above in connection with Formula I.

In another embodiment, Compounds of the Disclosure are compounds having Formula I, and the pharmaceutically acceptable salts or solvates, e.g., hydrates, thereof, wherein A is optionally substituted 4- to 14-membered heterocyclenyl.

In another embodiment, Compounds of the Disclosure are compounds having Formula VI:

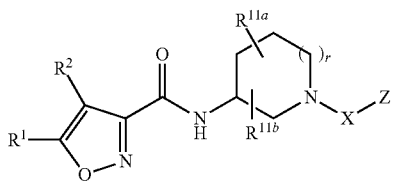

VI and the pharmaceutically acceptable salts or solvates, e.g., hydrates, thereof, wherein:

$R^{11a}$ and $R^{11b}$ are each independently selected from the group consisting of hydrogen, $C_{1-4}$ alkyl, and alkoxycarbonyl;

X is selected from the group consisting of —C(=O)—, —S(=O)$_2$—, and —C(=O)C($R^8$)(H)—;

Z is selected from the group consisting of (amino)alkyl, (alkylamino)alkyl, (dialkylamino)alkyl, optionally substituted $C_{3-12}$ cycloalkyl, and aralkyl; and r is 0 or 1, and $R^1$, $R^2$, and $R^8$ are as defined above in connection with Formula I.

In another embodiment, Compounds of the Disclosure are compounds having Formula XVI:

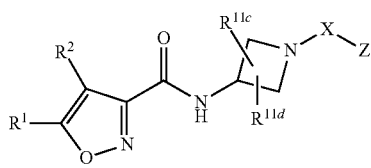

XVI and the pharmaceutically acceptable salts or solvates, e.g., hydrates, thereof, wherein:

$R^{11c}$ and $R^{11d}$ are each independently selected from the group consisting of hydrogen and $C_{1-4}$ alkyl;

X is selected from the group consisting of —C(=O)— and —S(=O)$_2$; or X is absent; and Z, $R^1$, and $R^2$ are as defined above in connection with Formula I.

In another embodiment, Compounds of the Disclosure are compounds having Formula XVI, and the pharmaceutically acceptable salts or solvates, e.g., hydrates, thereof, wherein $R^{11c}$ and $R^{11d}$ are hydrogen; X is absent; Z is selected from the group consisting of hydrogen, optionally substituted $C_{1-6}$ alkyl, fluoroalkyl, hydroxyalkyl, (amino)alkyl, (alkylamino) alkyl, (dialkylamino)alkyl, (heterocyclo)alkyl, (cycloalkyl) alkyl, (hydroxy)(aryl)alkyl, alkoxyalkyl, optionally substituted $C_{6-14}$ aryl, optionally substituted 4- to 14-membered heterocyclo, optionally substituted 5- to 14-membered heteroaryl, optionally substituted $C_{3-12}$ cycloalkyl, aralkyl, and (heteroaryl)alkyl; $R^2$ is hydrogen; and $R^1$ is as defined above in connection with Formula I. In another embodiment, Z is selected from the group consisting of aralkyl, and (heteroaryl)alkyl. In another embodiment, Z is (heteroaryl)alkyl that is substituted with an aralkyl, e.g.,

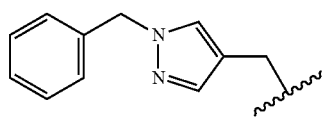

or

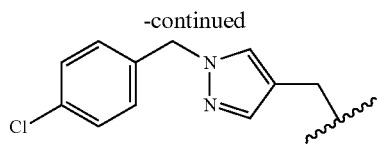

or (heteroaryl)alkyl, e.g.,

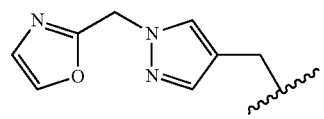

.

In another embodiment, $R^1$ is selected from the group consisting of $C_{1-6}$ alkyl and $C_{3-6}$ cycloalkyl.

In another embodiment, Compounds of the Disclosure are compounds having Formula XVII:

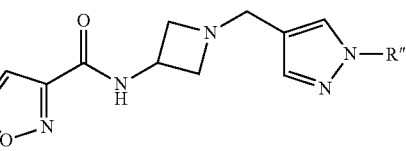

XVII and the pharmaceutically acceptable salts or solvates, e.g., hydrates, thereof, wherein:

R" is selected from the group consisting of aralkyl and (heteroaryl)alkyl; and $R^1$ is as defined above in connection with Formula I.

In another embodiment, Compounds of the Disclosure are compounds having Formula XVII, wherein $R^1$ is selected from the group consisting of $C_{1-6}$ alkyl and $C_{3-6}$ cycloalkyl. In another embodiment, R" is aralkyl. In another embodiment, R" is (heteroaryl)alkyl. In another embodiment, R" is benzyl wherein the phenyl group is optionally substituted with one or two substituents, e.g., —CH$_2$(4-Cl-Ph), —CH$_2$ (3-Cl-Ph), —CH$_2$(3,4-di-Cl-Ph), and —CH$_2$(4-CF$_3$-Ph).

In another embodiment, Compounds of the Disclosure are compounds having Formula I, and the pharmaceutically acceptable salts or solvates, e.g., hydrates, thereof, wherein A is —C(H)$R^3R^4$. In another embodiment, $R^3$ is selected from the group consisting of $C_{1-6}$ alkyl and optionally substituted $C_{3-12}$ cycloalkyl; and $R^4$ is selected from the group consisting of optionally substituted $C_{3-12}$ cycloalkyl and optionally substituted $C_{6-14}$ aryl. In another embodiment, $R^4$ is optionally substituted 4- to 14-membered heterocyclo. In another embodiment, $R^3$ is $C_{1-4}$ alkyl, hydroxyalkyl, alkoxyalkyl, alkoxycarbonyl, optionally substituted $C_{6-14}$ aryl, and aralkyl. In each of these embodiments, —X—Z replaces a hydrogen atom on the $R^4$ substituent. In certain instances, —X—Z can be hydrogen, when X is absent and Z is hydrogen.

In another embodiment, Compounds of the Disclosure are compounds having Formula VII, Formula VIII, or Formula IX:

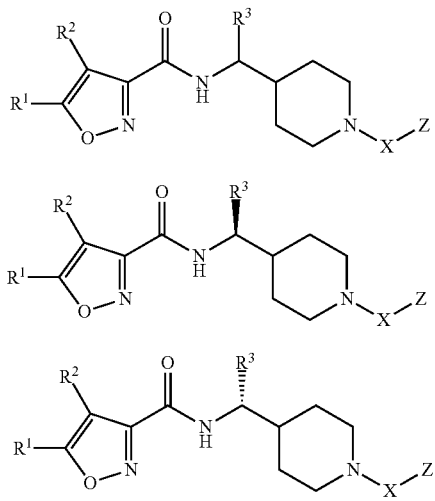

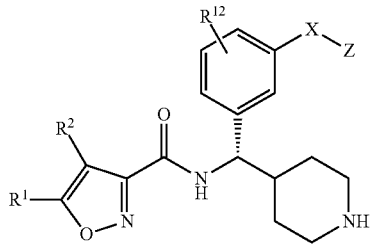

and the pharmaceutically acceptable salts or solvates, e.g., hydrates, thereof, wherein:

R³ is selected from the group consisting of hydrogen, $C_{1-4}$ alkyl, hydroxyalkyl, alkoxyalkyl, optionally substituted $C_{6-14}$ aryl, aryloxyalkyl, and aralkyl;

X is selected from the group consisting of —S(=O)₂—, —S(=O)₂N(R⁷)—, —S(=O)₂C(R⁸)(H)—, —C(=O)—, —C(=O)N(R⁷)—, —C(=O)O—, —OC(=O)—, and —C(=O)C(R⁸)(H)—; or X is absent;

R⁸ is selected from the group consisting of $C_{1-4}$ alkyl, amino, alkylamino, and dialkylamino; and Z is selected from the group consisting of $C_{1-6}$ alkyl, (amino)alkyl, (alkylamino)alkyl, (dialkylamino)alkyl, (heterocyclo)alkyl, hydroxyalkyl, optionally substituted $C_{3-12}$ cycloalkyl, aralkyl, and (heteroaryl)alkyl, and R¹, R², and R⁷ are as defined above in connection with Formula I. In another embodiment, R³ is selected from the group consisting of hydrogen and methyl.

In another embodiment, Compounds of the Disclosure are compounds having Formula X, Formula XI, or Formula XII:

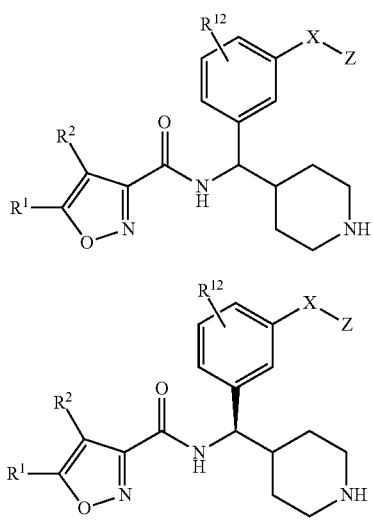

and the pharmaceutically acceptable salts or solvates, e.g., hydrates, thereof, wherein R¹² is selected from the group consisting of hydrogen, halo, (amino)alkyl, (alkylamino)alkyl, (dialkylamino)alkyl, hydroxyalkyl, (aralkyloxy)alkyl, alkoxyalkyl, heteroalkyl, (hydroxyalkylamino)alkyl, (heterocycloamino)alkyl, and carboxamido, and R¹, R², X, and Z are as defined above in connection with Formula I. In another embodiment, X is selected from the group consisting of —C(=O)N(R⁷)— and —S(=O)₂N(R⁷)—; Z is optionally substituted $C_{1-6}$ alkyl, hydroxyalkyl, (amino)alkyl, (alkylamino)alkyl, (dialkylamino)alkyl, (heterocyclo)alkyl, (cycloalkyl)alkyl, (amino)(hydroxy)alkyl, optionally substituted $C_{6-14}$ aryl, optionally substituted 4- to 14-membered heterocyclo, optionally substituted 5- to 14-membered heteroaryl, optionally substituted $C_{3-12}$ cycloalkyl, aralkyl, and (heteroaryl)alkyl; and R¹² is hydrogen. In another embodiment, X is absent; Z is hydrogen; and R¹² is selected from the group consisting of halo, (amino)alkyl, (alkylamino)alkyl, (dialkylamino)alkyl, hydroxyalkyl, (aralkyloxy)alkyl, alkoxyalkyl, heteroalkyl, (hydroxyalkylamino)alkyl, (heterocycloamino)alkyl, and carboxamido.

In another embodiment, Compounds of the Disclosure are compounds having Formula XIII, Formula XIV, or Formula XV:

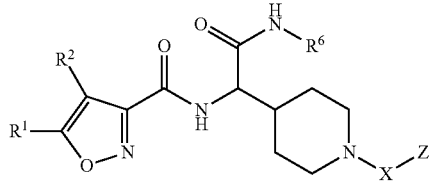

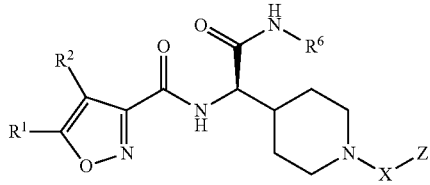

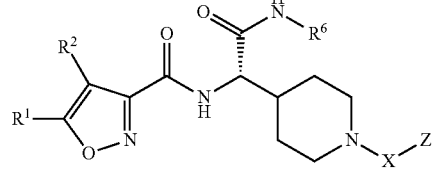

and the pharmaceutically acceptable salts or solvates, e.g., hydrates, thereof, wherein:

R⁶ is selected from the group consisting of optionally substituted $C_{1-6}$ alkyl, hydroxyalkyl, (amino)alkyl, (alkylamino)alkyl, (dialkylamino)alkyl, (heterocyclo)alkyl, (cycloalkyl)alkyl, (amino)(hydroxy)alkyl, optionally substituted $C_{6-14}$ aryl, optionally substituted 4- to 14-membered heterocyclo, optionally substituted 5- to 14-membered heteroaryl, optionally substituted $C_{3-12}$ cycloalkyl, aralkyl, and (heteroaryl)alkyl;

X is selected from the group consisting of —C(=O)N(R$^7$)—, —C(=O)C(R$^8$)(H)—, and —S(=O)$_2$N(R$^7$)—; or X is absent;

R$^8$ is selected from the group consisting of $C_{1-4}$ alkyl, amino, alkylamino, and dialkylamino;

Z is selected from the group consisting of $C_{1-4}$ alkyl, amino, alkylamino, dialkylamino, (amino)alkyl, (alkylamino)alkyl, (dialkylamino)alkyl, (amino)(heteroaryl)alkyl, and (amino)(hydroxy)alkyl, and R$^1$, R$^2$, and R$^7$ are as defined above in connection with Formula I.

In another embodiment, Compounds of the Disclosure are compounds having Formula I, and the pharmaceutically acceptable salts or solvates, e.g., hydrates, thereof, wherein:

X is selected from the group consisting of:

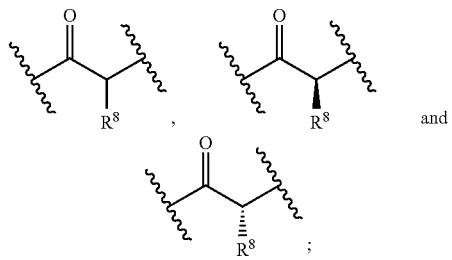

and

R$^8$ is selected from the group consisting of $C_{1-4}$ alkyl, amino, alkylamino, and dialkylamino, and R$^1$, R$^2$, A, and Z are as defined above in connection with Formula I.

In another embodiment, Compounds of the Disclosure are compounds having any one of Formulae I-XVII, and the pharmaceutically acceptable salts or solvates, e.g., hydrates, thereof, wherein R$^1$ is selected from the group consisting of $C_{1-4}$ alkyl and $C_{3-6}$ cycloalkyl. In another embodiment, R$^1$ is cyclopropyl. In another embodiment, R$^2$ is hydrogen.

In another embodiment, a Compound of the Disclosure is not 5-cyclopropyl-N-(pyridin-3-yl)-1,2-oxazole-3-carboxamide.

In another embodiment, Compounds of the Disclosure are compounds of Table 1, and the pharmaceutically acceptable salts or solvates, e.g., hydrates, thereof, or different pharmaceutically acceptable salt thereof. The chemical names of the compounds of Table 1 are provided in Table 1A.

In another embodiment, Compounds of the Disclosure are compounds of Table 1A, and the pharmaceutically acceptable salts or solvates, e.g., hydrates, thereof.

In another embodiment, Compounds of the Disclosure are compounds of Table 2, and the pharmaceutically acceptable salts or solvates, e.g., hydrates, thereof, or different pharmaceutically acceptable salt thereof.

In another embodiment, Compounds of the Disclosure is the compound of Table 3, and the pharmaceutically acceptable salts or solvates, e.g., hydrates, thereof.

In another embodiment, Compounds of the Disclosure are compounds of Tables 1 and 2, and the pharmaceutically acceptable salts or solvates, e.g., hydrates, thereof, or different pharmaceutically acceptable salt thereof.

In another embodiment, Compounds of the Disclosure are compounds of Tables 1-3, and the pharmaceutically acceptable salts or solvates, e.g., hydrates, thereof, or different pharmaceutically acceptable salt thereof.

In another embodiment, Compounds of the Disclosure are compounds of Table 1, Table 1A, Table 2, and Table 3, and the pharmaceutically acceptable salts or solvates, e.g., hydrates, thereof, or different pharmaceutically acceptable salt thereof.

It should be appreciated that the Compounds of the Disclosure in certain embodiments are the free base, various salts, and hydrate forms, and are not limited to the particular salt listed in Table 1, Table 2, and Table 3.

TABLE 1

| Cpd. No. | Structure | Salt Form |
|---|---|---|
| 2 | 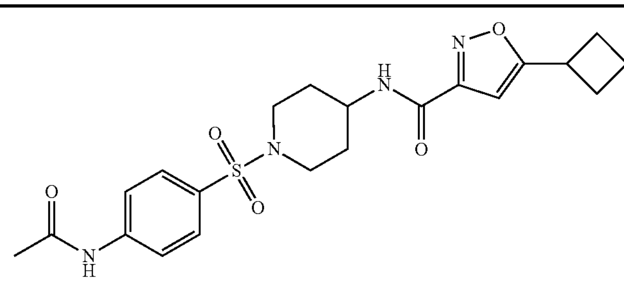 | None |
| 3 | 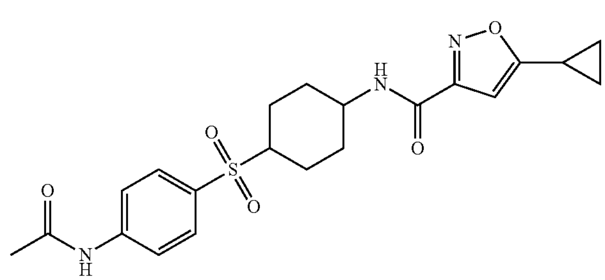 [SMILES: CC(=O)Nc1ccc(S(=O)(=O)C2CCC(NC(=O)c3cc(C4CC4)on3)CC2)cc1] | None |

TABLE 1-continued

| Cpd. No. | Structure | Salt Form |
|---|---|---|
| 4 | 5-cyclopropyl-N-((piperidin-4-yl)methyl)isoxazole-3-carboxamide | HCl |
| 5 | 5-cyclopropyl-N-((1-methylpiperidin-4-yl)methyl)isoxazole-3-carboxamide | None |
| 6 | N-(cis-3-(4-acetamidophenylsulfonamido)cyclobutyl)-5-cyclopropylisoxazole-3-carboxamide | TFA |
| 7 | N-(trans-3-(4-acetamidophenylsulfonamido)cyclobutyl)-5-cyclopropylisoxazole-3-carboxamide | TFA |
| 8 | N-(trans-4-aminocyclohexyl)-5-cyclopropyl-4-iodoisoxazole-3-carboxamide | HCl |
| 9 | N-(trans-4-aminocyclohexyl)-5-(2-hydroxyethyl)isoxazole-3-carboxamide | HCl |
| 10 | N3-(trans-4-aminocyclohexyl)-5-cyclopropyl-N4-isobutylisoxazole-3,4-dicarboxamide | HCl |
| 11 | N-(trans-4-aminocyclohexyl)-5-vinylisoxazole-3-carboxamide | HCl |

TABLE 1-continued

| Cpd. No. | Structure | Salt Form |
|---|---|---|
| 12 | 5-cyclopropyl-N-(2,2-dimethyl-1-phenylpropyl)isoxazole-3-carboxamide | None |
| 13 | 3-((4-aminocyclohexyl)carbamoyl)-5-cyclopropylisoxazole-4-carboxamide (trans) | HCl |
| 14 | N-(4-(aminomethyl)phenyl)-5-cyclopropylisoxazole-3-carboxamide | HCl |
| 15 | N-(1-(4-aminophenyl)ethyl)-5-cyclopropylisoxazole-3-carboxamide | HCl |
| 16 | N-(4-(1-aminoethyl)phenyl)-5-cyclopropylisoxazole-3-carboxamide | HCl |
| 17 | N-(3-aminocyclobutyl)-5-cyclopropylisoxazole-3-carboxamide | HCl |
| 18 | 5-cyclopropyl-N-(1-(4-fluorophenyl)propyl)isoxazole-3-carboxamide | None |

TABLE 1-continued

| Cpd. No. | Structure | Salt Form |
|---|---|---|
| 19 | 5-cyclopropyl-N-(1-(4-fluorophenyl)-2-methylpropyl)isoxazole-3-carboxamide | None |
| 20 | 5-cyclopropyl-N-(1-(4-methoxyphenyl)-2,2-dimethylpropyl)isoxazole-3-carboxamide | None |
| 21 | N-(trans-4-aminocyclohexyl)-5-(3-hydroxypropyl)isoxazole-3-carboxamide | HCl |
| 22 | N-(azepan-4-yl)-5-cyclopropylisoxazole-3-carboxamide | HCl |
| 23 | N-(3-(azetidin-3-ylamino)cyclobutyl)-5-cyclopropylisoxazole-3-carboxamide | TFA |
| 24 | N-(trans-4-aminocyclohexyl)-5-isopropylisoxazole-3-carboxamide | HCl |
| 25 | 5-cyclopropyl-N-(cyclopropyl(4-fluorophenyl)methyl)isoxazole-3-carboxamide | None |

TABLE 1-continued

| Cpd. No. | Structure | Salt Form |
|---|---|---|
| 26 | *5-cyclopropyl-N-(3,3-dimethylbutan-2-yl)isoxazole-3-carboxamide* | None |
| 27 | *N-(1-(4-aminophenyl)-2,2-dimethylpropyl)-5-cyclopropylisoxazole-3-carboxamide* | None |
| 28 | *5-cyclopropyl-N-(2,2-dimethyl-1-(pyridin-2-yl)propyl)isoxazole-3-carboxamide* | None |
| 29 | *5-cyclopropyl-N-(1-(4-fluorophenyl)ethyl)isoxazole-3-carboxamide* | None |
| 30 | *5-cyclopropyl-N-(2,2-dimethylpentan-3-yl)isoxazole-3-carboxamide* | None |
| 31 | *N-(1-(4-acetamidophenyl)-2,2-dimethylpropyl)-5-cyclopropylisoxazole-3-carboxamide* | None |

TABLE 1-continued

| Cpd. No. | Structure | Salt Form |
|---|---|---|
| 32 | 5-cyclopropyl-N-(1-(4-chlorophenyl)-2,2-dimethylpropyl)isoxazole-3-carboxamide | None |
| 33 | N-(4-(aminomethyl)-2-methylphenyl)-5-cyclopropylisoxazole-3-carboxamide | HCl |
| 34 | N-(4-(aminomethyl)-2-chlorophenyl)-5-cyclopropylisoxazole-3-carboxamide | HCl |
| 35 | N-((5-amino-1,3,3-trimethylcyclohexyl)methyl)-5-cyclopropylisoxazole-3-carboxamide | HCOOH |
| 36 | 5-cyclopropyl-N-(2,2-dimethyl-1-(p-tolyl)propyl)isoxazole-3-carboxamide | None |
| 37 | N-(4-(2-aminoethyl)phenyl)-5-cyclopropylisoxazole-3-carboxamide | HCl |
| 38 | N-(4-(1-aminopropyl)phenyl)-5-cyclopropylisoxazole-3-carboxamide | HCl |

TABLE 1-continued
| Cpd. No. | Structure | Salt Form |
|---|---|---|
| 39 | 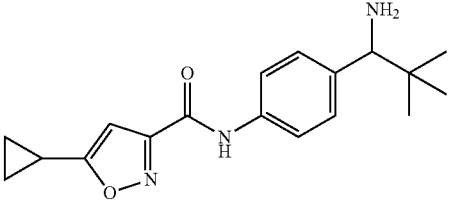 [SMILES: CC(C)(C)C(N)c1ccc(NC(=O)c2cc(C3CC3)on2)cc1] | HCl |
| 40 | 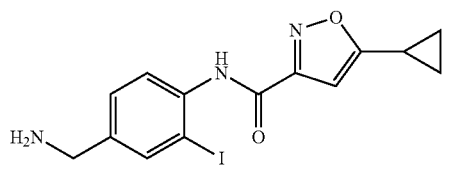 [SMILES: NCc1ccc(NC(=O)c2cc(C3CC3)on2)c(I)c1] | HCl |
| 41 | 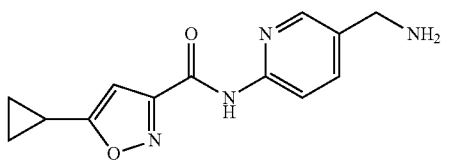 [SMILES: NCc1ccc(NC(=O)c2cc(C3CC3)on2)nc1] | HCl |
| 42 | 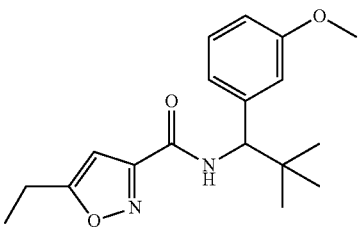 [SMILES: CCc1cc(C(=O)NC(c2cccc(OC)c2)C(C)(C)C)no1] | None |
| 43 | 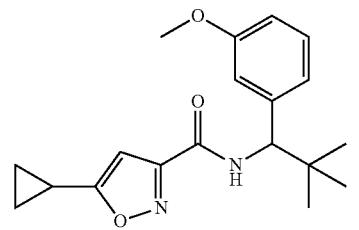 [SMILES: COc1cccc(C(NC(=O)c2cc(C3CC3)on2)C(C)(C)C)c1] | None |
| 44 | 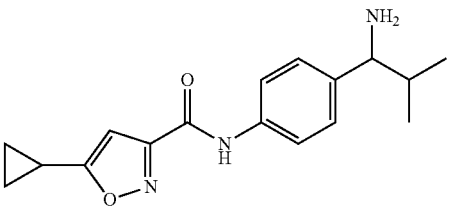 | HCl |
| 45 | 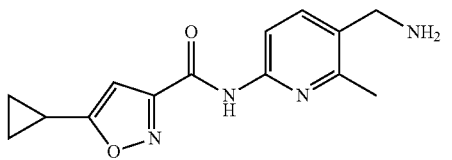 [SMILES: Cc1nc(NC(=O)c2cc(C3CC3)on2)ccc1CN] | HCl |

TABLE 1-continued

| Cpd. No. | Structure | Salt Form |
|---|---|---|
| 46 | 5-cyclopropyl-N-(2,2-dimethyl-1-(m-tolyl)propyl)isoxazole-3-carboxamide | None |
| 47 | 5-ethyl-N-(1-(3-fluorophenyl)-2,2-dimethylpropyl)isoxazole-3-carboxamide | None |
| 48 | 5-cyclopropyl-N-(1-(3-fluorophenyl)-2,2-dimethylpropyl)isoxazole-3-carboxamide | None |
| 49 | 5-cyclopropyl-N-(phenyl(piperidin-4-yl)methyl)isoxazole-3-carboxamide | HCl |
| 50 | 5-cyclopropyl-N-(2,2-dimethyl-1-(pyridin-3-yl)propyl)isoxazole-3-carboxamide | None |
| 51 | 5-cyclopropyl-N-(2,2-dimethyl-1-(pyridin-4-yl)propyl)isoxazole-3-carboxamide | None |

TABLE 1-continued

| Cpd. No. | Structure | Salt Form |
|---|---|---|
| 52 | 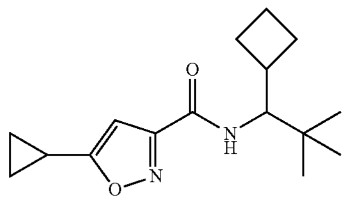 [SMILES: CC(C)(C)C(NC(=O)c1cc(C2CC2)on1)C1CCC1] | None |
| 53 | 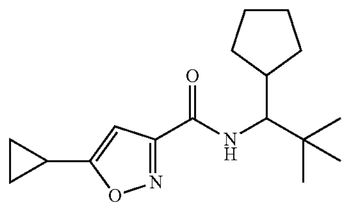 [SMILES: CC(C)(C)C(NC(=O)c1cc(C2CC2)on1)C1CCCC1] | None |
| 54 | 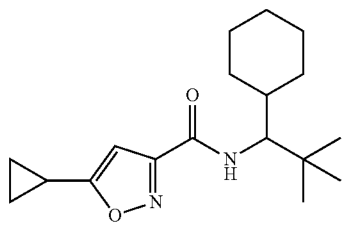 [SMILES: CC(C)(C)C(NC(=O)c1cc(C2CC2)on1)C1CCCCC1] | None |
| 55 | 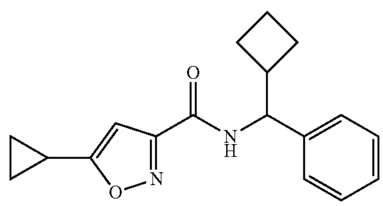 [SMILES: O=C(NC(c1ccccc1)C1CCC1)c1cc(C2CC2)on1] | None |
| 56 | 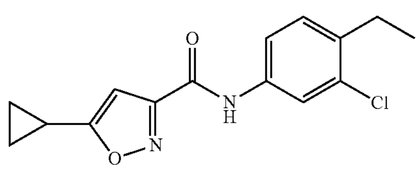 [SMILES: CCc1ccc(NC(=O)c2cc(C3CC3)on2)cc1Cl] | HCl |
| 57 | 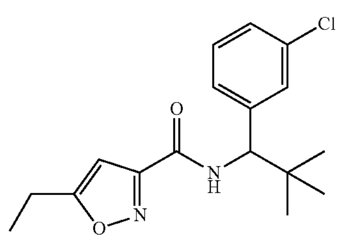 [SMILES: CCc1cc(C(=O)NC(c2cccc(Cl)c2)C(C)(C)C)no1] | None |
| 58 | 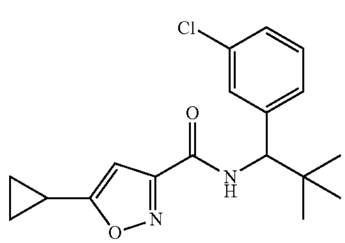 [SMILES: CC(C)(C)C(NC(=O)c1cc(C2CC2)on1)c1cccc(Cl)c1] | None |

TABLE 1-continued
| Cpd. No. | Structure | Salt Form |
|---|---|---|
| 59 | 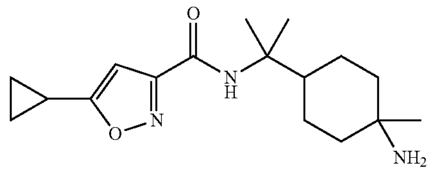 [SMILES: CC1(N)CCC(C(C)(C)NC(=O)c2cc(C3CC3)on2)CC1] | TFA |
| 60 | 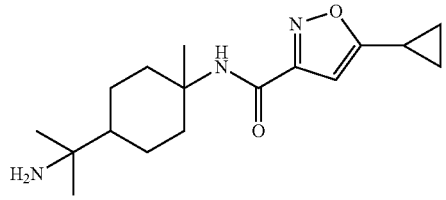 [SMILES: CC1(NC(=O)c2cc(C3CC3)on2)CCC(C(C)(C)N)CC1] | TFA |
| 61 | 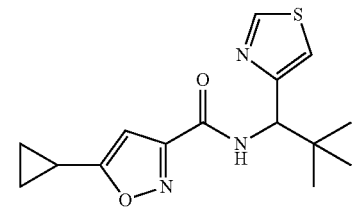 [SMILES: CC(C)(C)C(NC(=O)c1cc(C2CC2)on1)c1cscn1] | None |
| 62 | 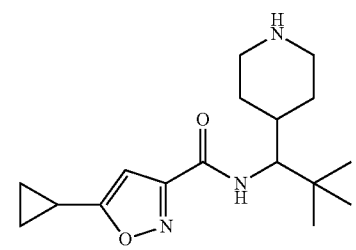 [SMILES: CC(C)(C)C(NC(=O)c1cc(C2CC2)on1)C1CCNCC1] | HCl |
| 63 | 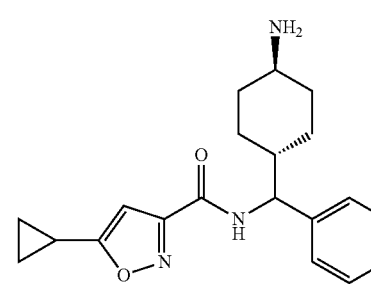 | HCl |
| 64 | 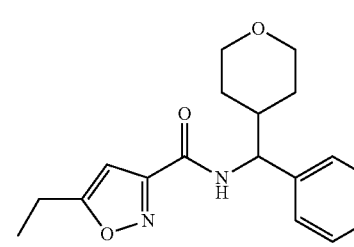 | None |
| 65 | 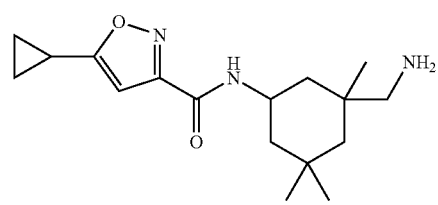 [SMILES: CC1(C)CC(NC(=O)c2cc(C3CC3)on2)CC(C)(CN)C1] | TFA |

TABLE 1-continued

| Cpd. No. | Structure | Salt Form |
|---|---|---|
| 66 | 5-cyclopropyl-N-[(S)-phenyl(pyrrolidin-2-yl)methyl]isoxazole-3-carboxamide | HCl |
| 67 | N-[(4-aminocyclohexyl)(phenyl)methyl]-5-cyclopropylisoxazole-3-carboxamide | HCl |
| 68 | 5-cyclopropyl-N-[3,3-dimethyl-1-(piperidin-3-yl)butan-2-yl]isoxazole-3-carboxamide | HCl |
| 69 | 5-cyclopropyl-N-[phenyl(piperidin-3-yl)methyl]isoxazole-3-carboxamide | HCl |
| 70 | N-[4-(aminomethyl)-3-methylphenyl]-5-cyclopropylisoxazole-3-carboxamide | HCl |
| 71 | 5-ethyl-N-[(1-methylpiperidin-4-yl)(phenyl)methyl]isoxazole-3-carboxamide | None |

TABLE 1-continued

| Cpd. No. | Structure | Salt Form |
|---|---|---|
| 72 | 5-ethyl-N-[(3-chlorophenyl)(piperidin-4-yl)methyl]isoxazole-3-carboxamide | HCl |
| 73 | 5-cyclopropyl-N-[(3-chlorophenyl)(piperidin-4-yl)methyl]isoxazole-3-carboxamide | HCl |
| 74 | 5-ethyl-N-[phenyl(piperidin-4-yl)methyl]isoxazole-3-carboxamide | HCl |
| 75 | 5-cyclopropyl-N-{[3-({[(4-chlorobenzyl)amino]carbonyl}phenyl)(piperidin-4-yl)methyl]}isoxazole-3-carboxamide | HCl |
| 76 | 5-cyclopropyl-N-{[3-({[(cyclohexylmethyl)amino]carbonyl}phenyl)(piperidin-4-yl)methyl]}isoxazole-3-carboxamide | HCl |
| 77 | 5-cyclopropyl-N-{[3-({[cyclohexylamino]carbonyl}phenyl)(piperidin-4-yl)methyl]}isoxazole-3-carboxamide | HCl |

TABLE 1-continued

| Cpd. No. | Structure | Salt Form |
|---|---|---|
| 78 | 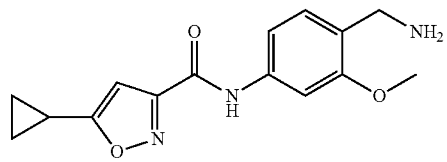 [SMILES: COc1cc(NC(=O)c2cc(C3CC3)on2)ccc1CN] | HCl |
| 79 | 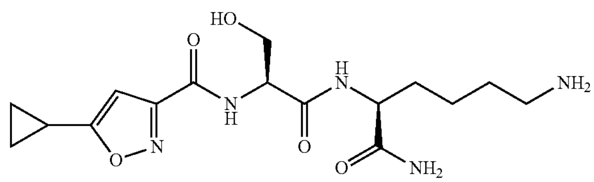 [SMILES: NCCCC[C@H](NC(=O)[C@H](CO)NC(=O)c1cc(C2CC2)on1)C(N)=O] | HCl |
| 80 | 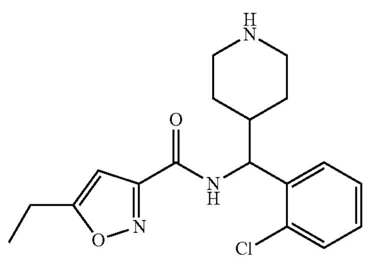 [SMILES: CCc1cc(C(=O)NC(c2ccccc2Cl)C2CCNCC2)no1] | HCl |
| 81 | 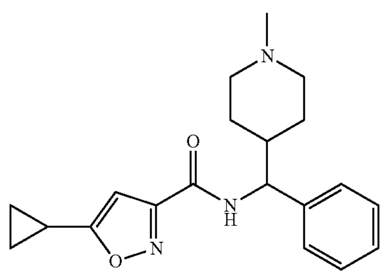 [SMILES: CN1CCC(C(NC(=O)c2cc(C3CC3)on2)c2ccccc2)CC1] | None |
| 82 | 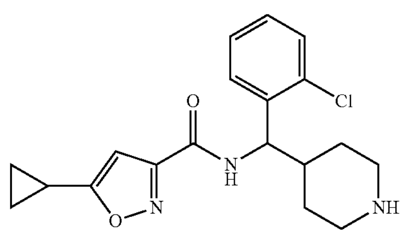 [SMILES: O=C(NC(c1ccccc1Cl)C1CCNCC1)c1cc(C2CC2)on1] | HCl |
| 83 | 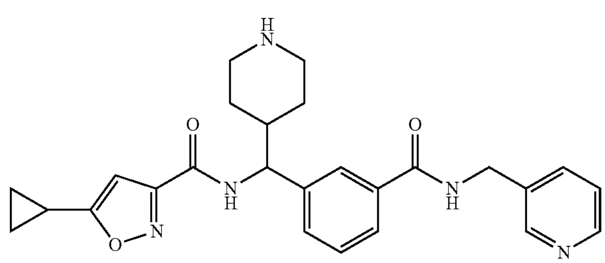 [SMILES: O=C(NCc1cccnc1)c1cccc(C(NC(=O)c2cc(C3CC3)on2)C2CCNCC2)c1] | HCl |

TABLE 1-continued

| Cpd. No. | Structure | Salt Form |
|---|---|---|
| 84 | [5-cyclopropyl-N-((3-((3-(pyrrolidin-1-yl)propyl)carbamoyl)phenyl)(piperidin-4-yl)methyl)isoxazole-3-carboxamide] | HCl |
| 85 | [5-cyclopropyl-N-((3-((2-(piperidin-1-yl)ethyl)carbamoyl)phenyl)(piperidin-4-yl)methyl)isoxazole-3-carboxamide] | HCl |
| 86 | [5-cyclopropyl-N-((3-((2-(methylsulfonyl)ethyl)carbamoyl)phenyl)(piperidin-4-yl)methyl)isoxazole-3-carboxamide] | HCl |
| 87 | [5-cyclopropyl-N-((3-((3-(dimethylamino)propyl)carbamoyl)phenyl)(piperidin-4-yl)methyl)isoxazole-3-carboxamide] | HCl |
| 88 | [5-cyclopropyl-N-((piperidin-4-yl)(3-((pyridin-4-ylmethyl)carbamoyl)phenyl)methyl)isoxazole-3-carboxamide] | HCl |

TABLE 1-continued

| Cpd. No. | Structure | Salt Form |
|---|---|---|
| 89 | 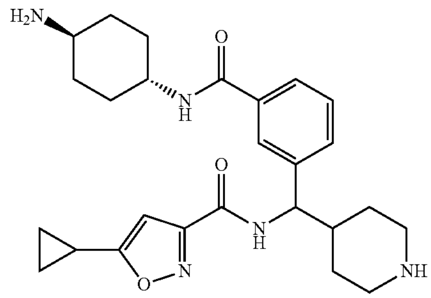 [SMILES: N[C@H]1CC[C@H](NC(=O)c2cccc(C(NC(=O)c3cc(C4CC4)on3)C3CCNCC3)c2)CC1] | HCl |
| 90 | 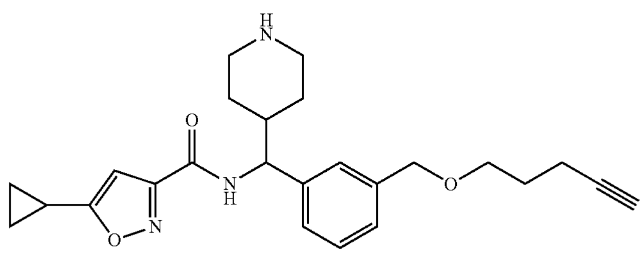 [SMILES: C#CCCCOCc1cccc(C(NC(=O)c2cc(C3CC3)on2)C2CCNCC2)c1] | HCl |
| 91 | 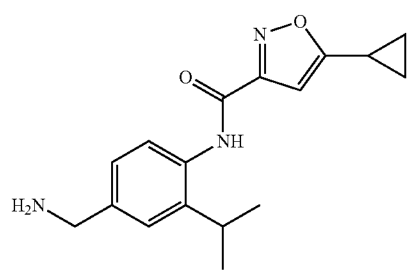 [SMILES: CC(C)c1cc(CN)ccc1NC(=O)c1cc(C2CC2)on1] | HCl |
| 92 | 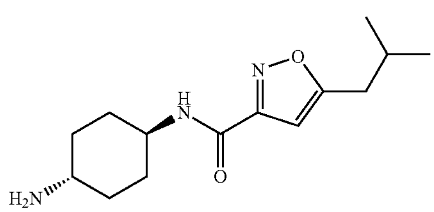 [SMILES: CC(C)Cc1cc(C(=O)N[C@H]2CC[C@H](N)CC2)no1] | HCl |
| 93 | 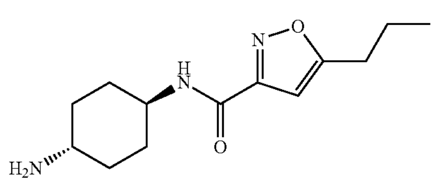 [SMILES: CCCc1cc(C(=O)N[C@H]2CC[C@H](N)CC2)no1] | HCl |
| 94 | 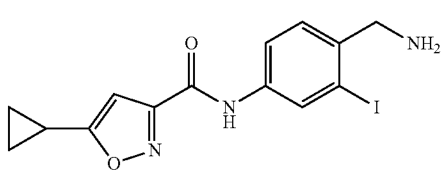 [SMILES: NCc1ccc(NC(=O)c2cc(C3CC3)on2)cc1I] | HCl |

TABLE 1-continued

| Cpd. No. | Structure | Salt Form |
|---|---|---|
| 95 | (5-cyclopropylisoxazole-3-carboxamide with N-(1-(1H-indazol-4-yl)-2,2-dimethylpropyl)) | None |
| 96 | (5-cyclopropyl-N-(piperidin-4-yl(3-((1-isopropylpiperidin-4-yl)carbamoyl)phenyl)methyl)isoxazole-3-carboxamide) | HCl |
| 97 | (5-cyclopropyl-N-((3-((3-hydroxybenzyl)carbamoyl)phenyl)(piperidin-4-yl)methyl)isoxazole-3-carboxamide) | HCl |
| 98 | (5-cyclopropyl-N-((3-(cyclopropylcarbamoyl)phenyl)(piperidin-4-yl)methyl)isoxazole-3-carboxamide) | HCl |
| 99 | (5-cyclopropyl-N-((piperidin-4-yl)(3-((prop-2-yn-1-yloxy)methyl)phenyl)methyl)isoxazole-3-carboxamide) | HCl |

TABLE 1-continued

| Cpd. No. | Structure | Salt Form |
|---|---|---|
| 100 | 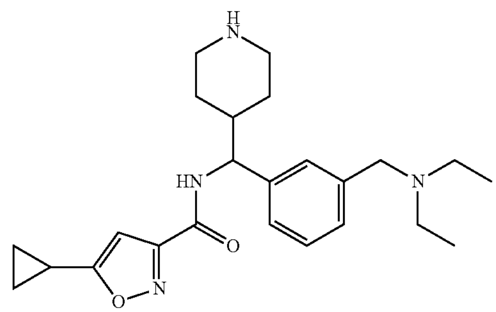 [SMILES: CCN(CC)Cc1cccc(C(NC(=O)c2cc(C3CC3)on2)C2CCNCC2)c1] | HCl |
| 101 | 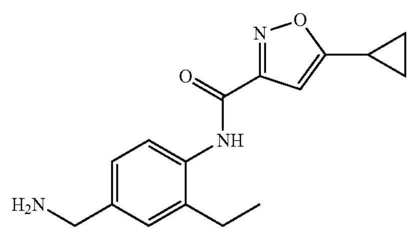 [SMILES: CCc1cc(CN)ccc1NC(=O)c1cc(C2CC2)on1] | HCl |
| 102 | 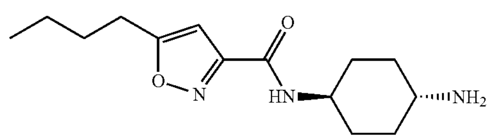 [SMILES: CCCCc1cc(C(=O)N[C@H]2CC[C@H](N)CC2)no1] | HCl |
| 103 | 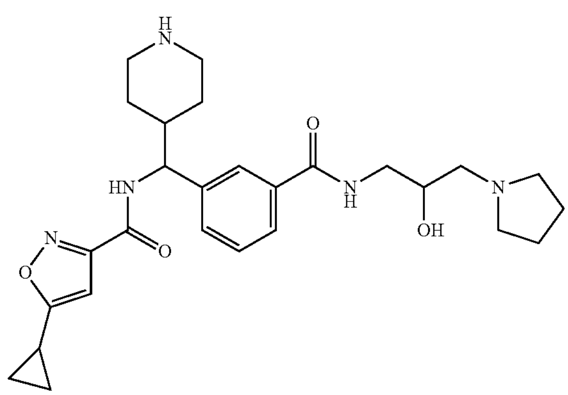 [SMILES: O=C(NCC(O)CN1CCCC1)c1cccc(C(NC(=O)c2cc(C3CC3)on2)C2CCNCC2)c1] | TFA |
| 104 | 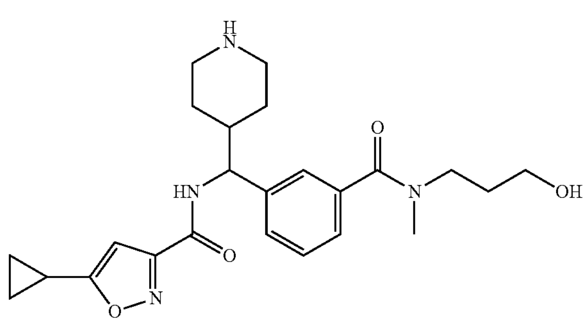 [SMILES: CN(CCCO)C(=O)c1cccc(C(NC(=O)c2cc(C3CC3)on2)C2CCNCC2)c1] | TFA |

US 10,428,029 B2
45    46
TABLE 1-continued
| Cpd. No. | Structure | Salt Form |
|---|---|---|
| 105 | 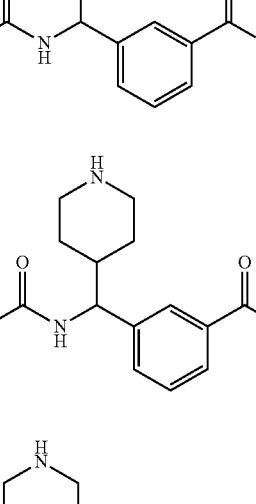 | HCl |
| 106 | 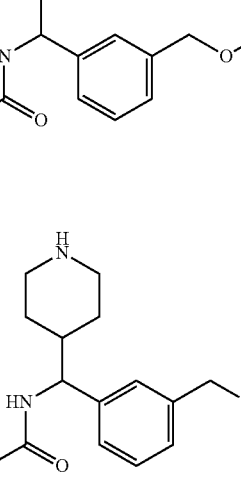 | HCl |
| 107 | 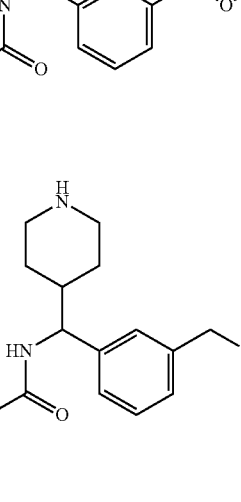 | TFA |
| 108 | 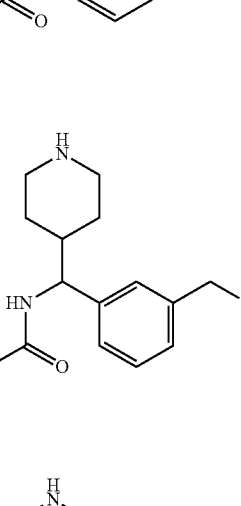 | TFA |
| 109 | 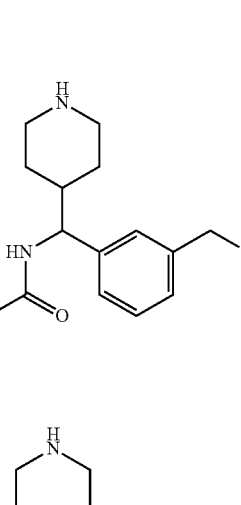 | HCl |

TABLE 1-continued

| Cpd. No. | Structure | Salt Form |
|---|---|---|
| 110 | 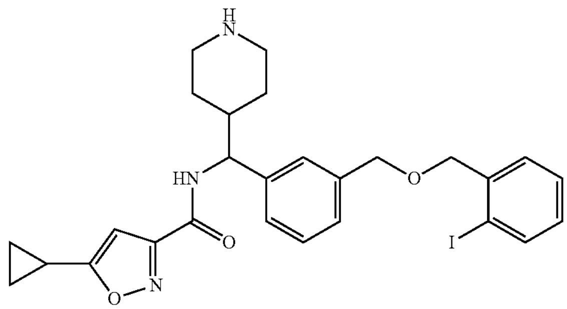 [SMILES: O=C(NC(c1cccc(COCc2ccccc2I)c1)C1CCNCC1)c1cc(C2CC2)on1] | HCl |
| 111 | 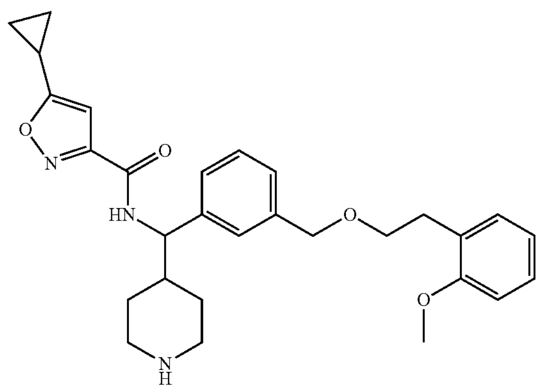 [SMILES: COc1ccccc1CCOCc1cccc(C(NC(=O)c2cc(C3CC3)on2)C2CCNCC2)c1] | HCl |
| 112 | 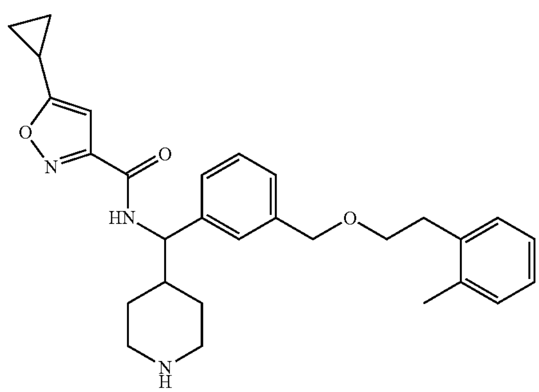 [SMILES: Cc1ccccc1CCOCc1cccc(C(NC(=O)c2cc(C3CC3)on2)C2CCNCC2)c1] | HCl |
| 113 | 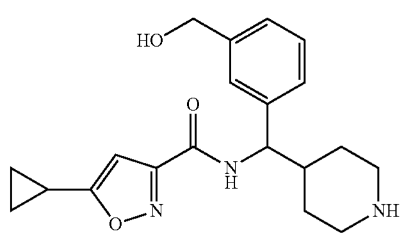 [SMILES: O=C(NC(c1cccc(CO)c1)C1CCNCC1)c1cc(C2CC2)on1] | HCl |
| 114 | 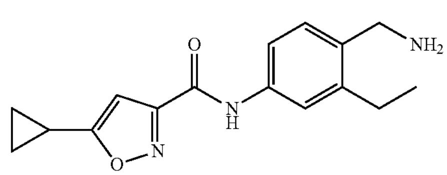 [SMILES: CCc1cc(NC(=O)c2cc(C3CC3)on2)ccc1CN] | HCl |

TABLE 1-continued

| Cpd. No. | Structure | Salt Form |
|---|---|---|
| 115 | 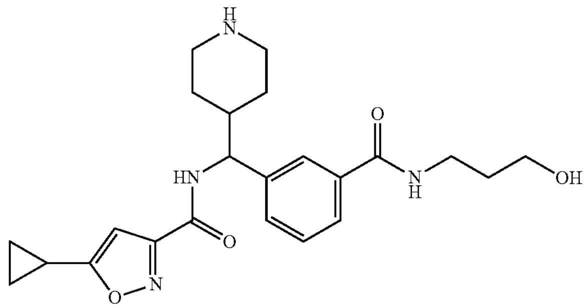 [SMILES: O=C(NCCCO)c1cccc(C(NC(=O)c2cc(C3CC3)on2)C2CCNCC2)c1] | HCl |
| 116 | 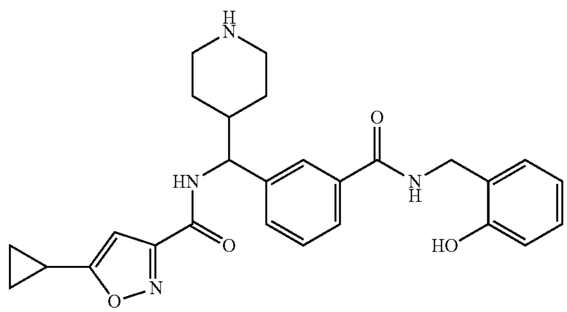 [SMILES: O=C(NCc1ccccc1O)c1cccc(C(NC(=O)c2cc(C3CC3)on2)C2CCNCC2)c1] | HCl |
| 117 | 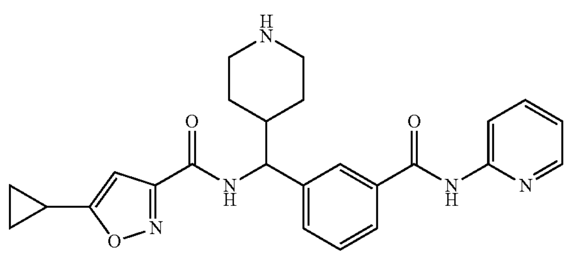 [SMILES: O=C(Nc1ccccn1)c1cccc(C(NC(=O)c2cc(C3CC3)on2)C2CCNCC2)c1] | HCl |
| 118 | 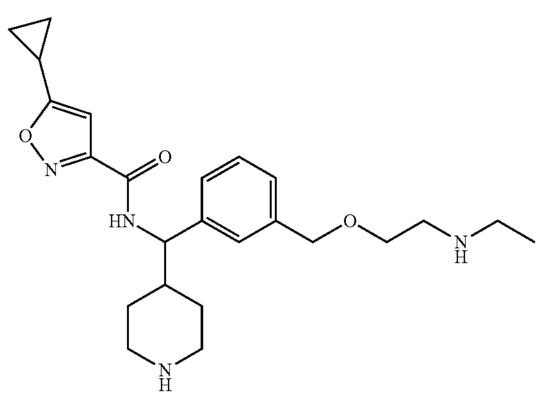 [SMILES: CCNCCOCc1cccc(C(NC(=O)c2cc(C3CC3)on2)C2CCNCC2)c1] | HCl |

TABLE 1-continued

| Cpd. No. | Structure | Salt Form |
|---|---|---|
| 119 | 5-cyclopropyl-isoxazole-3-carboxamide linked via NH to CH bearing a 4-piperidinyl group and a 3-(2-aminoethoxymethyl)phenyl group | TFA |
| 120 | 5-cyclopropyl-isoxazole-3-carboxamide linked via NH to CH bearing a 4-piperidinyl group and a 3-(propoxymethyl)phenyl group | HCl |
| 121 | 5-cyclopropyl-isoxazole-3-carboxamide N-linked to 4-(1-amino-4-hydroxybutyl)phenyl | HCl |
| 122 | 5-cyclopropyl-isoxazole-3-carboxamide linked via NH to 1-oxaspiro[5.5]undecan-4-yl | None |
| 123 | 5-cyclopropyl-isoxazole-3-carboxamide linked via NH to 1-ethoxy-spiro[3.5]nonan-3-yl | None |

TABLE 1-continued

| Cpd. No. | Structure | Salt Form |
|---|---|---|
| 124 | 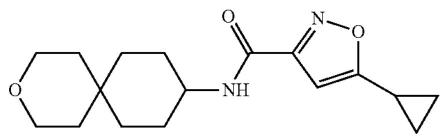 [SMILES: O=C(NC1CCC2(CCOCC2)CC1)c1cc(C2CC2)on1] | None |
| 125 | 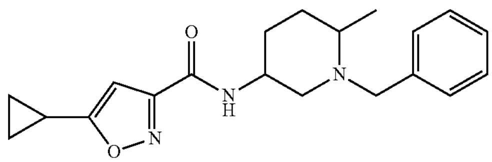 [SMILES: CC1CCC(NC(=O)c2cc(C3CC3)on2)CN1Cc1ccccc1] | None |
| 126 | 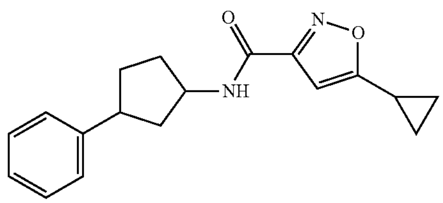 [SMILES: O=C(NC1CCC(c2ccccc2)C1)c1cc(C2CC2)on1] | None |
| 127 | 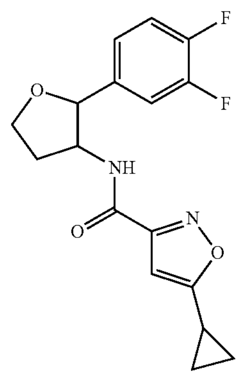 [SMILES: O=C(NC1CCOC1c1ccc(F)c(F)c1)c1cc(C2CC2)on1] | None |
| 128 | 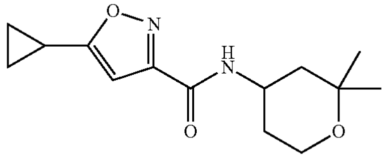 [SMILES: CC1(C)CC(NC(=O)c2cc(C3CC3)on2)CCO1] | None |
| 129 | 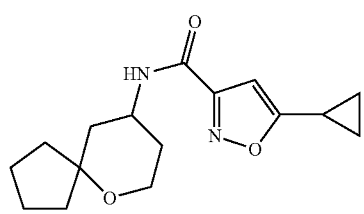 [SMILES: O=C(NC1CCOC2(CCCC2)C1)c1cc(C2CC2)on1] | None |
| 130 | 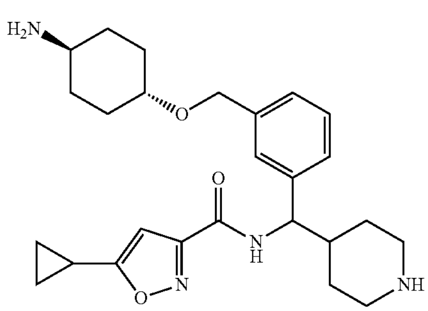 [SMILES: N[C@H]1CC[C@H](OCc2cccc(C(NC(=O)c3cc(C4CC4)on3)C3CCNCC3)c2)CC1] | TFA |

TABLE 1-continued

| Cpd. No. | Structure | Salt Form |
|---|---|---|
| 131 | 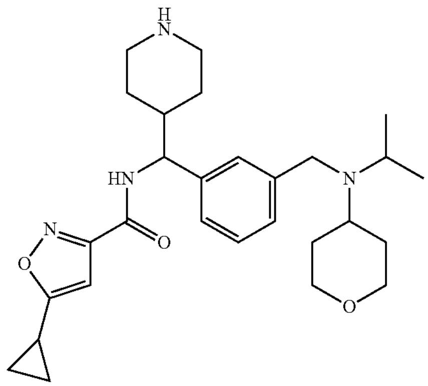 [SMILES: CC(C)N(Cc1cccc(C(NC(=O)c2cc(C3CC3)on2)C2CCNCC2)c1)C1CCOCC1] | HCl |
| 132 | 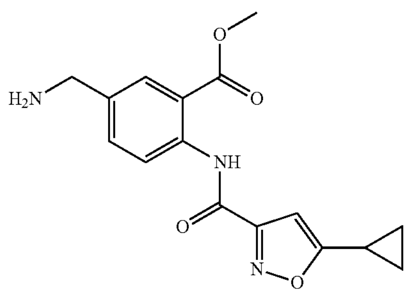 [SMILES: COC(=O)c1cc(CN)ccc1NC(=O)c1cc(C2CC2)on1] | HCl |
| 133 | 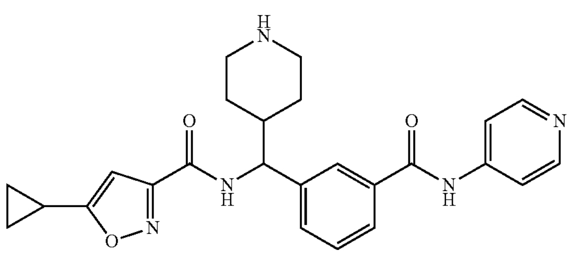 [SMILES: O=C(Nc1ccncc1)c1cccc(C(NC(=O)c2cc(C3CC3)on2)C2CCNCC2)c1] | HCl |
| 134 | 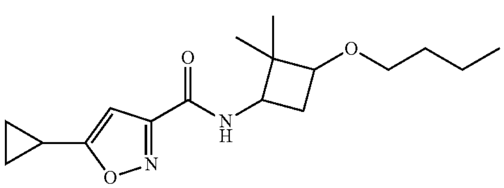 [SMILES: CCCCOC1CC(NC(=O)c2cc(C3CC3)on2)C1(C)C] | None |
| 135 | 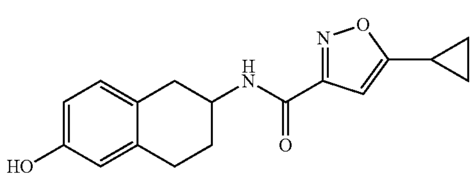 [SMILES: O=C(NC1CCc2cc(O)ccc2C1)c1cc(C2CC2)on1] | None |
| 136 | 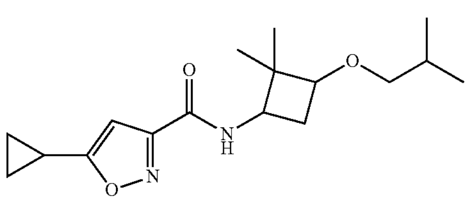 [SMILES: CC(C)COC1CC(NC(=O)c2cc(C3CC3)on2)C1(C)C] | None |

TABLE 1-continued

| Cpd. No. | Structure | Salt Form |
|---|---|---|
| 137 | 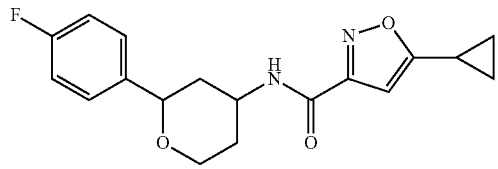 [SMILES: O=C(NC1CCOC(c2ccc(F)cc2)C1)c1cc(C2CC2)on1] | None |
| 138 | 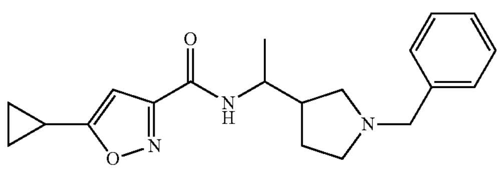 [SMILES: CC(NC(=O)c1cc(C2CC2)on1)C1CCN(Cc2ccccc2)C1] | None |
| 139 | 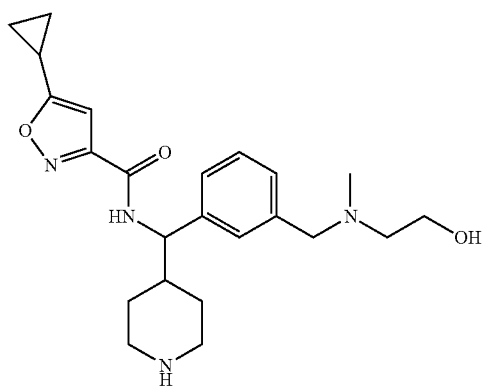 [SMILES: CN(CCO)Cc1cccc(C(NC(=O)c2cc(C3CC3)on2)C2CCNCC2)c1] | HCl |
| 140 | 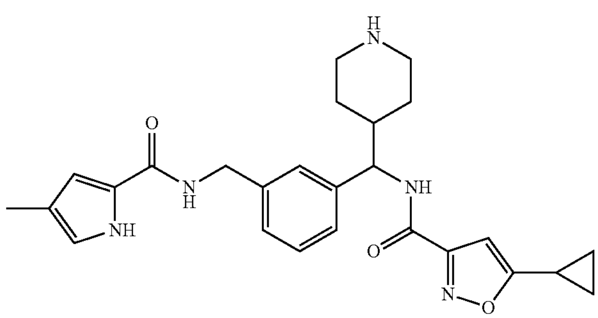 [SMILES: Cc1c[nH]c(C(=O)NCc2cccc(C(NC(=O)c3cc(C4CC4)on3)C3CCNCC3)c2)c1] | TFA |
| 141 | 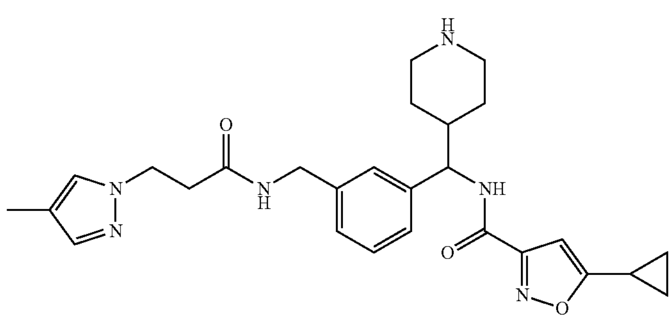 [SMILES: Cc1cnn(CCC(=O)NCc2cccc(C(NC(=O)c3cc(C4CC4)on3)C3CCNCC3)c2)c1] | HCl |

TABLE 1-continued

| Cpd. No. | Structure | Salt Form |
|---|---|---|
| 142 | 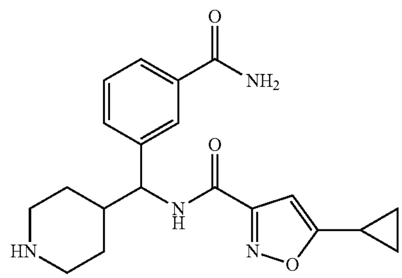 [SMILES: NC(=O)c1cccc(C(NC(=O)c2cc(C3CC3)on2)C2CCNCC2)c1] | TFA |
| 143 | 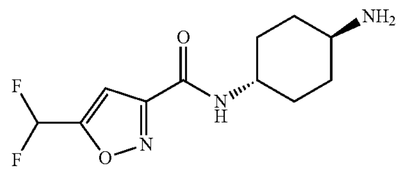 [SMILES: N[C@H]1CC[C@H](NC(=O)c2cc(C(F)F)on2)CC1] | None |
| 144 | 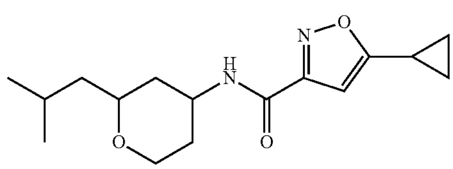 [SMILES: CC(C)CC1CC(NC(=O)c2cc(C3CC3)on2)CCO1] | None |
| 145 | 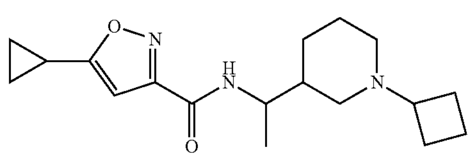 [SMILES: CC(NC(=O)c1cc(C2CC2)on1)C1CCCN(C2CCC2)C1] | None |
| 146 | 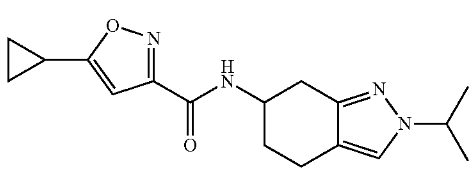 [SMILES: CC(C)n1cc2c(n1)CC(NC(=O)c1cc(C3CC3)on1)CC2] | None |
| 147 | 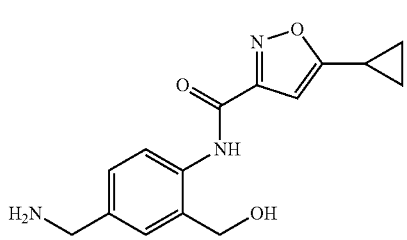 [SMILES: NCc1ccc(NC(=O)c2cc(C3CC3)on2)c(CO)c1] | TFA |
| 148 | 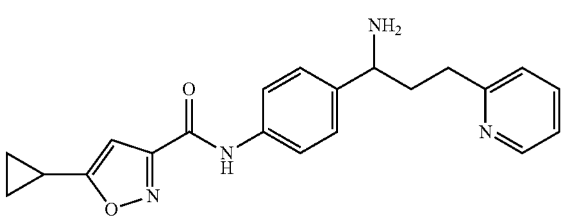 [SMILES: NC(CCc1ccccn1)c1ccc(NC(=O)c2cc(C3CC3)on2)cc1] | None |

TABLE 1-continued

| Cpd. No. | Structure | Salt Form |
|---|---|---|
| 149 | 5-cyclopropyl-N-(4-(1-amino-3-(pyridin-3-yl)propyl)phenyl)isoxazole-3-carboxamide | None |
| 150 | 5-cyclopropyl-N-(4-(1-amino-3-(pyridin-4-yl)propyl)phenyl)isoxazole-3-carboxamide | None |
| 151 | 5-cyclopropyl-N-(4-(1-amino-3-phenylpropyl)phenyl)isoxazole-3-carboxamide | None |
| 152 | 5-cyclopropyl-N-((1-(2-aminoacetyl)piperidin-4-yl)(phenyl)methyl)isoxazole-3-carboxamide | HCl |
| 153 | 5-cyclopropyl-N-((1-((S)-2-aminopropanoyl)piperidin-4-yl)(phenyl)methyl)isoxazole-3-carboxamide | TFA |

TABLE 1-continued

| Cpd. No. | Structure | Salt Form |
|---|---|---|
| 154 | 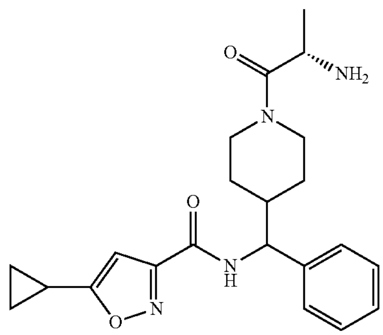 [SMILES: C[C@H](N)C(=O)N1CCC(C(NC(=O)c2cc(C3CC3)on2)c2ccccc2)CC1] | None |
| 155 | 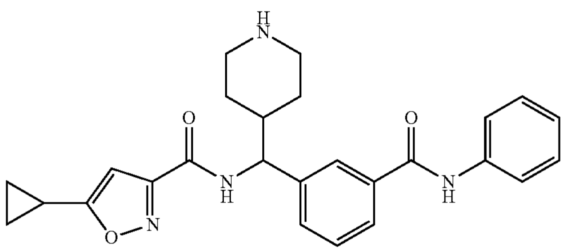 | HCOOH |
| 156 | 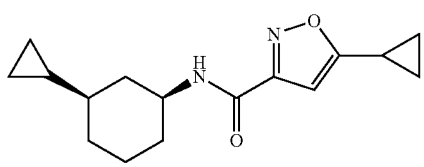 [SMILES: O=C(N[C@H]1CCC[C@@H](C2CC2)C1)c1cc(C2CC2)on1] | None |
| 157 | 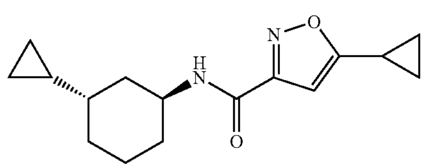 [SMILES: O=C(N[C@H]1CCC[C@H](C2CC2)C1)c1cc(C2CC2)on1] | None |
| 158 | 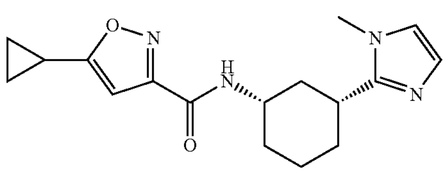 [SMILES: Cn1ccnc1[C@@H]1CCC[C@H](NC(=O)c2cc(C3CC3)on2)C1] | TFA |
| 159 | 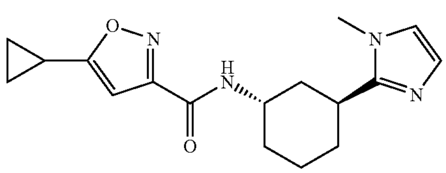 [SMILES: Cn1ccnc1[C@H]1CCC[C@H](NC(=O)c2cc(C3CC3)on2)C1] | TFA |
| 160 | 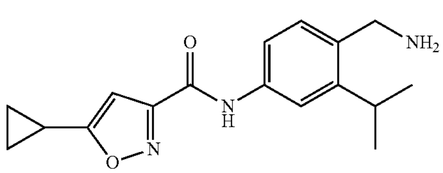 [SMILES: CC(C)c1cc(NC(=O)c2cc(C3CC3)on2)ccc1CN] | HCl |

TABLE 1-continued

| Cpd. No. | Structure | Salt Form |
|---|---|---|
| 161 | 5-cyclopropyl-N-(4-(aminomethyl)-3-(hydroxymethyl)phenyl)isoxazole-3-carboxamide | HCl |
| 162 | 5-cyclopropyl-N-((R)-(piperidin-4-yl)(3-(pyridin-3-ylcarbamoyl)phenyl)methyl)isoxazole-3-carboxamide | HCl |
| 163 | 5-cyclopropyl-N-((S)-(piperidin-4-yl)(3-(pyridin-3-ylcarbamoyl)phenyl)methyl)isoxazole-3-carboxamide | HCl |
| 164 | N-(4-((2-aminoacetamido)methyl)phenyl)-5-cyclopropylisoxazole-3-carboxamide | HCl |
| 165 | N-((1-benzyl-5-methylpyrrolidin-3-yl)methyl)-5-cyclopropylisoxazole-3-carboxamide | None |
| 166 | 5-cyclopropyl-N-((4-chlorophenyl)(4-methylmorpholin-2-yl)methyl)isoxazole-3-carboxamide | None |
| 167 | 5-cyclopropyl-N-(1,2-dimethylpiperidin-3-yl)isoxazole-3-carboxamide | None |

TABLE 1-continued

| Cpd. No. | Structure | Salt Form |
|---|---|---|
| 168 | 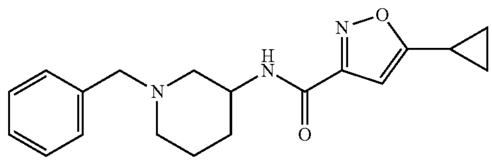 [SMILES: O=C(NC1CCCN(Cc2ccccc2)C1)c1cc(C2CC2)on1] | None |
| 169 | 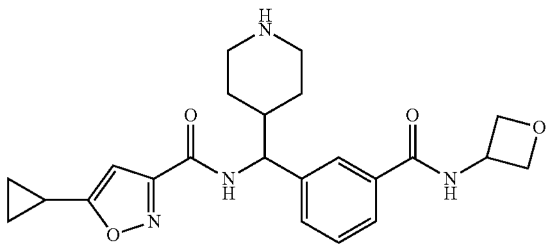 [SMILES: O=C(NC1COC1)c1cccc(C(NC(=O)c2cc(C3CC3)on2)C2CCNCC2)c1] | TFA |
| 170 | 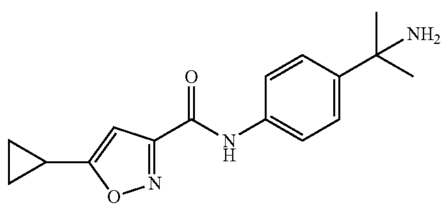 [SMILES: CC(C)(N)c1ccc(NC(=O)c2cc(C3CC3)on2)cc1] | HCl |
| 171 | 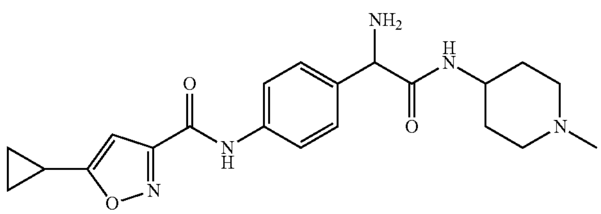 [SMILES: CN1CCC(NC(=O)C(N)c2ccc(NC(=O)c3cc(C4CC4)on3)cc2)CC1] | HCl |
| 172 | 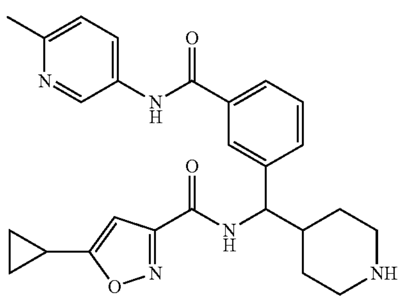 [SMILES: Cc1ccc(NC(=O)c2cccc(C(NC(=O)c3cc(C4CC4)on3)C3CCNCC3)c2)cn1] | HCl |
| 173 | 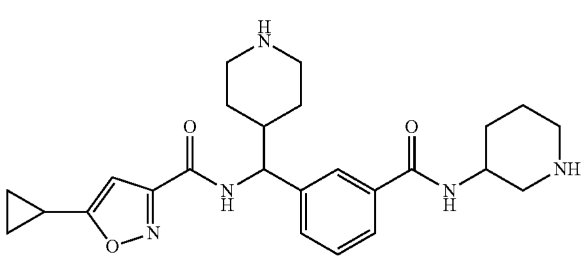 [SMILES: O=C(NC1CCCNC1)c1cccc(C(NC(=O)c2cc(C3CC3)on2)C2CCNCC2)c1] | HCl |

TABLE 1-continued

| Cpd. No. | Structure | Salt Form |
|---|---|---|
| 174 | 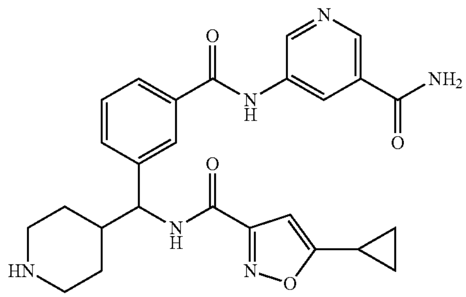 [SMILES: NC(=O)c1cncc(NC(=O)c2cccc(C(NC(=O)c3cc(C4CC4)on3)C3CCNCC3)c2)c1] | HCl |
| 175 | 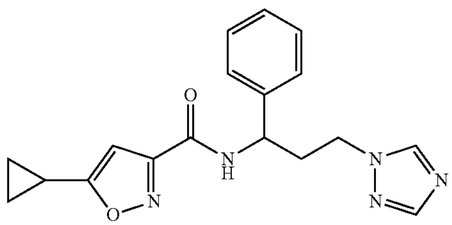 [SMILES: O=C(NC(CCn1cncn1)c1ccccc1)c1cc(C2CC2)on1] | None |
| 176 | 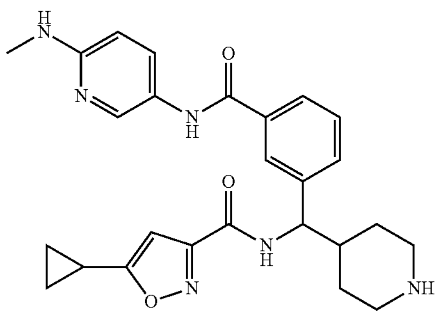 [SMILES: CNc1ccc(NC(=O)c2cccc(C(NC(=O)c3cc(C4CC4)on3)C3CCNCC3)c2)cn1] | HCl |
| 177 | 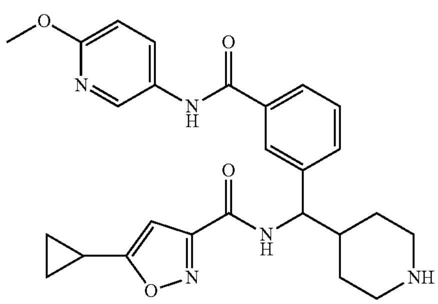 [SMILES: COc1ccc(NC(=O)c2cccc(C(NC(=O)c3cc(C4CC4)on3)C3CCNCC3)c2)cn1] | HCl |
| 178 | 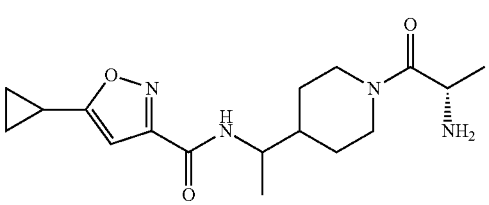 [SMILES: CC(NC(=O)c1cc(C2CC2)on1)C1CCN(C(=O)[C@H](C)N)CC1] | HCl |
| 179 | 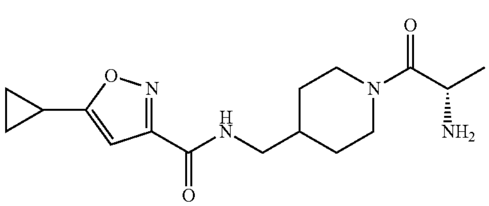 [SMILES: C[C@H](N)C(=O)N1CCC(CNC(=O)c2cc(C3CC3)on2)CC1] | HCl |

TABLE 1-continued

| Cpd. No. | Structure | Salt Form |
|---|---|---|
| 180 | 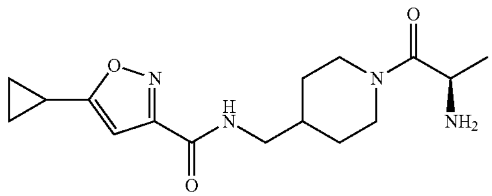 [SMILES: C[C@@H](N)C(=O)N1CCC(CNC(=O)c2cc(C3CC3)on2)CC1] | HCl |
| 181 | 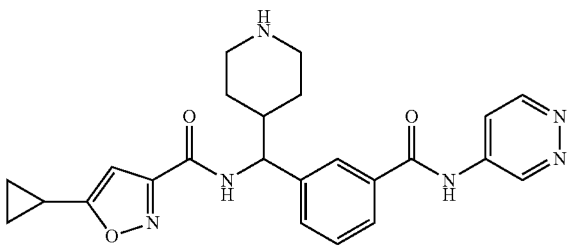 [SMILES: O=C(Nc1ccnnc1)c1cccc(C(NC(=O)c2cc(C3CC3)on2)C2CCNCC2)c1] | HCl |
| 182 | 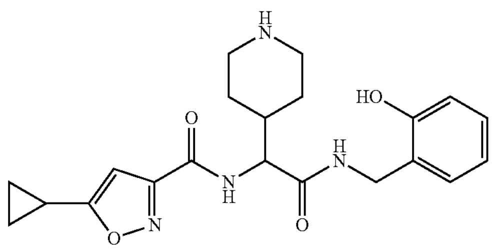 [SMILES: O=C(NC(C(=O)NCc1ccccc1O)C1CCNCC1)c1cc(C2CC2)on1] | HCl |
| 183 | 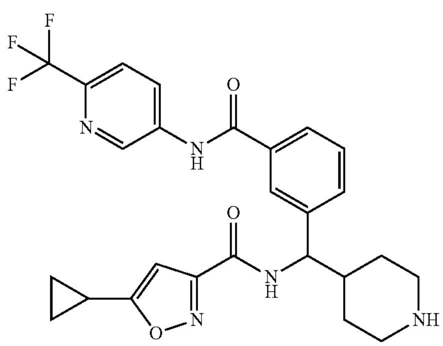 [SMILES: O=C(Nc1ccc(C(F)(F)F)nc1)c1cccc(C(NC(=O)c2cc(C3CC3)on2)C2CCNCC2)c1] | HCl |
| 184 | 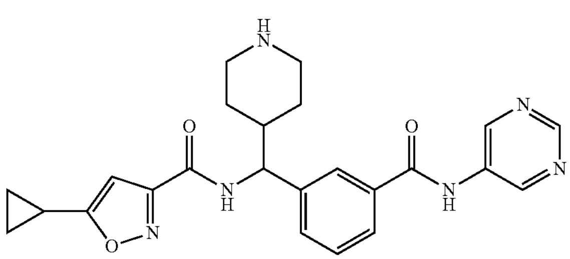 [SMILES: O=C(Nc1cncnc1)c1cccc(C(NC(=O)c2cc(C3CC3)on2)C2CCNCC2)c1] | HCl |
| 185 | 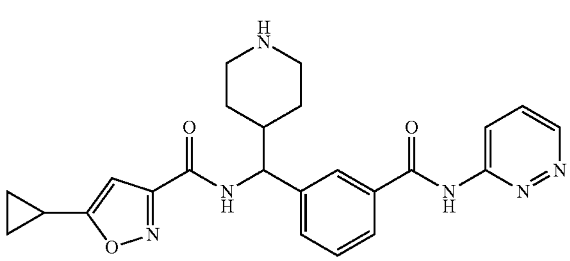 | HCl |

TABLE 1-continued

| Cpd. No. | Structure | Salt Form |
|---|---|---|
| 186 | 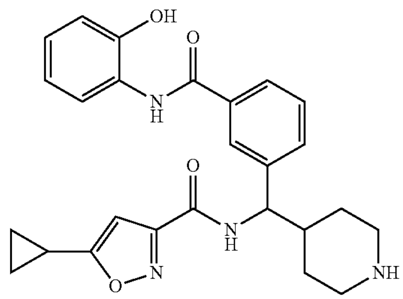 [SMILES: O=C(Nc1ccccc1O)c1cccc(C(NC(=O)c2cc(C3CC3)on2)C2CCNCC2)c1] | HCl |
| 187 | 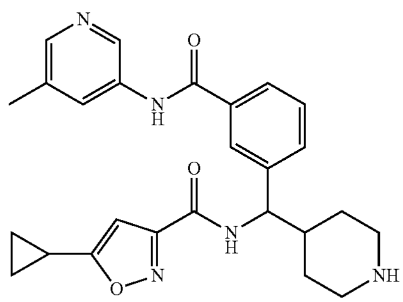 [SMILES: Cc1cncc(NC(=O)c2cccc(C(NC(=O)c3cc(C4CC4)on3)C3CCNCC3)c2)c1] | HCl |
| 188 | 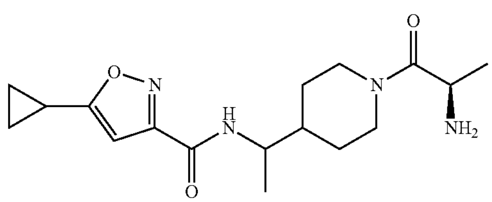 [SMILES: CC(NC(=O)c1cc(C2CC2)on1)C1CCN(C(=O)[C@@H](C)N)CC1] | HCl |
| 189 | 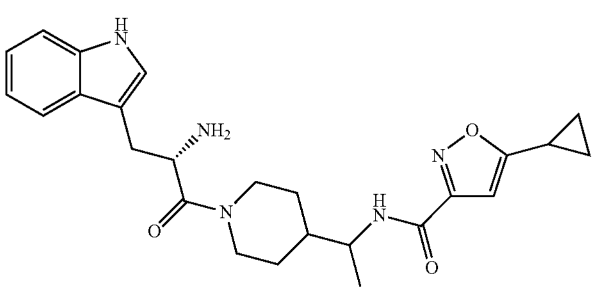 [SMILES: CC(NC(=O)c1cc(C2CC2)on1)C1CCN(C(=O)[C@@H](N)Cc2c[nH]c3ccccc23)CC1] | HCl |
| 190 | 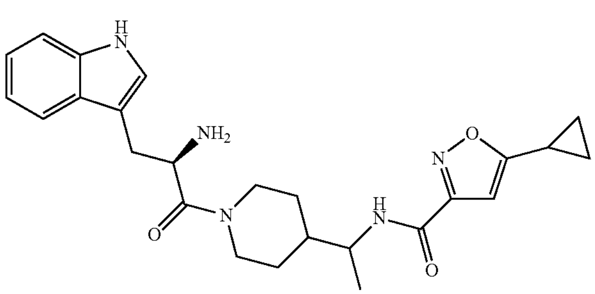 [SMILES: CC(NC(=O)c1cc(C2CC2)on1)C1CCN(C(=O)[C@H](N)Cc2c[nH]c3ccccc23)CC1] | HCl |

TABLE 1-continued

| Cpd. No. | Structure | Salt Form |
|---|---|---|
| 191 | (structure) | HCl |
| 192 | (structure) | HCl |
| 193 | (structure) | HCl |
| 194 | (structure) | HCl |

TABLE 1-continued
| Cpd. No. | Structure | Salt Form |
|---|---|---|
| 195 | 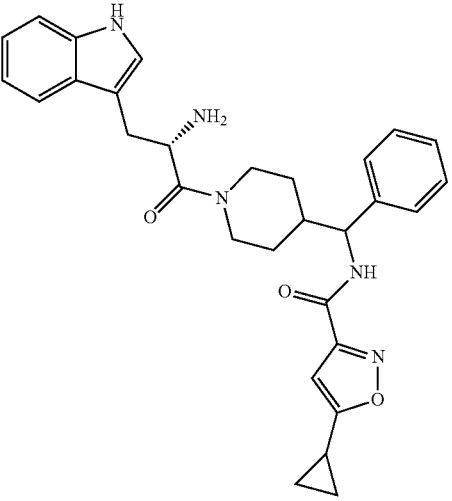 [SMILES: N[C@@H](Cc1c[nH]c2ccccc12)C(=O)N1CCC(C(NC(=O)c2cc(C3CC3)on2)c2ccccc2)CC1] | HCl |
| 196 | 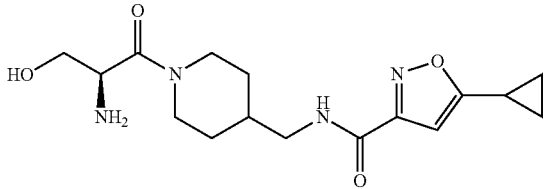 [SMILES: N[C@@H](CO)C(=O)N1CCC(CNC(=O)c2cc(C3CC3)on2)CC1] | HCl |
| 197 | 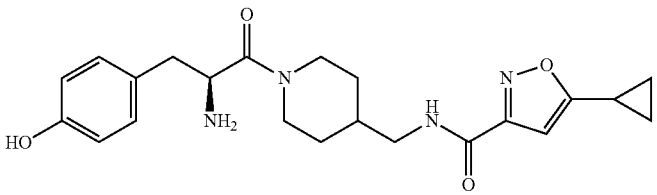 [SMILES: N[C@@H](Cc1ccc(O)cc1)C(=O)N1CCC(CNC(=O)c2cc(C3CC3)on2)CC1] | HCl |
| 198 | 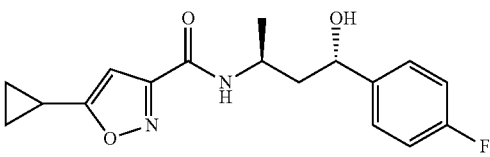 [SMILES: C[C@@H](C[C@H](O)c1ccc(F)cc1)NC(=O)c1cc(C2CC2)on1] | TFA |
| 199 | 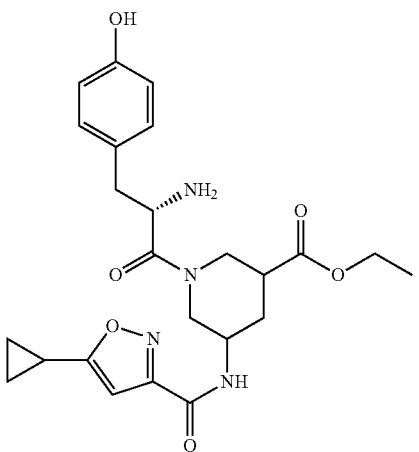 [SMILES: CCOC(=O)C1CC(NC(=O)c2cc(C3CC3)on2)CN(C(=O)[C@@H](N)Cc2ccc(O)cc2)C1] | TFA |

TABLE 1-continued

| Cpd. No. | Structure | Salt Form |
|---|---|---|
| 200 | 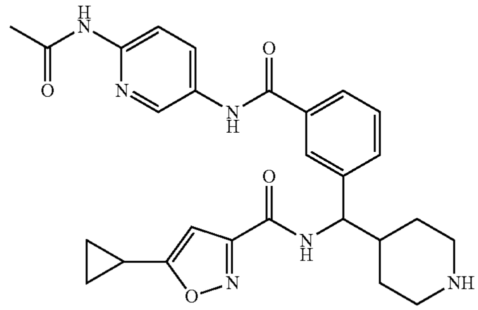 [SMILES: CC(=O)Nc1ccc(NC(=O)c2cccc(C(NC(=O)c3cc(C4CC4)on3)C3CCNCC3)c2)cn1] | HCl |
| 201 | 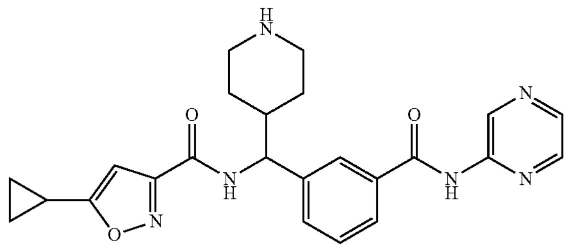 [SMILES: O=C(Nc1cnccn1)c1cccc(C(NC(=O)c2cc(C3CC3)on2)C2CCNCC2)c1] | HCl |
| 202 | 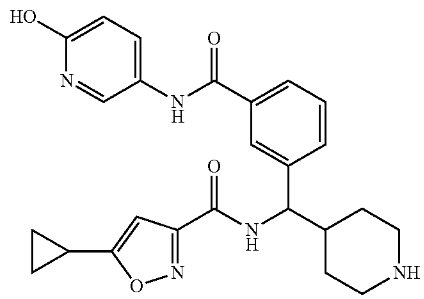 [SMILES: O=C(Nc1ccc(O)nc1)c1cccc(C(NC(=O)c2cc(C3CC3)on2)C2CCNCC2)c1] | HCl |
| 203 | 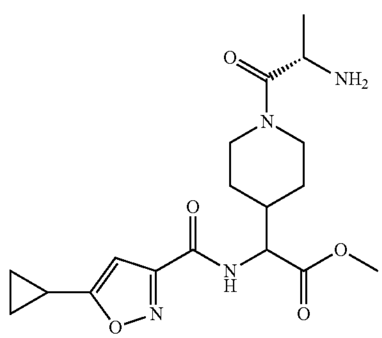 [SMILES: COC(=O)C(NC(=O)c1cc(C2CC2)on1)C1CCN(C(=O)[C@H](C)N)CC1] | HCl |
| 204 | 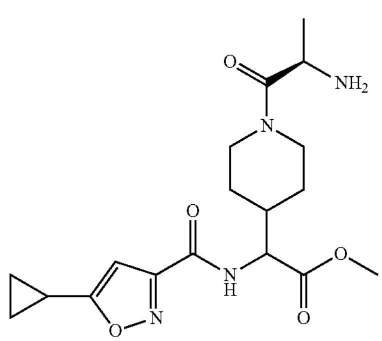 [SMILES: COC(=O)C(NC(=O)c1cc(C2CC2)on1)C1CCN(C(=O)[C@@H](C)N)CC1] | HCl |

TABLE 1-continued

| Cpd. No. | Structure | Salt Form |
|---|---|---|
| 205 | 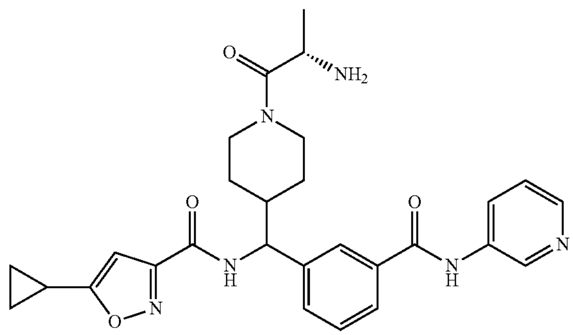 [SMILES: C[C@H](N)C(=O)N1CCC(C(NC(=O)c2cc(C3CC3)on2)c2cccc(C(=O)Nc3cccnc3)c2)CC1] | HCl |
| 206 | 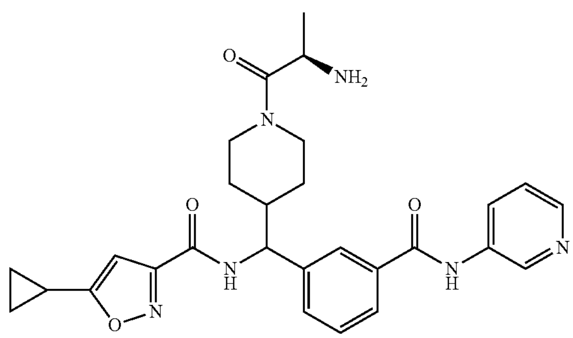 [SMILES: C[C@@H](N)C(=O)N1CCC(C(NC(=O)c2cc(C3CC3)on2)c2cccc(C(=O)Nc3cccnc3)c2)CC1] | HCl |
| 207 | 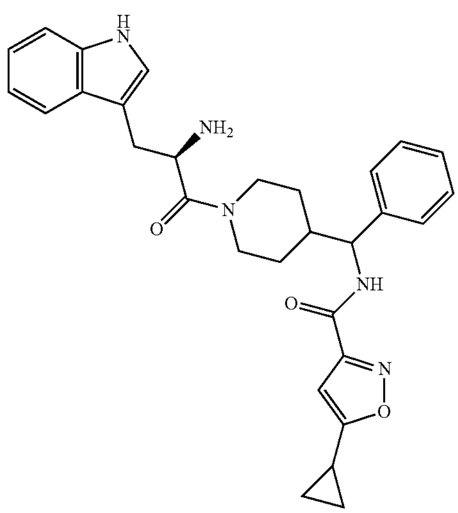 [SMILES: N[C@H](Cc1c[nH]c2ccccc12)C(=O)N1CCC(C(NC(=O)c2cc(C3CC3)on2)c2ccccc2)CC1] | HCl |
| 208 | 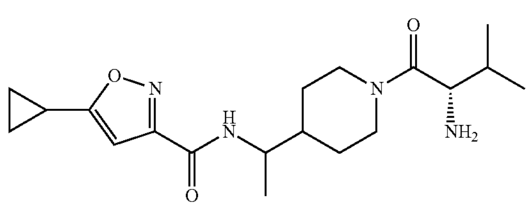 | HCl |
| 209 | 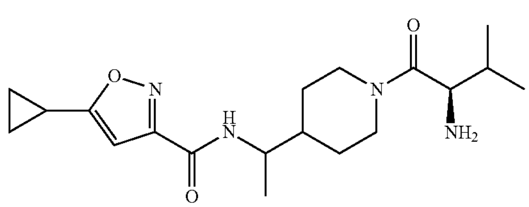 | HCl |

TABLE 1-continued
| Cpd. No. | Structure | Salt Form |
|---|---|---|
| 210 | 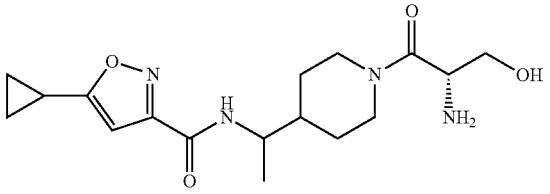 [SMILES: CC(NC(=O)c1cc(C2CC2)on1)C1CCN(C(=O)[C@@H](N)CO)CC1] | HCl |
| 211 | 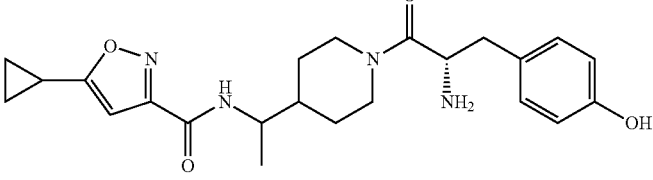 | HCl |
| 212 | 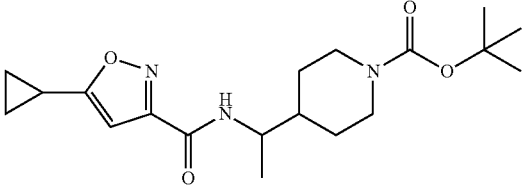 [SMILES: CC(NC(=O)c1cc(C2CC2)on1)C1CCN(C(=O)OC(C)(C)C)CC1] | None |
| 213 | 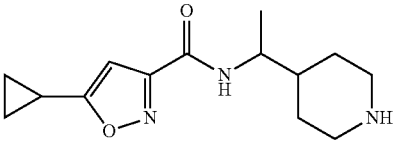 [SMILES: CC(NC(=O)c1cc(C2CC2)on1)C1CCNCC1] | HCl |
| 214 | 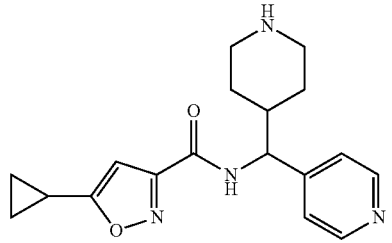 [SMILES: O=C(NC(c1ccncc1)C1CCNCC1)c1cc(C2CC2)on1] | HCl |
| 215 | 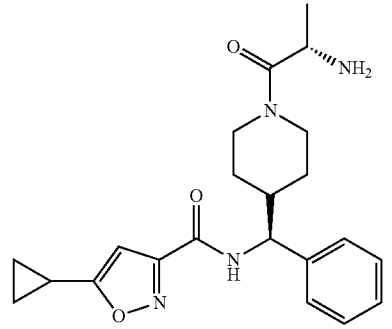 [SMILES: C[C@H](N)C(=O)N1CCC([C@H](NC(=O)c2cc(C3CC3)on2)c2ccccc2)CC1] | HCl |

TABLE 1-continued

| Cpd. No. | Structure | Salt Form |
|---|---|---|
| 216 | 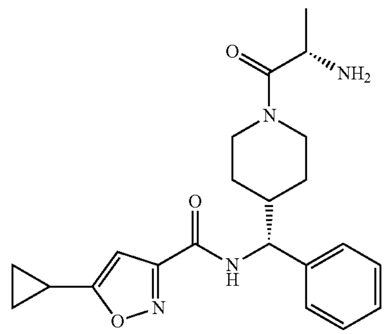 [SMILES: C[C@H](N)C(=O)N1CCC([C@@H](NC(=O)c2cc(C3CC3)on2)c2ccccc2)CC1] | HCl |
| 218 | 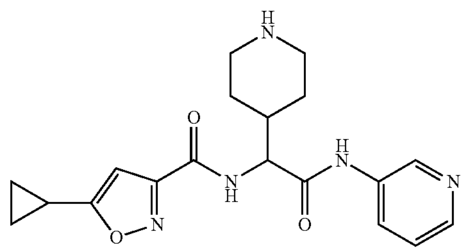 [SMILES: O=C(NC(C(=O)Nc1cccnc1)C1CCNCC1)c1cc(C2CC2)on1] | HCl |
| 219 | 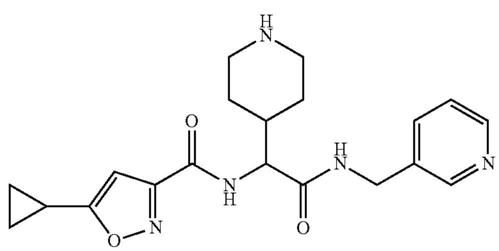 [SMILES: O=C(NC(C(=O)NCc1cccnc1)C1CCNCC1)c1cc(C2CC2)on1] | HCl |
| 220 | 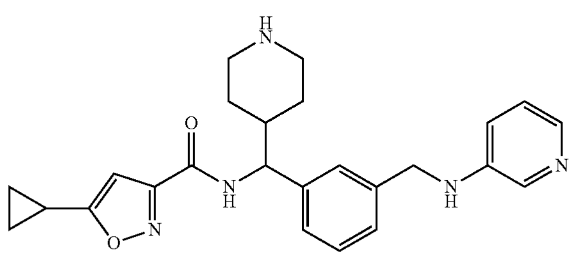 [SMILES: O=C(NC(c1cccc(CNc2cccnc2)c1)C1CCNCC1)c1cc(C2CC2)on1] | HCl |
| 221 | 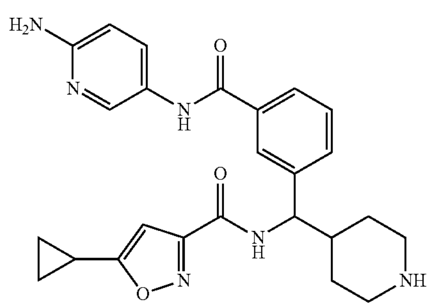 [SMILES: Nc1ccc(NC(=O)c2cccc(C(NC(=O)c3cc(C4CC4)on3)C3CCNCC3)c2)cn1] | HCl |

TABLE 1-continued

| Cpd. No. | Structure | Salt Form |
|---|---|---|
| 222 | 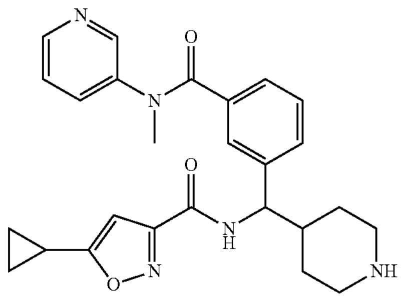 [SMILES: CN(C(=O)c1cccc(C(NC(=O)c2cc(C3CC3)on2)C2CCNCC2)c1)c1cccnc1] | HCl |
| 223 | 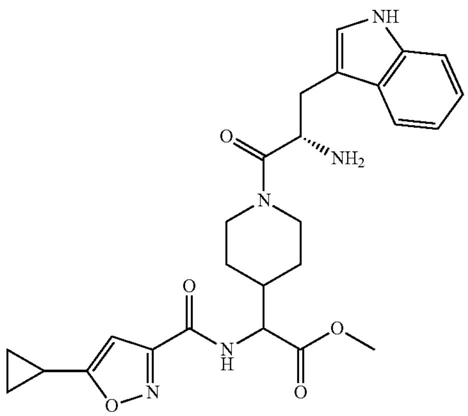 [SMILES: COC(=O)C(NC(=O)c1cc(C2CC2)on1)C1CCN(C(=O)[C@@H](N)Cc2c[nH]c3ccccc23)CC1] | HCl |
| 224 | 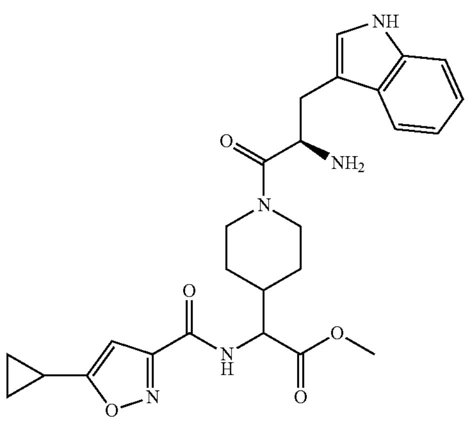 [SMILES: COC(=O)C(NC(=O)c1cc(C2CC2)on1)C1CCN(C(=O)[C@H](N)Cc2c[nH]c3ccccc23)CC1] | HCl |
| 225 | 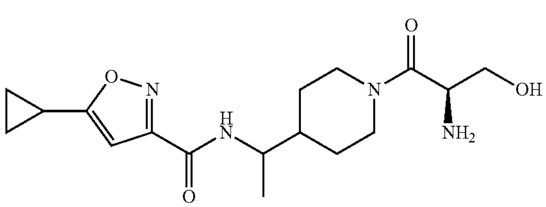 [SMILES: CC(NC(=O)c1cc(C2CC2)on1)C1CCN(C(=O)[C@H](N)CO)CC1] | HCl |
| 226 | 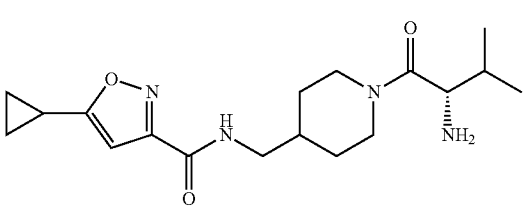 [SMILES: CC(C)[C@H](N)C(=O)N1CCC(CNC(=O)c2cc(C3CC3)on2)CC1] | HCl |

TABLE 1-continued

| Cpd. No. | Structure | Salt Form |
|---|---|---|
| 227 | 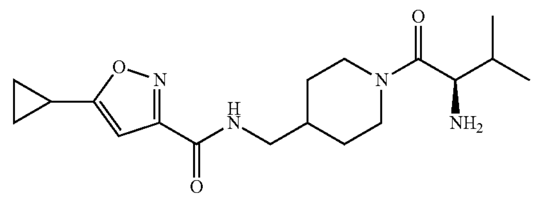 [SMILES: CC(C)[C@@H](N)C(=O)N1CCC(CNC(=O)c2cc(C3CC3)on2)CC1] | HCl |
| 228 | 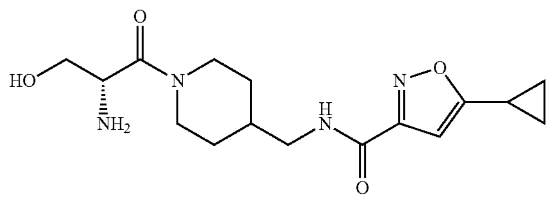 [SMILES: N[C@H](CO)C(=O)N1CCC(CNC(=O)c2cc(C3CC3)on2)CC1] | HCl |
| 229 | 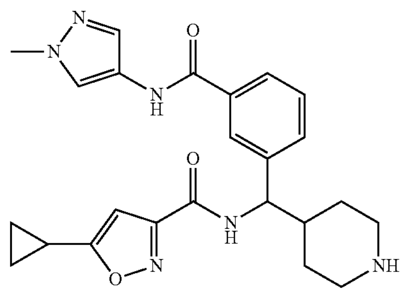 [SMILES: Cn1cc(NC(=O)c2cccc(C(NC(=O)c3cc(C4CC4)on3)C3CCNCC3)c2)cn1] | HCl |
| 230 | 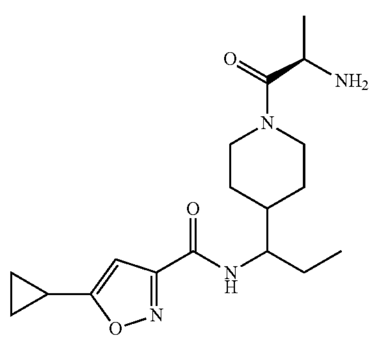 [SMILES: CCC(NC(=O)c1cc(C2CC2)on1)C1CCN(C(=O)[C@@H](C)N)CC1] | HCl |
| 231 | 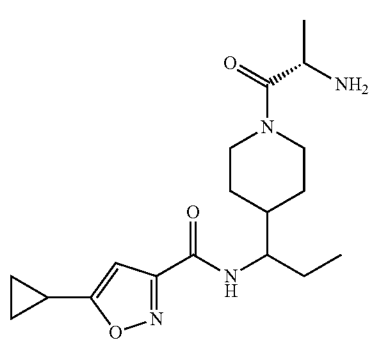 [SMILES: CCC(NC(=O)c1cc(C2CC2)on1)C1CCN(C(=O)[C@H](C)N)CC1] | HCl |

TABLE 1-continued

| Cpd. No. | Structure | Salt Form |
|---|---|---|
| 232 | 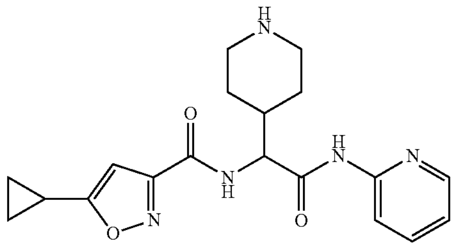 [SMILES: O=C(NC(C(=O)Nc1ccccn1)C1CCNCC1)c1cc(C2CC2)on1] | HCl |
| 233 | 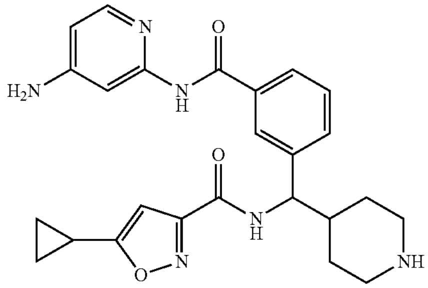 [SMILES: Nc1ccnc(NC(=O)c2cccc(C(NC(=O)c3cc(C4CC4)on3)C3CCNCC3)c2)c1] | TFA |
| 234 | 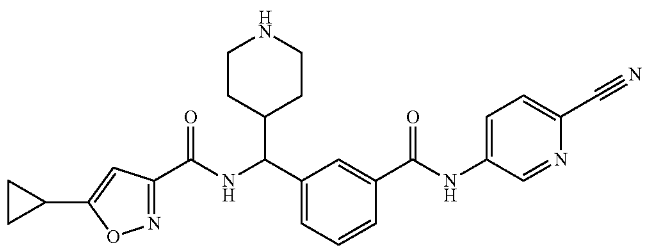 [SMILES: N#Cc1ccc(NC(=O)c2cccc(C(NC(=O)c3cc(C4CC4)on3)C3CCNCC3)c2)cn1] | HCl |
| 235 | 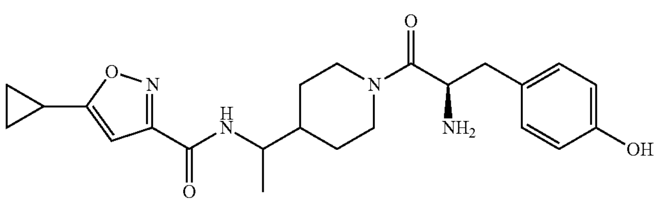 [SMILES: CC(NC(=O)c1cc(C2CC2)on1)C1CCN(C(=O)[C@H](N)Cc2ccc(O)cc2)CC1] | TFA |
| 236 | 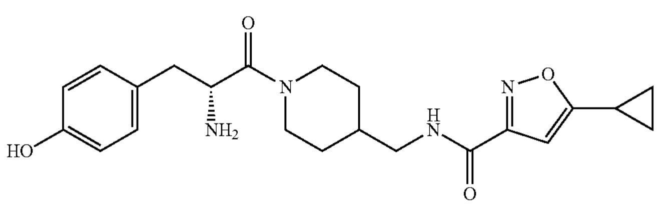 [SMILES: N[C@H](Cc1ccc(O)cc1)C(=O)N1CCC(CNC(=O)c2cc(C3CC3)on2)CC1] | TFA |
| 237 | 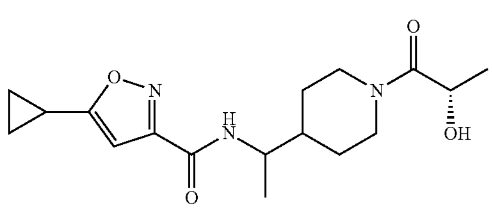 [SMILES: CC(NC(=O)c1cc(C2CC2)on1)C1CCN(C(=O)[C@H](C)O)CC1] | HCl |
| 238 | 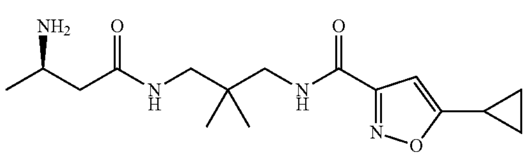 [SMILES: C[C@@H](N)CC(=O)NCC(C)(C)CNC(=O)c1cc(C2CC2)on1] | TFA |

TABLE 1-continued
| Cpd. No. | Structure | Salt Form |
|---|---|---|
| 239 | 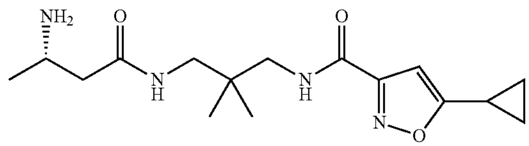 [SMILES: C[C@H](N)CC(=O)NCC(C)(C)CNC(=O)c1cc(C2CC2)on1] | TFA |
| 240 | 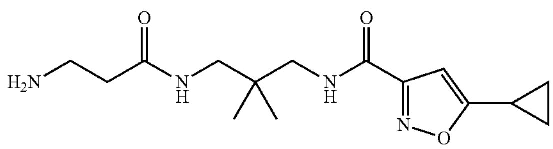 [SMILES: CC(C)(CNC(=O)CCN)CNC(=O)c1cc(C2CC2)on1] | TFA |
| 241 | 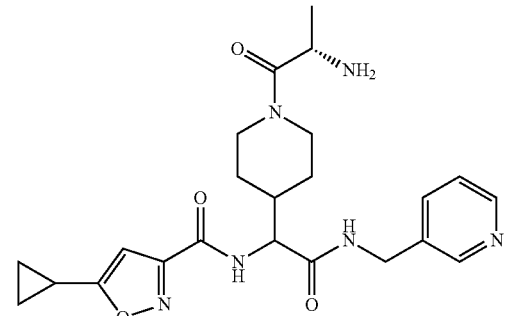 | HCl |
| 242 | 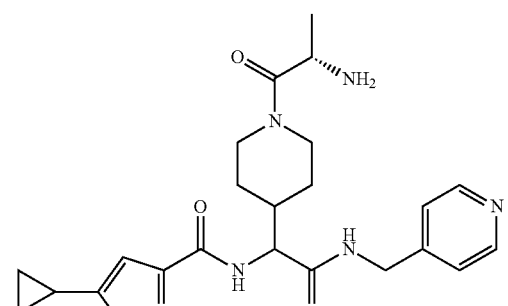 | HCl |
| 243 | 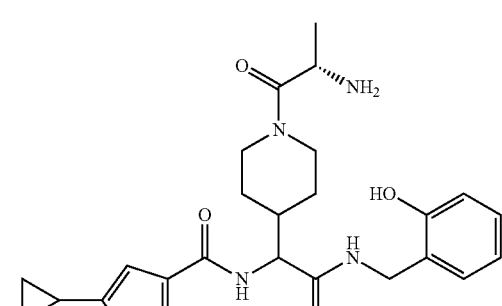 | HCl |
| 244 | 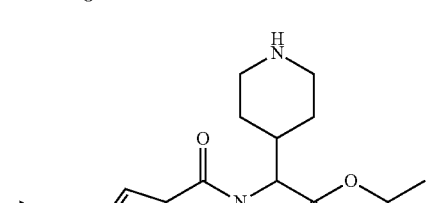 | TFA |

TABLE 1-continued

| Cpd. No. | Structure | Salt Form |
|---|---|---|
| 245 | 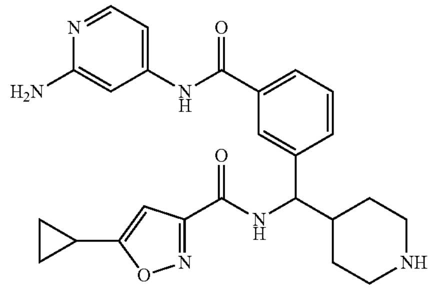 [SMILES: Nc1cc(NC(=O)c2cccc(C(NC(=O)c3cc(C4CC4)on3)C3CCNCC3)c2)ccn1] | TFA |
| 246 | 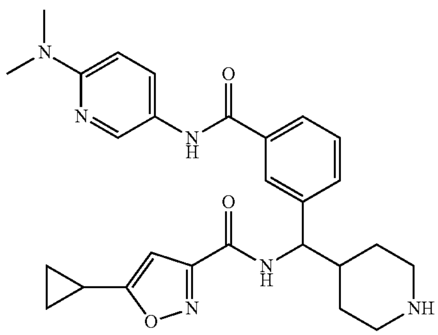 [SMILES: CN(C)c1ccc(NC(=O)c2cccc(C(NC(=O)c3cc(C4CC4)on3)C3CCNCC3)c2)cn1] | TFA |
| 247 | 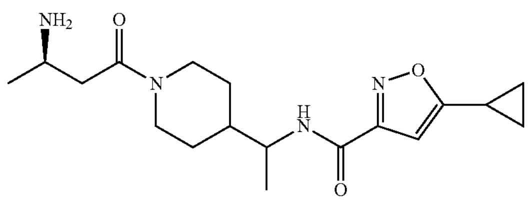 [SMILES: CC(NC(=O)c1cc(C2CC2)on1)C1CCN(C(=O)C[C@@H](C)N)CC1] | HCl |
| 248 | 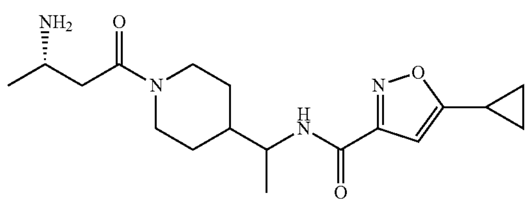 [SMILES: CC(NC(=O)c1cc(C2CC2)on1)C1CCN(C(=O)C[C@H](C)N)CC1] | HCOOH |
| 249 | 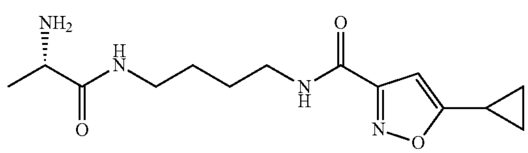 [SMILES: C[C@H](N)C(=O)NCCCCNC(=O)c1cc(C2CC2)on1] | HCl |
| 250 | 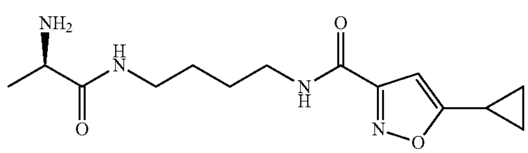 [SMILES: C[C@@H](N)C(=O)NCCCCNC(=O)c1cc(C2CC2)on1] | HCl |
| 251 | 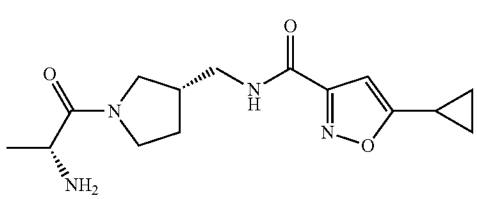 [SMILES: C[C@@H](N)C(=O)N1CC[C@@H](CNC(=O)c2cc(C3CC3)on2)C1] | HCl |

TABLE 1-continued

| Cpd. No. | Structure | Salt Form |
|---|---|---|
| 252 | 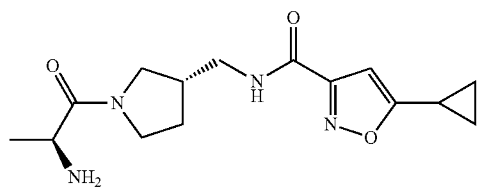 [SMILES: C[C@H](N)C(=O)N1CC[C@@H](CNC(=O)c2cc(C3CC3)on2)C1] | HCl |
| 253 | 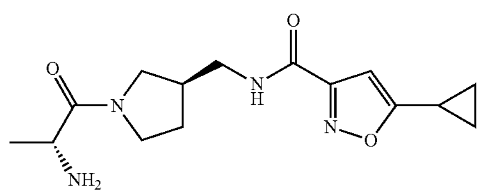 [SMILES: C[C@@H](N)C(=O)N1CC[C@H](CNC(=O)c2cc(C3CC3)on2)C1] | TFA |
| 254 | 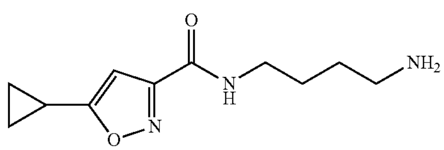 [SMILES: NCCCCNC(=O)c1cc(C2CC2)on1] | HCl |
| 255 | 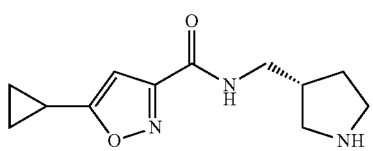 [SMILES: O=C(NC[C@@H]1CCNC1)c1cc(C2CC2)on1] | HCl |
| 256 | 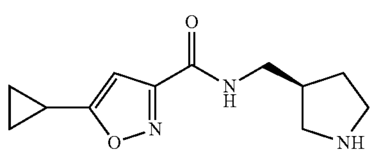 [SMILES: O=C(NC[C@H]1CCNC1)c1cc(C2CC2)on1] | HCl |
| 257 | 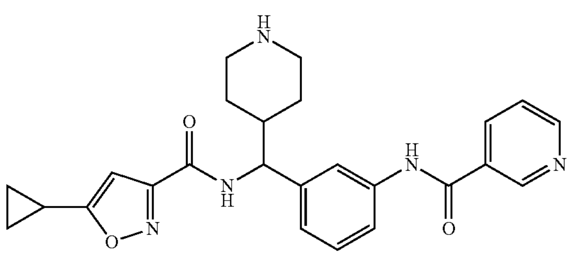 [SMILES: O=C(Nc1cccc(C(NC(=O)c2cc(C3CC3)on2)C2CCNCC2)c1)c1cccnc1] | TFA |
| 258 | 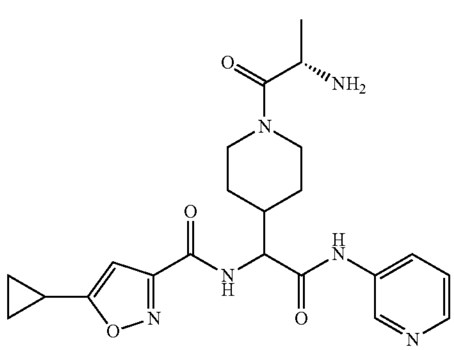 [SMILES: C[C@H](N)C(=O)N1CCC(C(NC(=O)c2cc(C3CC3)on2)C(=O)Nc2cccnc2)CC1] | TFA |

TABLE 1-continued

| Cpd. No. | Structure | Salt Form |
|---|---|---|
| 259 | 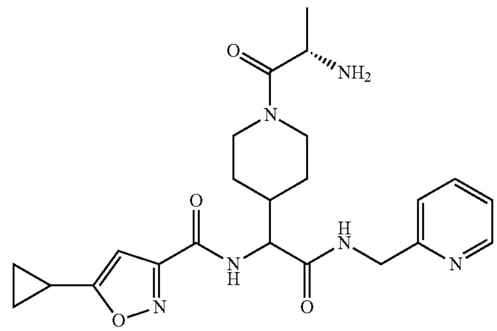 [SMILES: C[C@H](N)C(=O)N1CCC(C(NC(=O)c2cc(C3CC3)on2)C(=O)NCc2ccccn2)CC1] | TFA |
| 260 | 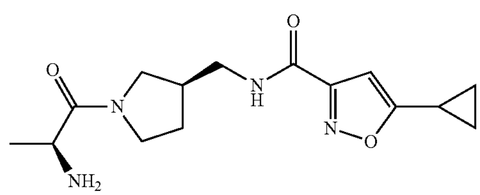 [SMILES: C[C@H](N)C(=O)N1CC[C@H](CNC(=O)c2cc(C3CC3)on2)C1] | TFA |
| 261 | 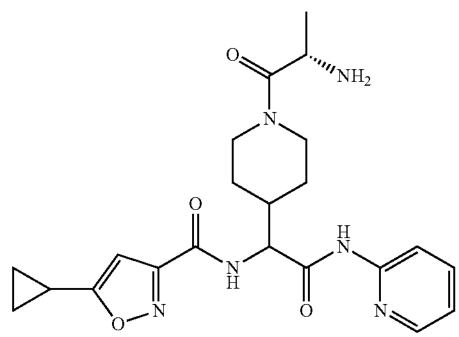 [SMILES: C[C@H](N)C(=O)N1CCC(C(NC(=O)c2cc(C3CC3)on2)C(=O)Nc2ccccn2)CC1] | HCl |
| 262 | 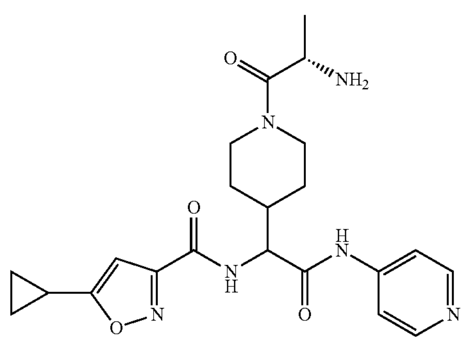 [SMILES: C[C@H](N)C(=O)N1CCC(C(NC(=O)c2cc(C3CC3)on2)C(=O)Nc2ccncc2)CC1] | TFA |
| 263 | 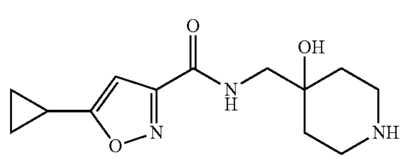 [SMILES: O=C(NCC1(O)CCNCC1)c1cc(C2CC2)on1] | TFA |
| 264 | 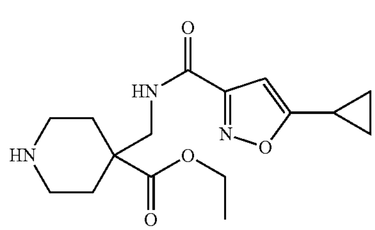 [SMILES: CCOC(=O)C1(CNC(=O)c2cc(C3CC3)on2)CCNCC1] | HCl |

TABLE 1-continued

| Cpd. No. | Structure | Salt Form |
|---|---|---|
| 265 | 5-cyclopropyl-N-((4-methylpiperidin-4-yl)methyl)isoxazole-3-carboxamide | TFA |
| 266 | 5-cyclopropyl-N-((4-fluoropiperidin-4-yl)methyl)isoxazole-3-carboxamide | HCl |
| 267 | N-((1-((S)-2-aminopropanoyl)-4-hydroxypiperidin-4-yl)methyl)-5-cyclopropylisoxazole-3-carboxamide | TFA |
| 268 | ethyl 1-((S)-2-aminopropanoyl)-4-(((5-cyclopropylisoxazole-3-carboxamido)methyl)piperidine-4-carboxylate | HCl |
| 269 | N-((1-((S)-2-aminopropanoyl)-4-methylpiperidin-4-yl)methyl)-5-cyclopropylisoxazole-3-carboxamide | TFA |
| 270 | N-((1-((S)-2-aminopropanoyl)-4-fluoropiperidin-4-yl)methyl)-5-cyclopropylisoxazole-3-carboxamide | HCl |
| 271 | N-(1-(1-((S)-2-aminopropanoyl)piperidin-4-yl)-2-hydroxyethyl)-5-cyclopropylisoxazole-3-carboxamide | TFA |

103
104
TABLE 1-continued
| Cpd. No. | Structure | Salt Form |
|---|---|---|
| 272 | 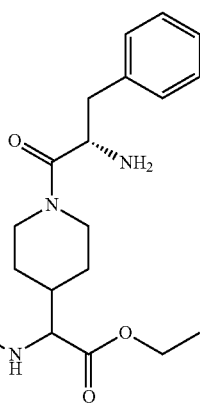 | TFA |
| 273 | 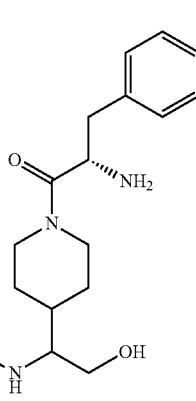 | TFA |
| 274 | 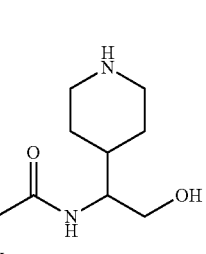 | TFA |
| 275 | 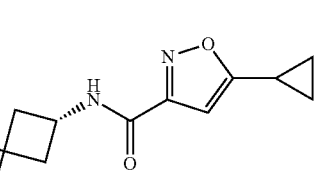 | TFA |
| 276 | 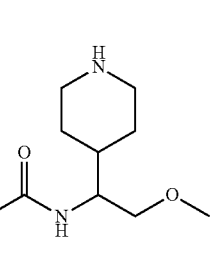 | TFA |

TABLE 1-continued

| Cpd. No. | Structure | Salt Form |
|---|---|---|
| 277 | 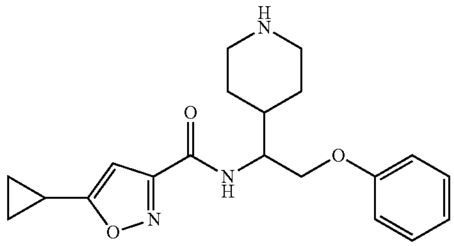 [SMILES: O=C(NC(COc1ccccc1)C1CCNCC1)c1cc(C2CC2)on1] | TFA |
| 278 | 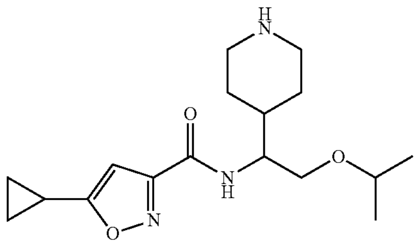 [SMILES: CC(C)OCC(NC(=O)c1cc(C2CC2)on1)C1CCNCC1] | TFA |
| 279 | 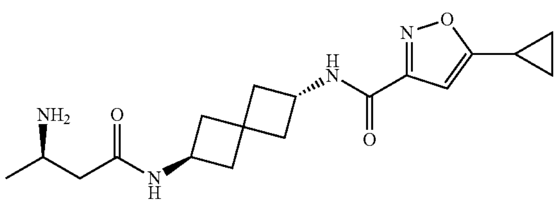 [SMILES: C[C@@H](N)CC(=O)N[C@H]1CC2(C1)C[C@H](NC(=O)c1cc(C3CC3)on1)C2] | TFA |
| 280 | 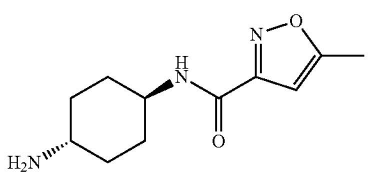 [SMILES: Cc1cc(C(=O)N[C@H]2CC[C@H](N)CC2)no1] | HCl |
| 281 | 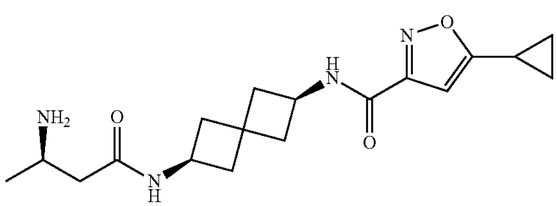 [SMILES: C[C@@H](N)CC(=O)N[C@H]1CC2(C1)C[C@H](NC(=O)c1cc(C3CC3)on1)C2] | HCl |
| 282 | 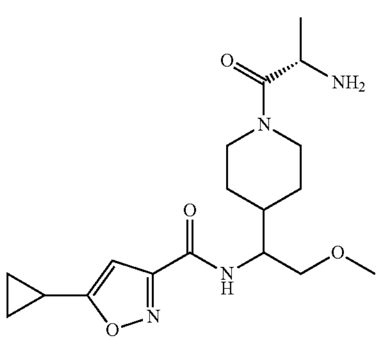 [SMILES: COCC(NC(=O)c1cc(C2CC2)on1)C1CCN(C(=O)[C@H](C)N)CC1] | TFA |

TABLE 1-continued

| Cpd. No. | Structure | Salt Form |
|---|---|---|
| 283 | (5-cyclopropylisoxazole-3-carboxamide N-linked to 1-(1-(alaninoyl)piperidin-4-yl)-2-phenoxyethyl) | TFA |
| 284 | (5-cyclopropylisoxazole-3-carboxamide N-linked to 1-(1-(alaninoyl)piperidin-4-yl)-2-isopropoxyethyl) | TFA |
| 285 | (5-cyclopropylisoxazole-3-carboxamide N-linked to 1-(1-(tyrosinoyl)piperidin-4-yl)-2-methoxyethyl) | TFA |
| 286 | (5-cyclopropylisoxazole-3-carboxamide N-linked to 1-(1-(tyrosinoyl)piperidin-4-yl)-2-phenoxyethyl) | TFA |

TABLE 1-continued
| Cpd. No. | Structure | Salt Form |
|---|---|---|
| 287 | 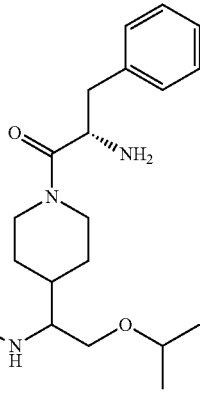 | TFA |
| 288 | 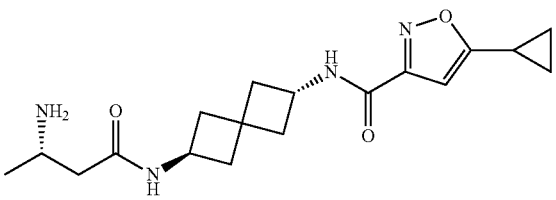 [SMILES: C[C@H](N)CC(=O)N[C@H]1CC2(C1)C[C@H](NC(=O)c1cc(C3CC3)on1)C2] | TFA |
| 290 | 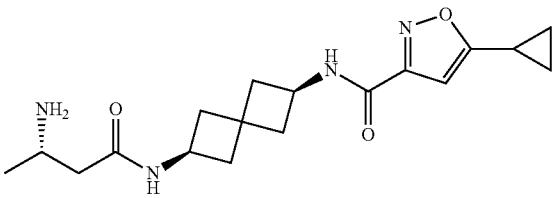 [SMILES: C[C@H](N)CC(=O)N[C@H]1CC2(C1)C[C@H](NC(=O)c1cc(C3CC3)on1)C2] | TFA |
| 291 | 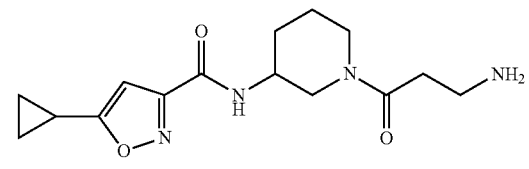 [SMILES: NCCC(=O)N1CCCC(NC(=O)c2cc(C3CC3)on2)C1] | HCl |
| 292 | 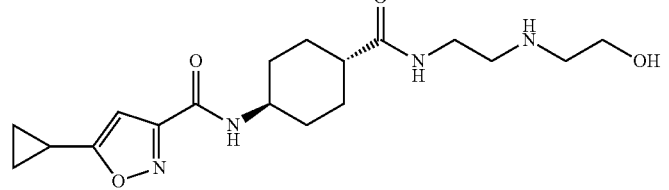 | None |
| 293 | 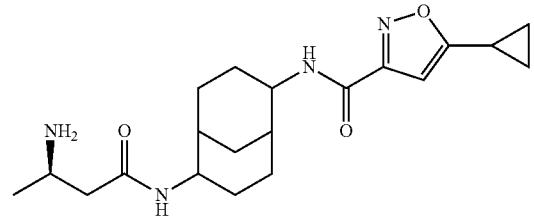 [SMILES: C[C@@H](N)CC(=O)NC1CCC2CC1CCC2NC(=O)c1cc(C2CC2)on1] | TFA |

TABLE 1-continued

| Cpd. No. | Structure | Salt Form |
|---|---|---|
| 294 | (structure) | TFA |
| 295 | (structure) | TFA |
| 296 | (structure) | TFA |
| 297 | (structure) | None |
| 298 | (structure) | None |
| 299 | (structure) | None |
| 300 | (structure) | HCl |

TABLE 1-continued

| Cpd. No. | Structure | Salt Form |
|---|---|---|
| 301 | 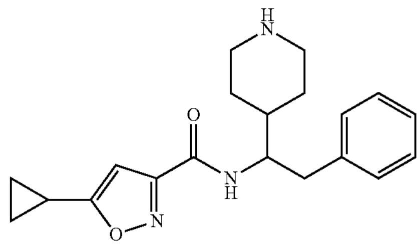 [SMILES: O=C(NC(Cc1ccccc1)C1CCNCC1)c1cc(C2CC2)on1] | HCl |
| 302 | 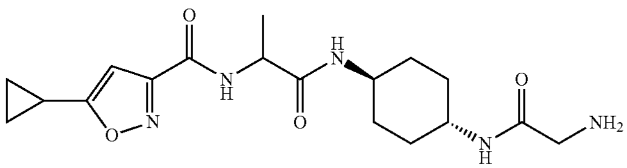 [SMILES: CC(NC(=O)c1cc(C2CC2)on1)C(=O)N[C@H]1CC[C@H](NC(=O)CN)CC1] | HCl |
| 303 | 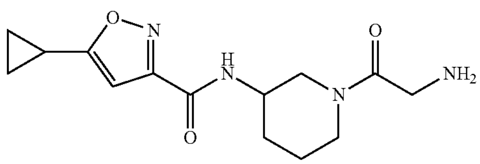 [SMILES: NCC(=O)N1CCCC(NC(=O)c2cc(C3CC3)on2)C1] | None |
| 304 | 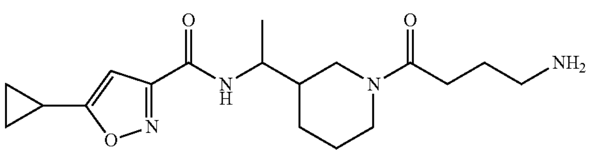 [SMILES: CC(NC(=O)c1cc(C2CC2)on1)C1CCCN(C(=O)CCCN)C1] | None |
| 305 | 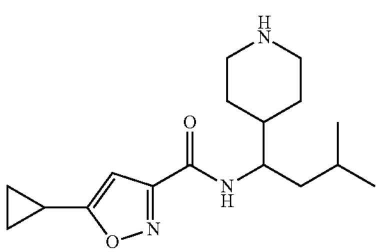 [SMILES: CC(C)CC(NC(=O)c1cc(C2CC2)on1)C1CCNCC1] | HCl |
| 306 | 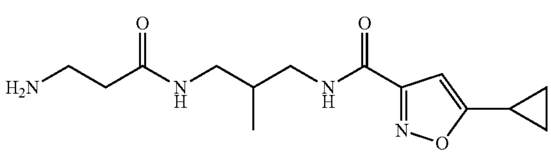 [SMILES: CC(CNC(=O)CCN)CNC(=O)c1cc(C2CC2)on1] | HCl |
| 307 | 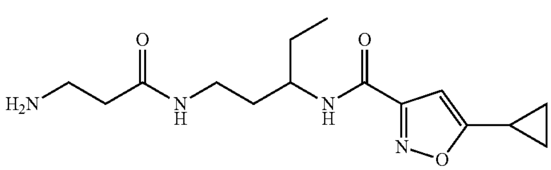 [SMILES: CCC(CCNC(=O)CCN)NC(=O)c1cc(C2CC2)on1] | HCl |
| 308 | 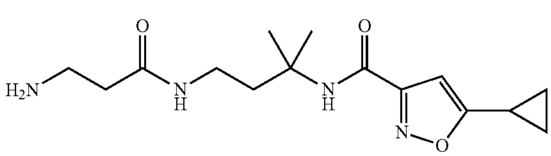 [SMILES: CC(C)(CCNC(=O)CCN)NC(=O)c1cc(C2CC2)on1] | HCl |

TABLE 1-continued

| Cpd. No. | Structure | Salt Form |
|---|---|---|
| 309 | 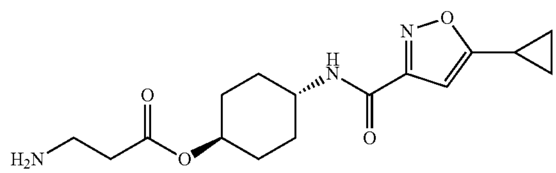 [SMILES: NCCC(=O)O[C@H]1CC[C@H](NC(=O)c2cc(C3CC3)on2)CC1] | HCl |
| 310 | 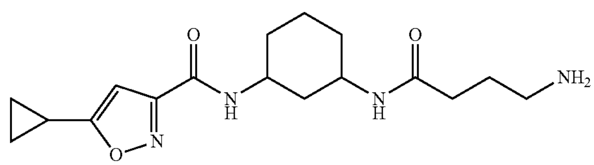 [SMILES: NCCCC(=O)NC1CCCC(NC(=O)c2cc(C3CC3)on2)C1] | HCl |
| 311 | 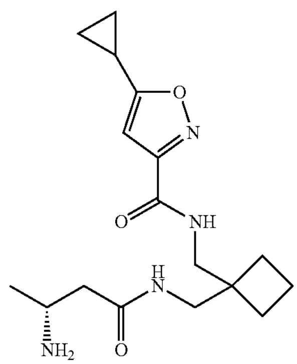 [SMILES: C[C@@H](N)CC(=O)NCC1(CNC(=O)c2cc(C3CC3)on2)CCC1] | None |
| 312 | 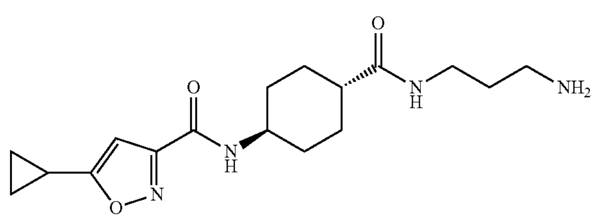 [SMILES: NCCCNC(=O)[C@H]1CC[C@H](NC(=O)c2cc(C3CC3)on2)CC1] | HCl |
| 313 | 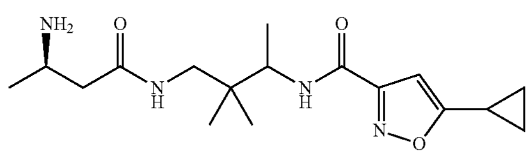 [SMILES: CC(NC(=O)c1cc(C2CC2)on1)C(C)(C)CNC(=O)C[C@@H](C)N] | HCl |
| 314 | 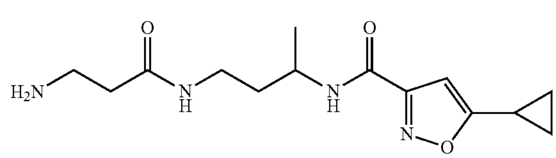 [SMILES: CC(CCNC(=O)CCN)NC(=O)c1cc(C2CC2)on1] | HCl |
| 315 | 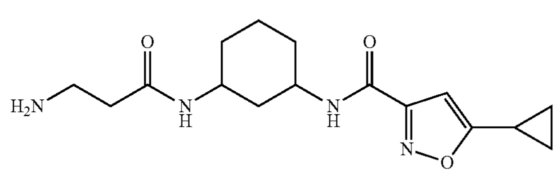 [SMILES: NCCC(=O)NC1CCCC(NC(=O)c2cc(C3CC3)on2)C1] | HCl |

TABLE 1-continued

| Cpd. No. | Structure | Salt Form |
|---|---|---|
| 316 | 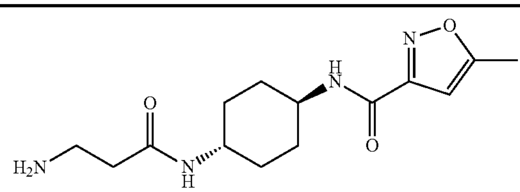 | None |
| 317 | 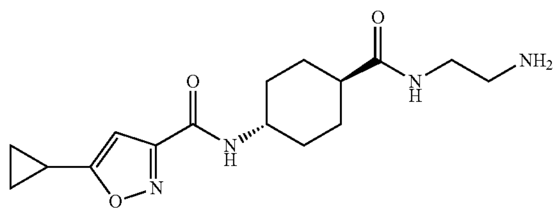 [SMILES: NCCNC(=O)[C@H]1CC[C@H](NC(=O)c2cc(C3CC3)on2)CC1] | HCl |
| 318 | 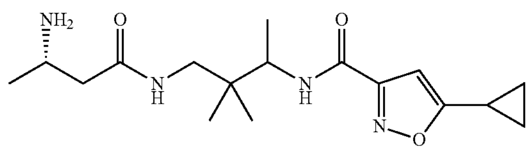 [SMILES: CC(NC(=O)c1cc(C2CC2)on1)C(C)(C)CNC(=O)C[C@H](C)N] | HCl |
| 319 | 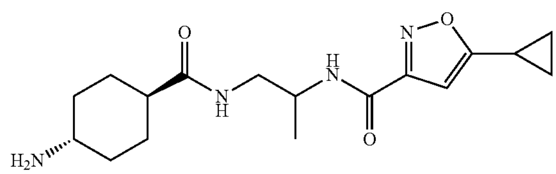 [SMILES: CC(CNC(=O)[C@H]1CC[C@H](N)CC1)NC(=O)c1cc(C2CC2)on1] | HCl |
| 320 | 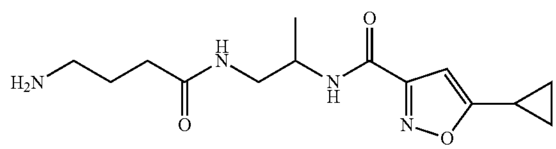 [SMILES: CC(CNC(=O)CCCN)NC(=O)c1cc(C2CC2)on1] | HCl |
| 321 | 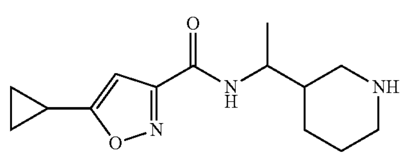 [SMILES: CC(NC(=O)c1cc(C2CC2)on1)C1CCCNC1] | HCl |
| 322 | 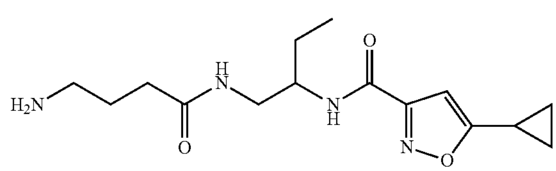 [SMILES: CCC(CNC(=O)CCCN)NC(=O)c1cc(C2CC2)on1] | HCl |
| 323 | 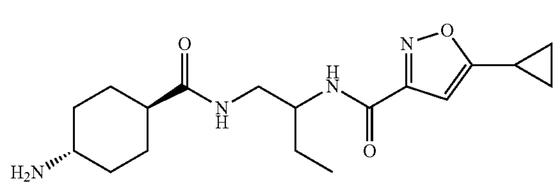 [SMILES: CCC(CNC(=O)[C@H]1CC[C@H](N)CC1)NC(=O)c1cc(C2CC2)on1] | None |
| 324 | 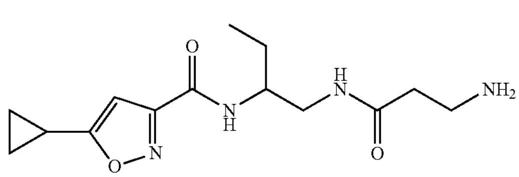 [SMILES: CCC(CNC(=O)CCN)NC(=O)c1cc(C2CC2)on1] | HCl |

TABLE 1-continued

| Cpd. No. | Structure | Salt Form |
|---|---|---|
| 325 | (5-cyclopropylisoxazole-3-carboxamide linked to 1,4-phenylenediamine with β-alanine amide) | None |
| 326 | (5-cyclopropylisoxazole-3-carboxamide linked to 1,4-phenylenediamine with glycine amide) | HCl |
| 327 | (5-cyclopropylisoxazole-3-carboxamide linked to 1,4-phenylenediamine with 4-aminobutyramide) | HCl |
| 328 | (5-cyclopropylisoxazole-3-carboxamide linked to 4-(3-aminopropylamino)aniline) | HCl |
| 329 | (5-cyclopropylisoxazole-3-carboxamide linked to 4-(2-aminoethylamino)aniline) | HCl |
| 330 | (β-alanine amide linked via 1,1-cyclopropanediyl-bis(methylene)diamine to 5-cyclopropylisoxazole-3-carboxamide) | HCl |
| 331 | (β-alanine amide linked to 2-amino-4-aminobutyl-1-ol with 5-cyclopropylisoxazole-3-carboxamide) | HCl |
| 332 | (5-cyclopropylisoxazole-3-carboxamide-phenyl-carboxamide-piperidin-4-yl) | None |

TABLE 1-continued

| Cpd. No. | Structure | Salt Form |
|---|---|---|
| 333 | 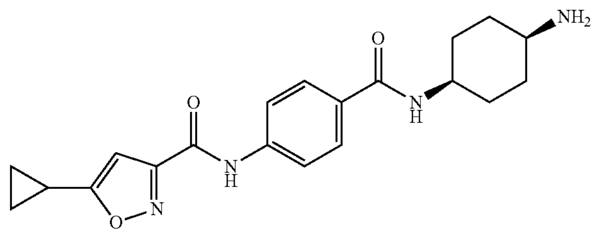 [SMILES: N[C@H]1CC[C@@H](NC(=O)c2ccc(NC(=O)c3cc(C4CC4)on3)cc2)CC1] | None |
| 334 | 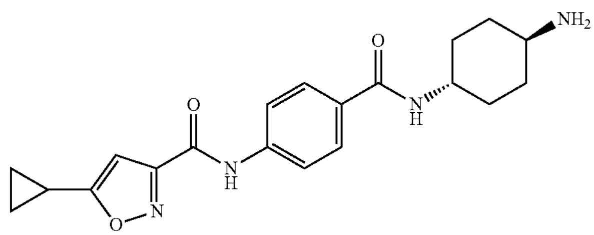 [SMILES: N[C@H]1CC[C@H](NC(=O)c2ccc(NC(=O)c3cc(C4CC4)on3)cc2)CC1] | HCl |
| 335 | 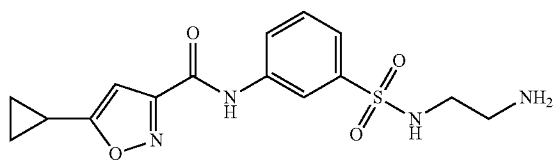 [SMILES: NCCNS(=O)(=O)c1cccc(NC(=O)c2cc(C3CC3)on2)c1] | HCl |
| 336 | 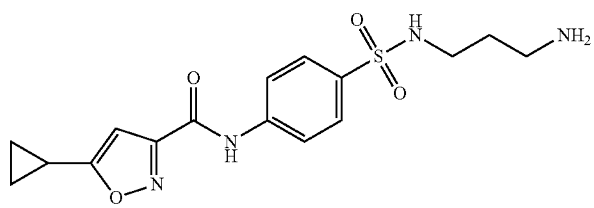 [SMILES: NCCCNS(=O)(=O)c1ccc(NC(=O)c2cc(C3CC3)on2)cc1] | HCl |
| 337 | 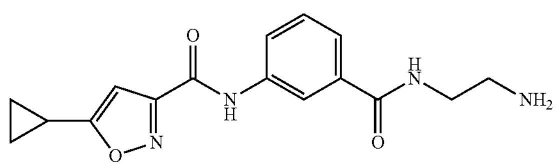 [SMILES: NCCNC(=O)c1cccc(NC(=O)c2cc(C3CC3)on2)c1] | HCl |
| 338 | 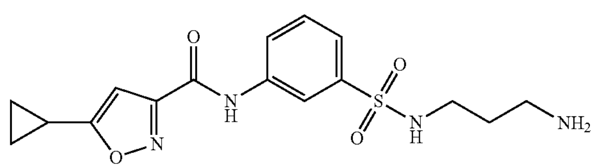 [SMILES: NCCCNS(=O)(=O)c1cccc(NC(=O)c2cc(C3CC3)on2)c1] | HCl |
| 339 | 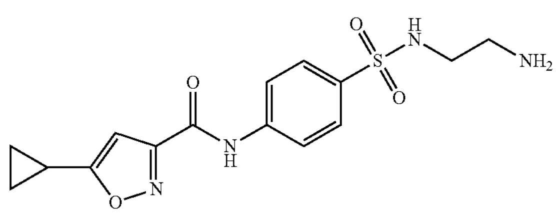 [SMILES: NCCNS(=O)(=O)c1ccc(NC(=O)c2cc(C3CC3)on2)cc1] | HCl |

TABLE 1-continued

| Cpd. No. | Structure | Salt Form |
|---|---|---|
| 340 | 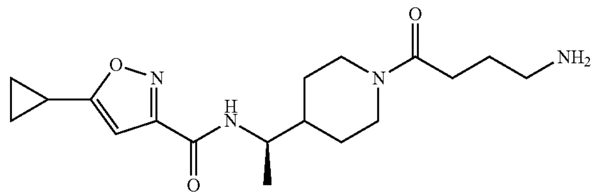 [SMILES: C[C@@H](NC(=O)c1cc(C2CC2)on1)C1CCN(C(=O)CCCN)CC1] | HCl |
| 341 | 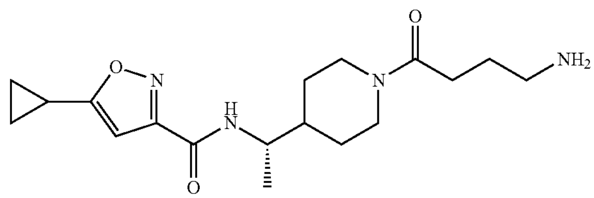 [SMILES: C[C@H](NC(=O)c1cc(C2CC2)on1)C1CCN(C(=O)CCCN)CC1] | HCl |
| 342 | 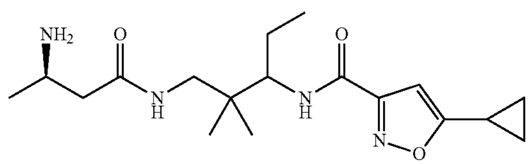 [SMILES: CCC(NC(=O)c1cc(C2CC2)on1)C(C)(C)CNC(=O)C[C@@H](C)N] | HCl |
| 343 | 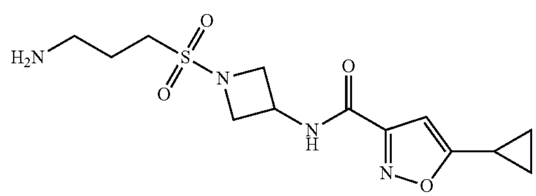 [SMILES: NCCCS(=O)(=O)N1CC(NC(=O)c2cc(C3CC3)on2)C1] | None |
| 344 | 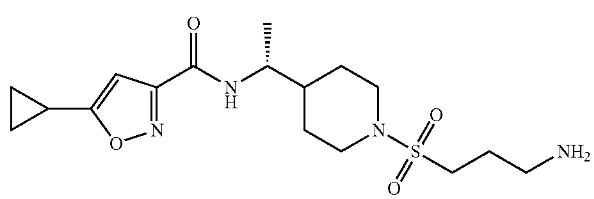 [SMILES: C[C@@H](NC(=O)c1cc(C2CC2)on1)C1CCN(S(=O)(=O)CCCN)CC1] | HCl |
| 345 | 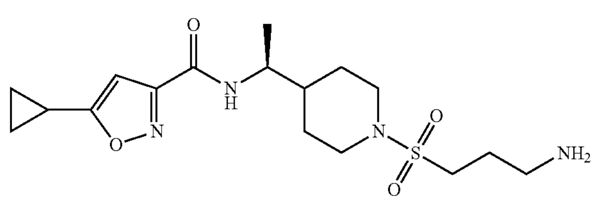 [SMILES: C[C@H](NC(=O)c1cc(C2CC2)on1)C1CCN(S(=O)(=O)CCCN)CC1] | HCl |
| 346 | 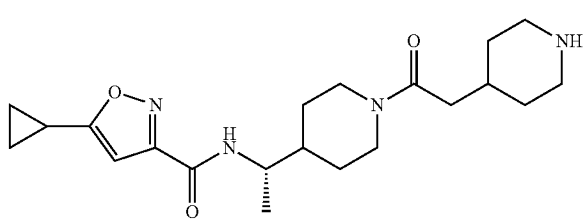 [SMILES: C[C@H](NC(=O)c1cc(C2CC2)on1)C1CCN(C(=O)CC2CCNCC2)CC1] | HCl |

TABLE 1-continued

| Cpd. No. | Structure | Salt Form |
|---|---|---|
| 347 | 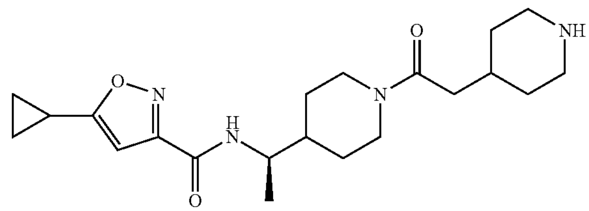 [SMILES: C[C@@H](NC(=O)c1cc(C2CC2)on1)C1CCN(C(=O)CC2CCNCC2)CC1] | HCl |
| 348 | 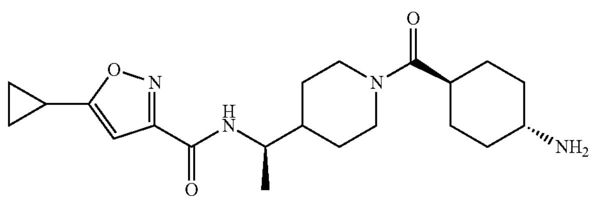 [SMILES: C[C@@H](NC(=O)c1cc(C2CC2)on1)C1CCN(C(=O)[C@H]2CC[C@H](N)CC2)CC1] | HCl |
| 349 | 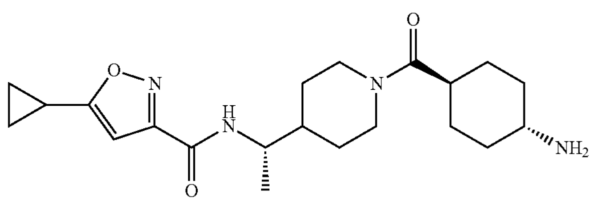 [SMILES: C[C@H](NC(=O)c1cc(C2CC2)on1)C1CCN(C(=O)[C@H]2CC[C@H](N)CC2)CC1] | HCl |
| 350 | 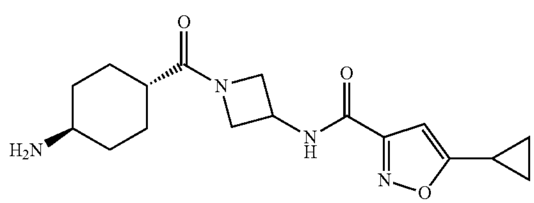 [SMILES: N[C@H]1CC[C@H](C(=O)N2CC(NC(=O)c3cc(C4CC4)on3)C2)CC1] | None |
| 351 | 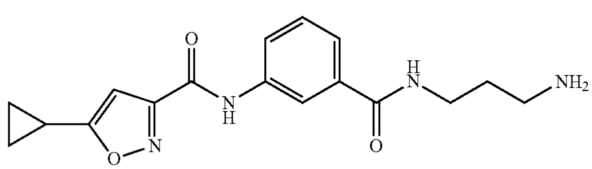 [SMILES: NCCCNC(=O)c1cccc(NC(=O)c2cc(C3CC3)on2)c1] | HCl |
| 352 | 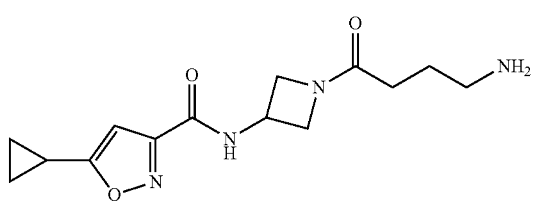 [SMILES: NCCCC(=O)N1CC(NC(=O)c2cc(C3CC3)on2)C1] | HCl |
| 353 | 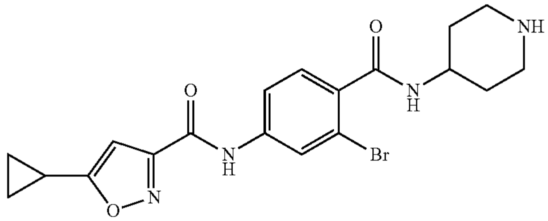 [SMILES: O=C(Nc1ccc(C(=O)NC2CCNCC2)c(Br)c1)c1cc(C2CC2)on1] | TFA |

TABLE 1-continued
| Cpd. No. | Structure | Salt Form |
|---|---|---|
| 354 | 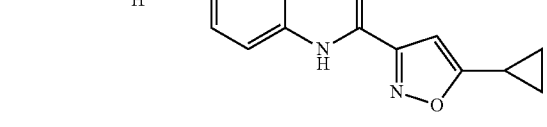 | HCl |
| 355 | 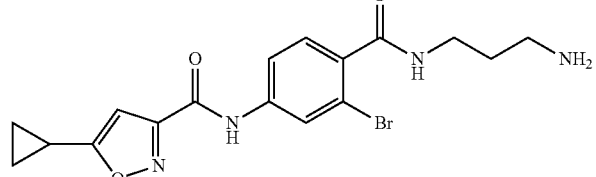 | TFA |
| 356 | 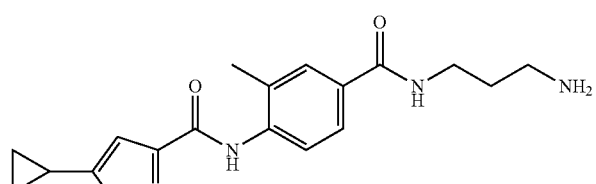 | HCl |
| 357 | 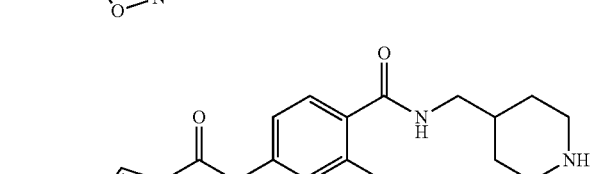 | None |
| 358 | 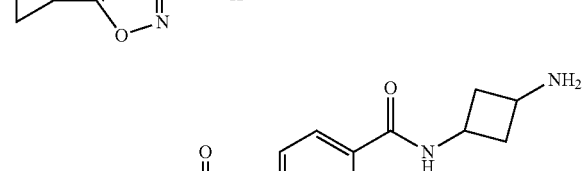 | TFA |
| 359 | 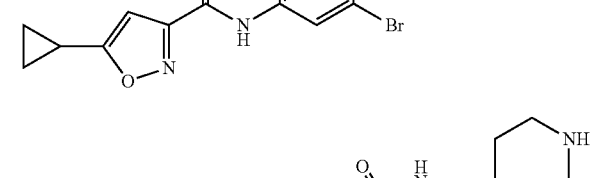 | TFA |
| 360 | 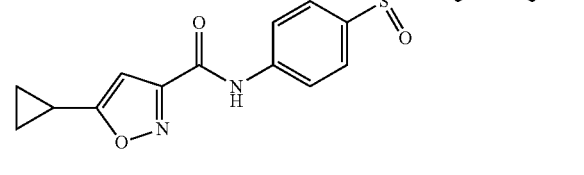 | HCl |

TABLE 1-continued

| Cpd. No. | Structure | Salt Form |
|---|---|---|
| 361 | 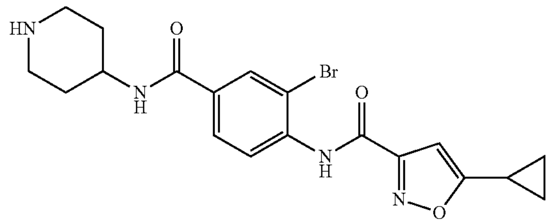 [SMILES: O=C(NC1CCNCC1)c1ccc(NC(=O)c2cc(C3CC3)on2)c(Br)c1] | HCl |
| 362 | 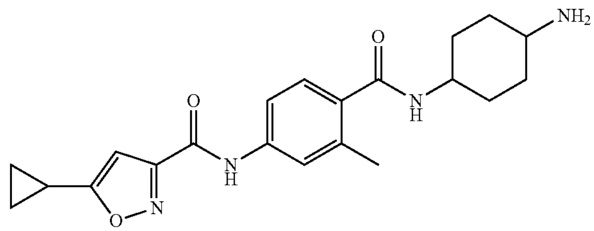 [SMILES: Cc1cc(NC(=O)c2cc(C3CC3)on2)ccc1C(=O)NC1CCC(N)CC1] | None |
| 363 | 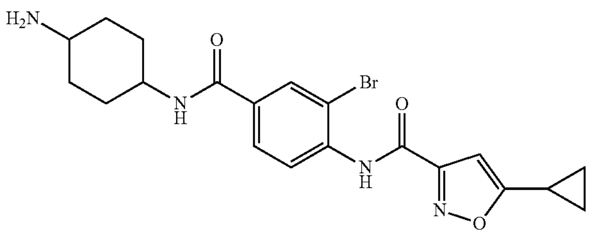 [SMILES: NC1CCC(NC(=O)c2ccc(NC(=O)c3cc(C4CC4)on3)c(Br)c2)CC1] | HCl |
| 364 | 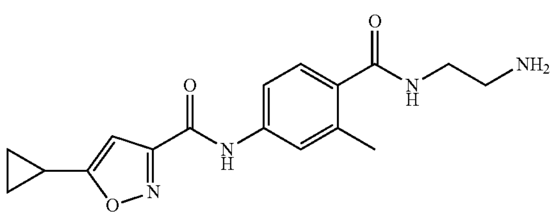 [SMILES: Cc1cc(NC(=O)c2cc(C3CC3)on2)ccc1C(=O)NCCN] | HCl |
| 365 | 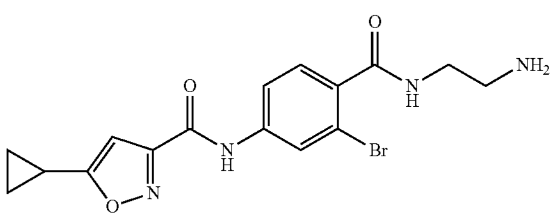 [SMILES: NCCNC(=O)c1ccc(NC(=O)c2cc(C3CC3)on2)cc1Br] | TFA |
| 366 | 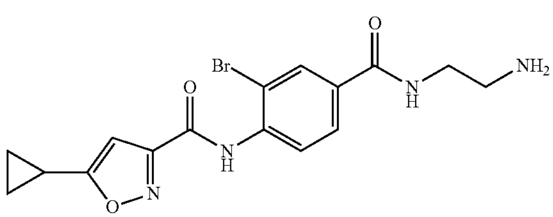 [SMILES: NCCNC(=O)c1ccc(NC(=O)c2cc(C3CC3)on2)c(Br)c1] | HCl |
| 367 | 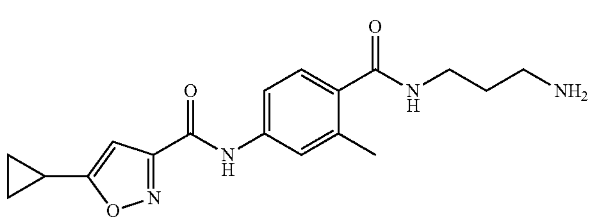 [SMILES: Cc1cc(NC(=O)c2cc(C3CC3)on2)ccc1C(=O)NCCCN] | HCl |

TABLE 1-continued

| Cpd. No. | Structure | Salt Form |
|---|---|---|
| 368 | (5-cyclopropylisoxazole-3-carboxamide linked to 2-bromo-4-aminobenzamide with pyrrolidin-3-yl amide) | None |
| 369 | (5-cyclopropylisoxazole-3-carboxamide linked to 2-methyl-4-aminobenzamide with piperidin-4-ylmethyl amide) | HCl |
| 370 | (3-aminocyclobutyl amide of 3-bromo-4-[(5-cyclopropylisoxazole-3-carbonyl)amino]benzamide) | HCl |
| 371 | (5-cyclopropylisoxazole-3-carboxamide linked to 2-bromo-4-aminobenzamide with 3-aminocyclohexyl amide) | None |
| 372 | (5-cyclopropylisoxazole-3-carboxamide linked to 4-aminobenzenesulfonamide with 4-aminocyclohexyl group) | TFA |
| 373 | (5-cyclopropylisoxazole-3-carboxamide linked to 4-aminobenzenesulfonamide with piperidin-4-yl group) | TFA |
| 374 | (5-cyclopropylisoxazole-3-carboxamide linked to 4-aminobenzenesulfonamide with pyrrolidin-3-yl group) | None |

TABLE 1-continued

| Cpd. No. | Structure | Salt Form |
|---|---|---|
| 375 | 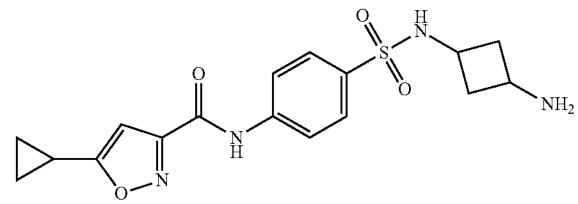 [SMILES: NC1CC(NS(=O)(=O)c2ccc(NC(=O)c3cc(C4CC4)on3)cc2)C1] | None |
| 376 | 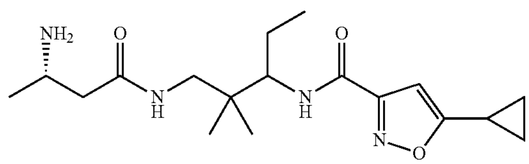 [SMILES: CCC(NC(=O)c1cc(C2CC2)on1)C(C)(C)CNC(=O)C[C@H](C)N] | HCl |
| 377 | 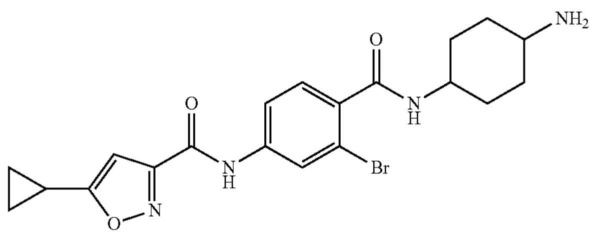 | None |
| 378 | 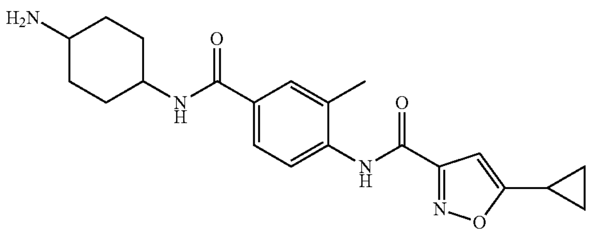 [SMILES: Cc1cc(C(=O)NC2CCC(N)CC2)ccc1NC(=O)c1cc(C2CC2)on1] | None |
| 379 | 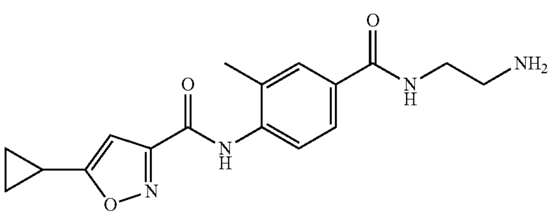 [SMILES: Cc1cc(C(=O)NCCN)ccc1NC(=O)c1cc(C2CC2)on1] | HCl |
| 380 | 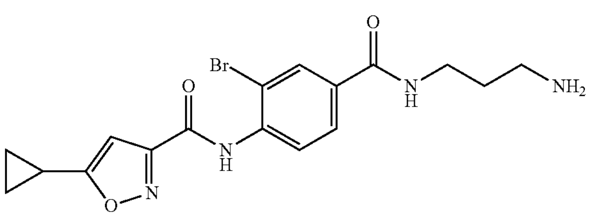 [SMILES: NCCCNC(=O)c1ccc(NC(=O)c2cc(C3CC3)on2)c(Br)c1] | HCl |
| 381 | 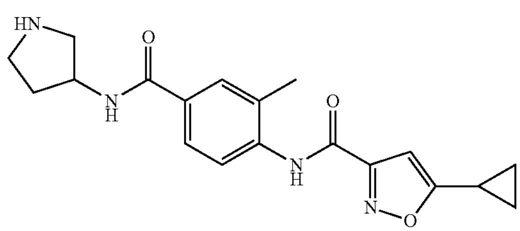 [SMILES: Cc1cc(C(=O)NC2CCNC2)ccc1NC(=O)c1cc(C2CC2)on1] | HCl |

TABLE 1-continued

| Cpd. No. | Structure | Salt Form |
|---|---|---|
| 382 | 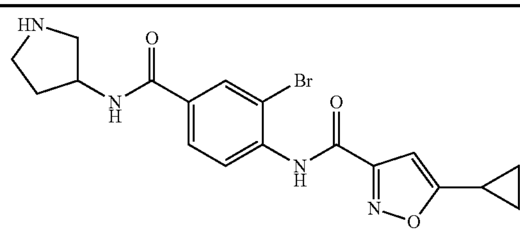 | None |
| 383 | 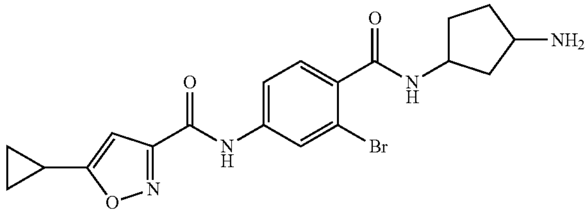 [SMILES: NC1CCC(NC(=O)c2ccc(NC(=O)c3cc(C4CC4)on3)cc2Br)C1] | None |
| 384 | 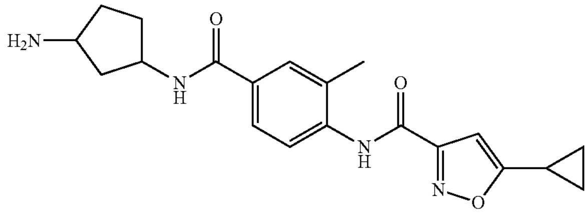 [SMILES: Cc1cc(C(=O)NC2CCC(N)C2)ccc1NC(=O)c1cc(C2CC2)on1] | HCl |
| 385 | 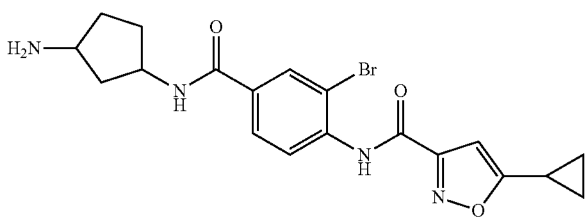 [SMILES: NC1CCC(NC(=O)c2ccc(NC(=O)c3cc(C4CC4)on3)c(Br)c2)C1] | HCl |
| 386 | 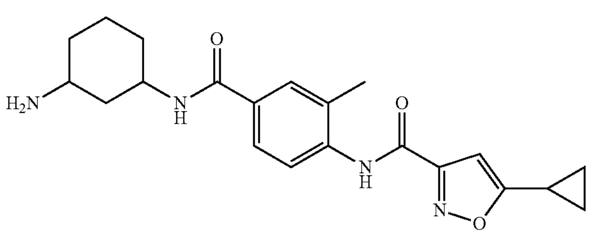 [SMILES: Cc1cc(C(=O)NC2CCCC(N)C2)ccc1NC(=O)c1cc(C2CC2)on1] | HCl |
| 387 | 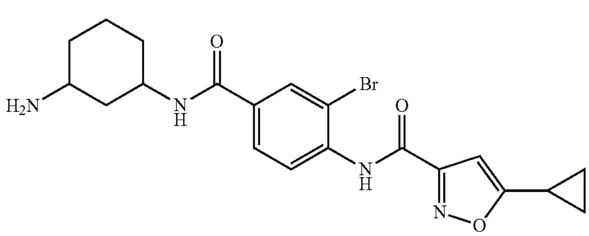 [SMILES: NC1CCCC(NC(=O)c2ccc(NC(=O)c3cc(C4CC4)on3)c(Br)c2)C1] | HCl |
| 388 | 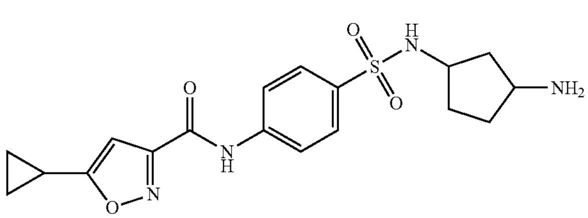 [SMILES: NC1CCC(NS(=O)(=O)c2ccc(NC(=O)c3cc(C4CC4)on3)cc2)C1] | None |

TABLE 1-continued

| Cpd. No. | Structure | Salt Form |
|---|---|---|
| 389 | 5-cyclopropyl-N-(4-(N-(3-aminocyclohexyl)sulfamoyl)phenyl)isoxazole-3-carboxamide | None |
| 390 | 5-cyclopropyl-N-(3-methyl-4-((pyrrolidin-3-yl)carbamoyl)phenyl)isoxazole-3-carboxamide | None |
| 391 | 5-cyclopropyl-N-(3-methyl-4-((piperidin-4-ylmethyl)carbamoyl)phenyl)isoxazole-3-carboxamide | None |
| 392 | 5-cyclopropyl-N-(2-bromo-4-((piperidin-4-ylmethyl)carbamoyl)phenyl)isoxazole-3-carboxamide | HCl |
| 393 | 5-cyclopropyl-N-(4-((3-aminocyclohexyl)carbamoyl)-3-methylphenyl)isoxazole-3-carboxamide | None |
| 394 | 5-cyclopropyl-N-(4-(N-(2-aminoethyl)sulfamoyl)cyclohexyl)isoxazole-3-carboxamide | None |
| 395 | 5-cyclopropyl-N-(4-((3-aminocyclopentyl)carbamoyl)-3-methylphenyl)isoxazole-3-carboxamide | None |

TABLE 1-continued

| Cpd. No. | Structure | Salt Form |
|---|---|---|
| 396 | 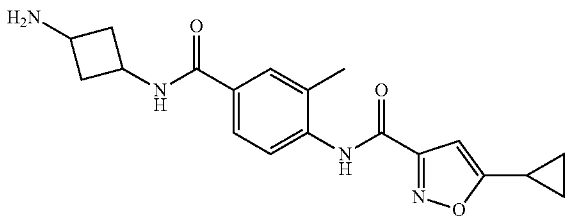 [SMILES: Cc1cc(C(=O)NC2CC(N)C2)ccc1NC(=O)c1cc(C2CC2)on1] | HCl |
| 397 | 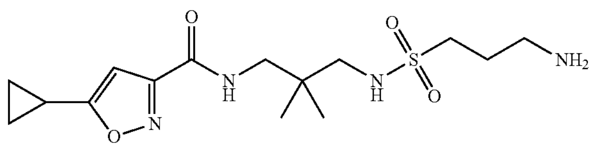 [SMILES: CC(C)(CNC(=O)c1cc(C2CC2)on1)CNS(=O)(=O)CCCN] | None |
| 398 | 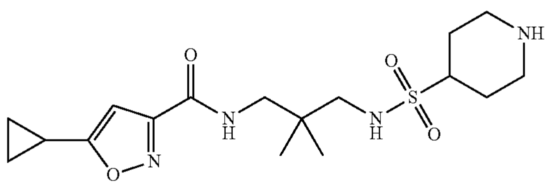 [SMILES: CC(C)(CNC(=O)c1cc(C2CC2)on1)CNS(=O)(=O)C1CCNCC1] | HCl |
| 399 | 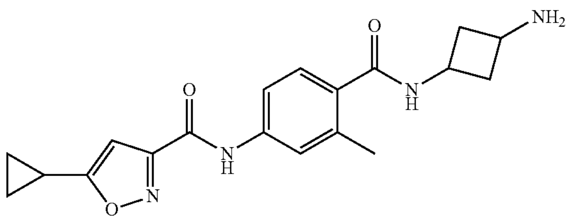 [SMILES: Cc1cc(NC(=O)c2cc(C3CC3)on2)ccc1C(=O)NC1CC(N)C1] | None |

TABLE 2

| Cpd. No. | Structure | Salt Form | Chemical Name | LCMS M + H | SMYD2 Biochem IC$_{50}$ (μM)* |
|---|---|---|---|---|---|
| 400 | 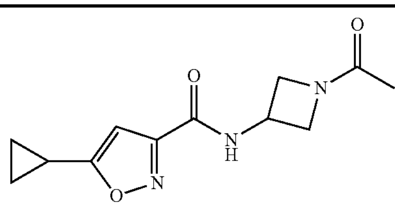 | None | N-(1-acetylazetidin-3-yl)-5-cyclopropyl-1,2-oxazole-3-carboxamide | 250.1 | >50.0 |
| 401 | 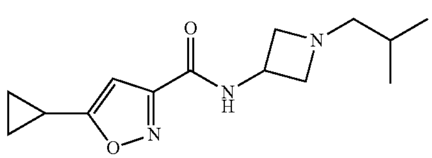 [SMILES: CC(C)CN1CC(NC(=O)c2cc(C3CC3)on2)C1] | None | 5-cyclopropyl-N-[1-(2-methylpropyl)azetidin-3-yl]-1,2-oxazole-3-carboxamide | 264.2 | 1.55823 |
| 402 | 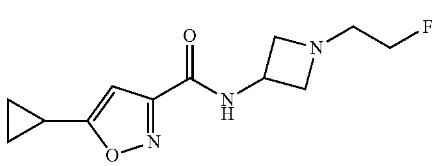 [SMILES: O=C(NC1CN(CCF)C1)c1cc(C2CC2)on1] | None | 5-cyclopropyl-N-[1-(2-fluoroethyl)azetidin-3-yl]-1,2-oxazole-3-carboxamide | 254.1 | 7.78955 |

TABLE 2-continued

| Cpd. No. | Structure | Salt Form | Chemical Name | LCMS M + H | SMYD2 Biochem IC$_{50}$ (μM)* |
|---|---|---|---|---|---|
| 403 | 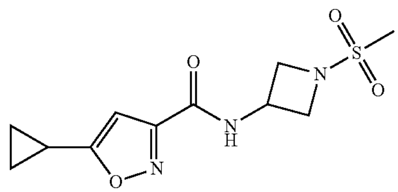 [SMILES: CS(=O)(=O)N1CC(NC(=O)c2cc(C3CC3)on2)C1] | None | 5-cyclopropyl-N-(1-methanesulfonylazetidin-3-yl)-1,2-oxazole-3-carboxamide | 286.1 | >50.0 |
| 404 | 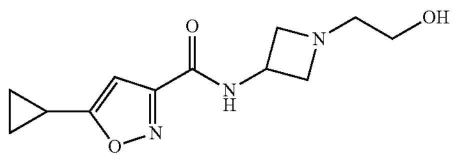 [SMILES: O=C(NC1CN(CCO)C1)c1cc(C2CC2)on1] | None | 5-cyclopropyl-N-[1-(2-hydroxyethyl)azetidin3--yl]-1,2-oxazole-3-carboxamide | 252.2 | 4.67695 |
| 405 | 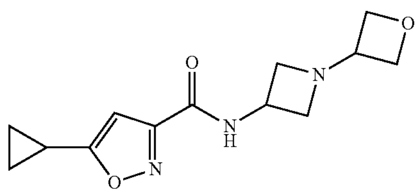 [SMILES: O=C(NC1CN(C2COC2)C1)c1cc(C2CC2)on1] | None | 5-cyclopropyl-N-[1-(oxetan-3-yl)azetidin-3-yl]-1,2-oxazole-3-carboxamide | 264.2 | >50.0 |
| 406 | 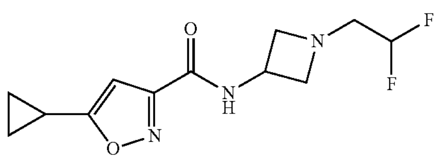 [SMILES: O=C(NC1CN(CC(F)F)C1)c1cc(C2CC2)on1] | None | 5-cyclopropyl-N-[1-(2,2-difluoroethyl)azetidin-3-yl]-1,2-oxazole-3-carboxamide | 272.2 | >50.0 |
| 407 | 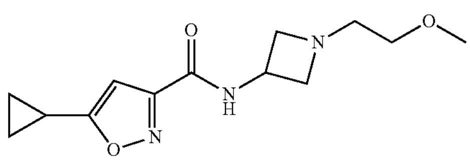 [SMILES: COCCN1CC(NC(=O)c2cc(C3CC3)on2)C1] | None | 5-cyclopropyl-N-[1-(2-methoxyethyl)azetidin-3-yl]-1,2-oxazole-3-carboxamide | 266.2 | 2.68352 |
| 408 | 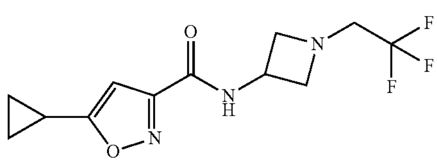 [SMILES: O=C(NC1CN(CC(F)(F)F)C1)c1cc(C2CC2)on1] | None | 5-cyclopropyl-N-[1-(2,2,2-trifluoroethyl)azetidin-3-yl]-1,2-oxazole-3-carboxamide | 290.2 | >50.0 |
| 409 | 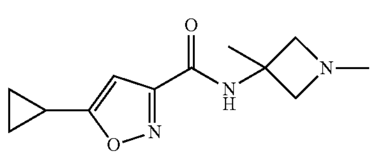 [SMILES: CN1CC(C)(NC(=O)c2cc(C3CC3)on2)C1] | None | 5-cyclopropyl-N-(1,3-dimethylazetidin-3-yl)-1,2-oxazole-3-carboxamide | 236.2 | >50.0 |
| 410 | 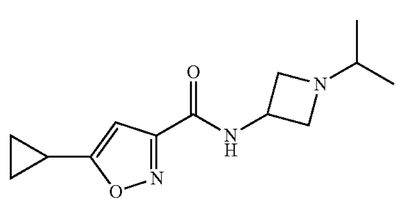 [SMILES: CC(C)N1CC(NC(=O)c2cc(C3CC3)on2)C1] | None | 5-cyclopropyl-N-[1-(propan-2-yl)azetidin-3-yl]-1,2-oxazole-3-carboxamide | 250.1 | 1.04736 |

TABLE 2-continued

| Cpd. No. | Structure | Salt Form | Chemical Name | LCMS M + H | SMYD2 Biochem IC$_{50}$ (μM)* |
|---|---|---|---|---|---|
| 411 | 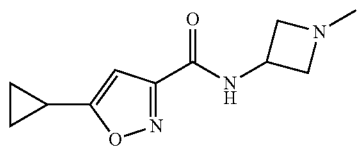 [SMILES: CN1CC(NC(=O)c2cc(C3CC3)on2)C1] | None | 5-cyclopropyl-N-(1-methylazetidin-3-yl)-1,2-oxazole-3-carboxamide | 222.1 | 5.33712 |
| 412 | 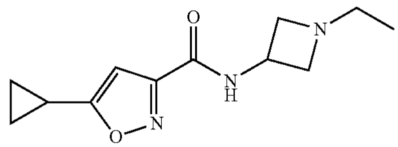 [SMILES: CCN1CC(NC(=O)c2cc(C3CC3)on2)C1] | None | 5-cyclopropyl-N-(1-ethylazetidin-3-yl)-1,2-oxazole-3-carboxamide | 236.2 | 1.50829 |
| 413 | 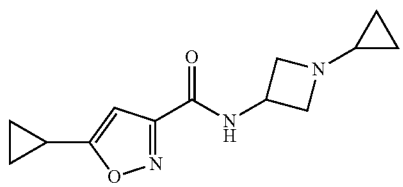 [SMILES: O=C(NC1CN(C2CC2)C1)c1cc(C2CC2)on1] | None | 5-cyclopropyl-N-(1-cyclopropylazetidin-3-yl)-1,2-oxazole-3-carboxamide | 248.1 | 1.46882 |
| 414 | 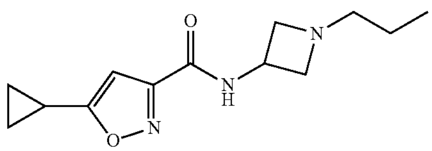 [SMILES: CCCN1CC(NC(=O)c2cc(C3CC3)on2)C1] | None | 5-cyclopropyl-N-(1-propylazetidin-3-yl)-1,2-oxazole-3-carboxamide | 250.2 | 1.70142 |
| 415 | 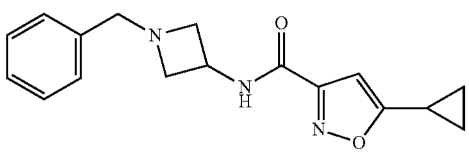 [SMILES: O=C(NC1CN(Cc2ccccc2)C1)c1cc(C2CC2)on1] | None | N-(1-benzylazetidin-3-yl)-5-cyclopropyl-1,2-oxazole-3-carboxamide | 298.1 | 2.47021 |
| 416 | 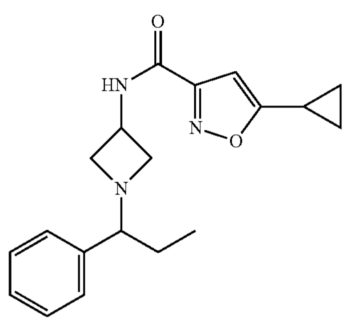 [SMILES: CCC(c1ccccc1)N1CC(NC(=O)c2cc(C3CC3)on2)C1] | None | 5-cyclopropyl-N-[1-(1-phenylpropyl)azetidin-3-yl]-1,2-oxazole-3-carboxamide | 326.1 | 0.61999 |
| 417 | 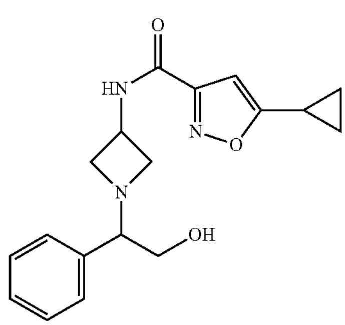 [SMILES: O=C(NC1CN(C(CO)c2ccccc2)C1)c1cc(C2CC2)on1] | None | 5-cyclopropyl-N-[1-(2-hydroxy-1-phenylethyl)azetidin-3-yl]-1,2-oxazole-3-carboxamide | 328.2 | 2.22554 |

TABLE 2-continued

| Cpd. No. | Structure | Salt Form | Chemical Name | LCMS M + H | SMYD2 Biochem IC$_{50}$ (μM)* |
|---|---|---|---|---|---|
| 418 | 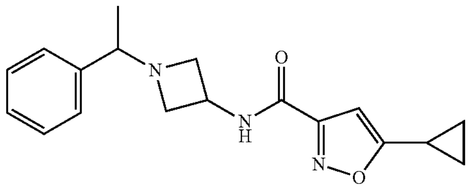 [SMILES: CC(c1ccccc1)N1CC(NC(=O)c2cc(C3CC3)on2)C1] | None | 5-cyclopropyl-N-[1-(1-phenylethyl)azetidin-3-yl]-1,2-oxazole-3-carboxamide | 312.1 | 0.58861 |
| 419 | 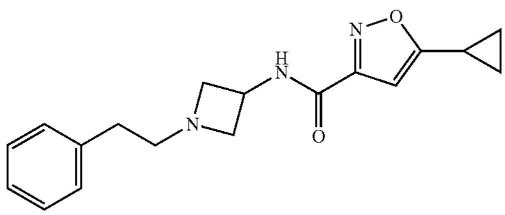 [SMILES: O=C(NC1CN(CCc2ccccc2)C1)c1cc(C2CC2)on1] | None | 5-cyclopropyl-N-[1-(2-phenylethyl)azetidin-3-yl]-1,2-oxazole-3-carboxamide | 312.1 | 2.18872 |
| 420 | 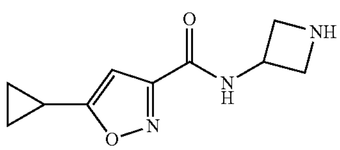 [SMILES: O=C(NC1CNC1)c1cc(C2CC2)on1] | HCl | N-(azetidin-3-yl)-5-cyclopropyl-1,2-oxazole-3-carboxamide | 208.1 | |
| 421 | 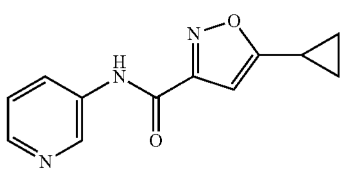 [SMILES: O=C(Nc1cccnc1)c1cc(C2CC2)on1] | None | 5-cyclopropyl-N-(pyridin-3-yl)-1,2-oxazole-3-carboxamide | 230.2 | >50.0 |
| 422 | 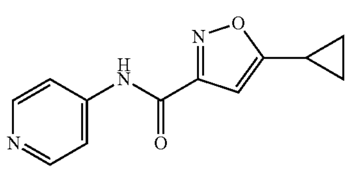 [SMILES: O=C(Nc1ccncc1)c1cc(C2CC2)on1] | None | 5-cyclopropyl-N-(pyridin-4-yl)-1,2-oxazole-3-carboxamide | 230.2 | >50.0 |
| 423 | 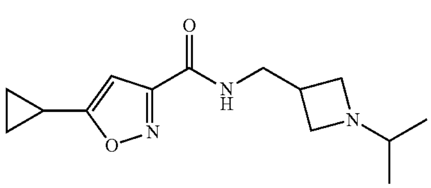 [SMILES: CC(C)N1CC(CNC(=O)c2cc(C3CC3)on2)C1] | None | 5-cyclopropyl-N-{[1-(propan-2-yl)azetidin-3-yl]methyl}-1,2-oxazole-3-carboxamide | 264.1 | >50.0 |
| 424 | 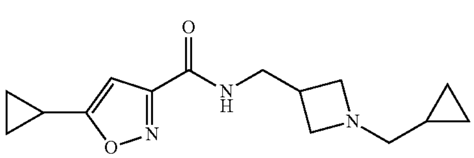 [SMILES: O=C(NCC1CN(CC2CC2)C1)c1cc(C2CC2)on1] | None | 5-cyclopropyl-N-{[1-(cyclopropylmethyl)azetidin-3-yl]methyl}-1,2-oxazole-3-carboxamide | 276.1 | >50.0 |
| 425 | 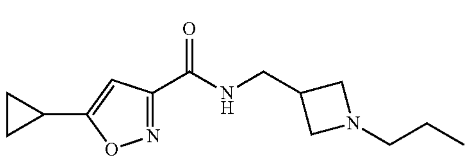 [SMILES: CCCN1CC(CNC(=O)c2cc(C3CC3)on2)C1] | None | 5-cyclopropyl-N-[(1-propylazetidin-3-yl)methyl]-1,2-oxazole-3-carboxamide | 264.1 | >50.0 |

TABLE 2-continued

| Cpd. No. | Structure | Salt Form | Chemical Name | LCMS M + H | SMYD2 Biochem IC$_{50}$ (μM)* |
|---|---|---|---|---|---|
| 426 | 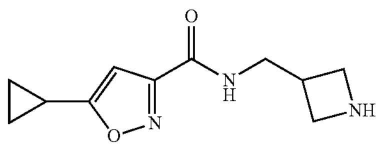 [SMILES: O=C(NCC1CNC1)c1cc(C2CC2)on1] | None | N-(azetidin-3-ylmethyl)-5-cyclopropyl-1,2-oxazole-3-carboxamide | 222.1 | 33.04122 |
| 427 | 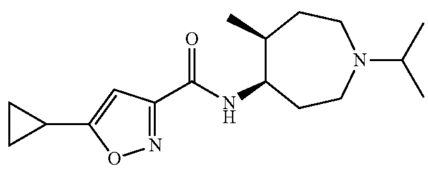 [SMILES: CC(C)N1CC[C@H](C)[C@H](NC(=O)c2cc(C3CC3)on2)CC1] | None | (±)-cis-5-cyclopropyl-N-[5-methyl-1-(propan-2-yl)azepan-4-yl]-1,2-oxazole-3-carboxamide | 306.2 | >50.0 |

*IC$_{50}$ values are an average of n = 1 to n = 50

TABLE 3

| Cpd. No. | Structure | Salt Form | Chemical Name | LCMS M + H | SMYD2 Biochem IC$_{50}$ (μM)* |
|---|---|---|---|---|---|
| 428 | 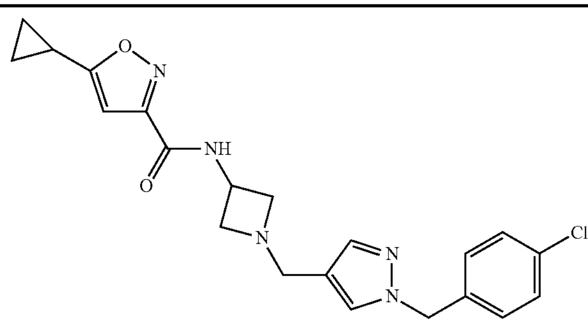 | none | N-(1-((1-(4-chlorobenzyl)-1H-pyrazol-4-yl)methyl)azetidin-3-yl)-5-cyclopropylisoxazole-3-carboxamide | 412.2 | 0.0095 |

*IC$_{50}$ values are an average of n = 1 to n = 50

TABLE 1A

| Cpd. No. | Chemical Name | LCMS M + H | SMYD3 Biochem IC$_{50}$ (μM)* | SMYD3 cell IC$_{50}$ (μM)* |
|---|---|---|---|---|
| 2 | N-(1-((4-acetamidophenyl)sulfonyl)piperidin-4-yl)-5-cyclobutylisoxazole-3-carboxamide | 447.15 | 48.11 | |
| 3 | N-(4-((4-acetamidophenyl)sulfonyl)cyclohexyl)-5-cyclopropylisoxazole-3-carboxamide | 431.91 | 23.37 | |
| 4 | 5-cyclopropyl-N-(piperidin-4-ylmethyl)isoxazole-3-carboxamide | 250.05 | 31.8 | |
| 5 | 5-cyclopropyl-N-((1-methylpiperidin-4-yl)methyl)isoxazole-3-carboxamide | 264.1 | 39.33 | |
| 6 | N-((1s,3s)-3-((4-acetamidophenyl)sulfonamido)cyclobutyl)-5-cyclopropylisoxazole-3-carboxamide | 419.25 | 32.91 | |
| 7 | N-((1r,3r)-3-((4-acetamidophenyl)sulfonamido)cyclobutyl)-5-cyclopropylisoxazole-3-carboxamide | 419.3 | 46.75 | |
| 8 | N-((1r,4r)-4-aminocyclohexyl)-5-cyclopropyl-4-iodoisoxazole-3-carboxamide | 375.83 | 20.73 | |
| 9 | N-((1r,4r)-4-aminocyclohexyl)-5-(2-hydroxyethyl)isoxazole-3-carboxamide | 254 | 33.25 | |

TABLE 1A-continued

| Cpd. No. | Chemical Name | LCMS M + H | SMYD3 Biochem IC$_{50}$ (μM)* | SMYD3 cell IC$_{50}$ (μM)* |
|---|---|---|---|---|
| 10 | N3-((1r,4r)-4-aminocyclohexyl)-5-cyclopropyl-N4-isobutylisoxazole-3,4-dicarboxamide | 349.1 | 38.97 | |
| 11 | N-((1r,4r)-4-aminocyclohexyl)-5-vinylisoxazole-3-carboxamide | 236.1 | 27.42 | |
| 12 | 5-cyclopropyl-N-(2,2-dimethyl-1-phenylpropyl)isoxazole-3-carboxamide | 299.05 | 12.75 | |
| 13 | N3-((1r,4r)-4-aminocyclohexyl)-5-cyclopropylisoxazole-3,4-dicarboxamide | 293.15 | 22.42 | |
| 14 | N-(4-(aminomethyl)phenyl)-5-cyclopropylisoxazole-3-carboxamide | 259.1 | 10.54 | |
| 15 | N-(1-(4-aminophenyl)ethyl)-5-cyclopropylisoxazole-3-carboxamide | 271.8 | 40.11 | |
| 16 | N-(4-(1-aminoethyl)phenyl)-5-cyclopropylisoxazole-3-carboxamide | 272.85 | 6.52 | |
| 17 | N-((1r,3r)-3-aminocyclobutyl)-5-cyclopropylisoxazole-3-carboxamide | 222.05 | 24.5 | |
| 18 | 5-cyclopropyl-N-(1-(4-fluorophenyl)propyl)isoxazole-3-carboxamide | 289.1 | 41.22 | |
| 19 | 5-cyclopropyl-N-(1-(4-fluorophenyl)-2-methylpropyl)isoxazole-3-carboxamide | 303.05 | 16.38 | |
| 20 | 5-cyclopropyl-N-(1-(4-methoxyphenyl)-2,2-dimethylpropyl)isoxazole-3-carboxamide | 329.1 | 5.85 | |
| 21 | N-((1r,4r)-4-aminocyclohexyl)-5-(3-hydroxypropyl)isoxazole-3-carboxamide | 268.1 | 40.64 | |
| 22 | N-(azepan-4-yl)-5-cyclopropylisoxazole-3-carboxamide | 250.15 | 14.88 | |
| 23 | N-(3-(azetidin-3-ylamino)cyclobutyl)-5-cyclopropylisoxazole-3-carboxamide | 277.1 | 32.38 | |
| 24 | N-((1r,4r)-4-aminocyclohexyl)-5-isopropylisoxazole-3-carboxamide | 234.79 (−NH$_2$) | 24.63 | |
| 25 | 5-cyclopropyl-N-(cyclopropyl(4-fluorophenyl)methyl)isoxazole-3-carboxamide | 301.05 | 16.21 | |
| 26 | 5-cyclopropyl-N-(3,3-dimethylbutan-2-yl)isoxazole-3-carboxamide | 237.05 | 45.92 | |
| 27 | N-(1-(4-aminophenyl)-2,2-dimethylpropyl)-5-cyclopropylisoxazole-3-carboxamide | 336.25 (+Na) | 8.54 | |
| 28 | 5-cyclopropyl-N-(2,2-dimethyl-1-(pyridin-2-yl)propyl)isoxazole-3-carboxamide | 300.15 | 38.32 | |
| 29 | 5-cyclopropyl-N-(1-(4-fluorophenyl)ethyl)isoxazole-3-carboxamide | 275 | 43.79 | |
| 30 | 5-cyclopropyl-N-(2,2-dimethylpentan-3-yl)isoxazole-3-carboxamide | 251.15 | 27.12 | |
| 31 | N-(1-(4-acetamidophenyl)-2,2-dimethylpropyl)-5-cyclopropylisoxazole-3-carboxamide | 356.25 | 12.82 | |
| 32 | N-(1-(4-chlorophenyl)-2,2-dimethylpropyl)-5-cyclopropylisoxazole-3-carboxamide | 333.15 | 9.03 | |
| 33 | N-(4-(aminomethyl)-2-methylphenyl)-5-cyclopropylisoxazole-3-carboxamide | 272.90 | 7.79 | |
| 34 | N-(4-(aminomethyl)-2-chlorophenyl)-5-cyclopropylisoxazole-3-carboxamide | 293.05 (295.00) | 6.45 | |
| 35 | N-((5-amino-1,3,3-trimethylcyclohexyl)methyl)-5-cyclopropylisoxazole-3-carboxamide | 306.3 | 12.99 | |
| 36 | 5-cyclopropyl-N-(2,2-dimethyl-1-(p-tolyl)propyl)isoxazole-3-carboxamide | 312.9 | 27.61 | |
| 37 | N-(4-(2-aminoethyl)phenyl)-5-cyclopropylisoxazole-3-carboxamide | 272.15 | 7.25 | |
| 38 | N-(4-(1-aminopropyl)phenyl)-5-cyclopropylisoxazole-3-carboxamide | 286.96 | 4.43 | |
| 39 | N-(4-(1-amino-2,2-dimethylpropyl)phenyl)-5-cyclopropylisoxazole-3-carboxamide | 297 (−NH$_3$) | 2.52 | |
| 40 | N-(4-(aminomethyl)-2-iodophenyl)-5-cyclopropylisoxazole-3-carboxamide | 366.9 (−NH$_3$) | 7.21 | |

TABLE 1A-continued

| Cpd. No. | Chemical Name | LCMS M + H | SMYD3 Biochem IC$_{50}$ (μM)* | SMYD3 cell IC$_{50}$ (μM)* |
|---|---|---|---|---|
| 41 | N-(5-(aminomethyl)pyridin-2-yl)-5-cyclopropylisoxazole-3-carboxamide | 259.15 | 22.53 | |
| 42 | 5-ethyl-N-(1-(3-methoxyphenyl)-2,2-dimethylpropyl)isoxazole-3-carboxamide | 317.2 | 24.62 | |
| 43 | 5-cyclopropyl-N-(1-(3-methoxyphenyl)-2,2-dimethylpropyl)isoxazole-3-carboxamide | 329.25 | 18.91 | |
| 44 | N-(4-(1-amino-2-methylpropyl)phenyl)-5-cyclopropylisoxazole-3-carboxamide | 300.04 | 2.5 | |
| 45 | N-(5-(aminomethyl)-6-methylpyridin-2-yl)-5-cyclopropylisoxazole-3-carboxamide | 273.15 | 29.74 | |
| 46 | 5-cyclopropyl-N-(2,2-dimethyl-1-(m-tolyl)propyl)isoxazole-3-carboxamide | 313.25 | 22.2 | |
| 47 | 5-ethyl-N-(1-(3-fluorophenyl)-2,2-dimethylpropyl)isoxazole-3-carboxamide | 305.15 | 7.26 | |
| 48 | 5-cyclopropyl-N-(1-(3-fluorophenyl)-2,2-dimethylpropyl)isoxazole-3-carboxamide | 317.25 | 7.92 | |
| 49 | 5-cyclopropyl-N-(phenyl(piperidin-4-yl)methyl)isoxazole-3-carboxamide | 326.25 | 8.09 | |
| 50 | 5-cyclopropyl-N-(2,2-dimethyl-1-(pyridin-3-yl)propyl)isoxazole-3-carboxamide | 300.15 | 9.99 | |
| 51 | 5-cyclopropyl-N-(2,2-dimethyl-1-(pyridin-4-yl)propyl)isoxazole-3-carboxamide | 300.2 | 4.08 | |
| 52 | N-(1-cyclobutyl-2,2-dimethylpropyl)-5-cyclopropylisoxazole-3-carboxamide | 277.2 | 7.4 | |
| 53 | N-(1-cyclopentyl-2,2-dimethylpropyl)-5-cyclopropylisoxazole-3-carboxamide | 291.25 | 10.58 | |
| 54 | N-(1-cyclohexyl-2,2-dimethylpropyl)-5-cyclopropylisoxazole-3-carboxamide | 305.01 | 15.14 | |
| 55 | N-(cyclobutyl(phenyl)methyl)-5-cyclopropylisoxazole-3-carboxamide | 297.2 | 38.47 | |
| 56 | N-(4-(aminomethyl)-3-chlorophenyl)-5-cyclopropylisoxazole-3-carboxamide | 291.95 | 16.4 | |
| 57 | N-(1-(3-chlorophenyl)-2,2-dimethylpropyl)-5-ethylisoxazole-3-carboxamide | 321.2 | 6.06 | |
| 58 | N-(1-(3-chlorophenyl)-2,2-dimethylpropyl)-5-cyclopropylisoxazole-3-carboxamide | 333.2 | 9.97 | |
| 59 | N-(2-(4-amino-4-methylcyclohexyl)propan-2-yl)-5-cyclopropylisoxazole-3-carboxamide | 306 | 10.23 | |
| 60 | N-(4-(2-aminopropan-2-yl)-1-methylcyclohexyl)-5-cyclopropylisoxazole-3-carboxamide | 306 | 2.98 | |
| 61 | 5-cyclopropyl-N-(2,2-dimethyl-1-(thiazol-4-yl)propyl)isoxazole-3-carboxamide | 306.15 | 6.29 | |
| 62 | 5-cyclopropyl-N-(2,2-dimethyl-1-(piperidin-4-yl)propyl)isoxazole-3-carboxamide | 306.25 | 4.35 | |
| 63 | N-(((1r,4r)-4-aminocyclohexyl)(phenyl)methyl)-5-cyclopropylisoxazole-3-carboxamide | 340.25 | 6.99 | |
| 64 | 5-ethyl-N-(phenyl(tetrahydro-2H-pyran-4-yl)methyl)isoxazole-3-carboxamide | 337.25 (+Na) | 37.06 | |
| 65 | N-(3-(aminomethyl)-3,5,5-trimethylcyclohexyl)-5-cyclopropylisoxazole-3-carboxamide | 306.15 | 14.07 | |
| 66 | 5-cyclopropyl-N-((S)-phenyl((S)-pyrrolidin-2-yl)methyl)isoxazole-3-carboxamide | 312.2 | 34.2 | |
| 67 | N-(((1s,4s)-4-aminocyclohexyl)(phenyl)methyl)-5-cyclopropylisoxazole-3-carboxamide | 340.25 | 13 | |
| 68 | 5-cyclopropyl-N-(2,2-dimethyl-1-(piperidin-3-yl)propyl)isoxazole-3-carboxamide | 306.25 | 4.38 | |
| 69 | 5-cyclopropyl-N-(phenyl(piperidin-3-yl)methyl)isoxazole-3-carboxamide | 326.25 | 12.68 | |

TABLE 1A-continued

| Cpd. No. | Chemical Name | LCMS M + H | SMYD3 Biochem IC$_{50}$ (μM)* | SMYD3 cell IC$_{50}$ (μM)* |
|---|---|---|---|---|
| 70 | N-(4-(aminomethyl)-3-methylphenyl)-5-cyclopropylisoxazole-3-carboxamide | 272.97 | 8.22 | |
| 71 | 5-ethyl-N-((1-methylpiperidin-4-yl)(phenyl)methyl)isoxazole-3-carboxamide | 328.25 | 20.51 | |
| 72 | N-((3-chlorophenyl)(piperidin-4-yl)methyl)-5-ethylisoxazole-3-carboxamide | 348.2 | 1.4 | |
| 73 | N-((3-chlorophenyl)(piperidin-4-yl)methyl)-5-cyclopropylisoxazole-3-carboxamide | 360.25 | 2.59 | |
| 74 | 5-ethyl-N-(phenyl(piperidin-4-yl)methyl)isoxazole-3-carboxamide | 314.2 | 7.44 | |
| 75 | N-((3-((4-chlorobenzyl)carbamoyl)phenyl)(piperidin-4-yl)methyl)-5-cyclopropylisoxazole-3-carboxamide | 493.3 | 13.58 | |
| 76 | N-((3-((cyclohexylmethyl)carbamoyl)phenyl)(piperidin-4-yl)methyl)-5-cyclopropylisoxazole-3-carboxamide | 465.35 | 34.82 | |
| 77 | N-((3-(cyclohexylcarbamoyl)phenyl)(piperidin-4-yl)methyl)-5-cyclopropylisoxazole-3-carboxamide | 451.4 | 49.05 | |
| 78 | N-(4-(aminomethyl)-3-methoxyphenyl)-5-cyclopropylisoxazole-3-carboxamide | 270.92 (−NH$_2$) | 32.1 | |
| 79 | 5-cyclopropyl-N-((S)-1-(((S)-1,6-diamino-1-oxohexan-2-yl)amino)-3-hydroxy-1-oxopropan-2-yl)isoxazole-3-carboxamide | 368.25 | 15.03 | |
| 80 | N-((2-chlorophenyl)(piperidin-4-yl)methyl)-5-ethylisoxazole-3-carboxamide | 348.15 | 15.86 | |
| 81 | 5-cyclopropyl-N-((1-methylpiperidin-4-yl)(phenyl)methyl)isoxazole-3-carboxamide | 340.2 | 22.81 | |
| 82 | N-((2-chlorophenyl)(piperidin-4-yl)methyl)-5-cyclopropylisoxazole-3-carboxamide | 360.2 | 9.05 | |
| 83 | 5-cyclopropyl-N-(piperidin-4-yl(3-((pyridin-3-ylmethyl)carbamoyl)phenyl)methyl)isoxazole-3-carboxamide | 460.3 | 30.8 | |
| 84 | 5-cyclopropyl-N-(piperidin-4-yl(3-((3-(pyrrolidin-1-yl)propyl)carbamoyl)phenyl)methyl)isoxazole-3-carboxamide | 480.4 | 10.57 | |
| 85 | 5-cyclopropyl-N-((3-((2-(piperidin-1-yl)ethyl)carbamoyl)phenyl)(piperidin-4-yl)methyl)isoxazole-3-carboxamide | 480.4 | 12.59 | |
| 86 | 5-cyclopropyl-N-((3-((2-(methylsulfonyl)ethyl)carbamoyl)phenyl)(piperidin-4-yl)methyl)isoxazole-3-carboxamide | 475.35 | 20.84 | |
| 87 | 5-cyclopropyl-N-((3-((3-(dimethylamino)propyl)carbamoyl)phenyl)(piperidin-4-yl)methyl)isoxazole-3-carboxamide | 454.35 | 24.56 | |
| 88 | 5-cyclopropyl-N-(piperidin-4-yl(3-((pyridin-4-ylmethyl)carbamoyl)phenyl)methyl)isoxazole-3-carboxamide | 460.35 | 37.32 | |
| 89 | N-((3-(((1r,4r)-4-aminocyclohexyl)carbamoyl)phenyl)(piperidin-4-yl)methyl)-5-cyclopropylisoxazole-3-carboxamide | 466.35 | 39.36 | |
| 90 | 5-cyclopropyl-N-((3-((pent-4-yn-1-yloxy)methyl)phenyl)(piperidin-4-yl)methyl)isoxazole-3-carboxamide | | 11.77 | |
| 91 | N-(4-(aminomethyl)-2-isopropylphenyl)-5-cyclopropylisoxazole-3-carboxamide | 283.02 (−NH2) | 6.08 | |
| 92 | N-((1r,4r)-4-aminocyclohexyl)-5-isobutylisoxazole-3-carboxamide | 266.1 | 38.15 | |

TABLE 1A-continued

| Cpd. No. | Chemical Name | LCMS M + H | SMYD3 Biochem IC$_{50}$ (μM)* | SMYD3 cell IC$_{50}$ (μM)* |
|---|---|---|---|---|
| 93 | N-((1r,4r)-4-aminocyclohexyl)-5-propylisoxazole-3-carboxamide | 252.1 | 9.93 | |
| 94 | N-(4-(aminomethyl)-3-iodophenyl)-5-cyclopropylisoxazole-3-carboxamide | 383.98 | 19.48 | |
| 95 | N-(1-(2H-indazol-4-yl)-2,2-dimethylpropyl)-5-cyclopropylisoxazole-3-carboxamide | 339.01 | 6.82 | |
| 96 | 5-cyclopropyl-N-((3-((1-isopropylpiperidin-4-yl)carbamoyl)phenyl)(piperidin-4-yl)methyl)isoxazole-3-carboxamide | 494.45 | 48.53 | |
| 97 | 5-cyclopropyl-N-((3-((3-hydroxybenzyl)carbamoyl)phenyl)(piperidin-4-yl)methyl)isoxazole-3-carboxamide | 475.4 | 25.88 | |
| 98 | 5-cyclopropyl-N-((3-(cyclopropylcarbamoyl)phenyl)(piperidin-4-yl)methyl)isoxazole-3-carboxamide | 409.3 | 46.85 | |
| 99 | 5-cyclopropyl-N-(piperidin-4-yl(3-((prop-2-yn-1-yloxy)methyl)phenyl)methyl)isoxazole-3-carboxamide | 394.24 | 11.9 | |
| 100 | 5-cyclopropyl-N-((3-((diethylamino)methyl)phenyl)(piperidin-4-yl)methyl)isoxazole-3-carboxamide | 411.3 | 17.98 | |
| 101 | N-(4-(aminomethyl)-2-ethylphenyl)-5-cyclopropylisoxazole-3-carboxamide | 268.99 (−NH$_2$) | 3 | |
| 102 | N-((1r,4r)-4-aminocyclohexyl)-5-butylisoxazole-3-carboxamide | 266.1 | 32.62 | |
| 103 | 5-cyclopropyl-N-((3-((2-hydroxy-3-(pyrrolidin-1-yl)propyl)carbamoyl)phenyl)(piperidin-4-yl)methyl)isoxazole-3-carboxamide | 496.4 | 14.1 | |
| 104 | 5-cyclopropyl-N-((3-((3-hydroxypropyl)(methyl)carbamoyl)phenyl)(piperidin-4-yl)methyl)isoxazole-3-carboxamide | 441.3 | 11.17 | |
| 105 | 5-cyclopropyl-N-(piperidin-4-yl(3-((pyridin-2-ylmethyl)carbamoyl)phenyl)methyl)isoxazole-3-carboxamide | 460.35 | 45.5 | |
| 106 | 5-cyclopropyl-N-(piperidin-4-yl(3-(pyridin-3-ylcarbamoyl)phenyl)methyl)isoxazole-3-carboxamide | 446.3 | 4.76 | |
| 107 | 5-cyclopropyl-N-((3-(((3-fluorobenzyl)oxy)methyl)phenyl)(piperidin-4-yl)methyl)isoxazole-3-carboxamide | 464.35 | 16.78 | |
| 108 | N-((3-((but-2-yn-1-yloxy)methyl)phenyl)(piperidin-4-yl)methyl)-5-cyclopropylisoxazole-3-carboxamide | 408.3 | 6.36 | |
| 109 | 5-cyclopropyl-N-((3-(((3-hydroxypropyl)(methyl)amino)methyl)phenyl)(piperidin-4-yl)methyl)isoxazole-3-carboxamide | 427.35 | 34.01 | |
| 110 | 5-cyclopropyl-N-((3-(((2-iodobenzyl)oxy)methyl)phenyl)(piperidin-4-yl)methyl)isoxazole-3-carboxamide | 572.3 | 4.98 | |
| 111 | 5-cyclopropyl-N-((3-((2-methoxyphenethoxy)methyl)phenyl)(piperidin-4-yl)methyl)isoxazole-3-carboxamide | 490.4 | 11.35 | |
| 112 | 5-cyclopropyl-N-((3-((2-methylphenethoxy)methyl)phenyl)(piperidin-4-yl)methyl)isoxazole-3-carboxamide | 474.4 | 11.25 | |
| 113 | 5-cyclopropyl-N-((3-(hydroxymethyl)phenyl)(piperidin-4-yl)methyl)isoxazole-3-carboxamide | 356.25 | 3.67 | |
| 114 | N-(4-(aminomethyl)-3-ethylphenyl)-5-cyclopropylisoxazole-3-carboxamide | 268.99 (−NH$_2$) | 13.86 | |

TABLE 1A-continued

| Cpd. No. | Chemical Name | LCMS M + H | SMYD3 Biochem IC$_{50}$ (μM)* | SMYD3 cell IC$_{50}$ (μM)* |
|---|---|---|---|---|
| 115 | 5-cyclopropyl-N-((3-((3-hydroxypropyl)carbamoyl)phenyl)(piperidin-4-yl)methyl)isoxazole-3-carboxamide | 427.3 | 17.42 | |
| 116 | 5-cyclopropyl-N-((3-((2-hydroxybenzyl)carbamoyl)phenyl)(piperidin-4-yl)methyl)isoxazole-3-carboxamide | 475.35 | 18.31 | |
| 117 | 5-cyclopropyl-N-(piperidin-4-yl(3-(pyridin-2-ylcarbamoyl)phenyl)methyl)isoxazole-3-carboxamide | 446.4 | 9.3 | |
| 118 | 5-cyclopropyl-N-((3-((2-(ethylamino)ethoxy)methyl)phenyl)(piperidin-4-yl)methyl)isoxazole-3-carboxamide | 427.35 | 19.37 | |
| 119 | N-((3-((2-aminoethoxy)methyl)phenyl)(piperidin-4-yl)methyl)-5-cyclopropylisoxazole-3-carboxamide | 399.3 | 13.19 | |
| 120 | 5-cyclopropyl-N-(piperidin-4-yl(3-(propoxymethyl)phenyl)methyl)isoxazole-3-carboxamide | 398.35 | 20.62 | |
| 121 | N-(4-(1-amino-4-hydroxybutyl)phenyl)-5-cyclopropylisoxazole-3-carboxamide | 316.10 | 4.36 | |
| 122 | 5-cyclopropyl-N-(1-oxaspiro[5.5]undecan-4-yl)isoxazole-3-carboxamide | 305.1 | 11.83 | |
| 123 | 5-cyclopropyl-N-(3-ethoxyspiro[3.5]nonan-1-yl)isoxazole-3-carboxamide | 319.3 | 4.79 | |
| 124 | 5-cyclopropyl-N-(3-oxaspiro[5.5]undecan-9-yl)isoxazole-3-carboxamide | 305.1 | 26.51 | |
| 125 | N-(1-benzyl-6-methylpiperidin-3-yl)-5-cyclopropylisoxazole-3-carboxamide | 340.1 | 21.2 | |
| 126 | 5-cyclopropyl-N-(3-phenylcyclopentyl)isoxazole-3-carboxamide | 297.1 | 29.97 | |
| 127 | 5-cyclopropyl-N-(2-(3,4-difluorophenyl)tetrahydrofuran-3-yl)isoxazole-3-carboxamide | 335.1 | 49.59 | |
| 128 | 5-cyclopropyl-N-(2,2-dimethyltetrahydro-2H-pyran-4-yl)isoxazole-3-carboxamide | 265.4 | 44.55 | |
| 129 | 5-cyclopropyl-N-(6-oxaspiro[4.5]decan-9-yl)isoxazole-3-carboxamide | 291.1 | 18.41 | |
| 130 | N-((3-((((1r,4r)-4-aminocyclohexyl)oxy)methyl)phenyl)(piperidin-4-yl)methyl)-5-cyclopropylisoxazole-3-carboxamide | | 1.38 | |
| 131 | 5-cyclopropyl-N-((3-((isopropyl(tetrahydro-2H-pyran-4-yl)amino)methyl)phenyl)(piperidin-4-yl)methyl)isoxazole-3-carboxamide | | 16.6 | |
| 132 | methyl 5-(aminomethyl)-2-(5-cyclopropylisoxazole-3-carboxamido)benzoate | 299.83 (M − NH$_2$) | 48.66 | |
| 133 | 5-cyclopropyl-N-(piperidin-4-yl(3-(pyridin-4-ylcarbamoyl)phenyl)methyl)isoxazole-3-carboxamide | 446.12 | 6.48 | |
| 134 | N-(3-butoxy-2,2-dimethylcyclobutyl)-5-cyclopropylisoxazole-3-carboxamide | 307.3 | 18.73 | |
| 135 | 5-cyclopropyl-N-(6-hydroxy-1,2,3,4-tetrahydronaphthalen-2-yl)isoxazole-3-carboxamide | 299.1 | 23.68 | |
| 136 | 5-cyclopropyl-N-(3-isobutoxy-2,2-dimethylcyclobutyl)isoxazole-3-carboxamide | 307.2 | 9.54 | |
| 137 | 5-cyclopropyl-N-(2-(4-fluorophenyl)tetrahydro-2H-pyran-4-yl)isoxazole-3-carboxamide | 331.3 | 2.56 | |

TABLE 1A-continued

| Cpd. No. | Chemical Name | LCMS M + H | SMYD3 Biochem IC$_{50}$ (μM)* | SMYD3 cell IC$_{50}$ (μM)* |
|---|---|---|---|---|
| 138 | N-(1-(1-benzylpyrrolidin-3-yl)ethyl)-5-cyclopropylisoxazole-3-carboxamide | 340.3 | 24.96 | |
| 139 | 5-cyclopropyl-N-((3-(((2-hydroxyethyl)(methyl)amino)methyl)phenyl)(piperidin-4-yl)methyl)isoxazole-3-carboxamide | 413.25 | 41.77 | |
| 140 | 5-cyclopropyl-N-((3-((4-methyl-1H-pyrrole-2-carboxamido)methyl)phenyl)(piperidin-4-yl)methyl)isoxazole-3-carboxamide | 462.17 | 28.35 | |
| 141 | 5-cyclopropyl-N-((3-((3-(4-methyl-1H-pyrazol-1-yl)propanamido)methyl)phenyl)(piperidin-4-yl)methyl)isoxazole-3-carboxamide | 491.35 | 25.42 | |
| 142 | N-((3-carbamoylphenyl)(piperidin-4-yl)methyl)-5-cyclopropylisoxazole-3-carboxamide | 369.15 | 3.6 | |
| 143 | N-((1r,4r)-4-aminocyclohexyl)-5-(difluoromethyl)isoxazole-3-carboxamide | 260.1 | 18.56 | |
| 144 | 5-cyclopropyl-N-(2-isobutyltetrahydro-2H-pyran-4-yl)isoxazole-3-carboxamide | 293.2 | 7.16 | |
| 145 | N-(1-(1-cyclobutylpiperidin-3-yl)ethyl)-5-cyclopropylisoxazole-3-carboxamide | 318.4 | 18.08 | |
| 146 | 5-cyclopropyl-N-(2-isopropyl-4,5,6,7-tetrahydro-2H-indazol-6-yl)isoxazole-3-carboxamide | 315.1 | 27.28 | |
| 147 | N-(4-(aminomethyl)-2-(hydroxymethyl)phenyl)-5-cyclopropylisoxazole-3-carboxamide | 310.15 (+Na) | 4.07 | |
| 148 | N-(4-(1-amino-3-(pyridin-2-yl)propyl)phenyl)-5-cyclopropylisoxazole-3-carboxamide | 363.3 | 0.97 | |
| 149 | N-(4-(1-amino-3-(pyridin-3-yl)propyl)phenyl)-5-cyclopropylisoxazole-3-carboxamide | 363.3 | 0.62 | |
| 150 | N-(4-(1-amino-3-(pyridin-4-yl)propyl)phenyl)-5-cyclopropylisoxazole-3-carboxamide | 363.3 | 1.39 | |
| 151 | N-(4-(1-amino-3-phenylpropyl)phenyl)-5-cyclopropylisoxazole-3-carboxamide | 345.12 (M − NH$_2$) | 2.34 | |
| 152 | 5-cyclopropyl-N-((1-glycylpiperidin-4-yl)(phenyl)methyl)isoxazole-3-carboxamide | 383.4 | 4.47 | |
| 153 | N-((1-(D-alanyl)piperidin-4-yl)(phenyl)methyl)-5-cyclopropylisoxazole-3-carboxamide | 397.35 | 1.27 | |
| 154 | N-((1-(L-alanyl)piperidin-4-yl)(phenyl)methyl)-5-cyclopropylisoxazole-3-carboxamide | 397.35 | 1.53 | |
| 155 | 5-cyclopropyl-N-((3-(phenylcarbamoyl)phenyl)(piperidin-4-yl)methyl)isoxazole-3-carboxamide | 445.4 | 4.15 | |
| 156 | (±)-cis-5-cyclopropyl-N-(3-cyclopropylcyclohexyl)isoxazole-3-carboxamide | 275.4 | 31.11 | |
| 157 | (±)-trans-5-cyclopropyl-N-(3-cyclopropylcyclohexyl)isoxazole-3-carboxamide | 275.3 | 39.9 | |
| 158 | (±)-cis-5-cyclopropyl-N-(3-(1-methyl-1H-imidazol-2-yl)cyclohexyl)isoxazole-3-carboxamide | 315.1 | 10.07 | |
| 159 | (±)-trans-5-cyclopropyl-N-((1S,3S)-3-(1-methyl-1H-imidazol-2-yl)cyclohexyl)isoxazole-3-carboxamide | 315.1 | 14.94 | |
| 160 | N-(4-(aminomethyl)-3-isopropylphenyl)-5-cyclopropylisoxazole-3-carboxamide | 322.2 (+Na) | 17.14 | |
| 161 | N-(4-(aminomethyl)-3-(hydroxymethyl)phenyl)-5-cyclopropylisoxazole-3-carboxamide | 310.2 (+Na) | 12.36 | |
| 162 | (R)-5-cyclopropyl-N-(piperidin-4-yl(3-(pyridin-3-ylcarbamoyl)phenyl)methyl)isoxazole-3-carboxamide | 446.3 | 49 | |

TABLE 1A-continued

| Cpd. No. | Chemical Name | LCMS M + H | SMYD3 Biochem IC$_{50}$ (μM)* | SMYD3 cell IC$_{50}$ (μM)* |
|---|---|---|---|---|
| 163 | (S)-5-cyclopropyl-N-(piperidin-4-yl(3-(pyridin-3-ylcarbamoyl)phenyl)methyl)isoxazole-3-carboxamide | 446.3 | 0.85 | |
| 164 | N-(4-((2-aminoacetamido)methyl)phenyl)-5-cyclopropylisoxazole-3-carboxamide | 337.1 (+Na) | 17.78 | |
| 165 | N-((1-benzyl-5-methylpyrrolidin-3-yl)methyl)-5-cyclopropylisoxazole-3-carboxamide | 340.2 | 43.84 | |
| 166 | N-((4-chlorophenyl)(4-methylmorpholin-2-yl)methyl)-5-cyclopropylisoxazole-3-carboxamide | 376.2 | 31.49 | |
| 167 | 5-cyclopropyl-N-(1,2-dimethylpiperidin-3-yl)isoxazole-3-carboxamide | 263.1 | 28.85 | |
| 168 | N-(1-benzylpiperidin-3-yl)-5-cyclopropylisoxazole-3-carboxamide | 326.1 | 26.38 | |
| 169 | 5-cyclopropyl-N-((3-(oxetan-3-ylcarbamoyl)phenyl)(piperidin-4-yl)methyl)isoxazole-3-carboxamide | 425.3 | 35.06 | |
| 170 | N-(4-(2-aminopropan-2-yl)phenyl)-5-cyclopropylisoxazole-3-carboxamide | 286.88 | 3.54 | |
| 171 | N-(4-(1-amino-2-((1-methylpiperidin-4-yl)amino)-2-oxoethyl)phenyl)-5-cyclopropylisoxazole-3-carboxamide | 398.25 | 24.39 | |
| 172 | 5-cyclopropyl-N-((3-((6-methylpyridin-3-yl)carbamoyl)phenyl)(piperidin-4-yl)methyl)isoxazole-3-carboxamide | 460.3 | 5.9 | |
| 173 | 5-cyclopropyl-N-((3-(piperidin-3-ylcarbamoyl)phenyl)(piperidin-4-yl)methyl)isoxazole-3-carboxamide | 452.3 | 38.93 | |
| 174 | N-((3-((5-carbamoylpyridin-3-yl)carbamoyl)phenyl)(piperidin-4-yl)methyl)-5-cyclopropylisoxazole-3-carboxamide | 489.3 | 10.82 | |
| 175 | 5-cyclopropyl-N-(1-phenyl-3-(1H-1,2,4-triazol-1-yl)propyl)isoxazole-3-carboxamide | 338.15 | 41.58 | |
| 176 | 5-cyclopropyl-N-((3-((6-(methylamino)pyridin-3-yl)carbamoyl)phenyl)(piperidin-4-yl)methyl)isoxazole-3-carboxamide | 475.35 | 3.45 | |
| 177 | 5-cyclopropyl-N-((3-((6-methoxypyridin-3-yl)carbamoyl)phenyl)(piperidin-4-yl)methyl)isoxazole-3-carboxamide | 476.35 | 4.59 | |
| 178 | N-(1-(1-(L-alanyl)piperidin-4-yl)ethyl)-5-cyclopropylisoxazole-3-carboxamide | 335.25 | 0.47 | |
| 179 | N-((1-(L-alanyl)piperidin-4-yl)methyl)-5-cyclopropylisoxazole-3-carboxamide | 321.25 | 0.75 | |
| 180 | N-((1-(D-alanyl)piperidin-4-yl)methyl)-5-cyclopropylisoxazole-3-carboxamide | 321.2 | 9.05 | |
| 181 | 5-cyclopropyl-N-(piperidin-4-yl(3-(pyridazin-4-ylcarbamoyl)phenyl)methyl)isoxazole-3-carboxamide | 447.35 | 7.34 | |
| 182 | 5-cyclopropyl-N-(2-((2-hydroxybenzyl)amino)-2-oxo-1-(pipendm-4-yl)ethyl)isoxazole-3-carboxamide | 399.3 | 14.19 | |
| 183 | 5-cyclopropyl-N-(piperidin-4-yl(3-((6-(trifluoromethyl)pyridin-3-yl)carbamoyl)phenyl)methyl)isoxazole-3-carboxamide | 514.35 | 8.28 | |
| 184 | 5-cyclopropyl-N-(piperidin-4-yl(3-(pyrimidin-5-ylcarbamoyl)phenyl)methyl)isoxazole-3-carboxamide | 447.85 | 2.16 | |
| 185 | 5-cyclopropyl-N-(piperidin-4-yl(3-(pyridazin-3-ylcarbamoyl)phenyl)methyl)isoxazole-3-carboxamide | 447.4 | 1.7 | |
| 186 | 5-cyclopropyl-N-((3-((2-hydroxypyridin-3-yl)carbamoyl)phenyl)(piperidin-4-yl)methyl)isoxazole-3-carboxamide | 462.35 | 29.68 | |

TABLE 1A-continued

| Cpd. No. | Chemical Name | LCMS M + H | SMYD3 Biochem IC$_{50}$ (μM)* | SMYD3 cell IC$_{50}$ (μM)* |
|---|---|---|---|---|
| 187 | 5-cyclopropyl-N-((3-((5-methylpyridin-3-yl)carbamoyl)phenyl)(piperidin-4-yl)methyl)isoxazole-3-carboxamide | 460.35 | 2.88 | |
| 188 | N-(1-(1-(D-alanyl)piperidin-4-yl)ethyl)-5-cyclopropylisoxazole-3-carboxamide | 335.25 | 3.69 | |
| 189 | N-(1-(1-(L-tryptophyl)piperidin-4-yl)ethyl)-5-cyclopropylisoxazole-3-carboxamide | 450.4 | 0.52 | |
| 190 | N-(1-(1-(D-tryptophyl)piperidin-4-yl)ethyl)-5-cyclopropylisoxazole-3-carboxamide | 450.4 | 10.09 | |
| 191 | N-((1-(L-tryptophyl)piperidin-4-yl)methyl)-5-cyclopropylisoxazole-3-carboxamide | 436.35 | 0.56 | |
| 192 | N-((1-(D-tryptophyl)piperidin-4-yl)methyl)-5-cyclopropylisoxazole-3-carboxamide | 435.35 | 6.5 | |
| 193 | N-((1-(L-seryl)piperidin-4-yl)(phenyl)methyl)-5-cyclopropylisoxazole-3-carboxamide | 413.35 | 3.51 | |
| 194 | N-((1-(L-tyrosyl)piperidin-4-yl)(phenyl)methyl)-5-cyclopropylisoxazole-3-carboxamide | 489.5 | 2.69 | |
| 195 | N-((1-(L-tryptophyl)piperidin-4-yl)(phenyl)methyl)-5-cyclopropylisoxazole-3-carboxamide | 512.29 | 1.42 | |
| 196 | N-((1-(L-seryl)piperidin-4-yl)methyl)-5-cyclopropylisoxazole-3-carboxamide | 337.25 | 3.28 | |
| 197 | N-((1-(L-tyrosyl)piperidin-4-yl)methyl)-5-cyclopropylisoxazole-3-carboxamide | 413.35 | 0.43 | |
| 198 | (±)-trans-5-cyclopropyl-N-(4-(4-fluorophenyl)-4-hydroxybutan-2-yl)isoxazole-3-carboxamide | 319.2 | 17.68 | |
| 199 | ethyl 1-(L-tyrosyl)-5-(5-cyclopropylisoxazole-3-carboxamido)piperidine-3-carboxylate | 471.4 | 43.3 | |
| 200 | N-((3-((6-acetamidopyridin-3-yl)carbamoyl)phenyl)(piperidin-4-yl)methyl)-5-cyclopropylisoxazole-3-carboxamide | 503.45 | 4.57 | |
| 201 | 5-cyclopropyl-N-(piperidin-4-yl(3-(pyrazin-2-ylcarbamoyl)phenyl)methyl)isoxazole-3-carboxamide | 447.3 | 18.97 | |
| 202 | 5-cyclopropyl-N-((3-((6-hydroxypyridin-3-yl)carbamoyl)phenyl)(piperidin-4-yl)methyl)isoxazole-3-carboxamide | 462.35 | 49.68 | |
| 203 | methyl 2-(1-(L-alanyl)piperidin-4-yl)-2-(5-cyclopropylisoxazole-3-carboxamido)acetate | 379.3 | 0.74 | |
| 204 | methyl 2-(1-(D-alanyl)piperidin-4-yl)-2-(5-cyclopropylisoxazole-3-carboxamido)acetate | 379.3 | 7.54 | |
| 205 | N-((1-(L-alanyl)piperidin-4-yl)(3-(pyridin-3-ylcarbamoyl)phenyl)methyl)-5-cyclopropylisoxazole-3-carboxamide | 517.35 | 0.29 | |
| 206 | N-((1-(D-alanyl)piperidin-4-yl)(3-(pyridin-3-ylcarbamoyl)phenyl)methyl)-5-cyclopropylisoxazole-3-carboxamide | 517.45 | 0.59 | |
| 207 | N-((1-(D-tryptophyl)piperidin-4-yl)(phenyl)methyl)-5-cyclopropylisoxazole-3-carboxamide | 534.5 (+Na) | 23.23 | |
| 208 | N-(1-(1-(L-valyl)piperidin-4-yl)ethyl)-5-cyclopropylisoxazole-3-carboxamide | 363.35 | 0.36 | |
| 209 | N-(1-(1-(D-valyl)piperidin-4-yl)ethyl)-5-cyclopropylisoxazole-3-carboxamide | 363.35 | 2.42 | |
| 210 | N-(1-(1-(L-seryl)piperidin-4-yl)ethyl)-5-cyclopropylisoxazole-3-carboxamide | 373.3 (+Na) | 1.2 | |
| 211 | N-(1-(1-(L-tyrosyl)piperidin-4-yl)ethyl)-5-cyclopropylisoxazole-3-carboxamide | 427.35 | 0.2 | |
| 212 | tert-butyl 4-(1-(5-cyclopropylisoxazole-3-carboxamido)ethyl)piperidine-1-carboxylate | 386.25 (+Na) | 28.43 | |
| 213 | 5-cyclopropyl-N-(1-(piperidin-4-yl)ethyl)isoxazole-3-carboxamide | 264.2 | 7.12 | |

TABLE 1A-continued

| Cpd. No. | Chemical Name | LCMS M + H | SMYD3 Biochem IC$_{50}$ (μM)* | SMYD3 cell IC$_{50}$ (μM)* |
|---|---|---|---|---|
| 214 | 5-cyclopropyl-N-(piperidin-4-yl(pyridin-4-yl)methyl)isoxazole-3-carboxamide | 327.25 | 3.15 | |
| 215 | N-((S)-(1-(L-alanyl)piperidin-4-yl)(phenyl)methyl)-5-cyclopropylisoxazole-3-carboxamide | 397.35 | 0.21 | |
| 216 | N-((R)-(1-(L-alanyl)piperidin-4-yl)(phenyl)methyl)-5-cyclopropylisoxazole-3-carboxamide | 397.35 | 4.48 | |
| 218 | 5-cyclopropyl-N-(2-oxo-1-(piperidin-4-yl)-2-(pyridin-3-ylamino)ethyl)isoxazole-3-carboxamide | 370.3 | 26.87 | |
| 219 | 5-cyclopropyl-N-(2-oxo-1-(piperidin-4-yl)-2-((pyridin-3-ylmethyl)amino)ethyl)isoxazole-3-carboxamide | 384.3 | 34.17 | |
| 220 | 5-cyclopropyl-N-(piperidin-4-yl(3-((pyridin-3-ylamino)methyl)phenyl)methyl)isoxazole-3-carboxamide | 432.35 | 2.22 | |
| 221 | N-((3-((6-aminopyridin-3-yl)carbamoyl)phenyl)(piperidin-4-yl)methyl)-5-cyclopropylisoxazole-3-carboxamide | 461.4 | 7.49 | |
| 222 | 5-cyclopropyl-N-((3-(methyl(pyridin-3-yl)carbamoyl)phenyl)(piperidin-4-yl)methyl)isoxazole-3-carboxamide | 460.4 | 31.99 | |
| 223 | methyl 2-(1-(L-tryptophyl)piperidin-4-yl)-2-(5-cyclopropylisoxazole-3-carboxamido)acetate | 494.18 | 3.15 | |
| 224 | methyl 2-(1-(D-tryptophyl)piperidin-4-yl)-2-(5-cyclopropylisoxazole-3-carboxamido)acetate | 494.23 | 29.42 | |
| 225 | N-(1-(1-(D-seryl)piperidin-4-yl)ethyl)-5-cyclopropylisoxazole-3-carboxamide | 351.3 | 5.82 | |
| 226 | N-((1-(L-valyl)piperidin-4-yl)methyl)-5-cyclopropylisoxazole-3-carboxamide | 349.3 | 0.57 | |
| 227 | N-((1-(D-valyl)piperidin-4-yl)methyl)-5-cyclopropylisoxazole-3-carboxamide | 349.25 | 4.01 | |
| 228 | N-((1-(D-seryl)piperidin-4-yl)methyl)-5-cyclopropylisoxazole-3-carboxamide | 337.25 | 13.18 | |
| 229 | 5-cyclopropyl-N-((3-((1-methyl-1H-pyrazol-4-yl)carbamoyl)phenyl)(piperidin-4-yl)methyl)isoxazole-3-carboxamide | 449.4 | 5.5 | |
| 230 | N-(1-(1-(D-alanyl)piperidin-4-yl)propyl)-5-cyclopropylisoxazole-3-carboxamide | 349.3 | 1.93 | |
| 231 | N-(1-(1-(L-alanyl)piperidin-4-yl)propyl)-5-cyclopropylisoxazole-3-carboxamide | 349.25 | 0.9 | |
| 232 | 5-cyclopropyl-N-(2-oxo-1-(piperidin-4-yl)-2-(pyridin-2-ylamino)ethyl)isoxazole-3-carboxamide | 370.2 | 6.36 | |
| 233 | N-((3-((4-aminopyridin-2-yl)carbamoyl)phenyl)(piperidin-4-yl)methyl)-5-cyclopropylisoxazole-3-carboxamide | 461.3 | 5.1 | |
| 234 | N-((3-((6-cyanopyridin-3-yl)carbamoyl)phenyl)(piperidin-4-yl)methyl)-5-cyclopropylisoxazole-3-carboxamide | 471.4 | 5.42 | |
| 235 | N-(1-(1-(D-tyrosyl)piperidin-4-yl)ethyl)-5-cyclopropylisoxazole-3-carboxamide | 427.3 | 6.5 | |
| 236 | N-((1-(D-tyrosyl)piperidin-4-yl)methyl)-5-cyclopropylisoxazole-3-carboxamide | 413.25 | 14.3 | |
| 237 | 5-cyclopropyl-N-(1-(1-((S)-2-hydroxypropanoyl)piperidin-4-yl)ethyl)isoxazole-3-carboxamide | 336.2 | 25.65 | |
| 238 | (R)—N-(3-(3-aminobutanamido)-2,2-dimethylpropyl)-5-cyclopropylisoxazole-3-carboxamide | 323.1 | 4.43 | |
| 239 | (S)—N-(3-(3-aminobutanamido)-2,2-dimethylpropyl)-5-cyclopropylisoxazole-3-carboxamide | 323.1 | 6.35 | |

TABLE 1A-continued

| Cpd. No. | Chemical Name | LCMS M + H | SMYD3 Biochem IC$_{50}$ (μM)* | SMYD3 cell IC$_{50}$ (μM)* |
|---|---|---|---|---|
| 240 | N-(3-(3-aminopropanamido)-2,2-dimethylpropyl)-5-cyclopropylisoxazole-3-carboxamide | 309.1 | 12.72 | |
| 241 | N-(1-(1-(L-alanyl)piperidin-4-yl)-2-oxo-2-((pyridin-3-ylmethyl)amino)ethyl)-5-cyclopropylisoxazole-3-carboxamide | 455.3 | 15.58 | |
| 242 | N-(1-(1-(L-alanyl)piperidin-4-yl)-2-oxo-2-((pyridin-4-ylmethyl)amino)ethyl)-5-cyclopropylisoxazole-3-carboxamide | 455.25 | 22.31 | |
| 243 | N-(1-(1-(L-alanyl)piperidin-4-yl)-2-((2-hydroxybenzyl)amino)-2-oxoethyl)-5-cyclopropylisoxazole-3-carboxamide | 470.35 | 2.72 | |
| 244 | ethyl 2-(5-cyclopropylisoxazole-3-carboxamido)-2-(piperidin-4-yl)acetate | 322.2 | 20.57 | |
| 245 | N-((3-((2-aminopyridin-4-yl)carbamoyl)phenyl)(piperidin-4-yl)methyl)-5-cyclopropylisoxazole-3-carboxamide | 461.3 | 4.13 | |
| 246 | 5-cyclopropyl-N-((3-((6-(dimethylamino)pyridin-3-yl)carbamoyl)phenyl)(piperidin-4-yl)methyl)isoxazole-3-carboxamide | 489.4 | 5.95 | |
| 247 | N-(1-(1-((R)-3-aminobutanoyl)piperidin-4-yl)ethyl)-5-cyclopropylisoxazole-3-carboxamide | 349.25 | 0.62 | |
| 248 | N-(1-(1-((S)-3-aminobutanoyl)piperidin-4-yl)ethyl)-5-cyclopropylisoxazole-3-carboxamide | 349.25 | 1.47 | |
| 249 | (S)—N-(4-(2-aminopropanamido)butyl)-5-cyclopropylisoxazole-3-carboxamide | 295.15 | 14.62 | |
| 250 | (R)—N-(4-(2-aminopropanamido)butyl)-5-cyclopropylisoxazole-3-carboxamide | 295.15 | 36.02 | |
| 251 | N-(((S)-1-(D-alanyl)pyrrolidin-3-yl)methyl)-5-cyclopropylisoxazole-3-carboxamide | 307.15 | 30.73 | |
| 252 | N-(((S)-1-(L-alanyl)pyrrolidin-3-yl)methyl)-5-cyclopropylisoxazole-3-carboxamide | 307.05 | 21.36 | |
| 253 | N-(((R)-1-(D-alanyl)pyrrolidin-3-yl)methyl)-5-cyclopropylisoxazole-3-carboxamide | 307.15 | 32.34 | |
| 254 | N-(4-aminobutyl)-5-cyclopropylisoxazole-3-carboxamide | 224.1 | 41.44 | |
| 255 | (R)-5-cyclopropyl-N-(pyrrolidin-3-ylmethyl)isoxazole-3-carboxamide | 236.1 | 39.25 | |
| 256 | (S)-5-cyclopropyl-N-(pyrrolidin-3-ylmethyl)isoxazole-3-carboxamide | 236.1 | 37.48 | |
| 257 | 5-cyclopropyl-N-((3-(nicotinamido)phenyl)(piperidin-4-yl)methyl)isoxazole-3-carboxamide | 446.35 | 7.37 | |
| 258 | N-(1-(1-(L-alanyl)piperidin-4-yl)-2-oxo-2-(pyridin-3-ylamino)ethyl)-5-cyclopropylisoxazole-3-carboxamide | 441.3 | 11.47 | |
| 259 | N-(1-(1-(L-alanyl)piperidin-4-yl)-2-oxo-2-((pyridin-2-ylmethyl)amino)ethyl)-5-cyclopropylisoxazole-3-carboxamide | 455.3 | 11.04 | |
| 260 | N-(((R)-1-(L-alanyl)pyrrolidin-3-yl)methyl)-5-cyclopropylisoxazole-3-carboxamide | 307.15 | 15.5 | |
| 261 | N-(1-(1-(L-alanyl)piperidin-4-yl)-2-oxo-2-(pyridin-2-ylamino)ethyl)-5-cyclopropylisoxazole-3-carboxamide | 441.3 | 0.39 | |
| 262 | N-(1-(1-(L-alanyl)piperidin-4-yl)-2-oxo-2-(pyridin-4-ylamino)ethyl)-5-cyclopropylisoxazole-3-carboxamide | 441.35 | 8.5 | |
| 263 | 5-cyclopropyl-N-((4-hydroxypiperidin-4-yl)methyl)isoxazole-3-carboxamide | 266.15 | 14.89 | |
| 264 | ethyl 4-((5-cyclopropylisoxazole-3-carboxamido)methyl)piperidine-4-carboxylate | 322.1 | 43.56 | |
| 265 | 5-cyclopropyl-N-((4-methylpiperidin-4-yl)methyl)isoxazole-3-carboxamide | 264.15 | 41.74 | |
| 266 | 5-cyclopropyl-N-((-fluoropiperidin-4-yl)methyl)isoxazole-3-carboxamide | 268.05 | 18.82 | |

TABLE 1A-continued

| Cpd. No. | Chemical Name | LCMS M + H | SMYD3 Biochem IC$_{50}$ (μM)* | SMYD3 cell IC$_{50}$ (μM)* |
|---|---|---|---|---|
| 267 | N-((1-(L-alanyl)-4-hydroxypiperidin-4-yl)methyl)-5-cyclopropylisoxazole-3-carboxamide | 337.35 | 5.47 | |
| 268 | ethyl 1-(L-alanyl)-4-((5-cyclopropylisoxazole-3-carboxamido)methyl)piperidine-4-carboxylate | 393.15 | 3.22 | |
| 269 | N-((1-(L-alanyl)-4-methylpiperidin-4-yl)methyl)-5-cyclopropylisoxazole-3-carboxamide | 335.15 | 1.67 | |
| 270 | N-((1-(L-alanyl)-4-fluoropiperidin-4-yl)methyl)-5-cyclopropylisoxazole-3-carboxamide | 339.15 | 4.15 | |
| 271 | N-(1-(1-(L-alanyl)piperidin-4-yl)-2-hydroxyethyl)-5-cyclopropylisoxazole-3-carboxamide | 351.3 | 2.23 | |
| 272 | ethyl 2-(1-(L-tyrosyl)piperidin-4-yl)-2-(5-cyclopropylisoxazole-3-carboxamido)acetate | 485.3 | 7.39 | |
| 273 | N-(1-(1-(L-tyrosyl)piperidin-4-yl)-2-hydroxyethyl)-5-cyclopropylisoxazole-3-carboxamide | 465.25 (+Na) | 2.37 | |
| 274 | 5-cyclopropyl-N-(2-hydroxy-1-(piperidin-4-yl)ethyl)isoxazole-3-carboxamide | 280.1 | 5.93 | |
| 275 | N-(6-(3-aminopropanamido)spiro[3.3]heptan-2-yl)-5-cyclopropylisoxazole-3-carboxamide [trans isomer] | 333.2 | 1.8 | |
| 276 | 5-cyclopropyl-N-(2-methoxy-1-(piperidin-4-yl)ethyl)isoxazole-3-carboxamide | 294.1 | 11.92 | |
| 277 | 5-cyclopropyl-N-(2-phenoxy-1-(piperidin-4-yl)ethyl)isoxazole-3-carboxamide | 356.1 | 10.51 | |
| 278 | 5-cyclopropyl-N-(2-isopropoxy-1-(piperidin-4-yl)ethyl)isoxazole-3-carboxamide | 322.2 | 15.25 | |
| 279 | N-(6-((R)-3-aminobutanamido)spiro[3.3]heptan-2-yl)-5-cyclopropylisoxazole-3-carboxamide [trans isomer] | 347.5 | 1.25 | |
| 280 | N-((1r,4r)-4-aminocyclohexyl)-5-methylisoxazole-3-carboxamide | 224.2 | 18.75 | |
| 281 | N-(6-((R)-3-aminobutanamido)spiro[3.3]heptan-2-yl)-5-cyclopropylisoxazole-3-carboxamide [cis isomer] | 347.1 | 5.6 | |
| 282 | N-(1-(1-(L-alanyl)piperidin-4-yl)-2-methoxyethyl)-5-cyclopropylisoxazole-3-carboxamide | 387 (+Na) | 2.08 | |
| 283 | N-(1-(1-(L-alanyl)piperidin-4-yl)-2-phenoxyethyl)-5-cyclopropylisoxazole-3-carboxamide | 427.35 | 2.67 | |
| 284 | N-(1-(1-(L-alanyl)piperidin-4-yl)-2-isopropoxyethyl)-5-cyclopropylisoxazole-3-carboxamide | 393.35 | 1.19 | |
| 285 | N-(1-(1-(L-tyrosyl)piperidin-4-yl)-2-methoxyethyl)-5-cyclopropylisoxazole-3-carboxamide | 457.25 | 1.07 | |
| 286 | N-(1-(1-(L-tyrosyl)piperidin-4-yl)-2-phenoxyethyl)-5-cyclopropylisoxazole-3-carboxamide | 519.3 | 4.35 | |
| 287 | N-(1-(1-(L-tyrosyl)piperidin-4-yl)-2-isopropoxyethyl)-5-cyclopropylisoxazole-3-carboxamide | 485.3 | 5.2 | |
| 288 | N-(6-((S)-3-aminobutanamido)spiro[3.3]heptan-2-yl)-5-cyclopropylisoxazole-3-carboxamide [trans isomer] | 347.58 | 3.94 | |
| 290 | N-(6-((S)-3-aminobutanamido)spiro[3.3]heptan-2-yl)-5-cyclopropylisoxazole-3-carboxamide[cis isomer] | 347.6 | 1.82 | |

TABLE 1A-continued

| Cpd. No. | Chemical Name | LCMS M + H | SMYD3 Biochem IC$_{50}$ (μM)* | SMYD3 cell IC$_{50}$ (μM)* |
|---|---|---|---|---|
| 291 | N-(1-(3-aminopropanoyl)piperidin-3-yl)-5-cyclopropylisoxazole-3-carboxamide | 307 | 25.86 | |
| 292 | 5-cyclopropyl-N-((1r,4r)-4-((2-((2-hydroxyethyl)amino)ethyl)carbamoyl)cyclohexyl)isoxazole-3-carboxamide | 365.1 | 4.88 | |
| 293 | N-(6-((R)-3-aminobutanamido)bicyclo[3.3.1]nonan-2-yl)-5-cyclopropylisoxazole-3-carboxamide | 375.4 | 0.56 | |
| 294 | N-(6-((S)-3-aminobutanamido)bicyclo[3.3.1]nonan-2-yl)-5-cyclopropylisoxazole-3-carboxamide | 375.3 | 0.66 | |
| 295 | N-(6-(3-aminopropanamido)bicyclo[3.3.1]nonan-2-yl)-5-cyclopropylisoxazole-3-carboxamide | 361.4 | 1.2 | |
| 296 | 5-cyclopropyl-N-((1-oxo-2-(pyridin-3-yl)-1,2,3,4-tetrahydroisoquinolin-5-yl)(piperidin-4-yl)methyl)isoxazole-3-carboxamide | 472.63 | 36.37 | |
| 297 | N-(1-(4-aminobutanoyl)piperidin-3-yl)-5-cyclopropylisoxazole-3-carboxamide | 321.05 | 18.59 | |
| 298 | N-(1-(1-(3-aminopropanoyl)piperidin-3-yl)ethyl)-5-cyclopropylisoxazole-3-carboxamide | 335.1 | 37.71 | |
| 299 | 5-cyclopropyl-N-(1-(1-glycylpiperidin-3-yl)ethyl)isoxazole-3-carboxamide | 321.1 | 21.81 | |
| 300 | 5-cyclopropyl-N-(1-(piperidin-4-yl)butyl)isoxazole-3-carboxamide | 292.1 | 8.7 | |
| 301 | 5-cyclopropyl-N-(2-phenyl-1-(piperidin-4-yl)ethyl)isoxazole-3-carboxamide | 340.1 | 36.88 | |
| 302 | N-(1-(((1r,4r)-4-(2-aminoacetamido)cyclohexyl)amino)-1-oxopropan-2-yl)-5-cyclopropylisoxazole-3-carboxamide | 378.1 | 27.66 | |
| 303 | 5-cyclopropyl-N-(1-glycylpiperidin-3-yl)isoxazole-3-carboxamide | 293.1 | 32.81 | |
| 304 | N-(1-(1-(4-aminobutanoyl)piperidin-3-yl)ethyl)-5-cyclopropylisoxazole-3-carboxamide | 349.1 | 21.81 | |
| 305 | 5-cyclopropyl-N-(3-methyl-1-(piperidin-4-yl)butyl)isoxazole-3-carboxamide | 306.15 | 9.24 | |
| 306 | N-(3-(3-aminopropanamido)-2-methylpropyl)-5-cyclopropylisoxazole-3-carboxamide | 295.1 | 41.9 | |
| 307 | N-(1-(3-aminopropanamido)pentan-3-yl)-5-cyclopropylisoxazole-3-carboxamide | 309.1 | 21.73 | |
| 308 | N-(4-(3-aminopropanamido)-2-methylbutan-2-yl)-5-cyclopropylisoxazole-3-carboxamide | 309.1 | 22.05 | |
| 309 | (1r,4r)-4-(5-cyclopropylisoxazole-3-carboxamido)cyclohexyl 3-aminopropanoate | 322.1 | 0.71 | |
| 310 | N-(3-(4-aminobutanamido)cyclohexyl)-5-cyclopropylisoxazole-3-carboxamide | 335.1 | 27.03 | |
| 311 | (R)—N-((1-((3-aminobutanamido)methyl)cyclobutyl)methyl)-5-cyclopropylisoxazole-3-carboxamide | 335.05 | 10.15 | |
| 312 | N-((1r,4r)-4-((3-aminopropyl)carbamoyl)cyclohexyl)-5-cyclopropylisoxazole-3-carboxamide | 335.1 | 2.75 | |
| 313 | N-(4-((R)-3-aminobutanamido)-3,3-dimethylbutan-2-yl)-5-cyclopropylisoxazole-3-carboxamide | 337.1 | 0.8 | |
| 314 | N-(4-(3-aminopropanamido)butan-2-yl)-5-cyclopropylisoxazole-3-carboxamide | 295.05 | 27.98 | |
| 315 | N-(3-(3-aminopropanamido)cyclohexyl)-5-cyclopropylisoxazole-3-carboxamide | 321.1 | 20.78 | |
| 316 | N-((1r,4r)-4-(3-aminopropanamido)cyclohexyl)-5-methylisoxazole-3-carboxamide | 295.1 | 8.58 | |

TABLE 1A-continued

| Cpd. No. | Chemical Name | LCMS M + H | SMYD3 Biochem IC$_{50}$ (μM)* | SMYD3 cell IC$_{50}$ (μM)* |
|---|---|---|---|---|
| 317 | N-((1r,4r)-4-((2-aminoethyl)carbamoyl)cyclohexyl)-5-cyclopropylisoxazole-3-carboxamide | 321.1 | 3.67 | |
| 318 | N-(4-((S)-3-aminobutanamido)-3,3-dimethylbutan-2-yl)-5-cyclopropylisoxazole-3-carboxamide | 337.1 | 2.03 | |
| 319 | N-(1-((1r,4r)-4-aminocyclohexane-1-carboxamido)propan-2-yl)-5-cyclopropylisoxazole-3-carboxamide | 335.1 | 1.83 | |
| 320 | N-(1-(4-aminobutanamido)propan-2-yl)-5-cyclopropylisoxazole-3-carboxamide | 295.1 | 12.94 | |
| 321 | 5-cyclopropyl-N-(1-(piperidin-3-yl)ethyl)isoxazole-3-carboxamide | 264 | 26.78 | |
| 322 | N-(1-(4-aminobutanamido)butan-2-yl)-5-cyclopropylisoxazole-3-carboxamide | 309.1 | 17.38 | |
| 323 | N-(1-((1r,4r)-4-aminocyclohexane-1-carboxamido)butan-2-yl)-5-cyclopropylisoxazole-3-carboxamide | 349.1 | 1.3 | |
| 324 | N-(1-(3-aminopropanamido)butan-2-yl)-5-cyclopropylisoxazole-3-carboxamide | 295.1 | 19.68 | |
| 325 | N-(4-(3-aminopropanamido)phenyl)-5-cyclopropylisoxazole-3-carboxamide | 315 | 1.06 | |
| 326 | N-(4-(2-aminoacetamido)phenyl)-5-cyclopropylisoxazole-3-carboxamide | 301.3 | 4.24 | |
| 327 | N-(4-(4-aminobutanamido)phenyl)-5-cyclopropylisoxazole-3-carboxamide | 329.05 | 1.19 | |
| 328 | N-(4-((3-aminopropyl)amino)phenyl)-5-cyclopropylisoxazole-3-carboxamide | 301.05 | 3.74 | |
| 329 | N-(4-((2-aminoethyl)amino)phenyl)-5-cyclopropylisoxazole-3-carboxamide | 287.05 | 4.69 | |
| 330 | N-((1-((3-aminopropanamido)methyl)cyclopropyl)methyl)-5-cyclopropylisoxazole-3-carboxamide | 307.1 | 37.55 | |
| 331 | N-(4-(3-aminopropanamido)-1-hydroxybutan-2-yl)-5-cyclopropylisoxazole-3-carboxamide | 311.1 | 13.31 | |
| 332 | 5-cyclopropyl-N-(4-(piperidin-4-ylcarbamoyl)phenyl)isoxazole-3-carboxamide | 355.1 | 1.37 | |
| 333 | N-(4-(((1s,4s)-4-aminocyclohexyl)carbamoyl)phenyl)-5-cyclopropylisoxazole-3-carboxamide | 369.1 | 8.34 | |
| 334 | N-(4-(((1r,4r)-4-aminocyclohexyl)carbamoyl)phenyl)-5-cyclopropylisoxazole-3-carboxamide | 369.1 | 3.83 | |
| 335 | N-(3-(N-(2-aminoethyl)sulfamoyl)phenyl)-5-cyclopropylisoxazole-3-carboxamide | 351 | 10 | |
| 336 | N-(4-(N-(3-aminopropyl)sulfamoyl)phenyl)-5-cyclopropylisoxazole-3-carboxamide | 365.1 | 5.89 | |
| 337 | N-(3-((2-aminoethyl)carbamoyl)phenyl)-5-cyclopropylisoxazole-3-carboxamide | 315 | >10 | |
| 338 | N-(3-(N-(3-aminopropyl)sulfamoyl)phenyl)-5-cyclopropylisoxazole-3-carboxamide | 365.1 | >10 | |
| 339 | N-(4-(N-(2-aminoethyl)sulfamoyl)phenyl)-5-cyclopropylisoxazole-3-carboxamide | 351.1 | 7.68 | |
| 340 | (R)—N-(1-(1-(4-aminobutanoyl)piperidin-4-yl)ethyl)-5-cyclopropylisoxazole-3-carboxamide | 349.15 | 1.29 | |
| 341 | (S)—N-(1-(1-(4-aminobutanoyl)piperidin-4-yl)ethyl)-5-cyclopropylisoxazole-3-carboxamide | 349.15 | 3.54 | |
| 342 | N-(1-((R)-3-aminobutanamido)-2,2-dimethylpentan-3-yl)-5-cyclopropylisoxazole-3-carboxamide | 351.2 | 1.31 | |
| 343 | N-(1-((3-aminopropyl)sulfonyl)azetidin-3-yl)-5-cyclopropylisoxazole-3-carboxamide | 329 | >10 | >40 |

TABLE 1A-continued

| Cpd. No. | Chemical Name | LCMS M + H | SMYD3 Biochem IC$_{50}$ (μM)* | SMYD3 cell IC$_{50}$ (μM)* |
|---|---|---|---|---|
| 344 | (R)—N-(1-(1-((3-aminopropyl)sulfonyl)piperidin-4-yl)ethyl)-5-cyclopropylisoxazole-3-carboxamide | 385 | 5.03 | 23.42 |
| 345 | (S)—N-(1-(1-((3-aminopropyl)sulfonyl)piperidin-4-yl)ethyl)-5-cyclopropylisoxazole-3-carboxamide | 385 | >10 | >40 |
| 346 | (S)-5-cyclopropyl-N-(1-(1-(2-(piperidin-4-yl)acetyl)piperidin-4-yl)ethyl)isoxazole-3-carboxamide | 389.1 | >10 | |
| 347 | (R)-5-cyclopropyl-N-(1-(1-(2-(piperidin-4-yl)acetyl)piperidin-4-yl)ethyl)isoxazole-3-carboxamide | 389.2 | 2.6 | |
| 348 | N-((R)-1-(1-((1r,4R)-4-aminocyclohexane-1-carbonyl)piperidin-4-yl)ethyl)-5-cyclopropylisoxazole-3-carboxamide | 389.2 | 0.46 | 5.16 |
| 349 | N-((S)-1-(1-((1r,4S)-4-aminocyclohexane-1-carbonyl)piperidin-4-yl)ethyl)-5-cyclopropylisoxazole-3-carboxamide | 389.2 | 2.79 | >40 |
| 350 | N-(1-((1r,4r)-4-aminocyclohexane-1-carbonyl)azetidin-3-yl)-5-cyclopropylisoxazole-3-carboxamide | 333 | >10 | >40 |
| 351 | N-(3-((3-aminopropyl)carbamoyl)phenyl)-5-cyclopropylisoxazole-3-carboxamide | 329.1 | >10 | >40 |
| 352 | N-(1-(4-aminobutanoyl)azetidin-3-yl)-5-cyclopropylisoxazole-3-carboxamide | 293.05 | >10 | |
| 353 | N-(3-bromo-4-(piperidin-4-ylcarbamoyl)phenyl)-5-cyclopropylisoxazole-3-carboxamide | 433.1/ (433) | 1.44 | |
| 354 | 5-cyclopropyl-N-(2-methyl-4-(piperidin-4-ylcarbamoyl)phenyl)isoxazole-3-carboxamide | 369.2 | 2.17 | |
| 355 | N-(4-((3-aminopropyl)carbamoyl)-3-bromophenyl)-5-cyclopropylisoxazole-3-carboxamide | 407.05/ (409) | 1.77 | |
| 356 | N-(4-((3-aminopropyl)carbamoyl)-2-methylphenyl)-5-cyclopropylisoxazole-3-carboxamide | 343.1 | 3.52 | |
| 357 | N-(3-bromo-4-((piperidin-4-ylmethyl)carbamoyl)phenyl)-5-cyclopropylisoxazole-3-carboxamide | 447.1/ (449) | 7.25 | |
| 358 | N-(4-((3-aminocyclobutyl)carbamoyl)-3-bromophenyl)-5-cyclopropylisoxazole-3-carboxamide | 419/ (421.05) | 1.4 | |
| 359 | 5-cyclopropyl-N-(4-(N-(piperidin-4-ylmethyl)sulfamoyl)phenyl)isoxazole-3-carboxamide | 405 | 5.81 | >40 |
| 360 | 5-cyclopropyl-N-(3-methyl-4-(piperidin-4-ylcarbamoyl)phenyl)isoxazole-3-carboxamide | 369.15 | 1.41 | |
| 361 | N-(2-bromo-4-(piperidin-4-ylcarbamoyl)phenyl)-5-cyclopropylisoxazole-3-carboxamide | 433 (435) | 1.77 | >40 |
| 362 | N-(4-((4-aminocyclohexyl)carbamoyl)-3-methylphenyl)-5-cyclopropylisoxazole-3-carboxamide | 383.4 | 3.74 | |
| 363 | N-(4((4-aminocyclohexyl)carbamoyl)-2-bromophenyl)-5-cyclopropylisoxazole-3-carboxamide | 447/ (449.0) | 5.59 | >40 |
| 364 | N-(4-((2-aminoethyl)carbamoyl)-3-methylphenyl)-5-cyclopropylisoxazole-3-carboxamide | 329.1 | 6 | |
| 365 | N-(4((2-aminoethyl)carbamoyl)-3-bromophenyl)-5-cyclopropylisoxazole-3-carboxamide | 393.05/ (395) | 4.5 | >40 |
| 366 | N-(4-((2-aminoethyl)carbamoyl)-2-bromophenyl)-5-cyclopropylisoxazole-3-carboxamide | 393/ (395.1) | 3.7 | 38.81 |
| 367 | N-(4-((3-aminopropyl)carbamoyl)-3-methylphenyl)-5-cyclopropylisoxazole-3-carboxamide | 343.1 | 5.23 | |

TABLE 1A-continued

| Cpd. No. | Chemical Name | LCMS M + H | SMYD3 Biochem IC$_{50}$ (μM)* | SMYD3 cell IC$_{50}$ (μM)* |
|---|---|---|---|---|
| 368 | N-(3-bromo-4-(pyrrolidin-3-ylcarbamoyl)phenyl)-5-cyclopropylisoxazole-3-carboxamide | 419.1/ (421) | 3.06 | >40 |
| 369 | 5-cyclopropyl-N-(2-methyl-4-((piperidin-4-ylmethyl)carbamoyl)phenyl)isoxazole-3-carboxamide | 383.1 | 8.43 | |
| 370 | N-(4-((3-aminocyclobutyl)carbamoyl)-2-bromophenyl)-5-cyclopropylisoxazole-3-carboxamide | 419.1/ (421) | 2.74 | >40 |
| 371 | N-(4-((3-aminocyclohexyl)carbamoyl)-3-bromophenyl)-5-cyclopropylisoxazole-3-carboxamide | 447/ (449.15) | 9.11 | |
| 372 | N-(4-(N-(4-aminocyclohexyl)sulfamoyl)phenyl)-5-cyclopropylisoxazole-3-carboxamide | 405 | 2.57 | 21.71 |
| 373 | 5-cyclopropyl-N-(4-(N-(piperidin-4-yl)sulfamoyl)phenyl)isoxazole-3-carboxamide | 391 | 6.04 | 39.07 |
| 374 | 5-cyclopropyl-N-(4-(N-(pyrrolidin-3-yl)sulfamoyl)phenyl)isoxazole-3-carboxamide | 377.2 | 4.03 | >40 |
| 375 | N-(4-(N-(3-aminocyclobutyl)sulfamoyl)phenyl)-5-cyclopropylisoxazole-3-carboxamide | 377 | 4.72 | >40 |
| 376 | N-(1-((S)-3-aminobutanamido)-2,2-dimethylpentan-3-yl)-5-cyclopropylisoxazole-3-carboxamide | 351.1 | 1.17 | |
| 377 | N-(4-((4-aminocyclohexyl)carbamoyl)-3-bromophenyl)-5-cyclopropylisoxazole-3-carboxamide | 447.3/ (449) | 2.81 | |
| 378 | N-(4-((4-aminocyclohexyl)carbamoyl)-2-methylphenyl)-5-cyclopropylisoxazole-3-carboxamide | 383.3 | 6.36 | |
| 379 | N-(4-((2-aminoethyl)carbamoyl)-2-methylphenyl)-5-cyclopropylisoxazole-3-carboxamide | 329 | 2.76 | |
| 380 | N-(4-((3-aminopropyl)carbamoyl)-2-bromophenyl)-5-cyclopropylisoxazole-3-carboxamide | 406.9/ (409) | 1.74 | |
| 381 | 5-cyclopropyl-N-(2-methyl-4-(pyrrolidin-3-ylcarbamoyl)phenyl)isoxazole-3-carboxamide | 355 | 2 | |
| 382 | N-(2-bromo-4-(pyrrolidin-3-ylcarbamoyl)phenyl)-5-cyclopropylisoxazole-3-carboxamide | 419/ (420.9) | 2.95 | |
| 383 | N-(4-((3-aminocyclopentyl)carbamoyl)-3-bromophenyl)-5-cyclopropylisoxazole-3-carboxamide | 433.1/ (435) | 3.23 | |
| 384 | N-(4-((3-aminocyclopentyl)carbamoyl)-2-methylphenyl)-5-cyclopropylisoxazole-3-carboxamide | 369.15 | 5.54 | |
| 385 | N-(4-((3-aminocyclopentyl)carbamoyl)-2-bromophenyl)-5-cyclopropylisoxazole-3-carboxamide | 433.15/ (435) | 3.29 | |
| 386 | N-(4-((3-aminocyclohexyl)carbamoyl)-2-methylphenyl)-5-cyclopropylisoxazole-3-carboxamide | 383.1 | 8.02 | |
| 387 | N-(4-((3-aminocyclohexyl)carbamoyl)-2-bromophenyl)-5-cyclopropylisoxazole-3-carboxamide | 447/ (449.0) | 5.37 | |
| 388 | N-(4-(N-(3-aminocyclopentyl)sulfamoyl)phenyl)-5-cyclopropylisoxazole-3-carboxamide | 391 | 5.11 | >40 |
| 389 | N-(4-(N-(3-aminocyclohexyl)sulfamoyl)phenyl)-5-cyclopropylisoxazole-3-carboxamide | 405.15 | 3.79 | 38.09 |
| 390 | 5-cyclopropyl-N-(3-methyl-4-(pyrrolidin-3-ylcarbamoyl)phenyl)isoxazole-3-carboxamide | 355.1 | 4.45 | |

TABLE 1A-continued

| Cpd. No. | Chemical Name | LCMS M + H | SMYD3 Biochem IC$_{50}$ (μM)* | SMYD3 cell IC$_{50}$ (μM)* |
|---|---|---|---|---|
| 391 | 5-cyclopropyl-N-(3-methyl-4-((piperidin-4-ylmethyl)carbamoyl)phenyl)isoxazole-3-carboxamide | 383.1 | >10 | |
| 392 | N-(2-bromo-4-((piperidin-4-ylmethyl)carbamoyl)phenyl)-5-cyclopropylisoxazole-3-carboxamide | 447/ (449.0) | 4.78 | |
| 393 | N-(4-((3-aminocyclohexyl)carbamoyl)-3-methylphenyl)-5-cyclopropylisoxazole-3-carboxamide | 383.1 | >10 | |
| 394 | N-((1s,4s)-4-(N-(2-aminoethyl)sulfamoyl)cyclohexyl)-5-cyclopropylisoxazole-3-carboxamide | 357 | 2.12 | |
| 395 | N-(4-((3-aminocyclopentyl)carbamoyl)-3-methylphenyl)-5-cyclopropylisoxazole-3-carboxamide | 369 | 4.61 | |
| 396 | N-(4-((3-aminocyclobutyl)carbamoyl)-2-methylphenyl)-5-cyclopropylisoxazole-3-carboxamide | 355.2 | 3.29 | |
| 397 | N-(3-((3-aminopropyl)sulfonamido)-2,2-dimethylpropyl)-5-cyclopropylisoxazole-3-carboxamide | 359.1 | 2.16 | |
| 398 | 5-cyclopropyl-N-(2,2-dimethyl-3-(piperidine-4-sulfonamido)propyl)isoxazole-3-carboxamide | 385.15 | 1.74 | |
| 399 | N-(4-((3-aminocyclobutyl)carbamoyl)-3-methylphenyl)-5-cyclopropylisoxazole-3-carboxamide | 355 | 4.56 | |

*IC$_{50}$ values are an average of n = 1 to n = 50

Definitions

For the purpose of the present disclosure, the term "alkyl" as used by itself or as part of another group refers to a straight- or branched-chain aliphatic hydrocarbon containing one to twelve carbon atoms (i.e., $C_{1-12}$ alkyl) or the number of carbon atoms designated (i.e., a $C_1$ alkyl such as methyl, a $C_2$ alkyl such as ethyl, a $C_3$ alkyl such as propyl or isopropyl, etc.). In one embodiment, the alkyl group is chosen from a straight chain $C_{1-10}$ alkyl group. In another embodiment, the alkyl group is chosen from a branched chain $C_{3-10}$ alkyl group. In another embodiment, the alkyl group is chosen from a straight chain $C_{1-6}$ alkyl group. In another embodiment, the alkyl group is chosen from a branched chain $C_{3-6}$ alkyl group. In another embodiment, the alkyl group is chosen from a straight chain $C_{1-4}$ alkyl group. In another embodiment, the alkyl group is chosen from a branched chain $C_{3-4}$ alkyl group. In another embodiment, the alkyl group is chosen from a straight or branched chain $C_{3-4}$ alkyl group. In another embodiment, the alkyl group is partially or completely deuterated, i.e., one or more hydrogen atoms of the alkyl group are replaced with deuterium atoms. Non-limiting exemplary $C_{1-10}$ alkyl groups include methyl (including —CD$_3$), ethyl, propyl, isopropyl, butyl, sec-butyl, tert-butyl, iso-butyl, 3-pentyl, hexyl, heptyl, octyl, nonyl, and decyl. Non-limiting exemplary $C_{1-4}$ alkyl groups include methyl, ethyl, propyl, isopropyl, butyl, sec-butyl, tert-butyl, and iso-butyl. Non-limiting exemplary $C_{1-4}$ groups include methyl, ethyl, propyl, isopropyl, and tert-butyl.

For the purpose of the present disclosure, the term "optionally substituted alkyl" as used by itself or as part of another group means that the alkyl as defined above is either unsubstituted or substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, ureido, guanidino, carboxy, alkoxycarbonyl, and carboxyalkyl. In one embodiment, the alkyl is a $C_{1-6}$ alkyl. In another embodiment, the alkyl is a $C_{1-4}$ alkyl. In one embodiment, the optionally substituted alkyl is substituted with two substituents. In another embodiment, the optionally substituted alkyl is substituted with one substituent. Non-limiting exemplary optionally substituted alkyl groups include —CH$_2$CH$_2$NO$_2$, —CH$_2$CH$_2$CO$_2$H, —CH$_2$CH$_2$SO$_2$CH$_3$, —CH$_2$CH$_2$COPh, and —CH$_2$C$_6$H$_{11}$.

For the purpose of the present disclosure, the term "alkylenyl" as used herein by itself or part of another group refers to a divalent form of an alkyl group as defined above. In one embodiment, the alkylenyl is a divalent form of a $C_{1-6}$ alkyl. In one embodiment, the alkylenyl is a divalent form of a $C_{1-4}$ alkyl. Non-limiting exemplary alkylenyl groups include —CH$_2$CH$_2$—, —CH$_2$CH$_2$CH$_2$—, —CH$_2$CH(CH$_3$)CH$_2$—, and —CH$_2$C(CH$_3$)$_2$CH$_2$—.

For the purpose of the present disclosure, the term "cycloalkyl" as used by itself or as part of another group refers to saturated and partially unsaturated (containing one or two double bonds) cyclic aliphatic hydrocarbons containing one to three rings having from three to twelve carbon atoms (i.e., $C_{3-12}$ cycloalkyl) or the number of carbons designated. In one embodiment, the cycloalkyl group has two rings. In one embodiment, the cycloalkyl group has one ring. In another embodiment, the cycloalkyl group is chosen from a $C_{3-8}$ cycloalkyl group. In another embodiment, the cycloalkyl group is chosen from a $C_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, spiro[3.3]heptane, and bicyclo[3.3.1]nonane.

For the purpose of the present disclosure, the term "optionally substituted cycloalkyl" as used by itself or as part of another group means that the cycloalkyl as defined above is either unsubstituted or substituted with one, two, or three substituents independently chosen from halo, nitro, cyano, hydroxy, amino, alkylamino, dialkylamino, cycloalkylamino, haloalkyl, hydroxyalkyl, alkoxy, haloalkoxy, aryloxy, aralkyl, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, or (heteroaryl)alkyl. In one embodiment, the optionally substituted cycloalkyl is substituted with two substituents. In another embodiment, the optionally substituted cycloalkyl is substituted with one substituent. In one embodiment, the optionally substituted cycloalkyl is an (amino)cycloalkyl. For the purpose of the present disclosure, the term "(amino)cycloalkyl" as used by itself or as part of another group means that the optionally substituted cycloalkyl as defined above is substituted with one amino or alkylamino group, and optionally one or two additional substituents. In one embodiment, the optionally substituted cycloalkyl is an (amino)cyclohexyl. For the purpose of the present disclosure, the term "(amino)cyclohexyl" as used by itself or as part of another group means that the optionally substituted cycloalkyl as defined above is a cyclohexyl group substituted with one amino or alkylamino group, and optionally one or two additional substituents. Non-limiting exemplary optionally substituted cycloalkyl groups include:

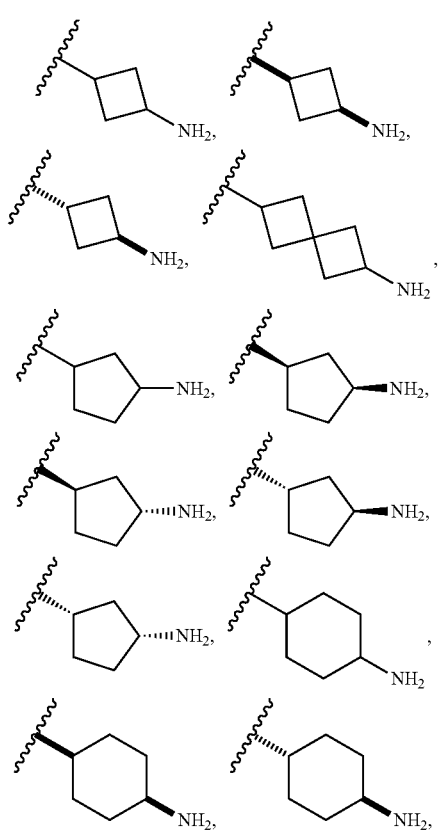

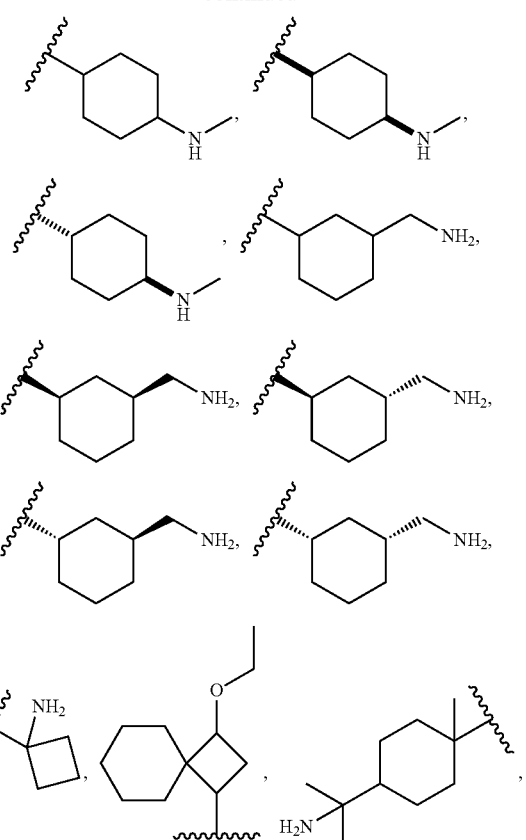

Non-limiting exemplary (amino)cycloalkyl groups include:

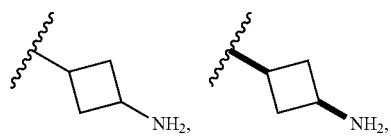

-continued

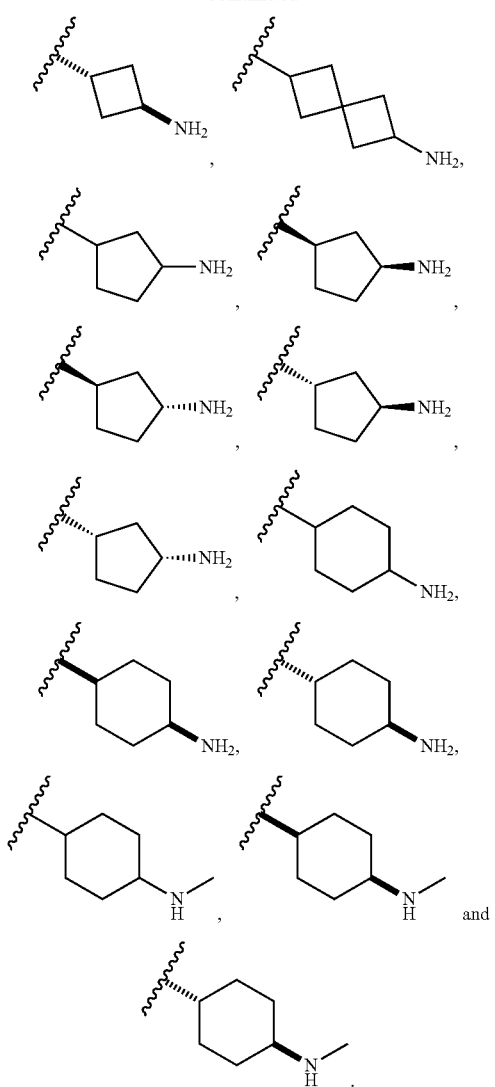

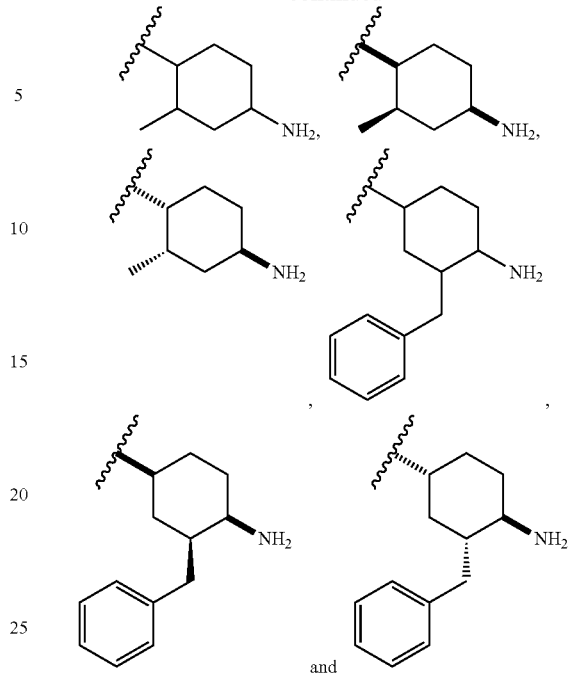

Non-limiting exemplary (amino)cyclohexyl groups include:

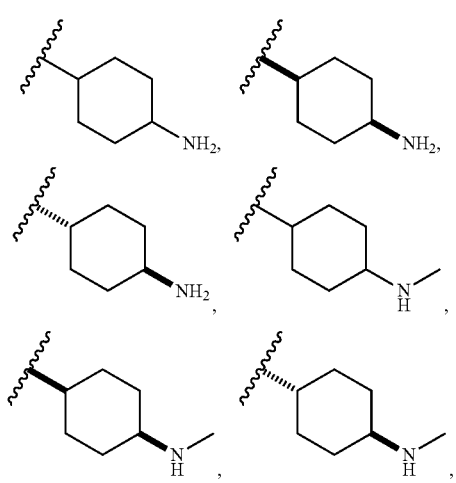

For the purpose of the present disclosure, the term "optionally substituted cyclohexyl" as used by itself or as part of another group means that the optionally substituted cycloalkyl as defined above is an optionally substituted cyclohexyl group.

For the purpose of the present disclosure, the term "cycloalkylenyl" as used herein by itself or part of another group refers to a divalent form of an optionally substituted cycloalkyl group as defined above. In one embodiment, the cycloalkylenyl is a "cyclohexylenyl." The term "cyclohexylenyl" as used herein by itself or part of another group refers to a divalent form of an optionally substituted cyclohexyl group.

Non-limiting exemplary cycloalkylenyl groups include:

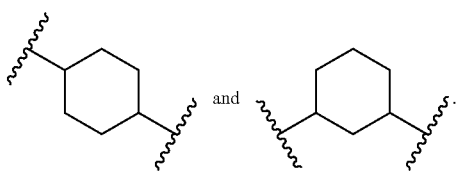 [SMILES: *C1CCC(*)CC1 ; *C1CCCC(*)C1]

For the purpose of the present disclosure, the term "1,4-cyclohexylenyl" as used herein by itself or part of another group refers to a cyclohexylenyl as defined above wherein the radicals are in the 1 and 4 positions of the cyclohexyl ring. Non-limiting exemplary 1,4-cyclohexylenyl groups include:

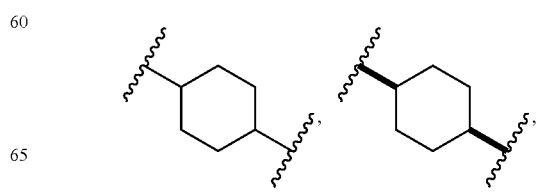

-continued

For the purpose of the present disclosure, the term "(cycloalkylenyl)alkyl" as used herein by itself or part of another group refers to an alkyl group substituted with a divalent form of an optionally substituted cycloalkyl group. In one embodiment, the cycloalkylenyl is a divalent form of optionally substituted cyclohexyl. In one embodiment, the alkyl is $C_{1-4}$ alkyl. Non-limiting exemplary (cycloalkylenyl)alkyl groups include:

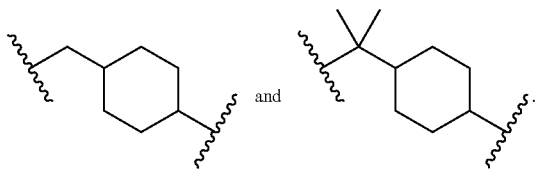 [SMILES: *CC1CCC(*)CC1 ; *C1CCC(C(*)(C)C)CC1]

For the purpose of the present disclosure, the term "cycloalkenyl" as used by itself or part of another group refers to a partially unsaturated cycloalkyl group as defined above. In one embodiment, the cycloalkenyl has one carbon-to-carbon double bond. In another embodiment, the cycloalkenyl group is chosen from a $C_{4-8}$ cycloalkenyl group. Exemplary cycloalkenyl groups include cyclopentenyl and cyclohexenyl.

For the purpose of the present disclosure, the term "optionally substituted cycloalkenyl" as used by itself or as part of another group means that the cycloalkenyl as defined above is either unsubstituted or substituted with one, two, or three substituents independently chosen from halo, nitro, cyano, hydroxy, amino, alkylamino, dialkylamino, haloalkyl, monohydroxyalkyl, dihydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. In one embodiment, the optionally substituted cycloalkenyl is substituted with two substituents. In another embodiment, the optionally substituted cycloalkenyl is substituted with one substituent. In another embodiment, the cycloalkenyl is unsubstituted.

For the purpose of the present disclosure, the term "alkenyl" as used by itself or as part of another group refers to an alkyl group as defined above containing one, two or three carbon-to-carbon double bonds. In one embodiment, the alkenyl group is chosen from a $C_{2-6}$ alkenyl group. In another embodiment, the alkenyl group is chosen from a $C_{2-4}$ alkenyl group. Non-limiting exemplary alkenyl groups include ethenyl, propenyl, isopropenyl, butenyl, sec-butenyl, pentenyl, and hexenyl.

For the purpose of the present disclosure, the term "optionally substituted alkenyl" as used herein by itself or as part of another group means the alkenyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, optionally substituted cycloalkyl, alkenyl, alkynyl, optionally substituted aryl, optionally substituted heteroaryl, or optionally substituted heterocyclo.

For the purpose of the present disclosure, the term "alkynyl" as used by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a $C_{2-6}$ alkynyl group. In another embodiment, the alkynyl group is chosen from a $C_{2-4}$ alkynyl group. Non-limiting exemplary alkynyl groups include ethynyl, propynyl, butynyl, 2-butynyl, pentynyl, and hexynyl groups.

For the purpose of the present disclosure, the term "optionally substituted alkynyl" as used herein by itself or as part of another group means the alkynyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, or heterocyclo.

For the purpose of the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is chosen from a $C_{1-4}$ haloalkyl group. Non-limiting exemplary haloalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

For the purpose of the present disclosure, the term "fluoroalkyl" as used by itself or as part of another group refers to an alkyl group substituted by one or more fluorine atoms. In one embodiment, the alkyl group is substituted by one, two, or three fluorine atoms. In another embodiment, the fluoroalkyl group is chosen from a $C_{1-4}$ fluoroalkyl group. Non-limiting exemplary fluoroalkyl groups include fluoromethyl, difluoromethyl, trifluoromethyl, pentafluoroethyl, 1,1-difluoroethyl, 2,2-difluoroethyl, 2,2,2-trifluoroethyl, 3,3,3-trifluoropropyl, and 4,4,4-trifluorobutyl.

For the purpose of the present disclosure, the term "hydroxyalkyl" as used by itself or as part of another group refers to an alkyl group substituted with one or more, e.g., one, two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups. In another embodiment, the hydroxyalkyl group is chosen from a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

For the purpose of the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is chosen from a $C_{1-4}$ alkoxy group. In another embodiment, the alkoxy group is chosen from a $C_{1-4}$ alkyl attached to a terminal oxygen atom, e.g., methoxy, ethoxy, tert-butoxy, —OCH$_2$C≡CH, —OCH$_2$C≡CCH$_3$, and —OCH$_2$CH$_2$CH$_2$C≡CH.

For the purpose of the present disclosure, the term "alkylthio" as used by itself or as part of another group refers to a sulfur atom substituted by an optionally substituted alkyl group. In one embodiment, the alkylthio group is chosen from a $C_{1-4}$ alkylthio group. Non-limiting exemplary alkylthio groups include —SCH$_3$, and —SCH$_2$CH$_3$.

For the purpose of the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, pentyloxymethyl, —CH$_2$OCH$_2$C≡CH and —CH$_2$OCH$_2$CH$_2$CH$_2$C≡CH.

For the purpose of the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

For the purpose of the present disclosure, the term "heteroalkyl" as used by itself or part of another group refers to a stable straight or branched chain hydrocarbon radical containing 1 to 10 carbon atoms and at least two heteroatoms, which can be the same or different, selected from O, N, or S, wherein: 1) the nitrogen atom(s) and sulfur atom(s) can optionally be oxidized; and/or 2) the nitrogen atom(s) can optionally be quaternized. The heteroatoms can be placed at any interior position of the heteroalkyl group or at a position at which the heteroalkyl group is attached to the remainder of the molecule. In one embodiment, the heteroalkyl group contains two oxygen atoms. In one embodiment, the heteroalkyl contains one oxygen and one nitrogen atom, e.g., a (hydroxyalkylamino)alkyl group, e.g., —CH$_2$N(CH$_3$)CH$_2$CH$_2$CH$_2$OH. In one embodiment, the heteroalkyl contains two nitrogen atoms. Non-limiting exemplary heteroalkyl groups include —CH$_2$OCH$_2$CH$_2$OCH$_3$, —OCH$_2$CH$_2$OCH$_2$CH$_2$OCH$_3$, —CH—$_2$NHCH$_2$CH$_2$OCH$_2$, —OCH$_2$CH$_2$NH$_2$, —NHCH$_2$CH$_2$N(H)CH$_3$, —NHCH$_2$CH$_2$OCH$_3$, —CH$_2$OCH$_2$CH$_2$NH$_2$, —CH$_2$OCH$_2$CH$_2$N(H)CH$_2$CH$_3$, and —OCH$_2$CH$_2$OCH$_3$.

For the purpose of the present disclosure, the term "aryl" as used by itself or as part of another group refers to a monocyclic or bicyclic aromatic ring system having from six to fourteen carbon atoms (i.e., $C_{6-14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl or naphthyl. In one embodiment, the aryl group is phenyl.

For the purpose of the present disclosure, the term "optionally substituted aryl" as used herein by itself or as part of another group means that the aryl as defined above is either unsubstituted or substituted with one to five substituents independently selected from the group consisting of halo, nitro, cyano, hydroxy, amino, alkylamino, dialkylamino, haloalkyl, hydroxyalkyl, alkoxy, haloalkoxy, aryloxy, heteroaryloxy, aralkyl aralkyloxy, (aralkyloxy)alkyl, alkylthio, carboxamido, sulfonamido, alkylcarbonyl, arylcarbonyl, alkylsulfonyl, arylsulfonyl, ureido, guanidino, carboxy, carboxyalkyl, heteroalkyl optionally substituted alkyl, optionally substituted cycloalkyl, alkenyl, alkynyl, optionally substituted aryl, optionally substituted heteroaryl, optionally substituted heterocyclo, ($C_{1-4}$ haloalkoxy)alkyl, alkoxyalkyl, (amino)alkyl, hydroxyalkylamino, (alkylamino)alkyl, (dialkylamino)alkyl, (cyano)alkyl, (carboxamido) alkyl, mercaptoalkyl, (heterocyclo)alkyl, (cycloalkylamino) alkyl, (hydroxyalkylamino)alkyl, (amino)(heteroaryl)alkyl, (heterocycloamino)alkyl (amino)(hydroxy)alkyl, (heteroaryl)alkyl, —N(R$^{43}$)(R$^{44}$), —CH$_2$N(H)C(=O)—R$^{45}$, and —N(H)C(=O)—R$^{45}$, wherein R$^{43}$ is hydrogen, $C_{1-4}$ alkyl, optionally substituted aryl, or optionally substituted heteroaryl; R$^{44}$ is alkoxyalkyl, (heterocyclo)alkyl, (amino) alkyl, (alkylamino)alkyl, or (dialkylamino)alkyl; and R$^{45}$ is alkyl, alkoxyalkyl, (heterocyclo)alkyl, (amino)alkyl, (alkylamino)alkyl, (dialkylamino)alkyl, optionally substituted aryl, optionally substituted heteroaryl, aralkyl, or (heteroaryl)alkyl In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. In another embodiment, the optionally substituted phenyl has at least one amino, alkylamino, dialkylamino, (amino) alkyl, (alkylamino)alkyl, (dialkylamino)alkyl, (amino)(heteroaryl)alkyl, or (amino)(hydroxy)alkyl substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, 3-chloro-4-fluorophenyl, and 2-phenylpropan-2-amine. The term optionally substituted aryl is meant to include aryl groups having fused optionally substituted cycloalkyl and fused optionally substituted heterocyclo rings. Examples include:

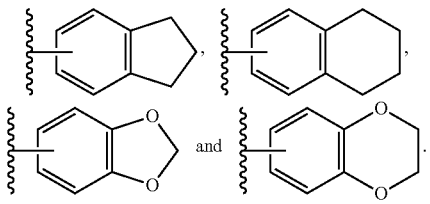

For the purpose of the present disclosure, the term "arylenyl" as used herein by itself or part of another group refers to a divalent form of an optionally substituted aryl group as defined above. In one embodiment, the arylenyl is a divalent form of an optionally substituted phenyl. In one embodiment, the arylenyl is a divalent form of phenyl. Non-limiting exemplary alkylenyl groups include:

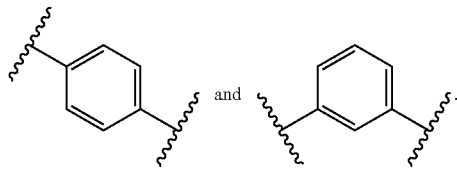 [SMILES: *c1ccc(*)cc1 ; *c1cccc(*)c1]

For the purpose of the present disclosure, the term "aryloxy" as used by itself or as part of another group refers to an optionally substituted aryl attached to a terminal oxygen atom. A non-limiting exemplary aryloxy group is PhO—.

For the purpose of the present disclosure, the term "heteroaryloxy" as used by itself or as part of another group refers to an optionally substituted heteroaryl attached to a terminal oxygen atom.

For the purpose of the present disclosure, the term "aralkyloxy" or "arylalkyloxy" as used by itself or as part of another group refers to an aralkyl group attached to a terminal oxygen atom. A non-limiting exemplary aralkyloxy group is PhCH$_2$O—.

For the purpose of the present disclosure, the term "(aralkyloxy)alkyl" as used by itself or as part of another group refers to an alkyl group substituted with an aralkyloxy group. In one embodiment, the alkyl is a $C_{1-4}$ alkyl. Non-limiting exemplary "(aralkyloxy)alkyl" groups include —CH$_2$OCH$_2$(3-F-Ph) and —CH$_2$OCH$_2$CH$_2$CH$_2$(2-OMe-Ph).

For the purpose of the present disclosure, the term "heteroaryl" or "heteroaromatic" refers to monocyclic and bicyclic aromatic ring systems having 5 to 14 ring members (i.e., a 5- to 14-membered heteroaryl) and 1, 2, 3, or 4 heteroatoms independently chosen from oxygen, nitrogen or sulfur. In one embodiment, the heteroaryl has three heteroatoms. In another embodiment, the heteroaryl has two heteroatoms. In another embodiment, the heteroaryl has one heteroatom. In one embodiment, the heteroaryl has 5 ring atoms, e.g., thienyl. In another embodiment, the heteroaryl has 6 ring atoms, e.g., pyridyl. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl) and isoxazolyl (e.g., isoxazol-3-yl, isoxazol-4-yl, and isoxazol-5-yl). The term "heteroaryl" is also meant to include possible N-oxides. Exemplary N-oxides include pyridyl N-oxide.

For the purpose of the present disclosure, the term "optionally substituted heteroaryl" as used by itself or as part of another group means that the heteroaryl as defined above is either unsubstituted or substituted with one to four substituents, e.g., one or two substituents, independently chosen from halo, nitro, cyano, hydroxy, amino, alkylamino, dialkylamino, haloalkyl, hydroxyalkyl, alkoxy, haloalkoxy, aralkyl, aryloxy, aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, (heteroaryl)alkyl, —N(R$^{43}$)(R$^{44}$), or —N(H)C(=O)—R$^{45}$, wherein R$^{43}$ is hydrogen or $C_{1-4}$ alkyl; R$^{44}$ is alkoxyalkyl, (heterocyclo)alkyl, (amino)alkyl, (alkylamino)alkyl, or (dialkylamino)alkyl; and R$^{45}$ is alkyl, optionally substituted aryl, or optionally substituted heteroaryl. In one embodiment, the optionally substituted heteroaryl has one substituent. In one embodiment, the substituent is amino, alkylamino, dialkylamino, (amino)alkyl, hydroxyalkylamino, (alkylamino)alkyl, (dialkylamino)alkyl, (heterocyclo)alkyl, —N(R$^{43}$)(R$^{44}$), or —N(H)C(=O)—R$^{45}$. In one embodiment, the substituent is aralkyl or (heteroaryl)alkyl. Examples include:

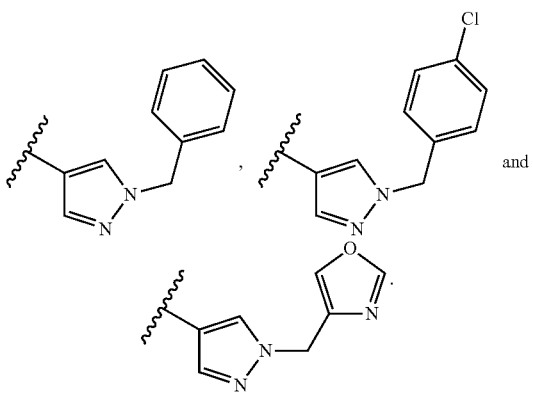

In one embodiment, the optionally substituted heteroaryl is an optionally substituted pyridyl, i.e., 2-, 3-, or 4-pyridyl. Any available carbon or nitrogen atom can be substituted. The term optionally substituted heteroaryl is meant to include heteroaryl groups having fused optionally substituted cycloalkyl and fused optionally substituted heterocyclo rings. Examples include:

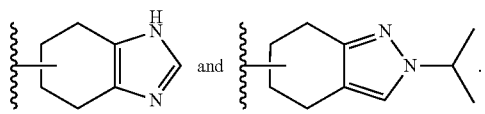

For the purpose of the present disclosure, the term "heteroarylenyl" as used herein by itself or part of another group refers to a divalent form of an optionally substituted heteroaryl group as defined above. In one embodiment, the heteroarylenyl is a divalent form of an optionally substituted pyridyl. Non-limiting exemplary heteroarylenyl groups include:

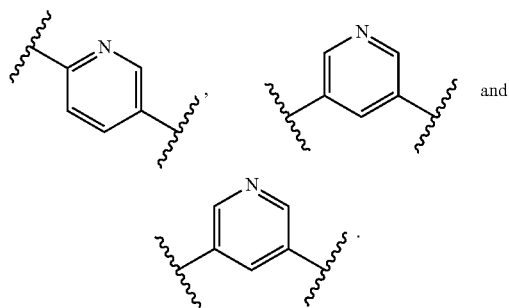

For the purpose of the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members (i.e., a 3- to 14-membered heterocyclo) and at least one heteroatom. Each heteroatom is independently selected from the group consisting of oxygen, sulfur, including sulfoxide and sulfone, and/or nitrogen atoms, which can be quaternized. The term "heterocyclo" is meant to include cyclic ureido groups such as imidazolidinyl-2-one, cyclic amide groups such as β-lactam, γ-lactam, δ-lactam and ε-lactam, and cyclic carbamate groups such as oxazolidinyl-2-one. The term "heterocyclo" is also meant to include groups having fused optionally substituted aryl groups, e.g., indolinyl, indolinyl-2-one, benzo[d]oxazolyl-2(3H)-one. In one embodiment, the heterocyclo group is chosen from a 4-, 5-, 6-, 7- or 8-membered cyclic group containing one ring and one or two oxygen and/or nitrogen atoms. In one embodiment, the heterocyclo group is chosen from a 5- or 6-membered cyclic group containing one ring and one or two nitrogen atoms. In one embodiment, the heterocyclo group is chosen from a 8-, 9-, 10-, 11-, or 12-membered cyclic group containing two rings and one or two nitrogen atoms. The heterocyclo can be optionally linked to the rest of the molecule through a carbon or nitrogen atom. Non-limiting exemplary heterocyclo groups include 2-oxopyrrolidin-3-yl, 2-imidazolidinone, piperidinyl, morpholinyl, piperazinyl, pyrrolidinyl, 8-azabicyclo[3.2.1]octane (nortropane), 6-azaspiro[2.5]octane, 6-azaspiro[3.4]octane, indolinyl, indolinyl-2-one, 1,3-dihydro-2H-benzo[d]imidazol-2-one For the purpose of the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyl aralkyloxy, alkylthio, carboxamido, sulfonamido, alkylcarbonyl, arylcarbonyl, alkylsulfonyl, arylsulfonyl, ureido, guanidino, carboxy, carboxyalkyl, alkyl, cycloalkyl, alkenyl, alkynyl, aryl, heteroaryl, heterocyclo, alkoxyalkyl, (amino)alkyl, hydroxyalkylamino, (alkylamino)alkyl, (dialkylamino)alkyl, (cyano)alkyl, (carboxamido)alkyl, mercaptoalkyl, (heterocyclo)alkyl, and (heteroaryl)alkyl. Substitution may occur on any available carbon or nitrogen atom, and may form a spirocycle. In one embodiment, the optionally substituted heterocyclo is substituted with at least one amino, alkylamino, or dialkylamino group. Non-limiting exemplary optionally substituted heterocyclo groups include:

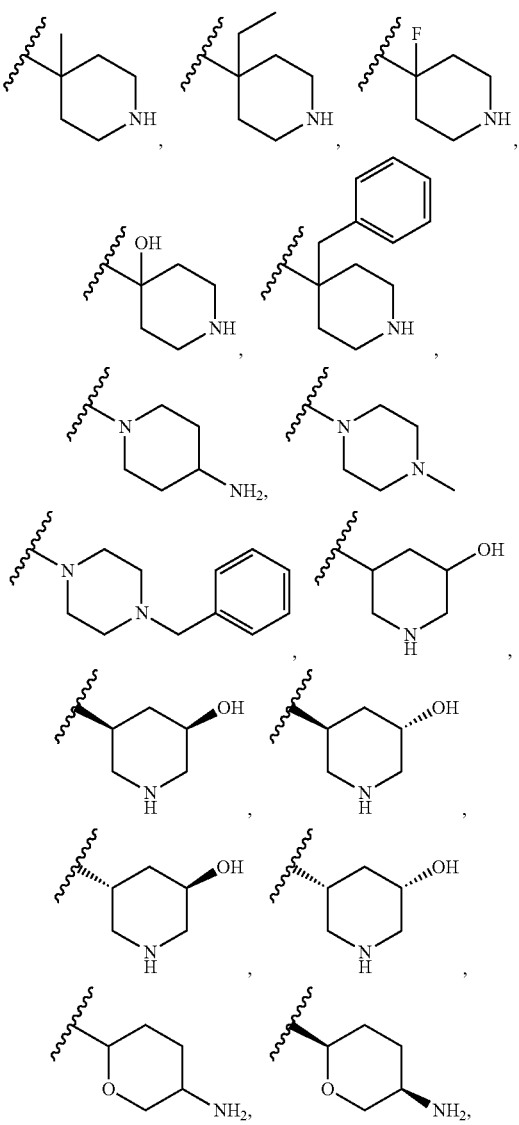

-continued

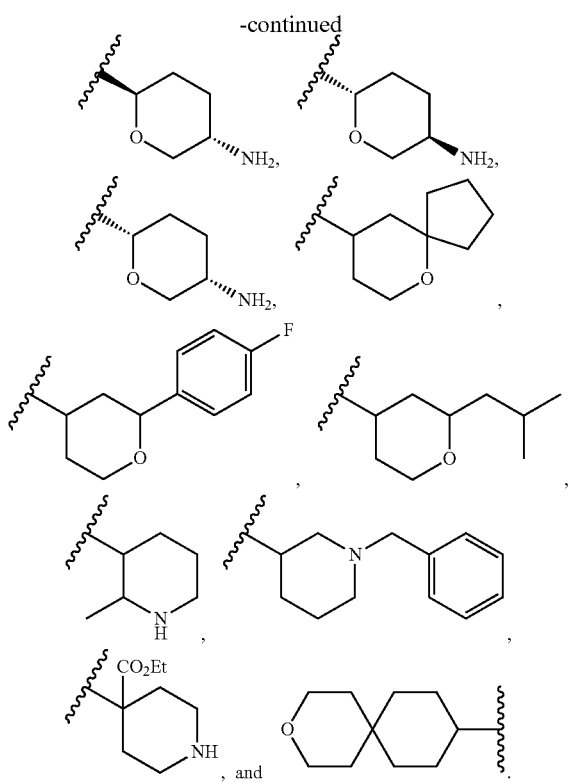

For the purpose of the present disclosure, the term "heterocyclenyl" as used herein by itself or part of another group refers to a divalent form of an optionally substituted heterocyclo group as defined above. In one embodiment, the heterocyclenyl is a divalent form of an optionally substituted azetidine. In one embodiment, the heterocyclenyl is a divalent form of an optionally substituted piperidinyl. Non-limiting exemplary heterocyclenyl groups include:

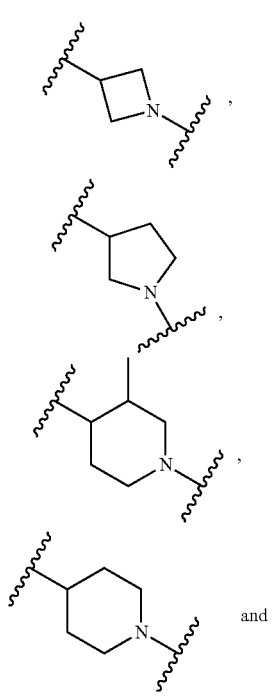

-continued

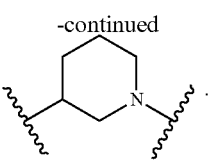

For the purpose of the present disclosure, the term "optionally substituted pyrrolidinyl" as used by itself or as part of another group means that the optionally substituted heterocyclo as defined above is an optionally substituted pyrrolidinyl group.

For the purpose of the present disclosure, the term "optionally substituted pyrrolidinenyl" as used herein by itself or part of another group refers to a divalent form of an optionally substituted pyrrolidinyl group as defined above. Non-limiting exemplary optionally substituted pyrrolidinenyl groups include:

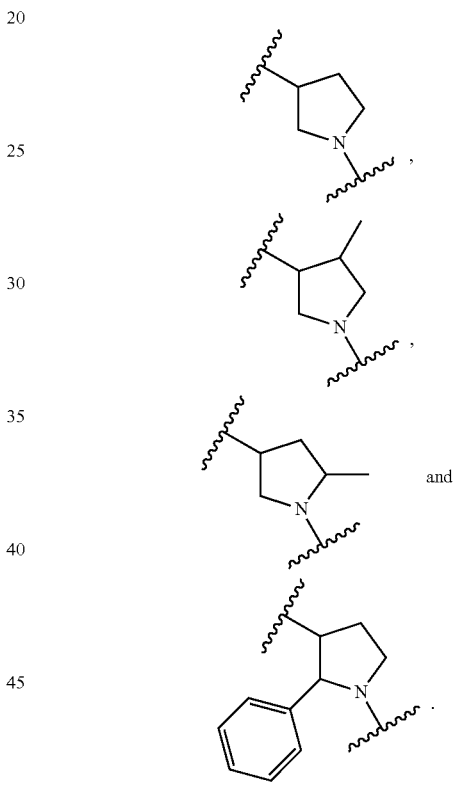

For the purpose of the present disclosure, the term "optionally substituted, optionally bridged piperidinenyl" as used by itself or as part of another group refers to a divalent form having the following structure:

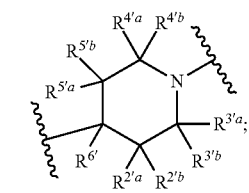

wherein:
$R^{2'a}$, $R^{2'b}$, $R^{3'a}$, $R^{3'b}$, $R^{4'a}$, $R^{4'b}$, $R^{5'a}$, and $R^{5'b}$ are each independently selected from the group consisting of hydrogen, halo, $C_{1-6}$ alkyl, $C_{3-12}$ cycloalkyl, haloalkyl, hydroxyalkyl, optionally substituted $C_{6-14}$ aryl, aralkyl, and alkoxycarbonyl; or $R^{2'a}$ and $R^{2'b}$ taken together with the carbon atom to which they are attached form a $C_{3-6}$ cycloalkyl; and $R^{3'a}$, $R^{3'b}$, $R^{4'a}$, $R^{4'b}$, $R^{5'a}$, and $R^{5'b}$ are each independently selected from the group consisting of hydrogen, halo, and $C_{1-4}$ alkyl; or $R^{3'a}$ and $R^{3'b}$ taken together with the carbon atom to which they are attached form a $C_{3-6}$ cycloalkyl; and $R^{2'a}$, $R^{2'b}$, $R^{4'a}$, $R^{4'b}$, $R^{5'a}$, and $R^{5'b}$ are each independently selected from the group consisting of hydrogen, halo, and $C_{1-4}$ alkyl; or $R^{4'a}$ and $R^{4'b}$ taken together with the carbon atom to which they are attached form a $C_{3-6}$ cycloalkyl; and $R^{2'a}$, $R^{2'b}$, $R^{3'a}$, $R^{3'b}$, $R^{5'a}$, and $R^{5'b}$ are each independently selected from the group consisting of hydrogen, halo, and $C_{1-4}$ alkyl; or $R^{5'a}$ and $R^{5'b}$ taken together with the carbon atom to which they are attached form a $C_{3-6}$ cycloalkyl; and $R^{2'a}$, $R^{2'b}$, $R^{3'a}$, $R^{3'b}$, $R^{4'a}$, and $R^{4'b}$ are each independently selected from the group consisting of hydrogen, halo, and $C_{1-4}$ alkyl; or $R^{2'a}$ and $R^{5'a}$ taken together form a $C_{1-4}$ bridge; and $R^{2'b}$, $R^{3'a}$, $R^{3'b}$, $R^{4'a}$, $R^{4'b}$, and $R^{5'b}$ are each independently selected from the group consisting of hydrogen, halo, and $C_{1-4}$ alkyl; or $R^{3'a}$ and $R^{4'a}$ taken together form a $C_1$-4 bridge; and $R^{2'a}$, $R^{2'b}$, $R^{3'b}$, $R^{4'b}$, $R^{5'a}$, and $R^{5'b}$ are each independently selected from the group consisting of hydrogen, halo, and $C_{1-4}$ alkyl; or $R^{2'a}$ and $R^{4'a}$ taken together form a $C_{1-4}$ bridge; and $R^{2'b}$, $R^{3a}$, $R^{3'b}$, $R^{4'b}$, $R^{5'a}$, and $R^{5'b}$ are each independently selected from the group consisting of hydrogen, halo, and $C_{1-4}$ alkyl; or $R^{3'a}$ and $R^{5'a}$ taken form a $C_{1-4}$ bridge; and $R^{2'a}$, $R^{2'b}$, $R^{3'b}$, $R^{4'a}$, $R^{4'b}$, and $R^{5'b}$ are each independently selected from the group consisting of hydrogen, halo, and $C_{1-4}$ alkyl;

$R^{6'}$ is selected from the group consisting of hydrogen and $C_{1-4}$ alkyl;

For the purpose of the present disclosure, the term "amino" as used by itself or as part of another group refers to $-NH_2$.

For the purpose of the present disclosure, the term "alkylamino" as used by itself or as part of another group refers to $-NHR^{22}$, wherein $R^{22}$ is $C_{1-6}$ alkyl. In one embodiment, $R^{22}$ is $C_{1-4}$ alkyl. Non-limiting exemplary alkylamino groups include $-N(H)CH_3$ and $-N(H)CH_2CH_3$.

For the purpose of the present disclosure, the term "dialkylamino" as used by itself or as part of another group refers to $-NR^{23a}R^{23b}$, wherein $R^{23a}$ and $R^{23b}$ are each independently $C_{1-6}$ alkyl. In one embodiment, $R^{23a}$ and $R^{23b}$ are each independently $C_{1-4}$ alkyl. Non-limiting exemplary dialkylamino groups include $-N(CH_3)_2$ and $-N(CH_3)CH_2CH(CH_3)_2$.

For the purpose of the present disclosure, the term "hydroxyalkylamino" as used by itself or as part of another group refers to $-NR^{24a}R^{24b}$, wherein $R^{24a}$ is hydrogen or $C_{1-4}$ alkyl, and $R^{24b}$ is hydroxyalkyl. Non-limiting exemplary hydroxyalkylamino groups include $-N(H)CH_2CH_2OH$, $-N(H)CH_2CH_2CH_2OH$, $-N(CH_3)CH_2CH_2OH$, and $-N(CH_3)CH_2CH_2CH_2OH$ For the purpose of the present disclosure, the term "(hydroxyalkylamino)alkyl" as used by itself or as part of another group refers to an alkyl group substituted with an hydroxyalkylamino group. In one embodiment, the alkyl is a $C_{1-4}$ alkyl. A non-limiting exemplary (hydroxyalkylamino)alkyl group is $-CH_2N(CH_3)CH_2CH_2CH_2OH$.

For the purpose of the present disclosure, the term "cycloalkylamino" as used by itself or as part of another group refers to $-NR^{25a}R^{25b}$, wherein $R^{25a}$ is optionally substituted cycloalkyl and $R^{25b}$ is hydrogen or $C_{1-4}$ alkyl.

For the purpose of the present disclosure, the term "heterocycloamino" as used by itself or as part of another group refers to $-NR^{25c}R^{25d}$, wherein $R^{25c}$ is optionally substituted heterocyclo and $R^{25d}$ is hydrogen or $C_{1-4}$ alkyl. Non-limiting exemplary heterocycloamino groups include:

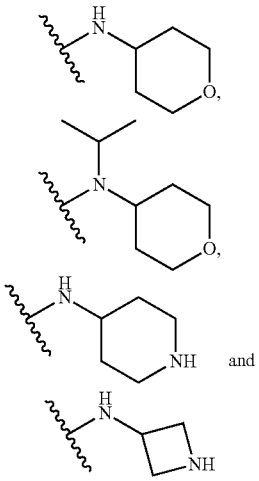

For the purpose of the present disclosure, the term "(heterocycloamino)alkyl" as used by itself or as part of another group refers to an alkyl group substituted with an heterocycloamino group. In one embodiment, the alkyl is a $C_{1-4}$ alkyl.

For the purpose of the present disclosure, the term "aralkylamino" as used by itself or as part of another group refers to $-NR^{26a}R^{26b}$, wherein $R^{26a}$ is aralkyl and $R^{26b}$ is hydrogen or $C_{1-4}$ alkyl. Non-limiting exemplary aralkylamino groups include $-N(H)CH_2Ph$ and $-N(CH_3)CH_2Ph$.

For the purpose of the present disclosure, the term "(amino)alkyl" as used by itself or as part of another group refers to an alkyl group substituted with an amino group. In one embodiment, the alkyl is a $C_{1-4}$ alkyl. Non-limiting exemplary (amino)alkyl groups include $-CH_2NH_2$, $-C(NH_2)(H)CH_3$, $-CH_2CH_2NH_2$, $-CH_2C(NH_2)(H)CH_3$, $-CH_2CH_2CH_2NH_2$, $-CH_2CH_2CH_2CH_2NH_2$, and $-CH_2C(CH_3)_2CH_2NH_2$.

For the purpose of the present disclosure, the term "(alkylamino)alkyl" as used by itself or as part of another group refers to an alkyl group substituted with an alkylamino group. In one embodiment, the alkyl is a $C_{1-4}$ alkyl. A non-limiting exemplary (alkylamino)alkyl group is $-CH_2CH_2N(H)CH_3$.

For the purpose of the present disclosure, the term "(dialkylamino)alkyl" as used by itself or as part of another group refers to an alkyl group substituted by a dialkylamino group. In one embodiment, the alkyl is a $C_{1-4}$ alkyl. Non-limiting exemplary (dialkylamino)alkyl groups are $-CH_2CH_2N(CH_3)_2$.

For the purpose of the present disclosure, the term "(cycloalkylamino)alkyl" as used by itself or as part of another group refers to an alkyl group substituted by a cycloalkylamino group. In one embodiment, the alkyl is a $C_{1-4}$ alkyl. Non-limiting exemplary (cycloalkylamino)alkyl groups include $-CH_2N(H)$cyclopropyl, $-CH_2N(H)$cyclobutyl, and $-CH_2N(H)$cyclohexyl.

For the purpose of the present disclosure, the term "(aralkylamino)alkyl" as used by itself or as part of another group refers to an alkyl group substituted with an aralkylamino group. In one embodiment, the alkyl is a $C_{1-4}$ alkyl. A non-limiting exemplary (aralkylamino)alkyl group is —CH₂CH₂CH₂N(H)CH₂Ph.

For the purpose of the present disclosure, the term "(hydroxyalkylamino)alkyl" as used by itself or as part of another group refers to an alkyl group substituted with an hydroxyalkylamino group. A non-limiting exemplary (hydroxyalkylamino)alkyl group is —CH₂CH₂NHCH₂CH₂OH For the purpose of the present disclosure, the term "(cyano)alkyl" as used by itself or as part of another group refers to an alkyl group substituted with one or more cyano, e.g., —CN, groups. In one embodiment, the alkyl is a $C_{1-4}$ alkyl. Non-limiting exemplary (cyano)alkyl groups include —CH₂CH₂CN, —CH₂CH₂CH₂CN, and —CH₂CH₂CH₂CH₂CN.

For the purpose of the present disclosure, the term "(amino)(hydroxy)alkyl" as used by itself or as part of another group refers to an alkyl group substituted with one amino, alkylamino, dialkylamino, or heterocyclo group and one hydroxy group. In one embodiment, the alkyl is a $C_{1-6}$ alkyl. In another embodiment, the alkyl is a $C_{1-4}$ alkyl.

Non-limiting exemplary (amino)(hydroxy)alkyl groups include:

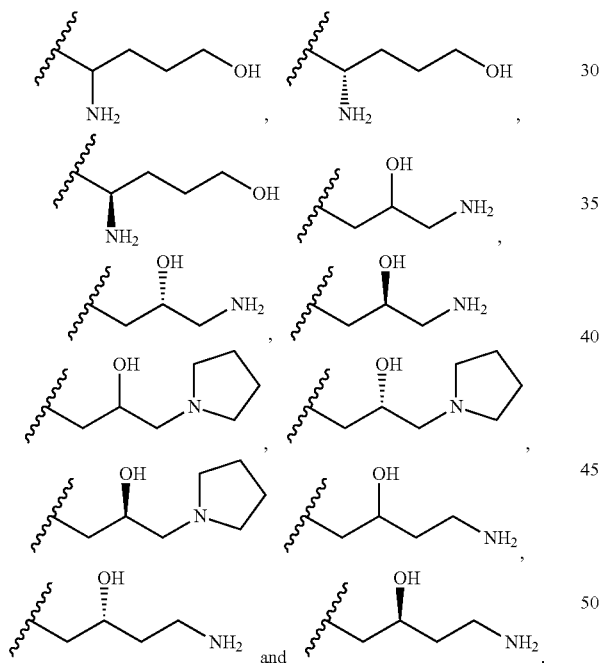

For the purpose of the present disclosure, the term "(amino)(carboxamido)alkyl" as used by itself or as part of another group refers to an alkyl group substituted with one amino, alkylamino, or dialkylamino, and one carboxamido group. In one embodiment, the alkyl is a $C_{1-6}$ alkyl. Non-limiting exemplary (amino)(carboxamido)alkyl groups include:

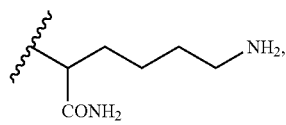

-continued

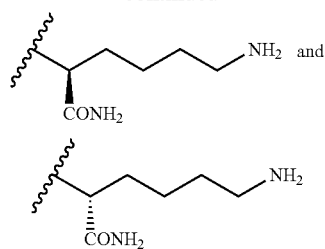

For the purpose of the present disclosure, the term "(amino)(aryl)alkyl" as used by itself or as part of another group refers to an alkyl group substituted with one amino, alkylamino, or dialkylamino group and one optionally substituted aryl group. In one embodiment, the alkyl is a $C_{1-6}$ alkyl. In one embodiment, the optionally substituted aryl group is an optionally substituted phenyl. Non-limiting exemplary (amino)(aryl)alkyl groups include:

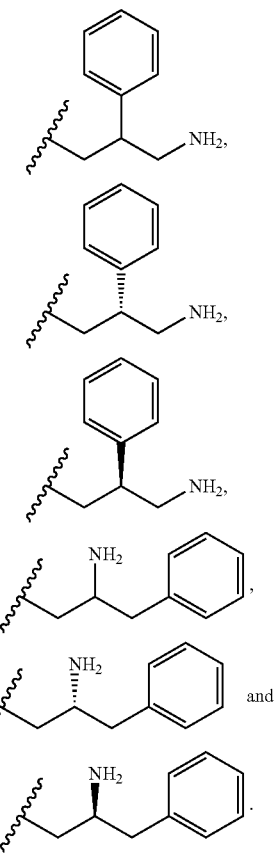

For the purpose of the present disclosure, the term "(amino)(heteroaryl)alkyl" as used by itself or as part of another group refers to an alkyl group substituted with one amino, alkylamino, or dialkylamino group and one optionally substituted heteroaryl group. In one embodiment, the alkyl is a $C_{1-6}$ alkyl. In one embodiment, the alkyl is a $C_{1-4}$ alkyl. In one embodiment, the optionally substituted heteroaryl group is an optionally substituted pyridyl. Non-limiting exemplary (amino)(heteroaryl)alkyl groups include:

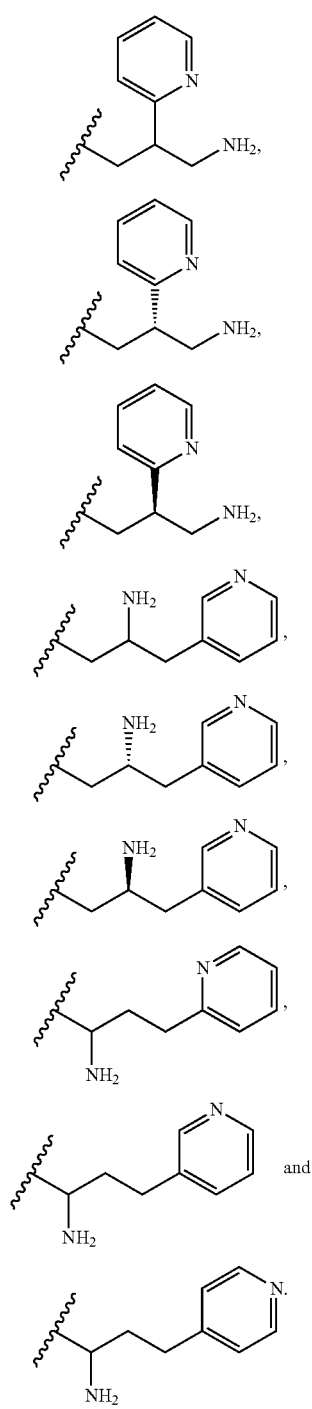

For the purpose of the present disclosure, the term "(hydroxy)(aryl)alkyl" as used by itself or as part of another group refers to an alkyl group substituted with one hydroxy group and one optionally substituted aryl group. In one embodiment, the alkyl is a $C_{1-6}$ alkyl. In one embodiment, the optionally substituted aryl group is an optionally substituted phenyl. Non-limiting exemplary (hydroxy)(aryl)alkyl groups include:

For the purpose of the present disclosure, the term "(cycloalkyl)alkyl" as used by itself or as part of another group refers to an alkyl group substituted with one optionally substituted cycloalkyl group. In one embodiment, the alkyl is a $C_{1-4}$ alkyl. In one embodiment, the cycloalkyl is a $C_{3-6}$ cycloalkyl. In one embodiment, the optionally substituted cycloalkyl group is substituted with an amino or (amino)alkyl group.

Non-limiting exemplary (cycloalkyl)alkyl groups include:

-continued

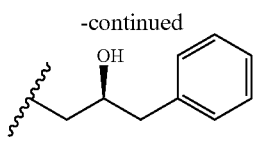

For the purpose of the present disclosure, the term "carboxamido" as used by itself or as part of another group refers to a radical of formula —C(=O)NR$^{26a}$R$^{26b}$, wherein R$^{26a}$ and R$^{26b}$ are each independently hydrogen, optionally substituted alkyl, optionally substituted aryl, aralkyl, (heteroaryl)alkyl, or optionally substituted heteroaryl, or R$^{26a}$ and R$^{26b}$ taken together with the nitrogen to which they are attached from a 3- to 8-membered heterocyclo group. In one embodiment, R$^{26a}$ and R$^{26b}$ are each independently hydrogen or optionally substituted alkyl. Non-limiting exemplary carboxamido groups include —CONH$_2$, —CON(H)CH$_3$, CON(CH$_3$)$_2$, and —CON(H)Ph.

For the purpose of the present disclosure, the term "(carboxamido)alkyl" as used by itself or as part of another group refers to an alkyl group substituted with a carboxamido group. Non-limiting exemplary (carboxamido)alkyl groups include —CH$_2$CONH$_2$, —C(H)CH$_3$—CONH$_2$, and —CH$_2$CON(H)CH$_3$.

For the purpose of the present disclosure, the term "sulfonamido" as used by itself or as part of another group refers to a radical of the formula —SO$_2$NR$^{27a}$R$^{27b}$, wherein R$^{27a}$ and R$^{27b}$ are each independently hydrogen, optionally substituted alkyl, or optionally substituted aryl, or R$^{27a}$ and R$^{27b}$ taken together with the nitrogen to which they are attached from a 3- to 8-membered heterocyclo group. Non-limiting exemplary sulfonamido groups include —SO$_2$NH$_2$, —SO$_2$N(H)CH$_3$, and —SO$_2$N(H)Ph.

For the purpose of the present disclosure, the term "alkylcarbonyl" as used by itself or as part of another group refers to a carbonyl group, i.e., —C(=O)—, substituted by an alkyl group. A non-limiting exemplary alkylcarbonyl group is —COCH$_3$.

For the purpose of the present disclosure, the term "arylcarbonyl" as used by itself or as part of another group refers to a carbonyl group, i.e., —C(=O)—, substituted by an optionally substituted aryl group. A non-limiting exemplary arylcarbonyl group is —COPh.

For the purpose of the present disclosure, the term "alkylsulfonyl" as used by itself or as part of another group refers to a sulfonyl group, i.e., —SO$_2$—, substituted by any of the above-mentioned optionally substituted alkyl groups. A non-limiting exemplary alkylsulfonyl group is —SO$_2$CH$_3$.

For the purpose of the present disclosure, the term "arylsulfonyl" as used by itself or as part of another group refers to a sulfonyl group, i.e., —SO$_2$—, substituted by any of the above-mentioned optionally substituted aryl groups. A non-limiting exemplary arylsulfonyl group is —SO$_2$Ph.

For the purpose of the present disclosure, the term "mercaptoalkyl" as used by itself or as part of another group refers to any of the above-mentioned alkyl groups substituted by a —SH group.

For the purpose of the present disclosure, the term "carboxy" as used by itself or as part of another group refers to a radical of the formula —COOH.

For the purpose of the present disclosure, the term "carboxyalkyl" as used by itself or as part of another group refers to any of the above-mentioned alkyl groups substituted with a —COOH. A non-limiting exemplary carboxyalkyl group is —CH$_2$CO$_2$H.

For the purpose of the present disclosure, the term "alkoxycarbonyl" as used by itself or as part of another group refers to a carbonyl group, i.e., —C(=O)—, substituted by an alkoxy group. Non-limiting exemplary alkoxycarbonyl groups are —CO$_2$Me and —CO$_2$Et.

For the purpose of the present disclosure, the term "aralkyl" or "arylalkyl" as used by itself or as part of another group refers to an alkyl group substituted with one, two, or three optionally substituted aryl groups. In one embodiment, the aralkyl group is a C$_{1-4}$ alkyl substituted with one optionally substituted aryl group. Non-limiting exemplary aralkyl groups include benzyl, phenethyl, —CHPh$_2$, —CH$_2$(4-OH-Ph), and —CH(4-F-Ph)$_2$.

For the purpose of the present disclosure, the term "ureido" as used by itself or as part of another group refers to a radical of the formula —NR$^{30a}$—C(=O)—NR$^{30b}$R$^{30c}$, wherein R$^{22a}$ is hydrogen, alkyl, or optionally substituted aryl, and R$^{30b}$ and R$^{30c}$ are each independently hydrogen, alkyl, or optionally substituted aryl, or R$^{30b}$ and R$^{30c}$ taken together with the nitrogen to which they are attached form a 4- to 8-membered heterocyclo group. Non-limiting exemplary ureido groups include —NH—C(C=O)—NH$_2$ and —NH—C(C=O)—NHCH$_3$.

For the purpose of the present disclosure, the term "guanidino" as used by itself or as part of another group refers to a radical of the formula —NR$^{28a}$—C(=NR$^{29}$)—NR$^{28b}$R$^{28}$, wherein R$^{28a}$, R$^{28b}$, and R$^{28c}$ are each independently hydrogen, alkyl, or optionally substituted aryl, and R$^{29}$ is hydrogen, alkyl, cyano, alkylsulfonyl, alkylcarbonyl, carboxamido, or sulfonamido. Non-limiting exemplary guanidino groups include —NH—C(C=NH)—NH$_2$, —NH—C(C=NCN)—NH$_2$, and —NH—C(C=NH)—NHCH$_3$.

For the purpose of the present disclosure, the term "(heterocyclo)alkyl" as used by itself or as part of another group refers to an alkyl group substituted with one, two, or three optionally substituted heterocyclo groups. In one embodiment, the (heterocyclo)alkyl is a C$_{1-4}$ alkyl substituted with one optionally substituted heterocyclo group. The heterocyclo can be linked to the alkyl group through a carbon or nitrogen atom. Non-limiting exemplary (heterocyclo)alkyl groups include:

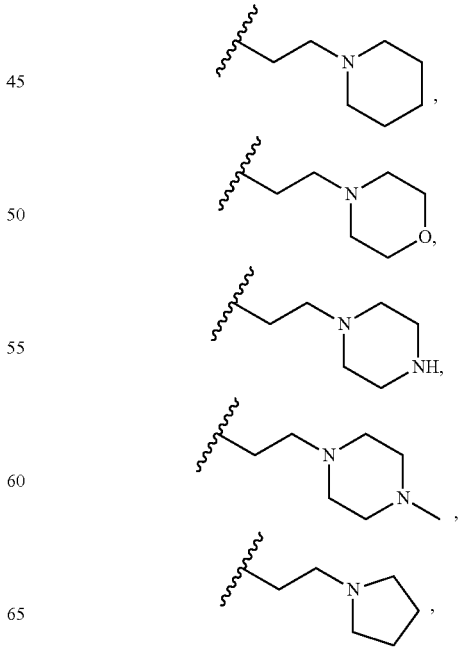

-continued

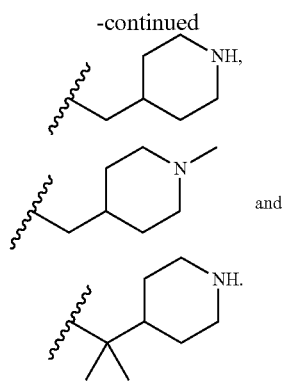

For the purpose of the present disclosure, the term "(heteroaryl)alkyl" as used by itself or as part of another group refers to an alkyl group substituted with one, two, or three optionally substituted heteroaryl groups. In one embodiment, the (heteroaryl)alkyl group is a $C_{1-4}$ alkyl substituted with one optionally substituted heteroaryl group.

Non-limiting exemplary (heteroaryl)alkyl groups include:

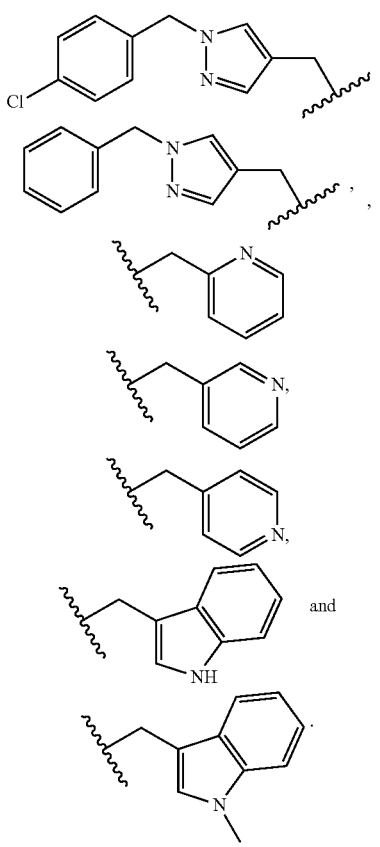

For the purpose of the present disclosure, the term "alkylcarbonylamino" as used by itself or as part of another group refers to an alkylcarbonyl group attached to an amino. A non-limiting exemplary alkylcarbonylamino group is —NHCOCH$_3$.

For the purpose of the present disclosure, the term "$C_{1-4}$ bridge" refers to a —CH$_2$—, —(CH$_2$)$_2$—, —(CH$_2$)$_3$—, or —(CH$_2$)$_4$— group that joins two carbon atoms of a piperidine to form an azabicyclo group. For example, in Formula I, $R^{3a}$ and $R^{4a}$ of B can be taken together to form a 6-azabicyclo[3.1.1]heptane, 8-azabicyclo[3.2.1]octane, 9-azabicyclo[3.3.1]nonane, or 10-azabicyclo[4.3.1]decane group. Each methylene unit of the $C_{1-4}$ bridge can be optionally substituted with one or two substituents independently selected from the group consisting of $C_{1-4}$ alkyl and halo.

The present disclosure encompasses any of the Compounds of the Disclosure being isotopically-labelled (i.e., radiolabeled) by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2$H (or deuterium (D)), $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively, e.g., $^3$H, $^{11}$C, and $^{14}$C. In one embodiment, provided is a composition wherein substantially all of the atoms at a position within the Compound of the Disclosure are replaced by an atom having a different atomic mass or mass number. In another embodiment, provided is a composition wherein a portion of the atoms at a position within the Compound of the disclosure are replaced, i.e., the Compound of the Disclosure is enriched at a position with an atom having a different atomic mass or mass number." Isotopically-labelled Compounds of the Disclosure can be prepared by methods known in the art.

Compounds of the Disclosure may contain one or more asymmetric centers and may thus give rise to enantiomers, diastereomers, and other stereoisomeric forms. The present disclosure is meant to encompass the use of all such possible forms, as well as their racemic and resolved forms and mixtures thereof. The individual enantiomers can be separated according to methods known in the art in view of the present disclosure. When the compounds described herein contain olefinic double bonds or other centers of geometric asymmetry, and unless specified otherwise, it is intended that they include both E and Z geometric isomers. All tautomers are intended to be encompassed by the present disclosure as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" or "asymmetric carbon atom" refers to a carbon atom to which four different groups are attached.

The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "absolute configuration" refers to the spatial arrangement of the atoms of a chiral molecular entity (or group) and its stereochemical description, e.g., R or S.

The stereochemical terms and conventions used in the specification are meant to be consistent with those described in *Pure & Appl. Chem* 68:2193 (1996), unless otherwise indicated.

The term "enantiomeric excess" or "ee" refers to a measure for how much of one enantiomer is present compared to the other. For a mixture of R and S enantiomers, the percent enantiomeric excess is defined as |R−S|*100, where R and S are the respective mole or weight fractions of enantiomers in a mixture such that R+S=1. With knowledge of the optical rotation of a chiral substance, the percent enantiomeric excess is defined as $([\alpha]_{obs}/[\alpha]_{max})*100$, where $[\alpha]_{obs}$ is the optical rotation of the mixture of enantiomers and $[\alpha]_{max}$ is the optical rotation of the pure enantiomer. Determination of enantiomeric excess is possible using a variety of analytical techniques, including NMR spectroscopy, chiral column chromatography or optical polarimetry.

The terms "enantiomerically pure" or "enantiopure" refer to a sample of a chiral substance all of whose molecules (within the limits of detection) have the same chirality sense.

The terms "enantiomerically enriched" or "enantioenriched" refer to a sample of a chiral substance whose enantiomeric ratio is greater than 50:50. Enantiomerically enriched compounds may be enantiomerically pure.

The terms "a" and "an" refer to one or more.

The term "about," as used herein, includes the recited number±10%. Thus, "about 10" means 9 to 11.

The present disclosure encompasses the preparation and use of salts of the Compounds of the Disclosure, including non-toxic pharmaceutically acceptable salts. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like. The term "pharmaceutically acceptable salt" as used herein, refers to any salt, e.g., obtained by reaction with an acid or a base, of a Compound of the Disclosure that is physiologically tolerated in the target patient (e.g., a mammal, e.g., a human).

Acid addition salts can be formed by mixing a solution of the particular Compound of the Disclosure with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the compound of the present disclosure with a solution of a pharmaceutically acceptable non-toxic base such as sodium hydroxide, potassium hydroxide, choline hydroxide, sodium carbonate and the like.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, ethanol, and the like, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1): Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

Since Compounds of the Disclosure are inhibitors of SMYD proteins, such as SMYD3 and SMYD2, a number of diseases, conditions, or disorders mediated by SMYD proteins, such as SMYD3 and SMYD2, can be treated by employing these compounds. The present disclosure is thus directed generally to a method for treating a disease, condition, or disorder responsive to the inhibition of SMYD proteins, such as SMYD3 and SMYD2, in an animal suffering from, or at risk of suffering from, the disorder, the method comprising administering to the animal an effective amount of one or more Compounds of the Disclosure.

The present disclosure is further directed to a method of inhibiting SMYD proteins in an animal in need thereof, the method comprising administering to the animal a therapeutically effective amount of at least one Compound of the Disclosure.

The present disclosure is further directed to a method of inhibiting SMYD3 in an animal in need thereof, the method comprising administering to the animal a therapeutically effective amount of at least one Compound of the Disclosure.

The present disclosure is further directed to a method of inhibiting SMYD2 in an animal in need thereof, the method comprising administering to the animal a therapeutically effective amount of at least one Compound of the Disclosure.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a Compound of the Disclosure to an individual in need of such treatment.

Within the meaning of the disclosure, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; modulate protein methylation in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

The term "disease" or "condition" or "disorder" denotes disturbances and/or anomalies that as a rule are regarded as being pathological conditions or functions, and that can manifest themselves in the form of particular signs, symptoms, and/or malfunctions. As demonstrated below, Compounds of the Disclosure inhibit SMYD proteins, such as SMYD3 and SMYD2 and can be used in treating diseases and conditions such as proliferative diseases, wherein inhibition of SMYD proteins, such as SMYD3 and SMYD2 provides a benefit.

In some embodiments, the Compounds of the Disclosure can be used to treat a "SMYD protein mediated disorder" (e.g., a SMYD3-mediated disorder or a SMYD2-mediated disorder). A SMYD protein mediated disorder is any pathological condition in which a SMYD protein is know to play a role. In some embodiments, a SMYD-mediated disorder is a proliferative disease.

In some embodiments inhibiting SMYD proteins, such as SMYD3 and SMYD2, is the inhibition of the activity of one or more activities of SMYD proteins such as SMYD3 and SMYD2. In some embodiments, the activity of the SMYD proteins such as SMYD3 and SMYD2 is the ability of the SMYD protein such as SMYD3 or SMYD2 to transfer a methyl group to a target protein (e.g., histone). It should be appreciated that the activity of the one or more SMYD proteins such as SMYD3 and SMYD2 may be inhibited in vitro or in vivo. Exemplary levels of inhibition of the activity one or more SMYD proteins such as SMYD3 and SMYD2 include at least 10% inhibition, at least 20% inhibition, at least 30% inhibition, at least 40% inhibition, at least 50% inhibition, at least 60% inhibition, at least 70% inhibition, at least 80% inhibition, at least 90% inhibition, and up to 100% inhibition.

The SMYD (SET and MYND domain) family of lysine methyltransferases (KMTs) plays pivotal roles in various cellular processes, including gene expression regulation and DNA damage response. The family of human SMYD proteins consists of SMYD1, SMYD2, SMYD3, SMYD4 and SMYD5. SMYD1, SMYD2, and SMYD3 share a high degree of sequence homology and, with the exception of SMYD5, human SMYD proteins harbor at least one C-terminal tetratrico peptide repeat (TPR) domain. (See e.g., Abu-Farha et al. *J Mol Cell Biol* (2011) 3 (5) 301-308). The SMYD proteins have been found to be linked to various cancers (See e.g., Hamamoto et al. *Nat Cell. Biol.* 2004, 6: 731-740), Hu et al. Cancer Research 2009, 4067-4072, and Komatsu et al. *Carcinogenesis* 2009, 301139-1146.)

SMYD3 is a protein methyltransferase found to be expressed at high levels in a number of different cancers (Hamamoto, R., et al., *Nat. Cell Biol.*, 6(8):731-40 (2004)). SMYD3 likely plays a role in the regulation of gene transcription and signal transduction pathways critical for survival of breast, liver, prostate and lung cancer cell lines (Hamamoto, R., et al., *Nat. Cell Biol.*, 6(8):731-40 (2004); Hamamoto, R., et al., *Cancer Sci.*, 97(2):113-8 (2006); Van Aller, G. S., et al., *Epigenetics*, 7(4):340-3 (2012); Liu, C., et al., *J. Natl. Cancer Inst.*, 105(22):1719-28 (2013); Mazur, P. K., et al., *Nature*, 510(7504):283-7 (2014)).

Genetic knockdown of SMYD3 leads to a decrease in proliferation of a variety of cancer cell lines (Hamamoto, R., et al., *Nat. Cell Biol.*, 6(8):731-40 (2004); Hamamoto, R., et al., *Cancer Sci.*, 97(2):113-8 (2006); Van Aller, G. S., et al., *Epigenetics*, 7(4):340-3 (2012); Liu, C., et al., *J. Natl. Cancer Inst.*, 105(22):1719-28 (2013); Mazur, P. K., et al., *Nature*, 510(7504):283-7 (2014)). Several studies employing RNAi-based technologies have shown that ablation of SMYD3 in hepatocellular carcinoma cell lines greatly reduces cell viability and that its pro-survival role is dependent on its catalytic activity (Hamamoto, R., et al., *Nat. Cell Biol.*, 6(8):731-40 (2004); Van Aller, G. S., et al., *Epigenetics*, 7(4):340-3 (2012)). Moreover, SMYD3 has also been shown to be a critical mediator of transformation resulting from gain of function mutations in the oncogene, KRAS for both pancreatic and lung adenocarcinoma in mouse models. The dependence of KRAS on SMYD3 was also shown to be dependent on its catalytic activity (Mazur, P. K., et al., *Nature*, 510(7504):283-7 (2014)). SMYD3 function has also been implicated in colerectal cancers and RNAi mediated knockdown of SMYD3 has been shown to impair colerectal cell proliferation. (Peserico et al., *Cell Physiol.* 2015 Feb. 28. doi: 10.1002/jcp.24975. [Epub ahead of print]).

Furthermore, SMYD3 function has also been shown to play a role in immunology and development. For instance, de Almeida reported that SMYD3 plays a role in generation of inducible regulatory T cells (iTreg) cells. In a mouse model of respiratory syncytial virus (RSV) infection, a model in which iTreg cells have a critical role in regulating lung pathogenesis, SMYD3−/− mice demonstrated exacerbation of RSV-induced disease related to enhanced proinflammatory responses and worsened pathogenesis within the lung (de Almeida et al. *Mucosal Immunol.* 2015 Feb. 11. doi: 10.1038/mi.2015.4. [Epub ahead of print]). In addition, as to development, Proserpio et al. have shown the importance of SMYD3 in the regulation of skeletal muscle atrophy (Proserpio et al. Genes Dev. 2013 Jun. 1; 27(11):1299-312), while Fujii et al. have elucidated the role of SMYD3 in cardiac and skeletal muscle development (Fujii et al. *PLoS One.* 2011; 6(8):e23491).

SMYD2 (SET and MYND domain-containing protein 2) was first characterized as protein that is a member of a sub-family of SET domain containing proteins which catalyze the site-specific transfer of methyl groups onto substrate proteins. SMYD2 was initially shown to have methyltransferase activity towards lysine 36 on histone H3 (H3K36) but has subsequently been shown to have both histone and non-histone methyltrasferase activity.

SMYD2 has been implicated in the pathogenesis of multiple cancers. It has been shown to be over-expressed, compared to matched normal samples, in tumors of the breast, cervix, colon, kidney, liver, head and neck, skin, pancreas, ovary, esophagus and prostate, as well as hematologic malignancies such as AML, B- and T-ALL, CLL and MCL, suggesting a role for SMYD2 in the biology of these cancers. More specifically, studies using genetic knockdown of SMYD2 have demonstrated anti-proliferative effects in esophageal squamous cell carcinoma (ESCC), bladder carcinoma and cervical carcinoma cell lines. (See e.g., Komatsu et al., *Carcinogenesis* 2009, 30, 1139, and Cho et al., *Neoplasia.* 2012 June; 14(6):476-86). Moreover, high expression of SMYD2 has been shown to be a poor prognostic factor in both ESCC and pediatric ALL. (See e.g., Komatsu et al. *Br J Cancer.* 2015 Jan. 20; 112(2):357-64, and Sakamoto et al., *Leuk Res.* 2014 April; 38(4):496-502). Recently, Nguyen et al., have shown that a small molecule inhibitor of SMYD2 (LLY-507) inhibited the proliferation of several esophageal, liver and breast cancer cell lines in a dose-dependent manner. (Nguyen et al. *J Biol Chem.* 2015 Mar. 30. pii: jbc.M114.626861. [Epub ahead of print]).

SMYD2 has also been implicated in immunology. For instance, Xu et al. have shown that SMYD2 is a negative regulator of macrophage activation by suppressing Interleukin-6 and TNF-alpha production. (Xu et al., J Biol Chem. 2015 Feb. 27; 290(9):5414-23).

In one aspect, the present disclosure provides a method of treating cancer in a patient comprising administering a therapeutically effective amount of a Compound of the Disclosure. While not being limited to a specific mechanism, in some embodiemtns, Compounds of the Disclosure can treat cancer by inhibiting SMYD proteins, such as SMYD3 and SMYD2. Examples of treatable cancers include, but are not limited to, adrenal cancer, acinic cell carcinoma, acoustic neuroma, acral lentigious melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In another embodiment, the cancer is breast, cervix, colon, kidney, liver, head and neck, skin, pancreas, ovary, esophagus, or prostate cancer.

In another embodiment, the cancer is a hematologic malignancy such as acute myeloid leukemia (AML), B- and T-acute lymphoblastic leukemia (ALL), chronic lymphocytic leukemia (CLL), or mantle cell lymphoma (MCL).

In another embodiment, the cancer is esophageal squamous cell carcinoma (ESCC), bladder carcinoma, or cervical carcinoma.

In another embodiment, the cancer is a leukemia, for example a leukemia selected from acute monocytic leukemia, acute myelogenous leukemia, chronic myelogenous leukemia, chronic lymphocytic leukemia and mixed lineage leukemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer.

In another embodiment, the present disclosure provides a therapeutic method of modulating protein methylation, gene expression, cell proliferation, cell differentiation and/or apoptosis in vivo in the cancers mentioned above by administering a therapeutically effective amount of a Compound of the Disclosure to a subject in need of such therapy.

Compounds of the Disclosure can be administered to a mammal in the form of a raw chemical without any other components present. Compounds of the Disclosure can also be administered to a mammal as part of a pharmaceutical composition containing the compound combined with a suitable pharmaceutically acceptable carrier. Such a carrier can be selected from pharmaceutically acceptable excipients and auxiliaries. The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

Pharmaceutical compositions within the scope of the present disclosure include all compositions where a Compound of the Disclosure is combined with one or more pharmaceutically acceptable carriers. In one embodiment, the Compound of the Disclosure is present in the composition in an amount that is effective to achieve its intended therapeutic purpose. While individual needs may vary, a determination of optimal ranges of effective amounts of each compound is within the skill of the art. Typically, a Compound of the Disclosure can be administered to a mammal, e.g., a human, orally at a dose of from about 0.0025 to about 1500 mg per kg body weight of the mammal, or an equivalent amount of a pharmaceutically acceptable salt or solvate thereof, per day to treat the particular disorder. A useful oral dose of a Compound of the Disclosure administered to a mammal is from about 0.0025 to about 50 mg per kg body weight of the mammal, or an equivalent amount of the pharmaceutically acceptable salt or solvate thereof. For intramuscular injection, the dose is typically about one-half of the oral dose.

A unit oral dose may comprise from about 0.01 mg to about 1 g of the Compound of the Disclosure, e.g., about 0.01 mg to about 500 mg, about 0.01 mg to about 250 mg, about 0.01 mg to about 100 mg, 0.01 mg to about 50 mg, e.g., about 0.1 mg to about 10 mg, of the compound. The unit dose can be administered one or more times daily, e.g., as one or more tablets or capsules, each containing from about 0.01 mg to about 1 g of the compound, or an equivalent amount of a pharmaceutically acceptable salt or solvate thereof.

A pharmaceutical composition of the present disclosure can be administered to any patient that may experience the beneficial effects of a Compound of the Disclosure. Foremost among such patients are mammals, e.g., humans and companion animals, although the disclosure is not intended to be so limited. In one embodiment, the patient is a human.

A pharmaceutical composition of the present disclosure can be administered by any means that achieves its intended purpose. For example, administration can be by the oral, parenteral, subcutaneous, intravenous, intramuscular, intraperitoneal, transdermal, intranasal, transmucosal, rectal, intravaginal or buccal route, or by inhalation. The dosage administered and route of administration will vary, depending upon the circumstances of the particular subject, and taking into account such factors as age, gender, health, and weight of the recipient, condition or disorder to be treated, kind of concurrent treatment, if any, frequency of treatment, and the nature of the effect desired.

In one embodiment, a pharmaceutical composition of the present disclosure can be administered orally. In another embodiment, a pharmaceutical composition of the present disclosure can be administered orally and is formulated into tablets, dragees, capsules, or an oral liquid preparation. In one embodiment, the oral formulation comprises extruded multiparticulates comprising the Compound of the Disclosure.

Alternatively, a pharmaceutical composition of the present disclosure can be administered rectally, and is formulated in suppositories.

Alternatively, a pharmaceutical composition of the present disclosure can be administered by injection.

Alternatively, a pharmaceutical composition of the present disclosure can be administered transdermally.

Alternatively, a pharmaceutical composition of the present disclosure can be administered by inhalation or by intranasal or transmucosal administration.

Alternatively, a pharmaceutical composition of the present disclosure can be administered by the intravaginal route.

A pharmaceutical composition of the present disclosure can contain from about 0.01 to 99 percent by weight, e.g., from about 0.25 to 75 percent by weight, of a Compound of the Disclosure, e.g., about 1%, about 5%, about 10%, about 15%, about 20%, about 25%, about 30%, about 35%, about 40%, about 45%, about 50%, about 55%, about 60%, about 65%, about 70%, or about 75% by weight of a Compound of the Disclosure.

A pharmaceutical composition of the present disclosure is manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries are typically flow-regulating agents and lubricants such as, for example, silica, talc, stearic acid or salts thereof (e.g., magnesium stearate or calcium stearate), and polyethylene glycol. Dragee cores are provided with suitable coatings that are resistant to gastric juices. For this purpose, concentrated saccharide solutions can be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate can be used. Dye stuffs or pigments can be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which can be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers can be added.

Possible pharmaceutical preparations for rectal administration include, for example, suppositories, which consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

Suitable formulations for parenteral administration include aqueous solutions of the active compound in a water-soluble form such as, for example, a water-soluble salt, alkaline solution, or acidic solution. Alternatively, a suspension of the active compound can be prepared as an oily suspension. Suitable lipophilic solvents or vehicles for such as suspension may include fatty oils (for example, sesame oil), synthetic fatty acid esters (for example, ethyl oleate), triglycerides, or a polyethylene glycol such as polyethylene glycol-400 (PEG-400). An aqueous suspension may contain one or more substances to increase the viscosity of the suspension, including, for example, sodium carboxymethyl cellulose, sorbitol, and/or dextran. The suspension may optionally contain stabilizers.

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration.

General Synthesis of Compounds

Compounds of the Disclosure are prepared using methods known to those skilled in the art in view of this disclosure, or by the illustrative methods shown in the General Schemes below. In the General Schemes, $R^1$, $R^2$, $R^3$, and Z of Formulae A-C are as defined in connection with Formula VII, unless otherwise indicated. In the General Schemes, suitable protecting can be employed in the synthesis, for example, when Z is (amino)alkyl or any other group that may require protection. (See, Wuts, P. G. M.; Greene, T. W., "Greene's Protective Groups in Organic Synthesis", 4th Ed., J. Wiley & Sons, N Y, 2007).

General Scheme 1

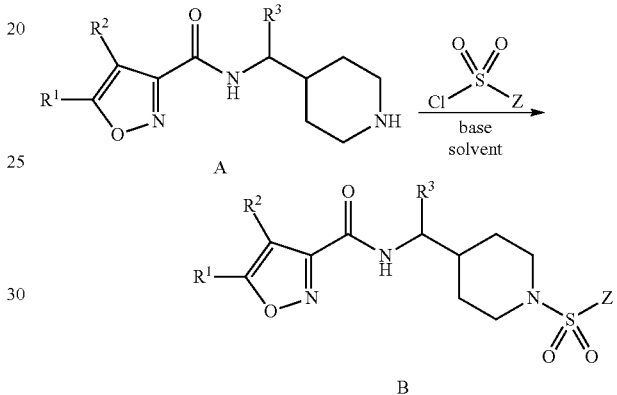

Compound A is converted to compound B (i.e, a compound having Formula VII, wherein X is —S(=O)$_2$—) by coupling with a suitable sulfonyl chloride (Z—SO$_2$Cl) in the presence of a suitable base such as TEA or DIPEA in a suitable solvent such as dichloromethane, acetonitrile, or DMF.

General Scheme 2

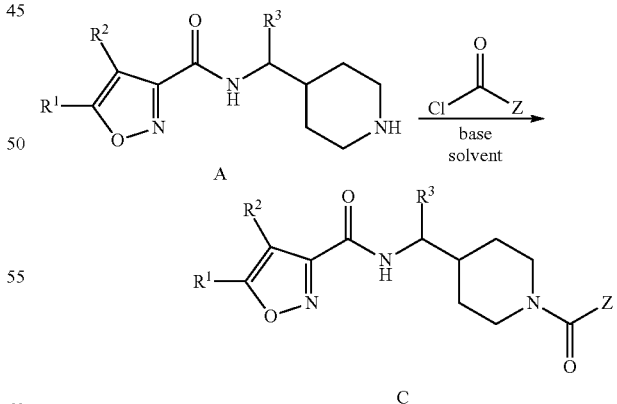

Compound A was converted to compound C by coupling with a suitable carboxylic acid (ZCO$_2$H) in the presence of a suitable coupling reagent such as HATU or HOBT in the presence of a suitable base such as TEA or DIPEA in a suitable solvent such as DMF. Compound A can also be converted to compound C by coupling with a suitable acid chloride (ZCOCl) in the presence of a suitable base such as TEA or DIPEA in the presence of a suitable solvent such as dichloromethane, acetonitrile or DMF.

EXAMPLES

General Synthetic Methods

General methods and experimental procedures for preparing and characterizing compounds of Tables 1 and 2 are set forth in the general schemes above and the examples below. Wherever needed, reactions were heated using conventional hotplate apparatus or heating mantle or microwave irradiation equipment. Reactions were conducted with or without stirring, under atmospheric or elevated pressure in either open or closed vessels. Reaction progress was monitored using conventional techniques such as TLC, HPLC, UPLC, or LCMS using instrumentation and methods described below. Reactions were quenched and crude compounds isolated using conventional methods as described in the specific examples provided. Solvent removal was carried out with or without heating, under atmospheric or reduced pressure, using either a rotary or centrifugal evaporator.

Compound purification was carried out as needed using a variety of traditional methods including, but not limited to, preparative chromatography under acidic, neutral, or basic conditions using either normal phase or reverse phase HPLC or flash columns or Prep-TLC plates. Compound purity and mass confirmations were conducted using standard HPLC and/or UPLC and/or MS spectrometers and/or LCMS and/or GC equipment (i.e., including, but not limited to the following instrumentation: Waters Alliance 2695 with 2996 PDA detector connected with ZQ detector and ESI source; Shimadzu LDMS-2020; Waters Acquity H Class with PDA detector connected with SQ detector and ESI source; Agilent 1100 Series with PDA detector; Waters Alliance 2695 with 2998 PDA detector; AB SCIEX API 2000 with ESI source; Agilent 7890 GC).

Compound structure confirmations were carried out using standard 300 or 400 MHz NMR spectrometers with nOe's conducted whenever necessary.

The following abbreviations are used herein:

| Abbreviation | Meaning |
|---|---|
| ACN | acetonitrile |
| atm. | atmosphere |
| DCM | dichloromethane |
| DHP | dihydropyran |
| DIBAL | diisobutyl aluminum hydride |
| DIEA | diisopropyl ethylamine |
| DMF | dimethyl formamide |
| DMF-DMA | dimethyl formamide dimethyl acetal |
| DMSO | dimethyl sulfoxide |
| Dppf | 1,1'-bis(diphenylphosphino)ferrocene |
| EA | ethyl acetate |
| ESI | electrospray ionization |
| EtOH | Ethanol |
| FA | formic acid |
| GC | gas chromatography |
| H | hour |
| Hex | hexanes |
| HMDS | hexamethyl disilazide |
| HPLC | high performance liquid chromatography |
| IPA | Isopropanol |
| LCMS | liquid chromatography/mass spectrometry |

-continued

| Abbreviation | Meaning |
|---|---|
| MeOH | Methanol |
| Min | Minutes |
| NBS | N-bromo succinimide |
| NCS | N-chloro succinimide |
| NIS | N-iodo succinimide |
| NMR | nuclear magnetic resonance |
| nOe | nuclear Overhauser effect |
| Prep. | Preparative |
| PTSA | para-toluene sulfonic acid |
| Rf | retardation factor |
| rt | room temperature |
| RT | retention time |
| sat. | Saturated |
| SGC | silica gel chromatography |
| TBAF | tetrabutyl ammonium fluoride |
| TEA | Triethylamine |
| TFA | trifluoroacetic acid |
| THF | Tetrahydrofuran |
| TLC | thin layer chromatography |
| UPLC | ultra performance liquid chromatography |

Example 1

Synthesis of 5-cyclopropylisoxazole-3-carboxylic acid

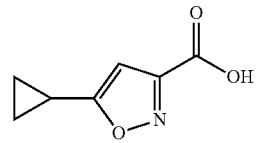 [SMILES: O=C(O)c1cc(C2CC2)on1]

Step 1: Synthesis of ethyl 4-cyclopropyl-2,4-dioxobutanoate

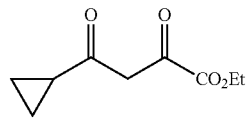 [SMILES: CCOC(=O)C(=O)CC(=O)C1CC1]

Into a 10-L 3-necked round-bottom flask purged and maintained with an inert atmosphere of nitrogen Na (164 g, 1.20 equiv) was added in portions to ethanol (5 L). A solution of $(CO_2Et)_2$ (869 g, 1.00 equiv) and 1-cyclopropylethan-1-one (500 g, 5.94 mol, 1.00 equiv) was added dropwise with stirring at 0-20° C. The resulting solution was stirred for 1 h at 20-30° C. and then for an additional 1 h at 80° C. The resulting solution was diluted with 15 L of $H_2O$. The pH was adjusted to 2 with hydrochloric acid (12N). The resulting mixture was extracted with ethyl acetate and the organic layers combined and washed with $NaHCO_3$ (sat. aq.). The extract was concentrated under vacuum yielding 820 g (crude) of ethyl 4-cyclopropyl-2,4-dioxobutanoate as yellow oil. TLC (ethyl acetate/petroleum ether=1/5): Rf=0.5.

Step 2: Synthesis of ethyl 5-cyclopropylisoxazole-3-carboxylate

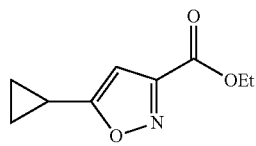 [SMILES: CCOC(=O)c1cc(C2CC2)on1]

Into a 10 L round-bottom flask, was placed a solution of ethyl 4-cyclopropyl-2,4-dioxobutanoate (177 g) in ethanol (1.1 L) and NH$_2$OH—HCl (200 g). The resulting solution was stirred for 1 h at 20-30° C. The resulting solution was allowed to react, with stirring, for an additional 1 h at 80° C. The resulting mixture was concentrated under vacuum. The residue was purified on a silica gel column with ethyl acetate/petroleum ether (1/10). This resulted in 143 g (the two step yield was 66.3%) of ethyl 5-cyclopropylisoxazole-3-carboxylate as a yellow oil. TLC (ethyl acetate/petroleum ether=1/5): Rf=0.2.

Step 3: Synthesis of 5-cyclopropylisoxazole-3-carboxylic acid

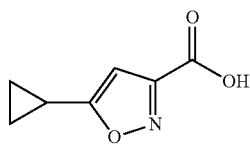 [SMILES: O=C(O)c1cc(C2CC2)on1]

Into a 10-L round-bottom flask was placed ethyl 5-cyclopropylisoxazole-3-carboxylate (280 g, 1.55 mol, 1.00 equiv) and a solution of sodium hydroxide (74.3 g, 1.20 equiv) in water (4 L). The resulting solution was stirred for 1 h at room temperature. The resulting mixture was washed with ether. The pH value of the aqueous solution was adjusted to 2-3 with hydrochloric acid (12N). The resulting solution was extracted with ethyl acetate and the organic layers combined and concentrated under vacuum. This resulted in 220 g (93%) of 5-cyclopropylisoxazole-3-carboxylic acid as an off-white solid. $^1$H-NMR (300 MHz CDCl$_3$): δ 8.42 (brs, 1H), 6.37 (s, 1H), 2.16-2.05 (m, 1H), 1.29-1.12 (m, 2H), 1.12-0.99 (m, 2H); LCMS m/z=153.9 [M+H]$^+$.

Example 2

Synthesis of 5-cyclopropylisoxazole-3-carbonyl chloride

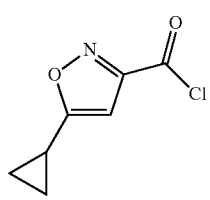 [SMILES: O=C(Cl)c1cc(C2CC2)on1]

To a stirred solution of 5-cyclopropylisoxazole-3-carboxylic acid (0.750 g, 4.90 mmol) in DCM (5 ml) was added oxalyl chloride (1.68 ml, 19.60 mmol) and 2 drops of DMF. The reaction was stirred at RT 2 hr. After complete consumption of starting material, the solvent was removed under reduced pressure to obtain 5-cyclopropylisoxazole-3-carbonyl chloride as a residue (0.6 g, crude). The material was used without further purification.

Example 3

Synthesis of 5-cyclopropyl-N-(1-(piperidin-4-yl) ethyl)isoxazole-3-carboxamide hydrochloride (Cpd. No. 213

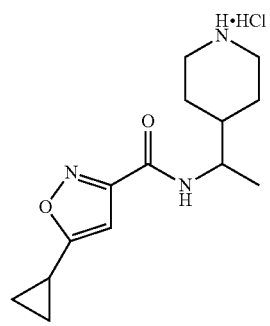

Step 1: Synthesis of tert-butyl 4-(methoxy(methyl) carbamoyl)piperidine-1-carboxylate

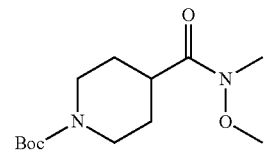 [SMILES: CON(C)C(=O)C1CCN(C(=O)OC(C)(C)C)CC1]

To a stirred solution of 1-(tert-butoxycarbonyl)piperidine-4-carboxylic acid (5.0 g, 21.7 mmol) in DMF (20 mL) was added HATU (12.39 g, 32.60 mmol) and diisopropylethylamine (18.94 ml, 108.6 mmol). The solution was stirred for 10 min at 0° C. After that N,O-dimethylhydroxylamine hydrochloride (2.12 g, 21.7 mmol) was added and stirred at RT for 2 h. The progress of the reaction was monitored by TLC. After complete consumption of starting material, the reaction was quenched with water and extracted with ethyl acetate. The organic layer was washed with brine, dried over anhydrous Na$_2$SO$_4$ and concentrated under reduced pressure to obtain a crude residue which was purified by column chromatography to afford tert-butyl 4-(methoxy(methyl)carbamoyl)piperidine-1-carboxylate (4.3 g, 71%). LCMS: m/z=173.05 (M-Boc)$^+$.

Step 2: Synthesis of tert-butyl 4-acetylpiperidine-1-carboxylate

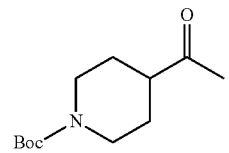 [SMILES: CC(=O)C1CCN(C(=O)OC(C)(C)C)CC1]

To a stirred solution of tert-butyl 4-(methoxy(methyl) carbamoyl)piperidine-1-carboxylate (4.3 g, 15.8 mmol) in dry THF (20 mL) was added a solution of methyl magnesium bromide (20 mL, 23.71 mmol, 1.6 M in THF:toluene) at −78° C. and the reaction was stirred at −78° C. for 2 h and RT for 2 h. The progress of the reaction was monitored by TLC. After complete consumption of starting material, the reaction was quenched with saturated NH$_4$Cl solution and extracted with ethyl acetate. The organic layer was washed with brine, dried over Na$_2$SO$_4$ and concentrated under reduced pressure to a crude residue which was purified by column chromatography to afford tert-butyl 4-acetylpiperidine-1-carboxylate (2.8 g, 62%).

Step 3: Synthesis of tert-butyl 4-(1-aminoethyl)piperidine-1-carboxylate

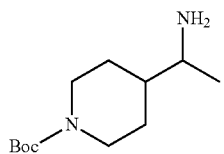 [SMILES: CC(N)C1CCN(C(=O)OC(C)(C)C)CC1]

To a stirred solution of compound tert-butyl 4-acetylpiperidine-1-(2.8 g, 9.68 mmol) in dry MeOH (6 mL) was added ammonium acetate (8.9 g, 16.2 mmol) and the reaction was stirred at RT for 15 min, sodium cyanoborohydride (2.43 g, 38.7 mmol) was then added. The reaction mixture was heated to reflux for 16 h. The progress of the reaction was monitored by TLC. After complete consumption of starting material, the reaction was quenched with 0.5 M NaOH solution and extracted with ethyl acetate. The organic layer was washed with brine, dried over Na$_2$SO$_4$ and concentrated under reduced pressure to obtain a residue of tert-butyl 4-(1-aminoethyl)piperidine-1-carboxylate (2.1 g, crude). This was used in the next step without further purification. LCMS: m/z=191.25 (M-Boc)$^+$.

Step 4: Synthesis of tert-butyl 4-(1-(5-cyclopropylisoxazole-3-carboxamido)ethyl)piperidine-1-carboxylate

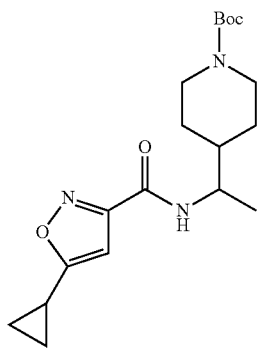 [SMILES: CC(NC(=O)c1cc(C2CC2)on1)C1CCN(C(=O)OC(C)(C)C)CC1]

To a stirred solution of 5-cyclopropylisoxazole-3-carboxylic acid (1.0 g, 6.5 mmol) in DMF (3 mL) was added HATU (3.72 g, 9.8 mmol) and diisopropylethylamine (3.5 ml, 19.6 mmol). The solution was stirred for 10 min at 0° C. tert-Butyl 4-(1-aminoethyl)piperidine-1-carboxylate (1.45 g, 6.5 mmol) was added and the reaction stirred at RT for 2 h. The progress of the reaction was monitored by TLC. After complete consumption of starting material, the reaction was quenched with water and extracted with ethyl acetate. The organic layer was separated, washed with brine, dried over anhydrous Na$_2$SO$_4$ and concentrated under reduced pressure to obtain a crude residue which was purified by column chromatography to afford compound tert-butyl 4-(1-(5-cyclopropylisoxazole-3-carboxamido)ethyl)piperidine-1-carboxylate (2.1 g, 84%). $^1$H NMR (400 MHz, DMSO-d$_6$) δ 8.44 (d, J=8.9 Hz, 1H), 6.46 (s, 1H), 3.98-3.90 (m, 2H), 3.79 (p, J=7.3 Hz, 1H), 2.53-2.47 (m, 2H), 2.19-2.16 (m, 1H), 1.6-1.58 (m, 3H), 1.38 (s, 9H), 1.18-0.86 (m, 9H); LCMS: m/z=386.25 (M+H)$^+$.

Step 5: Synthesis of 5-cyclopropyl-N-(1-(piperidin-4-yl)ethyl)isoxazole-3-carboxamide hydrochloride

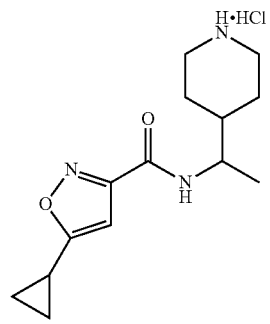

To a stirred solution of tert-butyl 4-(1-(5-cyclopropylisoxazole-3-carboxamido)ethyl)piperidine-1-carboxylate (2.1 g, 5.8 mmol) in dioxane (5 mL) was added 4 M dioxane:HCl (20 mL) at 0° C. and the reaction mixture was stirred at RT for 3 h. The progress of the reaction was monitored by TLC. After complete consumption of starting material, the solvent was removed under reduced pressure to obtain a crude residue which was purified by repeated washing with ether and pentane to obtain 5-cyclopropyl-N-(1-(piperidin-4-yl) ethyl)isoxazole-3-carboxamide hydrochloride (1.3 g, 86%). $^1$H NMR (400 MHz, DMSO-d$_6$) δ 8.95-8.86 (m, 1H), 8.54 (t, J=11.8 Hz, 2H), 6.49 (s, 1H), 3.91-3.77 (m, 1H), 3.24 (d, J=12.4 Hz, 2H), 2.88-2.66 (m, 2H), 2.18 (tt, J=8.4, 5.0 Hz, 1H), 1.86-1.60 (m, 3H), 1.44-1.27 (m, 2H), 1.15-1.03 (m, 5H), 0.95-0.84 (m, 2H); LCMS: m/z=264.20 (M+H)$^+$.

Example 4

Synthesis of 5-cyclopropyl-N-(phenyl(piperidin-4-yl)methyl)isoxazole-3-carboxamide (Cpd. No. 49)

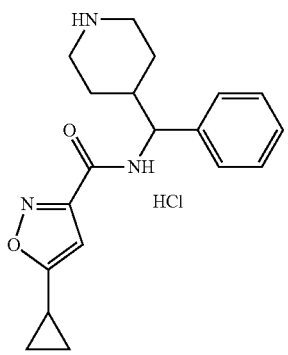 [SMILES: O=C(NC(c1ccccc1)C1CCNCC1)c1cc(C2CC2)on1 ; Cl]

Step 1: Synthesis of tert-butyl 4-benzoylpiperidine-1-carboxylate

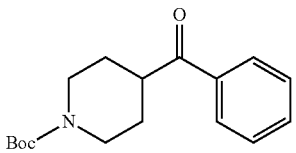 [SMILES: CC(C)(C)OC(=O)N1CCC(C(=O)c2ccccc2)CC1]

To a stirred solution of tert-butyl 4-(methoxy(methyl)carbamoyl)piperidine-1-carboxylate (0.5 g, 1.83 mmol) in THF (1.5 mL) was added a 1M solution of phenyl magnesium bromide in THF (3.67 mL, 3.67 mmol) at 0° C. The reaction was stirred overnight at RT. The reaction completion was monitored by TLC and the reaction was quenched with ammonium chloride solution and extracted with ethyl acetate. The organic layer was separated, washed with brine, dried using $Na_2SO_4$ and concentrated under reduced pressure to a residue. The residue was purified by column chromatography to obtain tert-butyl 4-benzoylpiperidine-1-carboxylate (0.188 g, 35.5%) LCMS: m/z=190.1 (M+H)$^+$.

Step 2: Synthesis of tert-butyl 4-(amino(phenyl)methyl)piperidine-1-carboxylate

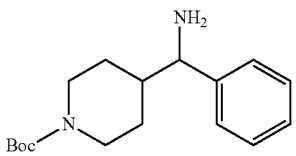 [SMILES: CC(C)(C)OC(=O)N1CCC(C(N)c2ccccc2)CC1]

To a solution of tert-butyl 4-benzoylpiperidine-1-carboxylate (0.188 g, 0.65 mmol) in MeOH (5 mL) was added ammonium acetate (0.6 g, 7.8 mmol). The reaction was stirred for 10 minutes at 25° C., then sodium cyanoborohydride (0.163 g, 2.59 mmol) was added. The reaction heated to 60° C. for 16 hours. The reaction completion was monitored by TLC and the reaction was quenched with 0.5N NaOH solution and extracted with ethyl acetate. The organic layer was separated, washed with brine, dried using $Na_2SO_4$ and concentrated under reduced pressure to a residue which was purified by column chromatography to obtain tert-butyl 4-(amino(phenyl)methyl)piperidine-1-carboxylate (0.2 g, 40%). LCMS: m/z=190.3 (M+H)$^+$.

Step 3: Synthesis of tert-butyl 4-((5-cyclopropylisoxazole-3-carboxamido)(phenyl)methyl)piperidine-1-carboxylate

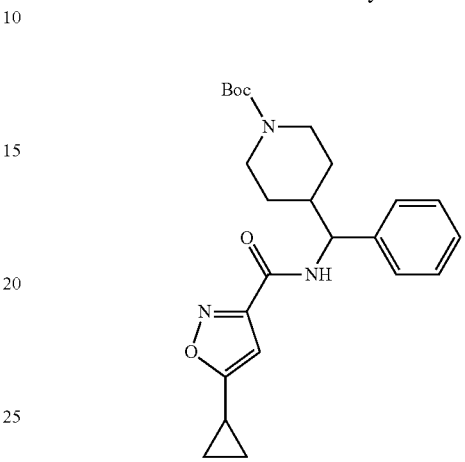

To a stirred solution of 5-cyclopropylisoxazole-3-carboxylic acid (0.1 g, 0.34 mmol) in DCM (5 ml) was added oxalyl chloride (0.2 ml, 0.68 mmol) and 2 drops of DMF. The reaction was stirred at RT 2 hr. After complete consumption of starting material, the solvent was removed under reduced pressure to obtain a residue. The residue was dissolved in DCM and cooled to 0° C. tert-Butyl 4-(amino(phenyl)methyl)piperidine-1-carboxylate was added (0.070 g, 0.41 mmol) in DCM (5 mL) followed by triethylamine (0.23 mL, 0.17 mmol). The reaction was stirred at RT for 1 hr. The progress of the reaction was monitored by TLC. After complete consumption of starting material, the reaction was quenched with sodium bicarbonate and, extracted with DCM. The organic layer was separated, washed with brine, dried using $Na_2SO_4$ and concentrated under reduced pressure to obtain a residue which was purified by column chromatography to obtain tert-butyl 4-((5-cyclopropylisoxazole-3-carboxamido)(phenyl)methyl)piperidine-1-carboxylate (0.057 g, 50%) LCMS: m/z=326.23 (M+H)$^+$.

Step 4: Synthesis of 5-cyclopropyl-N-(phenyl(piperidin-4-yl)methyl)isoxazole-3-carboxamide hydrochloride

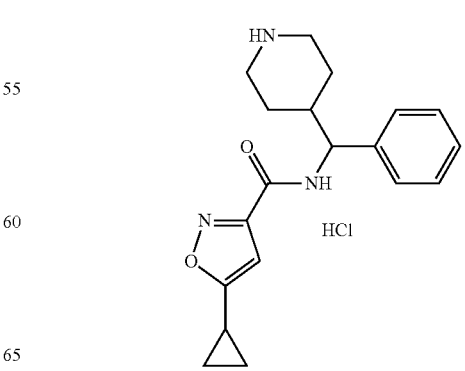

To a stirred solution of tert-butyl 4-((5-cyclopropylisoxazole-3-carboxamido)(phenyl)methyl)piperidine-1-carboxylate (0.057 g, 0.13 mmol) in dioxane (1 mL) at 0° C. was added 4 M dioxane:HCl (2 mL). The reaction was stirred at rt for 2 h. The progress of the reaction was monitored by TLC. After complete consumption of starting material, the solvent was removed under reduced pressure and the residue was purified by washing with ether and pentane to obtain 5-cyclopropyl-N-(phenyl(piperidin-4-yl)methyl)isoxazole-3-carboxamide hydrochloride (0.028 g, 65%). $^1$H NMR (400 MHz, DMSO-$d_6$) δ 9.21 (d, J=9.0 Hz, 1H), 8.70 (d, J=11.2 Hz, 1H), 8.36 (d, J=11.7 Hz, 1H), 7.46-7.37 (m, 2H), 7.39-7.22 (m, 3H), 6.47 (s, 1H), 4.71 (t, J=9.5 Hz, 1H), 3.22-3.13 (m, 2H), 2.77 (q, J=11.0, 10.1 Hz, 2H), 2.23-2.03 (m, 3H), 1.47-1.19 (m, 3H), 1.14-1.02 (m, 2H), 0.94-0.83 (m, 2H); LCMS: m/z=326.25 (M+H)$^+$.

Example 5

Synthesis of N-(1-(1-((S)-2-amino-3-(4-hydroxyphenyl)propanoyl)piperidin-4-yl)ethyl)-5-cyclopropylisoxazole-3-carboxamide (Cpd. No. 211

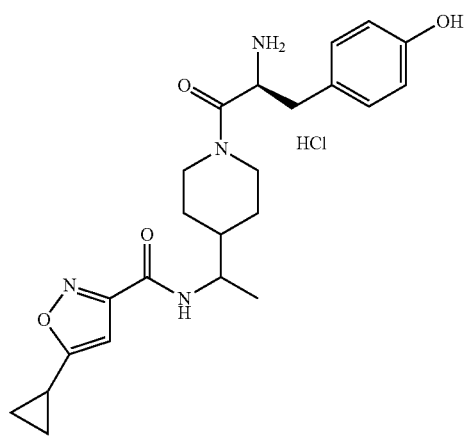 [SMILES: CC(NC(=O)c1cc(C2CC2)on1)C1CCN(C(=O)[C@@H](N)Cc2ccc(O)cc2)CC1 ; Cl]

Step 1: Synthesis of tert-butyl ((2S)-1-(4-(1-(5-cyclopropylisoxazole-3-carboxamido)ethyl)piperidin-1-yl)-3-(4-hydroxyphenyl)-1-oxopropan-2-yl)carbamate

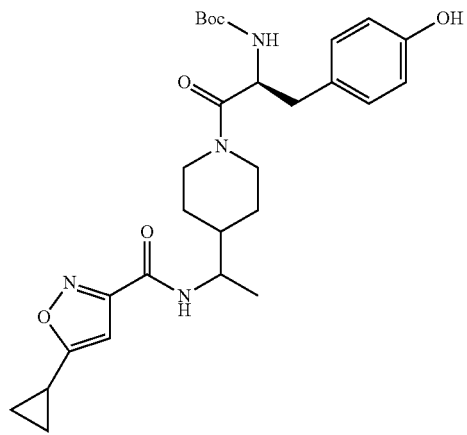 [SMILES: CC(NC(=O)c1cc(C2CC2)on1)C1CCN(C(=O)[C@H](Cc2ccc(O)cc2)NC(=O)OC(C)(C)C)CC1]

To a stirred solution of (S)-2-((tert-butoxycarbonyl)amino)-3-(4-hydroxyphenyl) propanoic acid (0.188 g, 0.68 mmol) in DMF (2 mL) was added EDCI (0.191 g, 1.10 mmol), HOBt (0.135 g, 1.10 mmol), and triethylamine (0.3 mL, 2.27 mmol). The solution was stirred for 30 min at 0° C. 5-Cyclopropyl-N-(1-(piperidin-4-yl)ethyl)isoxazole-3-carboxamide hydrochloride (0.2 g, 0.66 mmol) was then added and the reaction stirred at rt overnight. The progress of the reaction was monitored by TLC. After complete consumption of starting material, the reaction was quenched with water and extracted with ethyl acetate. The organic layer was separated, washed with brine, dried over anhydrous $Na_2SO_4$ and concentrated under reduced pressure to obtain a crude residue which was purified by column chromatography to afford tert-butyl ((2S)-1-(4-(1-(5-cyclopropylisoxazole-3-carboxamido)ethyl)piperidin-1-yl)-3-(4-hydroxyphenyl)-1-oxopropan-2-yl)carbamate (0.09 g, 25%). LCMS: m/z=428.05 (M-Boc)$^+$.

Step 2: Synthesis of N-(1-(1-((S)-2-amino-3-(4-hydroxyphenyl)propanoyl)piperidin-4-yl)ethyl)-5-cyclopropylisoxazole-3-carboxamide hydrochloride

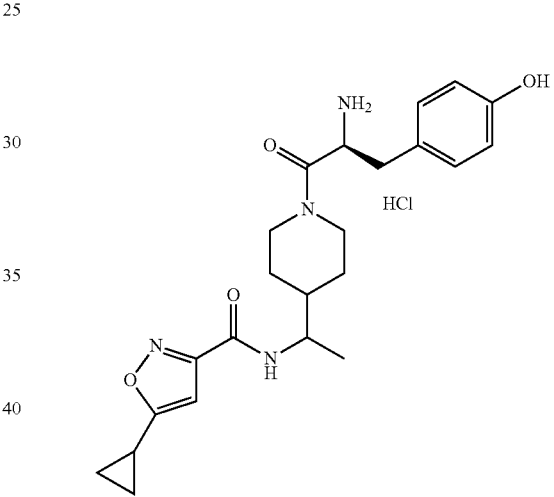

To a stirred solution of tert-butyl ((2S)-1-(4-(1-(5-cyclopropylisoxazole-3-carboxamido)ethyl)piperidin-1-yl)-3-(4-hydroxyphenyl)-1-oxopropan-2-yl)carbamate (0.09 g, 0.17 mmol) in dioxane (1 mL) was added 4 M dioxane:HCl (5 mL) at 0° C. and the reaction mixture stirred at rt for 3 h. The progress of the reaction was monitored by TLC. After complete consumption of starting material, the solvent was removed under reduced pressure to obtain a crude residue which was purified by repeated washing with ether and pentane to obtain N-(1-(1-((S)-2-amino-3-(4-hydroxyphenyl)propanoyl)piperidin-4-yl)ethyl)-5-cyclopropylisoxazole-3-carboxamide hydrochloride (0.020 g, 28%). $^1$H NMR (400 MHz, DMSO-$d_6$) δ 9.44-9.35 (m, 1H), 8.46 (q, J=7.3 Hz, 1H), 8.12 (s, 3H), 6.99 (dd, J=17.3, 7.9 Hz, 2H), 6.75-6.66 (m, 2H), 6.46 (d, J=3.5 Hz, 1H), 4.52 (p, J=6.8, 6.2 Hz, 1H), 4.37 (d, J=12.8 Hz, 1H), 3.83-3.59 (m, 2H), 2.96-2.73 (m, 2H), 2.47-2.33 (m, 2H), 2.27-2.12 (m, 1H), 1.76-1.62 (m, 1H), 1.62-1.35 (m, 2H), 1.14-0.81 (m, 9H); LCMS: m/z=427.35 (M+H)$^+$.

Example 6

Synthesis N—((S)-(1-((S)-2-aminopropanoyl)piperidin-4-yl)(phenyl)methyl)-5-cyclopropylisoxazole-3-carboxamide hydrochloride (Cpd. No. 215)

And

N—((R)-(1-((S)-2-aminopropanoyl)piperidin-4-yl)(phenyl)methyl)-5-cyclopropylisoxazole-3-carboxamide hydrochloride (Cpd. No. 216

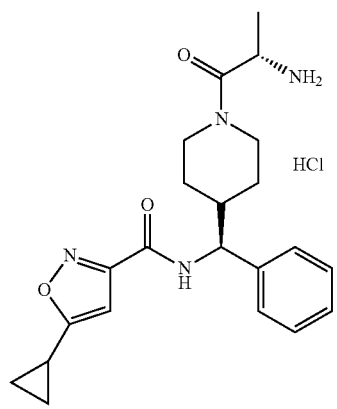

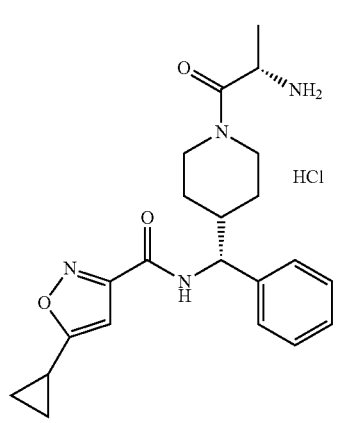

Step 1: Synthesis of tert-butyl ((S)-1-(4-((S)-(5-cyclopropylisoxazole-3-carboxamido)(phenyl)methyl)piperidin-1-yl)-1-oxopropan-2-yl)carbamate and tert-butyl ((S)-1-(4-((R)-(5-cyclopropylisoxazole-3-carboxamido)(phenyl)methyl)piperidin-1-yl)-1-oxopropan-2-yl)carbamate

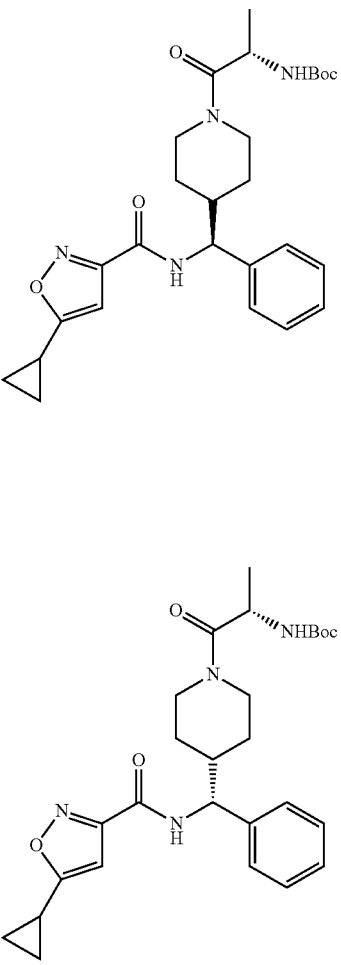

To a stirred solution of (S)-2-((tert-butoxycarbonyl)amino)propanoic acid (0.044 g, 0.230 mmol) in DMF (1 mL) was added HATU (0.131 g, 0.34 mmol) and diisopropyl ethylamine (0.12 mL, 0.69 mmol). The solution was stirred for 10 min at 0° C. Next, 5-cyclopropyl-N-(phenyl(piperidin-4-yl)methyl)isoxazole-3-carboxamide ((0.1 g, 0.277 mmol) was added and the reaction stirred at rt for 2 h. The progress of the reaction was monitored by TLC. After complete consumption of starting material, the reaction was quenched with water and extracted with ethyl acetate. The organic layer was washed with brine, dried over anhydrous $Na_2SO_4$ and concentrated under reduced pressure to obtain a crude residue which was purified by preparative chiral HPLC to afford tert-butyl ((S)-1-(4-((S)-(5-cyclopropylisoxazole-3-carboxamido)(phenyl)methyl)piperidin-1-yl)-1-oxopropan-2-yl)carbamate (0.13 g, 18%) and tert-butyl ((S)-1-(4-((R)-(5-cyclopropylisoxazole-3-carboxamido)(phenyl)methyl)piperidin-1-yl)-1-oxopropan-2-yl)carbamate (0.12 g, 17.4%).

Step 2: Synthesis of N—((S)-(1-((S)-2-aminopropanoyl)piperidin-4-yl)(phenyl)methyl)-5-cyclopropylisoxazole-3-carboxamide hydrochloride

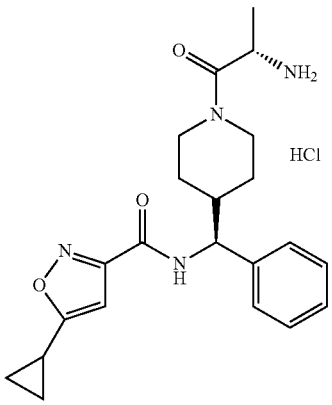 [SMILES: C[C@H](N)C(=O)N1CCC([C@H](NC(=O)c2cc(C3CC3)on2)c2ccccc2)CC1 ; Cl]

To a stirred solution of tert-butyl ((S)-1-(4-((S)-(5-cyclopropylisoxazole-3-carboxamido)(phenyl)methyl)piperidin-1-yl)-1-oxopropan-2-yl)carbamate (0.05 g, 0.126 mmol) in dioxane (1 mL) at 0° C. was added 4 M dioxane:HCl (3 mL). The reaction mixture was stirred at RT for 1 h. The progress of the reaction was monitored by TLC. After complete consumption of starting material the solvent was removed under reduced pressure to obtain a crude residue. The material was purified by repeated washing with ether and pentane to obtain N—((S)-(1-((S)-2-aminopropanoyl)piperidin-4-yl)(phenyl)methyl)-5-cyclopropylisoxazole-3-carboxamide hydrochloride (0.035 g, 50%). $^1$H NMR (400 MHz, DMSO-$d_6$): δ 9.19 (dd, J=9.0, 6.3 Hz, 1H), 8.09 (s, 3H), 7.44-7.21 (m, 5H), 6.46 (s, 1H), 4.69 (q, J=10.0 Hz, 1H), 4.29 (s, 2H), 3.76 (d, J=13.7 Hz, 1H), 2.98-2.96 (m, 1H), 2.66-2.50 (m, 1H), 2.23-2.06 (m, 2H), 2.02-1.91 (m, 1H), 1.30 (d, J=6.8 Hz, 1H), 1.21 (dd, J=24.0, 9.9 Hz, 4H), 1.14-0.83 (m, 5H); LCMS: m/z=397.35 (M+H)$^+$.

Step 2: Synthesis of N—((R)-(1-((S)-2-aminopropanoyl)piperidin-4-yl)(phenyl)methyl)-5-cyclopropylisoxazole-3-carboxamide hydrochloride

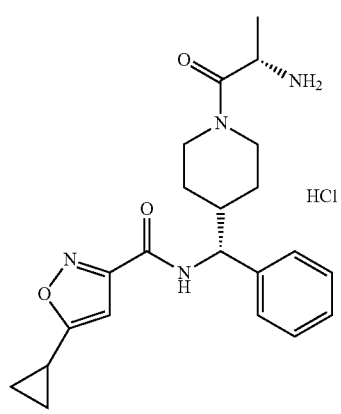 [SMILES: C[C@H](N)C(=O)N1CCC([C@@H](NC(=O)c2cc(C3CC3)on2)c2ccccc2)CC1 ; Cl]

To a stirred solution of tert-butyl ((S)-1-(4-((R)-(5-cyclopropylisoxazole-3-carboxamido)(phenyl)methyl)piperidin-1-yl)-1-oxopropan-2-yl)carbamate (0.06 g, 0.12 mmol) in dioxane (1 mL) at 0° C. was added 4 M dioxane:HCl (3 mL). The reaction mixture was stirred at RT for 1 h. The progress of the reaction was monitored by TLC. After complete consumption of starting material the solvent was removed under reduced pressure to obtain a crude residue. The material was purified by repeated washing with ether and pentane to obtain N—((R)-(1-((S)-2-aminopropanoyl)piperidin-4-yl)(phenyl)methyl)-5-cyclopropylisoxazole-3-carboxamide (0.02 g, 30%). $^1$H NMR (400 MHz, DMSO-$d_6$): δ 9.20 (t, J=8.8 Hz, 1H), 8.08 (s, 3H), 7.46-7.21 (m, 5H), 6.46 (d, J=1.5 Hz, 1H), 4.7-4.68 (m, 1H), 4.35-4.32 (m, 2H), 3.90 (d, J=13.7 Hz, 1H), 3.07-2.87 (m, 1H), 2.66-2.51 (m, 1H), 2.23-2.06 (m, 2H), 1.95 (d, J=11.4 Hz, 1H), 1.36-1.00 (m, 8H), 1.01-0.82 (m, 2H); LCMS: m/z=397.22 (M+H)$^+$.

Example 7

Synthesis of N-((1-((S)-2-aminopropanoyl)piperidin-4-yl)(3-(pyridin-3-ylcarbamoyl)phenyl)methyl)-5-cyclopropylisoxazole-3-carboxamide hydrochloride (Cpd. No. 205

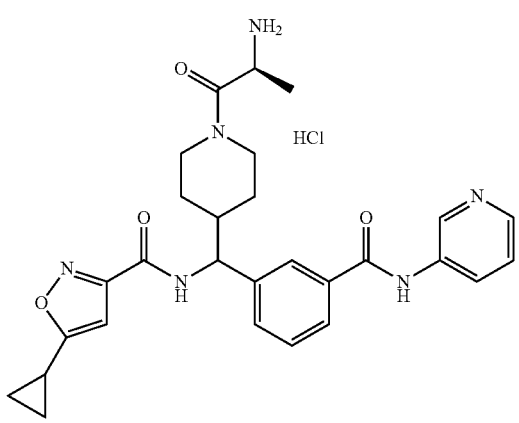 [SMILES: C[C@H](N)C(=O)N1CCC(C(NC(=O)c2cc(C3CC3)on2)c2cccc(C(=O)Nc3cccnc3)c2)CC1 ; Cl]

Step 1: Synthesis of tert-butyl 4-(hydroxy(3-(methoxycarbonyl)phenyl)methyl) piperidine-1-carboxylate

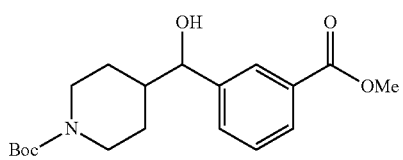 [SMILES: COC(=O)c1cccc(C(O)C2CCN(C(=O)OC(C)(C)C)CC2)c1]

To a stirred solution of methyl 3-iodobenzoate (3.0 g, 11.45 mmol) in anhydrous THF (100 mL) was added isopropyl magnesium chloride (6.27 mL, 12.59 mmol, 2M solution in THF) at −40° C. tert-Butyl 4-formylpiperidine-1-carboxylate (2.68 g, 12.59 mmol) was added. The reaction was stirred at rt overnight. The reaction was quenched with saturated NH$_4$Cl solution and extracted with ethyl acetate. The organic layer was washed with brine, dried over Na$_2$SO$_4$ and concentrated under reduced pressure to obtain a crude residue which was purified by column chromatography to afford tert-butyl 4-(hydroxy(3-(methoxycarbonyl)phenyl)methyl)piperidine-1-carboxylate (2.91 g, 73%). LCMS: m/z=350.15 (M+H)$^+$.

229

Step 2: Synthesis of tert-butyl 4-(3-(methoxycarbonyl)benzoyl)piperidine-1-carboxylate

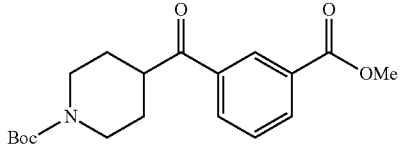 [SMILES: COC(=O)c1cccc(C(=O)C2CCN(C(=O)OC(C)(C)C)CC2)c1]

To a stirred solution of 4-(hydroxy(3-(methoxycarbonyl)phenyl)methyl)piperidine-1-carboxylate (1.9 g, 5.44 mmol) in DCM (30 mL) was added Dess Martin periodane (3.0 g, 7.07 mmol) at 0° C. The reaction mixture was stirred at rt for 1 h. The progress of the reaction was monitored by TLC. After complete consumption of starting material, the reaction was quenched by the addition of a mixture of saturated solution of $Na_2S_2O_3$ (10 mL) and $NaHCO_3$ (10 mL). The organic layer was extracted, dried over anhydrous $Na_2SO_4$, concentrated under reduced pressure to obtain a crude residue which was purified by column chromatography to afford tert-butyl 4-(3-(methoxycarbonyl)benzoyl)piperidine-1-carboxylate (1.78 g, 94%). LCMS: m/z=348.15 (M+H)$^+$.

Step 3: Synthesis of tert-butyl 4-(amino(3-(methoxycarbonyl)phenyl)methyl)piperidine-1-carboxylate

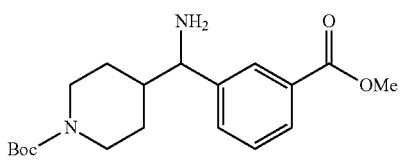 [SMILES: COC(=O)c1cccc(C(N)C2CCN(C(=O)OC(C)(C)C)CC2)c1]

To a stirred solution of tert-butyl 4-(3-(methoxycarbonyl)benzoyl)piperidine-1-carboxylate (1.5 g, 4.32 mmol) in methanol (30 mL) at 0° C. was added ammonium acetate (4.0 g, 51.8 mmol) followed by portionwise addition of sodium cyanoborohydride (1.0 g, 17.2 mmol). The reaction mixture was heated to reflux at 80° C. for 12 h. The progress of the reaction was monitored by TLC. After complete consumption of starting material, the reaction was quenched with dilute HCl solution and extracted with ethyl acetate. The organic layer was separated, washed with brine, dried over $Na_2SO_4$ and concentrated under reduced pressure to obtain a crude residue which was purified by column chromatography to afford tert-butyl 4-(amino(3-(methoxycarbonyl)phenyl)methyl)piperidine-1-carboxylate (1.05 g, 70%).

230

Step 4: Synthesis of tert-butyl 4-((5-cyclopropylisoxazole-3-carboxamido)(3-(methoxycarbonyl)phenyl)methyl)piperidine-1-carboxylate

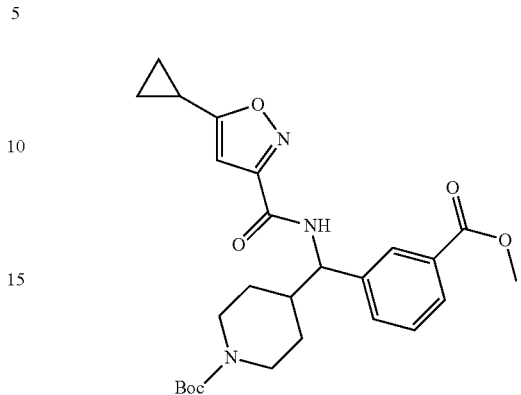

To a stirred solution of 5-cyclopropylisoxazole-3-carboxylic acid (0.65 g, 1.86 mmol) in DMF (10 mL) was added HATU (1.0 g, 2.8 mmol) and diisopropylethylamine (1.2 ml, 7.44 mmol). The reaction mixture was stirred for 10 min at 0° C. and then tert-butyl 4-(amino(3-(methoxycarbonyl)phenyl)methyl)piperidine-1-carboxylate (0.284 g, 1.86 mmol) was added. The reaction mixture was stirred at rt for 2 h. The progress of the reaction was monitored by TLC. After complete consumption of starting material, the reaction was quenched with water and extracted with ethyl acetate. The organic layer was separated, washed with brine, dried over $Na_2SO_4$ and concentrated under reduced pressure to obtain a crude residue which was purified by column chromatography to afford tert-butyl 4-((5-cyclopropylisoxazole-3-carboxamido)(3-(methoxycarbonyl) phenyl)methyl)piperidine-1-carboxylate (0.789 g, 95%).

Step 5: Synthesis of 3-((1-(tert-butoxycarbonyl)piperidin-4-yl)(5-cyclopropylisoxazole-3-carboxamido)methyl)benzoic acid

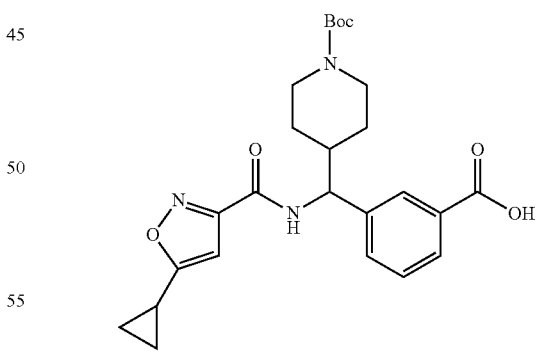

To a stirred solution of tert-butyl 4-((5-cyclopropylisoxazole-3-carboxamido)(3-(methoxycarbonyl)phenyl)methyl) piperidine-1-carboxylate (0.77 g, 1.59 mmol) in THF:MeOH:H$_2$O (1:1:1, 15 mL) was added lithium hydroxide (0.133 g, 3.18 mmol). The reaction mixture was then stirred at rt for 12 h. The progress of the reaction was monitored by TLC. After complete consumption of starting material the solvent was removed under reduced pressure to obtain a crude residue. The residue was taken up in MeOH and acidified with dilute HCl to pH=2. The reaction mixture was filtered and the filtrate was concentrated under reduced pressure to obtain 3-((1-(tert-butoxycarbonyl)piperidin-4-yl)(5-cyclopropylisoxazole-3-carboxamido)methyl)benzoic acid (0.580 g, crude).

Step 6: Synthesis of tert-butyl 4-((5-cyclopropylisoxazole-3-carboxamido)(3-(pyridin-3-ylcarbamoyl)phenyl)methyl)piperidine-1-carboxylate

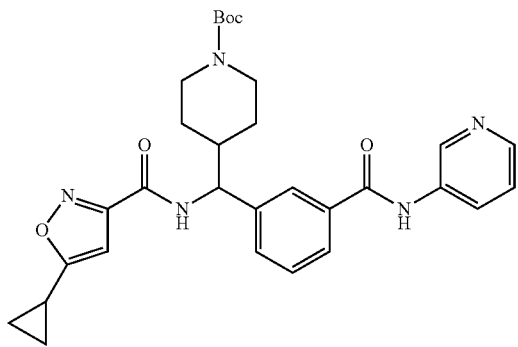 [SMILES: CC(C)(C)OC(=O)N1CCC(C(NC(=O)c2cc(C3CC3)on2)c2cccc(C(=O)Nc3cccnc3)c2)CC1]

To a stirred solution of 3-((1-(tert-butoxycarbonyl)piperidin-4-yl)(5-cyclopropylisoxazole-3-carboxamido)methyl)benzoic acid (0.5 g, 1.06 mmol) in DMF (3 mL) was added HATU (0.607 g, 1.59 mmol) and diisopropylethylamine (0.63 mL, 3.73 mmol). The solution was stirred for 10 min at 0° C. Then pyridin-3-amine (0.14 g, 1.49 mmol) was added and stirred at rt for 2 h. The progress of the reaction was monitored by TLC. After complete consumption of starting material, the reaction was quenched with water and extracted with ethyl acetate. The organic layer was washed with brine, dried over anhydrous Na$_2$SO$_4$ and concentrated under reduced pressure to obtain a crude residue which was purified by column chromatography to afford tert-butyl-4-((5-cyclopropylisoxazole-3-carboxamido)(3-(pyridin-3-ylcarbamoyl)phenyl)methyl)piperidine-1-carboxylate (0.445 g, 76%). LCMS: m/z=446.4 (M-Boc)$^+$.

Step 7: Synthesis of 5-cyclopropyl-N-(piperidin-4-yl(3-(pyridin-3-ylcarbamoyl)phenyl)methyl)isoxazole-3-carboxamide hydrochloride

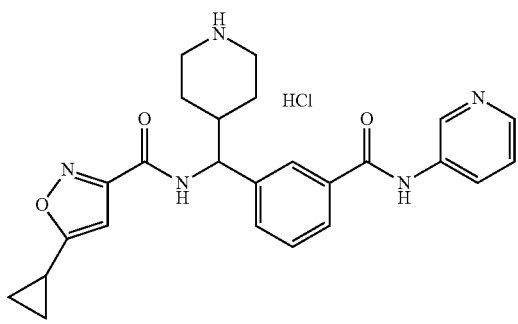 [SMILES: O=C(Nc1cccnc1)c1cccc(C(NC(=O)c2cc(C3CC3)on2)C2CCNCC2)c1 ; Cl]

To a stirred solution of tert-butyl-4-((5-cyclopropylisoxazole-3-carboxamido)(3-(pyridin-3-ylcarbamoyl)phenyl)methyl)piperidine-1-carboxylate (0.445 g, 0.81 mmol) in dioxane (4 mL) at 0° C. was added 4 M dioxane:HCl (8 mL) and the reaction mixture stirred at rt for 3 h. The progress of the reaction was monitored by TLC. After complete consumption of starting material the solvent was removed under reduced pressure to obtain a crude residue which was purified by repeated washing with ether and pentane to obtain 5-cyclopropyl-N-(piperidin-4-yl(3-(pyridin-3-ylcarbamoyl)phenyl)methyl) isoxazole-3-carboxamide hydrochloride (0.380 g, 96%). LCMS: m/z=446.25 (M+H)$^+$.

Step 8: Synthesis of tert-butyl ((2S)-1-(4-((5-cyclopropylisoxazole-3-carboxamido)(3-(pyridin-3-ylcarbamoyl)phenyl)methyl)piperidin-1-yl)-1-oxopropan-2-yl)carbamate

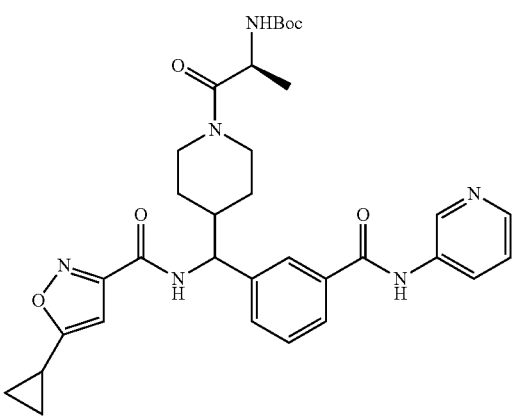 [SMILES: C[C@H](NC(=O)OC(C)(C)C)C(=O)N1CCC(C(NC(=O)c2cc(C3CC3)on2)c2cccc(C(=O)Nc3cccnc3)c2)CC1]

To a stirred solution of (S)-2-((tert-butoxycarbonyl)amino)propanoic acid (0.089 g, 0.474 mmol) in DMF (3 mL) was added HATU (0.225 g, 0.592 mmol) and diisopropylethylamine (0.23 mL, 1.38 mmol). The solution was stirred for 10 min at 0° C. Next 5-cyclopropyl-N-(piperidin-4-yl(3-(pyridin-3-ylcarbamoyl)phenyl)methyl) isoxazole-3-carboxamide hydrochloride (0.19 g, 0.395 mmol) was added and the reaction stirred at rt for 2 h. The progress of the reaction was monitored by TLC. After complete consumption of starting material, the reaction was quenched with water and extracted with ethyl acetate. The organic layer was separated, washed with brine, dried over anhydrous Na$_2$SO$_4$ and concentrated under reduced pressure to obtain a crude residue which was purified by column chromatography to afford tert-butyl ((2S)-1-(4-((5-cyclopropylisoxazole-3-carboxamido)(3-(pyridin-3-ylcarbamoyl)phenyl)methyl)piperidin-1-yl)-1-oxopropan-2-yl)carbamate (0.170 g, 83%). LCMS: m/z=517.4 (M-Boc)$^+$.

Step 9: Synthesis of N-((1-((S)-2-aminopropanoyl)piperidin-4-yl)(3-(pyridin-3-ylcarbamoyl)phenyl)methyl)-5-cyclopropylisoxazole-3-carboxamide hydrochloride

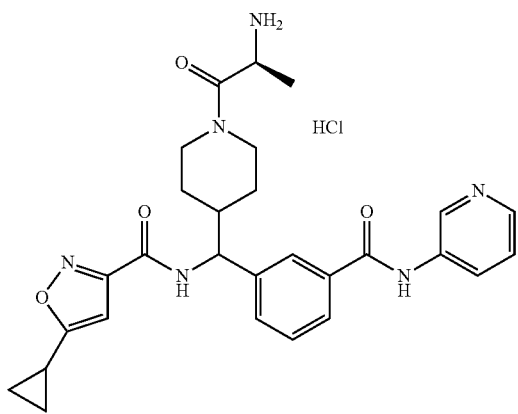 [SMILES: C[C@H](N)C(=O)N1CCC(C(NC(=O)c2cc(C3CC3)on2)c2cccc(C(=O)Nc3cccnc3)c2)CC1 ; Cl]

To a stirred solution of tert-butyl ((2S)-1-(4-((5-cyclopropylisoxazole-3-carboxamido)(3-(pyridin-3-ylcarbamoyl)phenyl)methyl)piperidin-1-yl)-1-oxopropan-2-yl)carbamate (0.170 g, 0.275 mmol) in dioxane (3 mL) at 0° C. was added 4 M dioxane:HCl (2 mL) and the reaction mixture stirred at rt for 3 h. The progress of the reaction was monitored by TLC. After complete consumption of starting material the solvent was removed under reduced pressure to obtain a crude residue which was purified by repeated washing with ether and pentane to obtain N-((1-((S)-2-aminopropanoyl)piperidin-4-yl)(3-(pyridin-3-ylcarbamoyl)phenyl)methyl)-5-cyclopropylisoxazole-3-carboxamide hydrochloride (0.135 g, 83%). $^1$H NMR (400 MHz, DMSO-$d_6$)(mixture of diastereomers): δ 11.09 (d, J=14.5 Hz, 1H), 9.38-9.24 (m, 2H), 8.64 (d, J=8.0 Hz, 1H), 8.55 (dd, J=5.4, 1.4 Hz, 1H), 8.17-8.09 (m, 4H), 8.03-7.94 (m, 1H), 7.84 (dd, J=8.4, 5.2 Hz, 1H), 7.71 (dd, J=7.7, 5.0 Hz, 1H), 7.56 (td, J=7.7, 4.2 Hz, 1H), 6.51 (d, J=3.7 Hz, 1H), 4.90-4.74 (m, 1H), 4.48-4.32 (m, 1H), 4.35-4.23 (m, 2H), 3.92 (d, J=13.6 Hz, 1H), 3.79 (dd, J=13.8, 9.2 Hz, 1H), 3.69-3.53 (m, 1H), 3.18-2.91 (m, 2H), 2.67-2.51 (m, 2H), 2.19-2.17 (m, 3H), 1.97 (d, J=12.6 Hz, 1H), 1.35-0.97 (m, 2H), 0.95-0.82 (m, 2H); LCMS: m/z=517.35 (M+H)$^+$.

Example 8

Synthesis of 5-cyclopropyl-N-(piperidin-4-ylmethyl)isoxazole-3-carboxamide hydrochloride (Cpd. No. 4)

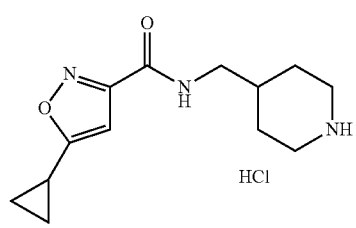 [SMILES: O=C(NCC1CCNCC1)c1cc(C2CC2)on1 ; Cl]

Step 1: Synthesis of tert-butyl 4-((5-cyclopropylisoxazole-3-carboxamido)methyl) piperidine-1-carboxylate

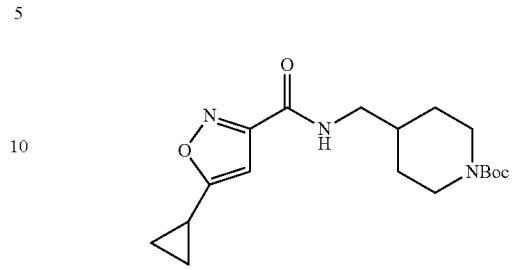

To a stirred solution of tert-butyl 4-(aminomethyl)piperidine-1-carboxylate (0.514 g, 2.43 mmol) in DCM (10 mL) was added triethylamine (0.68 mL, 4.87 mmol) and the solution was stirred at 0° C. for 10 min. 5-Cyclopropylisoxazole-3-carbonyl chloride (0.6 g, 3.166 mmol) in DCM (5 mL) was added dropwise and the reaction mixture stirred at rt overnight. The progress of the reaction was monitored by TLC. After complete consumption of starting material, the reaction was diluted with excess of DCM and washed with water and, the organic layer was separated, washed with brine, dried using Na$_2$SO$_4$ and concentrated under reduced pressure to obtain a residue which was purified by column chromatography to afford tert-butyl 4-((5-cyclopropylisoxazole-3-carboxamido)methyl)piperidine-1-carboxylate (0.750 g, 89%). $^1$H NMR (DMSO-$d_6$, 400 MHz) δ 8.69-8.66 (t, J=5.8 Hz, 1H) 6.46 (s, 1H), 3.90 (d, J=12.4 Hz, 2H), 3.11-3.08 (m, J=6.4 Hz, 2H), 2.67 (brs, 2H), 2.19-2.15 (m, 1H), 1.70-1.68 (m, 1H), 1.6 (brs, 1H), 1.58 (brs, 1H), 1.38 (s, 9H), 1.11-1.06 (m, 2H), 0.90-0.89 (m, 4H).

Step 2: Synthesis of 5-cyclopropyl-N-(piperidin-4-ylmethyl)isoxazole-3-carboxamide hydrochloride

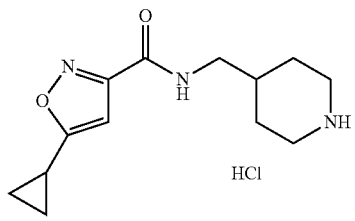 [SMILES: O=C(NCC1CCNCC1)c1cc(C2CC2)on1 ; Cl]

To a stirred solution of tert-butyl 4-((5-cyclopropylisoxazole-3-carboxamido)methyl)piperidine-1-carboxylate (0.750 g, 2.148 mmol) in MeOH (4 mL) at 0° C. was added 4 M methanolic HCl (6 mL). The reaction was stirred at rt for 16 hours. The progress of the reaction was monitored by TLC. After complete consumption of starting material the solvent was removed under reduced pressure and the residue was washed with DCM and hexanes to obtain 5-cyclopropyl-N-(piperidin-4-ylmethyl)isoxazole-3-carboxamide hydrochloride (0.590 g, 96%). $^1$H NMR (400 MHz, DMSO-$d_6$) δ 8.88 (s, 1H), 8.78 (t, J=6.1 Hz, 1H), 8.59 (m, 1H), 6.49 (s, 1H), 3.27-3.09 (m, 4H), 2.80 (q, J=11.8 Hz, 2H), 2.18 (m, 1H), 1.79 (m, 3H), 1.41-1.26 (m, 2H), 1.09 (m, 2H), 1.00-0.87 (m, 2H); LCMS: m/z=250.05 (M+H)$^+$.

Example 9

Synthesis of (S)—N-((1-(2-amino-3-methylbutanoyl)piperidin-4-yl)methyl)-5-cyclopropylisoxazole-3-carboxamide hydrochloride (Cpd. No. 226)

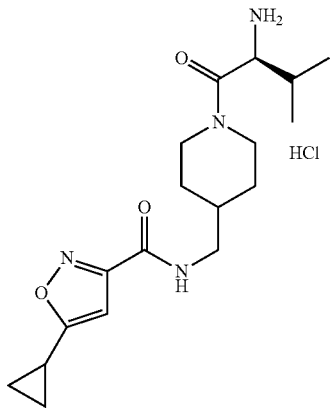 [SMILES: CC(C)[C@H](N)C(=O)N1CCC(CNC(=O)c2cc(C3CC3)on2)CC1 ; Cl]

Step 1: Synthesis of (S)-tert-butyl (1-(4-((5-cyclopropylisoxazole-3-carboxamido)methyl)piperidin-1-yl)-3-methyl-1-oxobutan-2-yl)carbamate

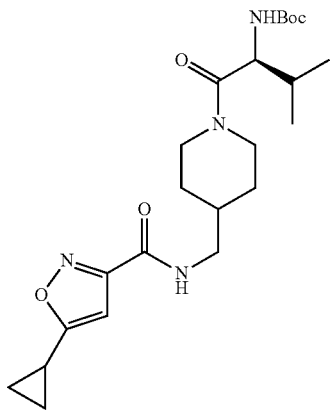 [SMILES: CC(C)[C@H](NC(=O)OC(C)(C)C)C(=O)N1CCC(CNC(=O)c2cc(C3CC3)on2)CC1]

To a stirred solution of (S)-2-((tert-butoxycarbonyl)amino)-3-methylbutanoic acid (0.156 g, 0.72 mmol) in DMF (2 mL) was added EDCI (0.172 g, 0.9 mmol), HOBt (0.121 g, 0.9 mmol), and triethylamine (0.3 mL, 1.8 mmol). The solution was stirred for 30 min at 0° C. 5-Cyclopropyl-N-(piperidin-4-ylmethyl)isoxazole-3-carboxamide (0.15 g, 0.6 mmol) was added and the reaction stirred at rt overnight. The progress of the reaction was monitored by TLC. After complete consumption of starting material, the reaction was quenched with water and extracted with ethyl acetate. The organic layer was washed with brine, dried over anhydrous $Na_2SO_4$ and concentrated under reduced pressure to obtain a crude residue which was purified by column chromatography to afford (S)-tert-butyl (1-(4-((5-cyclopropylisoxazole-3-carboxamido)methyl)piperidin-1-yl)-3-methyl-1-oxobutan-2-yl)carbamate (0.185 g, 68%). LCMS m/z=349.1 (M-Boc)$^+$.

Step 2: Synthesis of (S)—N-((1-(2-amino-3-methylbutanoyl)piperidin-4-yl)methyl)-5-cyclopropylisoxazole-3-carboxamide hydrochloride

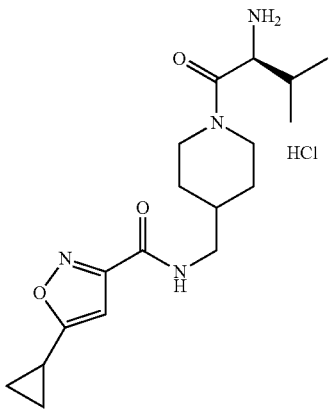 [SMILES: CC(C)[C@H](N)C(=O)N1CCC(CNC(=O)c2cc(C3CC3)on2)CC1 ; Cl]

To a stirred solution of (S)-tert-butyl (1-(4-((5-cyclopropylisoxazole-3-carboxamido)methyl)piperidin-1-yl)-3-methyl-1-oxobutan-2-yl)carbamate (0.185 g, 0.33 mmol) in dioxane (1 mL) at 0° C. was added 4M dioxane:HCl (3 mL). The reaction mixture was stirred at rt for 3 h. The progress of the reaction was monitored by TLC. After complete consumption of starting material the solvent was removed under reduced pressure to obtain a crude residue. The material was purified by repeated washing with ether and pentane to obtain (S)—N-((1-(2-amino-3-methylbutanoyl)piperidin-4-yl)methyl)-5-cyclopropylisoxazole-3-carboxamide hydrochloride (0.1 g, 69%). $^1$H NMR (400 MHz, DMSO-$d_6$): δ 8.75 (dt, J=7.1, 3.4 Hz, 1H), 8.03 (s, 3H), 6.48 (s, 1H), 4.43-4.31 (m, 1H), 4.27 (s, 1H), 3.93 (d, J=13.6 Hz, 1H), 3.21-2.97 (m, 3H), 2.66-2.53 (m, 1H), 2.18 (tt, J=8.4, 5.0 Hz, 1H), 2.01 (h, J=6.9 Hz, 1H), 1.89-1.78 (m, 1H), 1.70 (t, J=12.7 Hz, 1H), 1.26 (dd, J=10.3, 4.4 Hz, 1H), 1.16-0.82 (m, 12H); LCMS: m/z=349.3 (M+H)$^+$.

Example 10

Synthesis of N-(4-(1-amino-3-(pyridin-3-yl)propyl)phenyl)-5-cyclopropylisoxazole-3-carboxamide (Cpd. No. 149)

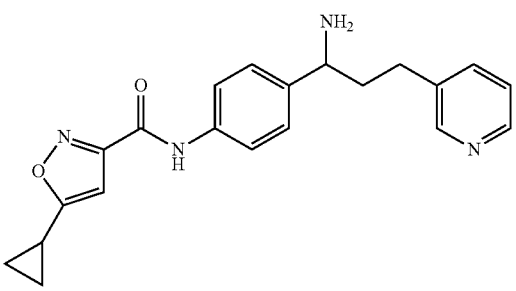 [SMILES: NC(CCc1cccnc1)c1ccc(NC(=O)c2cc(C3CC3)on2)cc1]

Step 1: Synthesis of (E)-1-(4-aminophenyl)-3-(pyridin-3-yl)prop-2-en-1-one

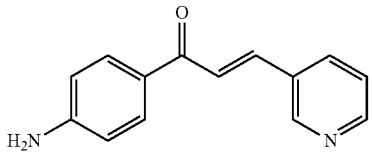 [SMILES: Nc1ccc(C(=O)/C=C/c2cccnc2)cc1]

To a stirred solution of 1-(4-aminophenyl)ethanone (2.0 g, 14.81 mmol) in MeOH:Water (1:1, 30 mL) was added nicotinaldehyde (1.58 g, 14.81 mmol) and potassium hydroxide (1.24 g, 22.22 mmol). The reaction mixture was stirred at rt for 12 h. The progress of the reaction was monitored by TLC. After complete consumption of starting material, the reaction was quenched with dilute HCl and extracted with ethyl acetate. The organic layer was separated, washed with brine, dried over anhydrous $Na_2SO_4$ and concentrated under reduced pressure to obtain a crude residue which was purified by column chromatography to afford (E)-1-(4-aminophenyl)-3-(pyridin-3-yl)prop-2-en-1-one (2.0 g, 60%). LCMS: m/z=225.3 $(M+H)^+$.

Step 2: Synthesis of 1-(4-aminophenyl)-3-(pyridin-3-yl)propan-1-one

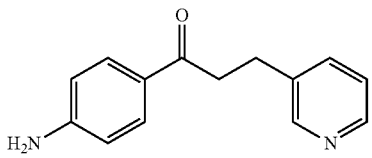 [SMILES: Nc1ccc(C(=O)CCc2cccnc2)cc1]

To a stirred solution of (E)-1-(4-aminophenyl)-3-(pyridin-3-yl)prop-2-en-1-one (2.0 g, 8.9 mmol) in methanol (20 mL), 10% palladium-carbon (0.2 g) was added and the reaction mixture stirred under hydrogen atmosphere at 1 atm pressure at rt for 3 h. The progress of the reaction was monitored by TLC. After complete consumption of starting material, the reaction mixture was filtered through a pad of Celite and the filtrate was concentrated under reduced pressure to obtain a crude residue of 1-(4-aminophenyl)-3-(pyridin-3-yl)propan-1-one (1.5 g) which was used in the next step without purification. LCMS: m/z=227.05 $(M+H)^+$.

Step 3: Synthesis of 5-cyclopropyl-N-(4-(3-(pyridin-3-yl)propanoyl)phenyl)isoxazole-3-carboxamide

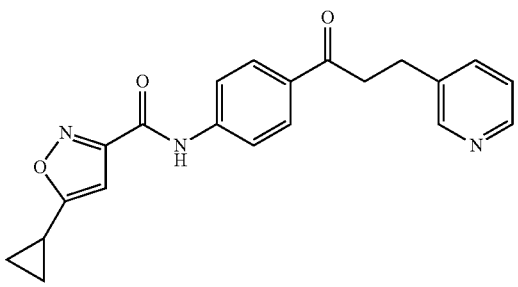 [SMILES: O=C(CCc1cccnc1)c1ccc(NC(=O)c2cc(C3CC3)on2)cc1]

To a stirred solution of 5-cyclopropylisoxazole-3-carboxylic acid (0.2 g, 1.3 mmol) and 2 drops of DMF in DCM (10 mL) was added oxalyl chloride (1 mL). The reaction mixture was stirred at rt for 2 h. After complete consumption of starting material, the solvent was removed under reduced pressure to obtain a crude residue. The residue was redissolved in DCM (5 mL). Triethylamine (0.35 mL, 2.61 mmol) and a solution of 1-(4-aminophenyl)-3-(pyridin-3-yl)propan-1-one (0.354 g, 1.56 mmol) in DCM (1 mL) was added at 0° C. to the reaction mixture. The mixture was stirred at rt for 1 h. The progress of the reaction was monitored by TLC. After complete consumption of starting material, the reaction mixture was quenched with saturated $NaHCO_3$ solution and extracted with DCM. The organic layer was separated, washed with brine, dried over $Na_2SO_4$ and concentrated under reduced pressure to obtain a crude residue which was purified by column chromatography to afford 5-cyclopropyl-N-(4-(3-(pyridin-3-yl)propanoyl)phenyl)isoxazole-3-carboxamide (0.4 g, 42%). LCMS: m/z=362.05 $(M+H)^+$.

Step 4: Synthesis of N-(4-(1-amino-3-(pyridin-3-yl)propyl)phenyl)-5-cyclopropylisoxazole-3-carboxamide

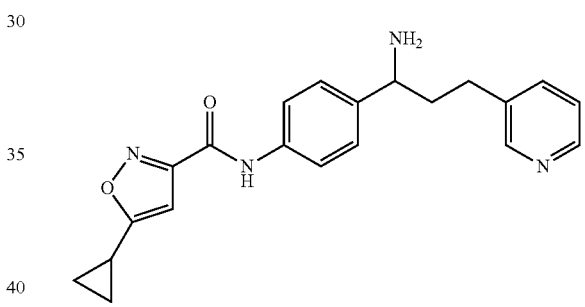

To a stirred solution of 5-cyclopropyl-N-(4-(3-(pyridin-3-yl)propanoyl)phenyl)isoxazole-3-carboxamide (0.05 g, 0.13 mmol) in dry MeOH (10 mL) was added ammonium acetate (0.127 g, 1.66 mmol) and the reaction stirred at rt for 15 min. Sodium cyanoborohydride (0.034 g, 0.55 mmol) was then added. The reaction mixture was heated to reflux for 16 h. The progress of the reaction was monitored by TLC. After complete consumption of starting material, the reaction was quenched with 0.5 M NaOH solution and extracted with ethyl acetate. The organic layer was washed with brine, dried over $Na_2SO_4$ and concentrated under reduced pressure to obtain a crude residue which was purified by prep HPLC to afford compound N-(4-(1-amino-3-(pyridin-3-yl)propyl)phenyl)-5-cyclopropylisoxazole-3-carboxamide (0.030 g, 12%). $^1$H NMR (400 MHz, Methanol-d4): δ 8.41-8.29 (m, 2H), 7.88-7.79 (m, 2H), 7.69-7.65 (m, 1H), 7.49-7.41 (m, 2H), 7.39-7.35 (m, 1H), 6.48 (s, 1H), 4.21 (dd, J=8.8, 6.3 Hz, 1H), 2.70-2.51 (m, 2H), 2.34-2.23 (m, 2H), 2.2-2.15 (m, 1H), 1.31 (d, J=18.9 Hz, 1H), 1.21-1.11 (m, 2H), 1.04-0.95 (m, 2H); LCMS: m/z=362.17 $(M+1)^+$.

Example 11

Synthesis of N-(4-aminobutyl)-5-cyclopropylisoxazole-3-carboxamide hydrochloride (Cpd. No. 254)

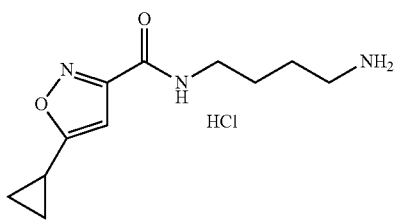 [SMILES: NCCCCNC(=O)c1cc(C2CC2)on1 ; Cl]

Step 1: Synthesis of tert-butyl (4-(5-cyclopropylisoxazole-3-carboxamido)butyl)carbamate

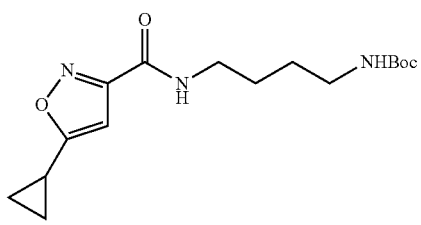 [SMILES: CC(C)(C)OC(=O)NCCCCNC(=O)c1cc(C2CC2)on1]

To a stirred solution of 5-cyclopropylisoxazole-3-carboxylic acid (0.5 g, 3.2 mmol) in DMF (3 mL) was added EDCI.HCl (0.93 g, 4.9 mmol), HOBt (0.66 g, 4.9 mmol) and triethylamine (1.41 mL, 9.8 mmol). The solution was stirred for 10 min at 0° C. After that tert-butyl (4-aminobutyl) carbamate (0.67 g, 3.5 mmol) was added and the reaction stirred at rt for 16 h. The progress of the reaction was monitored by TLC. After complete consumption of starting material, the reaction was quenched with water and extracted with ethyl acetate. The organic layer was washed with brine, dried over anhydrous $Na_2SO_4$ and concentrated under reduced pressure to obtain a crude residue which was purified by column chromatography to afford tert-butyl (4-(5-cyclopropylisoxazole-3-carboxamido)butyl)carbamate (0.25 g, 20%). LCMS: m/z=234.05 (M-Boc)$^+$.

Step 2: Synthesis of N-(4-aminobutyl)-5-cyclopropylisoxazole-3-carboxamide hydrochloride

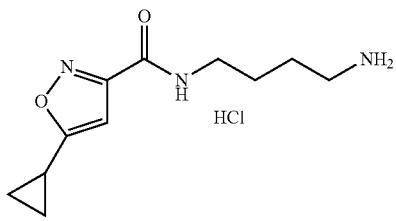 [SMILES: NCCCCNC(=O)c1cc(C2CC2)on1 ; Cl]

To a stirred solution of tert-butyl (4-(5-cyclopropylisoxazole-3-carboxamido)butyl)carbamate (0.24 g, 0.74 mmol) in dioxane (2 mL), was added 4M dioxane:HCl (2 mL) at 0° C. and the reaction mixture was stirred at rt for 5 h. The progress of the reaction was monitored by TLC. After complete consumption of starting material, the solvent was removed under reduced pressure to obtain a crude residue which was purified by Prep HPLC to obtain N-(4-aminobutyl)-5-cyclopropylisoxazole-3-carboxamide hydrochloride (0.16 g, 96%). $^1$H NMR (400 MHz, DMSO-$d_6$): δ 8.71 (t, J=5.9 Hz, 1H), 7.76 (s, 2H), 6.48 (s, 1H), 3.23 (q, J=6.0 Hz, 2H), 2.78 (q, J=6.1 Hz, 2H), 2.18 (td, J=8.6, 4.5 Hz, 1H), 1.54 (p, J=3.4 Hz, 4H), 1.1-1.08 (m, 2H), 0.96-0.87 (m, 2H); LCMS (method A, ESI): m/z=224.10 (M+H).

Example 12

Synthesis of (S)—N-(4-(2-aminopropanamido)butyl)-5-cyclopropylisoxazole-3-carboxamide hydrochloride (Cpd. No. 249)

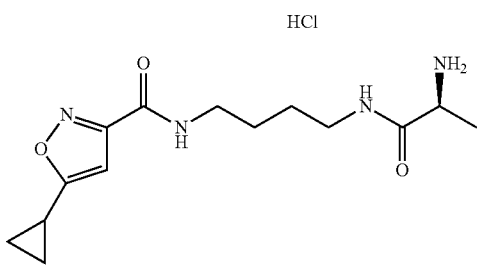 [SMILES: Cl ; C[C@H](N)C(=O)NCCCCNC(=O)c1cc(C2CC2)on1]

Step 1: Synthesis of (S)-tert-butyl (1-((4-(5-cyclopropylisoxazole-3-carboxamido)butyl) amino)-1-oxopropan-2-yl)carbamate

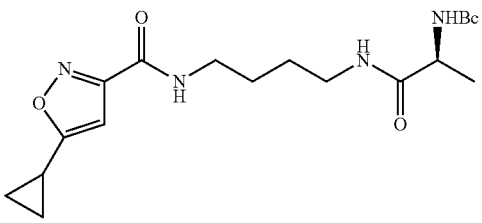

To a stirred solution of (S)-2-((tert-butoxycarbonyl)amino)propanoic acid (0.08 g, 0.37 mmol) in DMF (2 mL) was added EDCI.HCl (0.098 g, 0.51 mmol), HOBt (0.069 g, 0.51 mmol), and triethylamine (0.14 mL, 1.0 mmol). The solution was stirred for 10 min at 0° C. N-(4-Aminobutyl)-5-cyclopropylisoxazole-3-carboxamide (0.065 g, 0.34 mmol) was added and the reaction stirred at rt for 16 h. The progress of the reaction was monitored by TLC. After complete consumption of starting material, the reaction was quenched with water and extracted with ethyl acetate. The organic layer was washed with brine, dried over anhydrous $Na_2SO_4$ and concentrated under reduced pressure to obtain a crude residue which was purified by column chromatography to afford (S)-tert-butyl (1-((4-(5-cyclopropylisoxazole-3-carboxamido)butyl)amino)-1-oxopropan-2-yl)carbamate (0.08 g, 59%). LCMS: m/z=296.15 (M-Boc)$^+$.

Step 2: Synthesis of (S)—N-(4-(2-aminopropanamido)butyl)-5-cyclopropylisoxazole-3-carboxamide hydrochloride

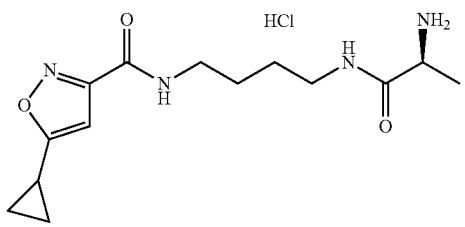 [SMILES: C[C@H](N)C(=O)NCCCCNC(=O)c1cc(C2CC2)on1 ; Cl]

To a stirred solution of (S)-tert-butyl (1-((4-(5-cyclopropylisoxazole-3-carboxamido)butyl)amino)-1-oxopropan-2-yl)carbamate (0.08 g, 0.20 mmol) in dioxane (2 mL) at 0° C. was added 4M dioxane:HCl solution (4 mL). The reaction mixture was stirred at rt for 5 h. The progress of the reaction was monitored by TLC. After complete consumption of starting material, the solvent was removed under reduced pressure to obtain a crude residue which was purified by repeated washing with ether and pentane to obtain (S)—N-(4-(2-aminopropanamido)butyl)-5-cyclopropylisoxazole-3-carboxamide hydrochloride (0.049 g, 83%). $^1$H NMR (400 MHz, DMSO-$d_6$): δ 8.67 (t, J=5.9 Hz, 1H), 8.39 (t, J=5.6 Hz, 1H), 8.10 (s, 3H), 6.47 (s, 1H), 3.80-3.70 (m, 1H), 3.26-3.03 (m, 4H), 2.24-2.12 (m, 1H), 1.56-1.36 (m, 4H), 1.33 (d, J=6.9 Hz, 3H), 1.16-1.02 (m, 2H), 0.96-0.87 (m, 2H); LCMS (method A, ESI): m/z=295.15 (M+H)$^+$.

Example 13

Synthesis of N-((1r,4r)-4-aminocyclohexyl)-5-(2-hydroxyethyl)isoxazole-3-carboxamide hydrochloride (Cpd. No. 9)

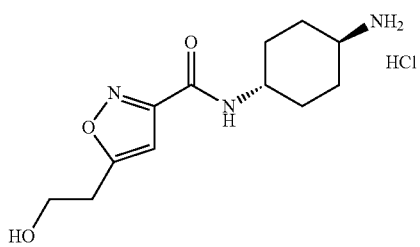 [SMILES: N[C@H]1CC[C@H](NC(=O)c2cc(CCO)on2)CC1 ; Cl]

Step 1: Synthesis of ethyl 5-(2-hydroxyethyl)isoxazole-3-carboxylate

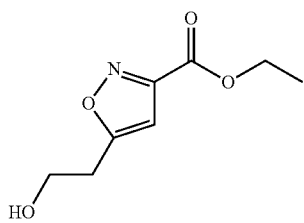

To a stirred solution of but-3-yn-1-ol (2 g, 28.5 mmol) in ethanol (15 mL), was added ethyl nitro acetate (7.59 g, 57.06 mmol) and DABCO (0.32 g, 2.85 mmol). The reaction was heated in a sealed tube at 80° C. The progress of the reaction was monitored by TLC. After complete consumption of staring material the reaction was quenched with water and extracted with ethyl acetate, the organic layer was separated, washed with brine, dried using $Na_2SO_4$ and concentrated under reduced pressure to obtain a residue which was purified by column chromatography to obtain ethyl 5-(2-hydroxyethyl)isoxazole-3-carboxylate (3.1 g, 59%). LCMS: m/z=186 (M+H)$^+$.

Step 2: Synthesis of 5-(2-hydroxyethyl)isoxazole-3-carboxylic acid

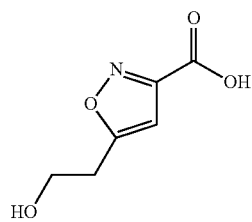 [SMILES: O=C(O)c1cc(CCO)on1]

To a stirred solution of ethyl 5-(2-hydroxyethyl)isoxazole-3-carboxylate (0.7 g, 3.78 mmol) in THF:MeOH:$H_2O$ (1:1:1, 15 ml) was added LiOH (0.317 g, 7.56 mmol). The reaction was stirred at rt for 16 hr. The progress of the reaction was monitored by TLC. After complete consumption of starting material, the solvent was removed under reduced pressure and the residue was acidified with dilute HCl to pH 2. The solid precipitated was collected by filtration and dried under reduced pressure to obtain 5-(2-hydroxyethyl)isoxazole-3-carboxylic acid (0.529 g, crude). $^1$H NMR (400 MHz, DMSO-$d_6$): δ 11.0 (brs, 1H), 6.40 (s, 1H), 3.69-3.65 (m, 2H), 3.0-2.95 (m, 2H).

Step 3: Synthesis of pentafluorophenyl 5-(2-hydroxyethyl)isoxazole-3-carboxylate

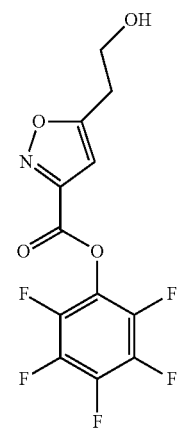 [SMILES: O=C(Oc1c(F)c(F)c(F)c(F)c1F)c1cc(CCO)on1]

To a solution of 5-(2-hydroxyethyl)isoxazole-3-carboxylic acid (0.529 g, 1.27 mmol) in DMF (5 mL) at 0° C. under an $N_2$ atmosphere was added DCC (0.26 g, 1.27 mmol) followed by pentafluorophenol (0.233 g, 1.27 mmol). The reaction was stirred at rt for 2 h. The progress of the reaction was monitored by TLC. After complete consumption of starting material, the reaction was quenched with water and extracted with ethyl acetate. The organic layer was separated, washed with brine, dried using $Na_2SO_4$ and concentrated under reduced pressure to obtain a residue which was purified by column chromatography to give pentafluorophenyl 5-(2-hydroxyethyl)isoxazole-3-carboxylate (0.26 g, 63%). $^1$H NMR (400 MHz, DMSO-$d_6$): δ 6.40 (s, 1H), 3.7-3.65 (m, 2H), 3.0-2.96 (m, 2H).

Step 4: Synthesis of tert-butyl ((1r,4r)-4-(5-(2-hydroxyethyl)isoxazole-3-carboxamido)cyclohexyl)carbamate

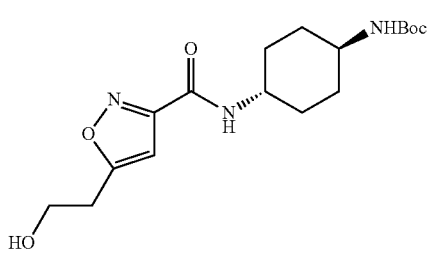 [SMILES: CC(C)(C)OC(=O)N[C@H]1CC[C@H](NC(=O)c2cc(CCO)on2)CC1]

To a stirred solution of pentafluorophenyl 5-(2-hydroxyethyl)isoxazole-3-carboxylate (0.25 g, 0.77 mmol) in DMF (5 mL) was added tert-butyl ((1r, 4r)-4-aminocyclohexyl)carbamate (0.16 g, 0.77 mmol). The reaction was stirred at rt for 2 hr. and the progress of the reaction was monitored by TLC. After complete consumption of starting material, the reaction was quenched with water and extracted with ethyl acetate. The organic layer was separated, washed with brine, dried using $Na_2SO_4$ and concentrated under reduced pressure to obtain a residue which was purified by column chromatography to obtain tert-butyl ((1r,4r)-4-(5-(2-hydroxyethyl)isoxazole-3-carboxamido)cyclohexyl)carbamate (0.130 g, 47%). LCMS: m/z=254 (M+H)$^+$.

Step 5: Synthesis of N-((1r,4r)-4-aminocyclohexyl)-5-(2-hydroxyethyl)isoxazole-3-carboxamide hydrochloride

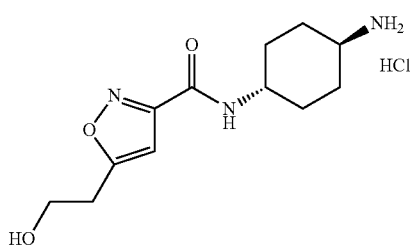 [SMILES: N[C@H]1CC[C@H](NC(=O)c2cc(CCO)on2)CC1 ; Cl]

To a stirred solution of tert-butyl ((1r,4r)-4-(5-(2-hydroxyethyl)isoxazole-3-carboxamido)cyclohexyl)carbamate (0.1 g, 0.28 mmol) in methanol (1 mL) at 0° C. was added 4 M methanol:HCl (10 mL). The reaction was at rt stirred for 2 h. The progress of the reaction was monitored by TLC. After complete consumption of starting material, the solvent was removed under reduced pressure and the residue was purified by washings with diethyl ether and hexane to obtain compound N-((1r,4r)-4-aminocyclohexyl)-5-(2-hydroxyethyl)isoxazole-3-carboxamide hydrochloride (0.060 g, 83%). $^1$H NMR (400 MHz, DMSO-$d_6$) δ 8.62-8.54 (m, 1H), 8.04 (d, J=5.6 Hz, 3H), 6.58 (s, 1H), 4.89 (s, 1H), 3.70 (t, J=6.3 Hz, 3H), 2.93 (t, J=6.3 Hz, 3H), 2.02-1.95 (m, 2H), 1.85 (d, J=7.1 Hz, 2H), 1.51-1.34 (m, 4H); LCMS: m/z=254 (M+H)$^+$.

Example 14

Synthesis of N-((1r,4r)-4-aminocyclohexyl)-5-cyclopropyl-4-iodoisoxazole-3-carboxamide hydrochloride (Cpd. No. 8

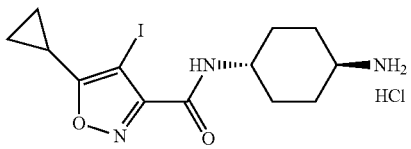 [SMILES: N[C@H]1CC[C@H](NC(=O)c2noc(C3CC3)c2I)CC1 ; Cl]

Step 1: Synthesis of ethyl 5-cyclopropyl-4-iodoisoxazole-3-carboxylate

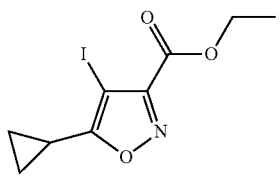

To the stirred solution of ethyl 5-cyclopropylisoxazole-3-carboxylate (1 g, 5.52 mmol) in TFA (16 ml), was added N-iodosuccinimide (1.48 g, 6.62 mmol) and reaction mixture stirred at rt for 2 h. The progress of the reaction was monitored by TLC. After complete consumption of starting material, the reaction was quenched with water and extracted with ethyl acetate. The organic layer was dried over sodium sulphate and evaporated under reduced pressure. The material was purified by column chromatography to afford ethyl 5-cyclopropyl-4-iodoisoxazole-3-carboxylate (1.27 g, 75%).

Step 2: Synthesis of 5-cyclopropyl-4-iodoisoxazole-3-carboxylic acid

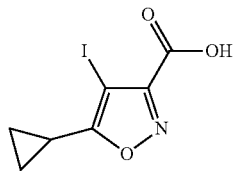 [SMILES: O=C(O)c1noc(C2CC2)c1I]

To a stirred solution of ethyl 5-cyclopropyl-4-iodoisoxazole-3-carboxylate (1.27 g, 4.14 mmol) in THF:MeOH:$H_2O$ (1:1:1, 9 ml) was added LiOH (1.04 g, 24.8 mmol). The solution was stirred at rt for 16 hr. After complete consumption of starting material, the residue was acidified to pH 2 with Amberlyst. The reaction mixture was filtration and

245 concentrated under reduced pressure to obtain a compound 5-cyclopropyl-4-iodoisoxazole-3-carboxylic acid (1.01 g, 87%). LCMS: m/z=278.9 (M+H)$^+$.

Step 3: Synthesis of tert-butyl ((1r,4r)-4-(5-cyclopropyl-4-iodoisoxazole-3-carboxamido)cyclohexyl)carbamate

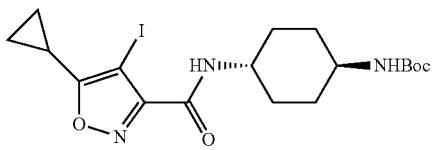 [SMILES: CC(C)(C)OC(=O)N[C@H]1CC[C@H](NC(=O)c2noc(C3CC3)c2I)CC1]

To a stirred solution of 5-cyclopropyl-4-iodoisoxazole-3-carboxylic acid (1.0 g, 3.59 mmol) in DMF (10 ml) was added EDCI (0.892 g, 4.66 mmol) and HOBT (0.533 g, 3.94 mmol). The solution was stirred for 10 min at 0° C. Next tert-butyl ((1r,4r)-4-aminocyclohexyl)carbamate (0.769 g, 3.59 mmol) was added and the reaction was stirred at rt for 2 hr. The progress of the reaction was monitored by TLC. After complete consumption of starting material, the reaction was quenched with water and the solid precipitated was collected by filtration and dried under reduced pressure to obtain a residue. The material was purified by column chromatography to afford tert-butyl ((1r,4r)-4-(5-cyclopropyl-4-iodoisoxazole-3-carboxamido)cyclohexyl)carbamate (0.48 g, 28%).

Step 4: Synthesis of N-((1r,4r)-4-aminocyclohexyl)-5-cyclopropyl-4-iodoisoxazole-3-carboxamide hydrochloride

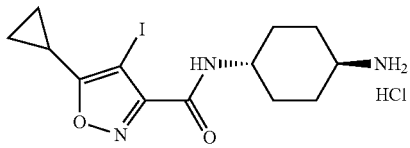

To a stirred solution of tert-butyl ((1r,4r)-4-(5-cyclopropyl-4-iodoisoxazole-3-carboxamido)cyclohexyl)carbamate (0.1 g, 0.210 mmol) in methanol (3 ml) at 0° C. was added 4 M methanolic:HCl (3 ml). The reaction was stirred for at rt for 1 h. The progress of the reaction was monitored by TLC. After complete consumption of starting material, the solvent was removed under reduced pressure and the residue was purified by washing with diethyl ether to obtain N-((1r,4r)-4-aminocyclohexyl)-5-cyclopropyl-4-iodoisoxazole-3-carboxamide hydrochloride (0.008 g, 10%). $^1$H NMR (400 MHz, DMSO-d$_6$) δ 8.70 (d, J=7.9 Hz, 1H), 7.92 (s, 3H), 3.67 (d, J=10.0 Hz, 1H), 2.96 (t, J=9.5 Hz, 1H), 2.20-2.17 (m, 1H), 1.97 (d, J=9.4 Hz, 2H), 1.87 (d, J=10.4 Hz, 2H), 1.39 (q, J=12.2, 11.2 Hz, 4H), 1.21-1.11 (m, 2H), 1.07-0.98 (m, 2H); LCMS (method C, ESI): m/z=375 (M+H)$^+$.

Example 15

Synthesis of N3-((1r,4r)-4-aminocyclohexyl)-5-cyclopropylisoxazole-3,4-dicarboxamide hydrochloride (Cpd. No. 13)

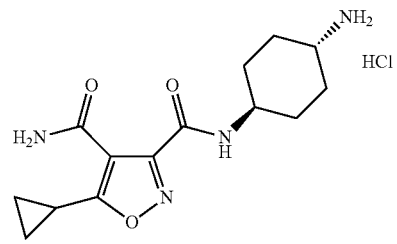 [SMILES: NC(=O)c1c(C(=O)N[C@H]2CC[C@H](N)CC2)noc1C1CC1 ; Cl]

Step 1: Synthesis of 3-(((1r,4r)-4-((tert-butoxycarbonyl)amino)cyclohexyl)carbamoyl)-5-cyclopropylisoxazole-4-carboxylic acid

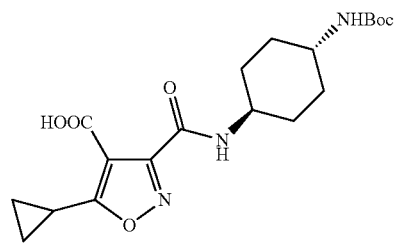 [SMILES: CC(C)(C)OC(=O)N[C@H]1CC[C@H](NC(=O)c2noc(C3CC3)c2C(=O)O)CC1]

To the stirred solution of tert-butyl ((1r,4r)-4-(5-cyclopropyl-4-iodoisoxazole-3-carboxamido)cyclohexyl)carbamate (1.6 g, 3.37 mmol) in DMF:H$_2$O (4:1, 10 ml) was added Pd(OAc)$_2$ (0.037 g, 0.168 mmol) and dppf (0.186 g, 0.337 mmol) and the reaction heated at 55° C. under CO balloon pressure overnight. The progress of the reaction was monitored by TLC. After complete consumption of starting material, the reaction was filtered, diluted with water and extracted with ethyl acetate. The organic layer was separated, washed with brine, dried using Na$_2$SO$_4$ and concentrated under reduced pressure to obtain a residue which was purified by column chromatography to obtain 3-(((1r,4r)-4-((tert-butoxycarbonyl)amino)cyclohexyl)carbamoyl)-5-cyclopropylisoxazole-4-carboxylic acid (0.350 g, 26%).

Step 2: Synthesis of pentafluorophenyl 3-(((1r,4r)-4-((tert-butoxycarbonyl)amino) cyclohexyl)carbamoyl)-5-cyclopropylisoxazole-4-carboxylate

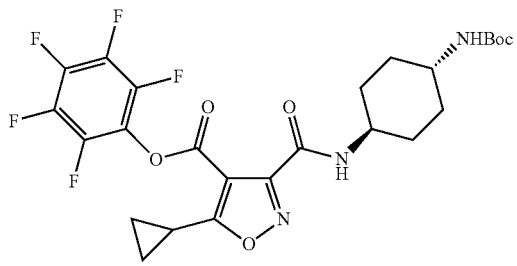 [SMILES: CC(C)(C)OC(=O)N[C@H]1CC[C@H](NC(=O)c2noc(C3CC3)c2C(=O)Oc2c(F)c(F)c(F)c(F)c2F)CC1]

To the stirred solution of 3-(((1r,4r)-4-((tert-butoxycarbonyl)amino) cyclohexyl)carbamoyl)-5-cyclopropylisoxazole-4-carboxylic acid (0.2 g, 0.508 mmol) in DMF (2 mL) at 0° C. was added pentafluorophenol (0.093 g, 0.508 mmol) and DCC (0.054 g, 0.508 mmol). The reaction was stirred at rt for 30 min. After complete consumption of starting material, the reaction was quenched with water and extracted with DCM; the organic layer was separated, washed with sodium bicarbonate solution, dried using $Na_2SO_4$ and concentrated under reduced pressure to obtain pentafluorophenyl 3-(((1r,4r)-4-((tert-butoxycarbonyl)amino)cyclohexyl)carbamoyl)-5-cyclopropylisoxazole-4-carboxylate (0.250 g). The material was used without further purification LCMS: m/z=583.12 $(M+Na)^+$.

Step 3: Synthesis of tert-butyl ((1r,4r)-4-(4-carbamoyl-5-cyclopropylisoxazole-3-carboxamido)cyclohexyl)carbamate

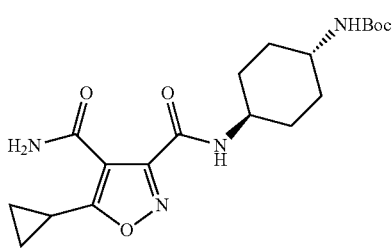 [SMILES: CC(C)(C)OC(=O)N[C@H]1CC[C@H](NC(=O)c2noc(C3CC3)c2C(N)=O)CC1]

Ammonia was bubbled through a stirred solution of pentafluorophenyl 3-(((1r,4r)-4-((tert-butoxycarbonyl)amino)cyclohexyl)carbamoyl)-5-cyclopropylisoxazole-4-carboxylate (0.08 g, 0.143 mmol) in DCM (2 mL) at 0° C. for 30 min. The reaction was then stirred at rt for 2 h. The progress of the reaction was monitored by TLC. After complete consumption of starting material, the reaction was evaporated to complete dryness. The material was purified by trituration with hexane and diethyl ether to obtain tert-butyl ((1r,4r)-4-(4-carbamoyl-5-cyclopropylisoxazole-3-carboxamido)cyclohexyl) carbamate (0.040 g, 71%).

Step 4: Synthesis of N3-((1r,4r)-4-aminocyclohexyl)-5-cyclopropylisoxazole-3,4-dicarboxamide hydrochloride

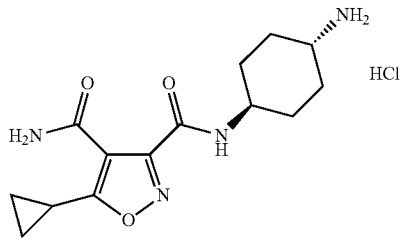 [SMILES: NC(=O)c1c(C(=O)N[C@H]2CC[C@H](N)CC2)noc1C1CC1 ; Cl]

To a stirred solution of tert-butyl ((1r,4r)-4-(4-carbamoyl-5-cyclopropylisoxazole-3-carboxamido)cyclohexyl)carbamate (0.040 g, 0.101 mmol) in dioxane (2 mL) at 0° C. was added 4 M dioxane:HCl (3 mL). The reaction was stirred at rt for 1 h and progress monitored by TLC. After complete consumption of starting material, the solvent was removed under reduced pressure and the residue was purified by washing with diethyl ether to obtain N3-((1r,4r)-4-aminocyclohexyl)-5-cyclopropylisoxazole-3,4-dicarboxamide hydrochloride (0.022 g, 75%). $^1$H NMR (400 MHz, DMSO-$d_6$) δ 9.10 (d, J=7.8 Hz, 1H), 8.50-8.45 (m, 1H), 7.91 (s, 3H), 7.64 (s, 1H), 3.83 (brs, 1H), 3.0-2.97 (m, 2H), 1.96 (d, J=7.6 Hz, 2H), 1.91-1.84 (m, 2H), 1.49-1.36 (m, 4H), 1.24-1.21 (m, 2H), 1.15-1.10 (m, 2H); LCMS: m/z=293.15 $(M+H)^+$.

Example 16

Synthesis of N-(6-((R)-3-aminobutanamido)bicyclo[3.3.1]nonan-2-yl)-5-cyclopropylisoxazole-3-carboxamide (Cpd. No. 293)

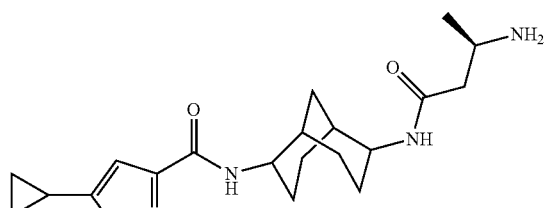

Step 1: Synthesis of $N^2,N^6$-dibenzylbicyclo[3.3.1]nonane-2,6-diamine

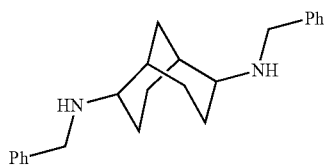 [SMILES: c1ccc(CNC2CCC3CC2CCC3NCc2ccccc2)cc1]

To a solution of bicyclo[3.3.1]nonane-2,6-dione (1.0 g, 6.5707 mmol) in THF (10 mL) was added benzyl amine (2.87 mL, 26.283 mmol) under $N_2$ atmosphere at rt and stirred for 5 minutes. AcOH (0.8 mL, 1.3798 mmol) was added and mixture was cooled to 0° C. Sodium triacetoxy borohydride (5.57 g, 26.283 mmol) was added portionwise over 30 min. The reaction was allowed to stir at rt overnight. The reaction was diluted with water (20 mL) and neutralized with saturated aq. solution of $NaHCO_3$ (80 mL). The mixture was extracted with DCM (40 mL×4). The combined organic layer was washed with saturated aq. solution of $NaHCO_3$ (50 mL), brine (50 mL), dried over $Na_2SO_4$ and concentrated under reduced pressure to give crude product, which was purified by column chromatography using mobile phase 0.3% methanol in DCM to obtain $N^2,N^6$-dibenzylbicyclo[3.3.1]nonane-2,6-diamine (1.3 g, yield 59.14%) LCMS: m/z=335.16 $[M+H]^+$.

Step 2: Synthesis of bicyclo[3.3.1]nonane-2,6-diamine

To a suspension of 10% Pd/C (dry) in MeOH (3 mL) was added solution of $N^2,N^6$-dibenzylbicyclo[3.3.1]nonane-2,6-diamine (1.3 g, 3.886 mmol) in MeOH (10 mL). The reaction was stirred overnight under a $H_2$ atmosphere. The reaction was filtered through a celite pad and washed with MeOH (50 mL). The filtrate was concentrated under reduced pressure to obtain title compound (0.5 g, yield 83.4%). LCMS: m/z=155.20 [M+H]$^+$.

Step 3: Synthesis of tert-Butyl (6-aminobicyclo[3.3.1]nonan-2-yl)carbamate

To a solution of bicyclo[3.3.1]nonane-2,6-diamine (500 mg, 3.241 mmol) in a mixture of MeOH (10 mL) and THF (20 mL) at 0° C. under $N_2$ atmosphere was added a solution of Boc-anhydride (0.37 mL, 1.620 mmol) in mixture of MeOH (20 mL) and THF (50 mL) over a period of 6 hours. The reaction was allowed to stir at rt overnight. The reaction was concentrated under reduced pressure to give crude product which was purified by column chromatography using basic alumina as stationary phase and 0-4% MeOH in DCM as mobile phase to obtain title compound (290 mg, yield 35.17%). LCMS: m/z=255.25 [M+H]$^+$.

Step 4: Synthesis of tert-Butyl (6-(5-cyclopropylisoxazole-3-carboxamido)bicyclo[3.3.1]nonan-2-yl)carbamate

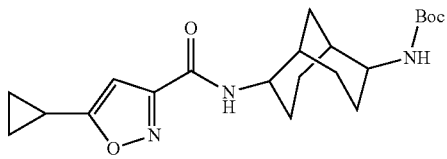 [SMILES: CC(C)(C)OC(=O)NC1CCC2CC1CCC2NC(=O)c1cc(C2CC2)on1]

To a solution of 5-cyclopropylisoxazole-3-carboxylic acid (175 mg, 1.14 mmol) in DMF at 0° C. under $N_2$ atmosphere was added HATU (650 mg, 1.71 mmol). The reaction stirred for 20 min. and then tert-butyl (6-aminobicyclo[3.3.1]nonan-2-yl)carbamate (290 mg, 1.14 mmol) was added followed by addition of DIPEA (0.6 mL, 3.42 mmol). The reaction was brought to rt and stirred overnight. The reaction was diluted with water (50 mL) and extracted with ethyl acetate (50 mL×3). The combined organic layer was washed with brine (20 mL), dried over $Na_2SO_4$ and concentrated to give crude product which was purified by column chromatography using mobile phase to 0-12% ethyl acetate in hexane to obtain the title compound (300 mg, yield 75.5%). LCMS: m/z=334.36 [M−56]$^+$.

Step 5: Synthesis of N-(6-aminobicyclo[3.3.1]nonan-2-yl)-5-cyclopropylisoxazole-3-carboxamide TFA Salt

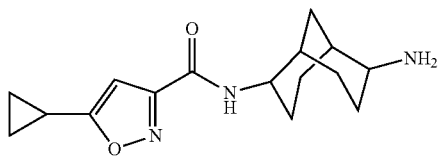 [SMILES: NC1CCC2CC1CCC2NC(=O)c1cc(C2CC2)on1]

To a solution of tert-butyl (6-(5-cyclopropylisoxazole-3-carboxamido)bicyclo[3.3.1]nonan-2-yl)carbamate (300 mg, 0.7702 mmol) in DCM (3 mL) at 0° C. under $N_2$ atmosphere was added TFA (1.5 mL). The reaction was allowed to stir at rt for 2 hours. The reaction was concentrated under reduced pressure and triturated with diethyl ether to obtain the title compound as the TFA salt (300 mg, yield 96.5%). LCMS: m/z=290.36 [M+H]$^+$.

Step 6: Synthesis of tert-butyl ((2R)-4-((6-(5-cyclopropylisoxazole-3-carboxamido) bicyclo[3.3.1]nonan-2-yl)amino)-4-oxobutan-2-yl)carbamate

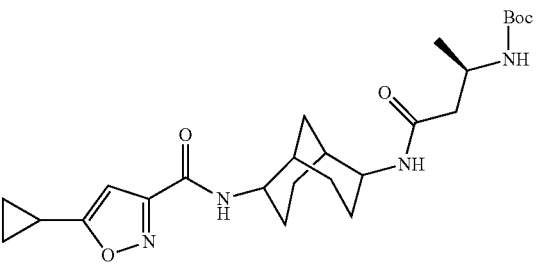 [SMILES: C[C@H](CC(=O)NC1CCC2CC1CCC2NC(=O)c1cc(C2CC2)on1)NC(=O)OC(C)(C)C]

To a solution of the TFA salt of (R)-3-((tert-butoxycarbonyl) amino)butanoic acid (50 mg, 0.246 mmol) in DMF (1.0 mL) at 0° C. was added HATU (140 mg, 0.369 mmol). After stirring for 15 minutes, the TFA salt of N-(6-aminobicyclo[3.3.1]nonan-2-yl)-5-cyclopropylisoxazole-3-carboxamide (100 mg, 0.246 mmol) was added followed by addition of DIPEA (0.126 mL, 0.738 mmol). The reaction was brought to rt and stirred overnight. The reaction was diluted with water (20 mL) and extracted with ethyl acetate (20 mL×3). The combined organic layer was dried over $Na_2SO4$ and concentrated under reduced pressure to give crude product which was purified by column chromatography using mobile phase 0-70% ethyl acetate in hexane to obtain the title compound (80 mg, 67.9%). LCMS: m/z=475.16 [M+H]$^+$.

Step 7: Synthesis of N-(6-((R)-3-aminobutanamido) bicyclo[3.3.1]nonan-2-yl)-5-cyclopropylisoxazole-3-carboxamide

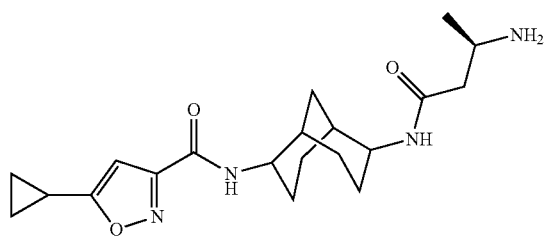 [SMILES: C[C@@H](N)CC(=O)NC1CCC2CC1CCC2NC(=O)c1cc(C2CC2)on1]

To a solution of tert-butyl ((2R)-4-((6-(5-cyclopropylisoxazole-3-carboxamido)bicyclo[3.3.1]nonan-2-yl)amino)-4-oxobutan-2-yl)carbamate (80 mg, 0.1686 mmol) in DCM (0.8 mL) at 0° C. under $N_2$ atmosphere was added TFA (0.4 mL) dropwise. The reaction was allowed to stir at room temperature for 2 hours. The reaction was concentrated under reduced pressure to give crude product which was triturated with diethyl ether (10 mL) and hexanes (10 mL) to obtain the title compound as TFA salt (50 mg, 60.7%). $^1$H NMR (400 MHz, DMSO-$d_6$) δ 8.667 (d, 1H), 8.180 (d, 1H), 7.792 (s, 3H), 6.478 (s, 1H), 4.067 (s, 1H), 3.907 (s, 1H), 3.39 (s, 1H), 2.42 (s, 2H), 2.18 (s, 2H), 2.42 (s, 2H), 1.91-1.88 (m, 4H), 1.78-1.65 (m, 4H), 1.54-1.50 (m, 4H), 1.16-1.09 (m, 5H), 0.917 (s, 1H); LCMS: m/z=375.4 [M+1]+.

Example 17

Synthesis of N-(4-(3-aminopropanamido)phenyl)-5-cyclopropylisoxazole-3-carboxamide hydrochloride (Cpd. No. 325)

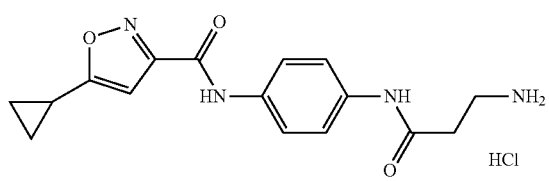 [SMILES: NCCC(=O)Nc1ccc(NC(=O)c2cc(C3CC3)on2)cc1 ; Cl]

Step 1: Synthesis of N-(4-aminophenyl)-5-cyclopropylisoxazole-3-carboxamide

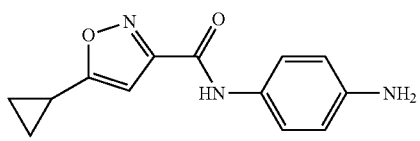 [SMILES: Nc1ccc(NC(=O)c2cc(C3CC3)on2)cc1]

Into a 250-mL round-bottom flask purged and maintained with an inert atmosphere of nitrogen was placed dichloromethane (40 mL) and benzene-1,4-diamine (1.059 g, 9.79 mmol, 1.05 equiv); then 5-cyclopropyl-1,2-oxazole-3-carbonyl chloride (1.6 g, 9.33 mmol, 1.00 equiv) in 10 mL DCM was added dropwise. The resulting solution was stirred for 12 h at room temperature. The resulting mixture was concentrated under vacuum. The solids were filtered off. The filtrate was extracted with 2×100 mL of ethyl acetate and the organic layers combined and concentrated under vacuum. The residue was purified on a silica gel column with ethyl acetate/petroleum ether (10:1). This resulted in 750 mg (33%) of N-(4-aminophenyl)-5-cyclopropylisoxazole-3-carboxamide as a yellow solid. LCMS: rt=1.04 min, m/z=285.0 [M+CN]+.

Step 2: Synthesis of tert-butyl 3-(4-(5-cyclopropylisoxazole-3-carboxamido) phenylamino)-3-oxopropylcarbamate

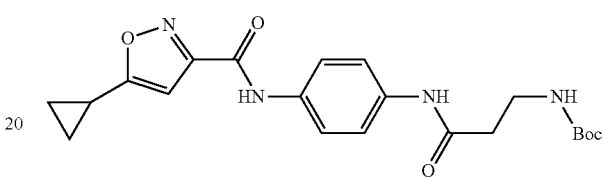

Into a 100-mL round-bottom flask purged and maintained with an inert atmosphere of nitrogen was placed N-(4-aminophenyl)-5-cyclopropylisoxazole-3-carboxamide (170 mg, 0.70 mmol, 1.00 equiv), tetrahydrofuran (5 mL), dichloromethane (5 mL), EDCI (401 mg, 2.09 mmol, 2.99 equiv), DIEA (271 mg, 2.10 mmol, 3.00 equiv), HOBT (283 mg, 2.09 mmol, 3.00 equiv), and 3-[[(tert-butoxy)carbonyl]amino]propanoic acid (264 mg, 1.40 mmol, 2.00 equiv). The resulting solution was stirred for 6 h at room temperature. The mixture was concentrated under vacuum. The residue was diluted with 50 mL of $H_2O$ and extracted with DCM. The organic phase was collected and dried over anhydrous sodium sulfate. The residue was purified on a silica gel column with ethyl acetate/petroleum ether (5:1). This resulted in 120 mg (41%) of tert-butyl 3-(4-(5-cyclopropylisoxazole-3-carboxamido)phenylamino)-3-oxopropylcarbamate as a light yellow solid. LCMS: m/z=437.1 [M+Na]+.

Step 3: Synthesis of N-(4-(3-aminopropanamido) phenyl)-5-cyclopropylisoxazole-3-carboxamide hydrochloride

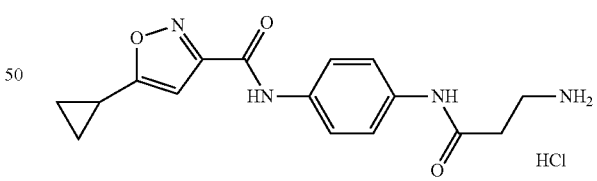

Into a 50-mL round-bottom flask purged and maintained with an inert atmosphere of nitrogen was placed tert-butyl 3-(4-(5-cyclopropylisoxazole-3-carboxamido)phenylamino)-3-oxopropylcarbamate (120 mg, 0.29 mmol, 1.00 equiv) and 1,4-dioxane (5 mL). Then hydrogen chloride was introduced into the mixture. The resulting solution was stirred for 2 h at room temperature. The mixture was then concentrated under vacuum. The crude product was purified by Flash-Prep-HPLC with the following conditions (IntelFlash-1): Column, silica gel; mobile phase, detector, UV 254 nm. The result solution was acidified by dilute hydrochloric acid (1N), then concentrated and dried. This resulted in 21.4 mg (24%) of N-(4-(3-aminopropanamido)phenyl)-5-cyclopropylisoxazole-3-carboxamide hydrochloride as a white solid. $^1$H-NMR (300 MHz, D$_2$O): δ 7.54-7.37 (m, 4H), 6.36 (s, 1H), 3.25 (t, J=6.6 Hz, 2H), 2.77 (t, J=6.6 Hz, 2H), 2.12-2.04 (m, 1H), 1.08-1.02 (m, 2H), 0.97-0.92 (m, 2H). LCMS: m/z=315.0 [M+H]$^+$.

Example 18

Synthesis of N-(1-((1-(4-chlorobenzyl)-1H-pyrazol-4-yl)methyl)azetidin-3-yl)-5-cyclopropylisoxazole-3-carboxamide (Cpd. No. 428)

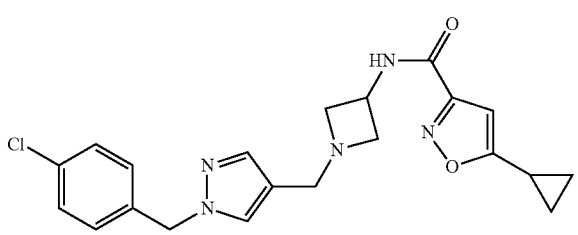 [SMILES: O=C(NC1CN(Cc2cnn(Cc3ccc(Cl)cc3)c2)C1)c1cc(C2CC2)on1]

Step 1: Synthesis of tert-butyl 3-(5-cyclopropylisoxazole-3-carboxamido)azetidine-1-carboxylate

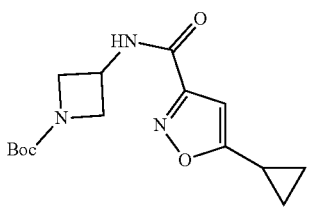 [SMILES: CC(C)(C)OC(=O)N1CC(NC(=O)c2cc(C3CC3)on2)C1]

To a solution of 5-cyclopropylisoxazole-3-carboxylic acid (1.53 g) in DMF (20 mL) was added HATU (6.84 g, DIPEA (3.87 g) and tert-butyl 3-aminoazetidine-1-carboxylate (2.58 g). The resulting mixture was stirred at r.t. overnight. The reaction mixture was diluted with ethyl acetate (120 mL), washed with brine (30 mL×4), dried over Na$_2$SO$_4$ and concentrated under reduced pressure. The residue was purified by flash column chromatography (eluant petroleum ether: ethyl acetate gradient elution 100:0 to 50:50) to afford tert-butyl 3-(5-cyclopropylisoxazole-3-carboxamido)azetidine-1-carboxylate (2.55 g, 83%) as a pale yellow solid. ESI-LCMS (m/z): 330[M+Na]$^+$.

Step 2: Synthesis of N-(azetidin-3-yl)-5-cyclopropylisoxazole-3-carboxamide

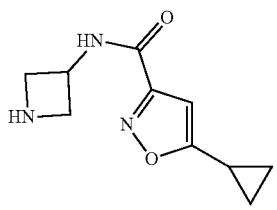 [SMILES: O=C(NC1CNC1)c1cc(C2CC2)on1]

To a solution of tert-butyl 3-(5-cyclopropylisoxazole-3-carboxamido)azetidine-1-carboxylate (2.55 g) in DCM (10 mL) was added TFA (4 mL) drop-wise. The resulting mixture was stirred at r.t. overnight. The reaction mixture was concentrated under reduced pressure and the residue was treated with ammonia in MeOH (7N, 30 mL) and the solution concentrated under reduced pressure. The residue was purified by flash column chromatography (eluant: DCM:MeOH (MeOH:7N NH$_3$ 100:1) 10:1) to afford N-(azetidin-3-yl)-5-cyclopropylisoxazole-3-carboxamide (1.35 g, 78%) as a white solid. ESI-LCMS (m/z): 208[M+H]$^+$.

Step 3: Synthesis of N-(1-((1-(4-chlorobenzyl)-1H-pyrazol-4-yl)methyl)azetidin-3-yl)-5-cyclopropylisoxazole-3-carboxamide

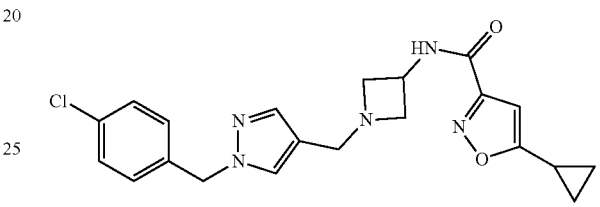

Into the stirred solution of N-(azetidin-3-yl)-5-cyclopropylisoxazole-3-carboxamide (400 mg, 1.9 mmol) and 1-(4-chlorobenzyl)-1H-pyrazole-4-carbaldehyde (425 mg, 1.9 mmol) in MeOH (10 mL) was added NaBH$_3$CN (363 mg, 5.8 mmol). The mixture was stirred at 60° C. for 20 h. The product was purified by reversed phased pre-HPLC (NH$_4$HCO3, CH$_3$CN:H$_2$O=5%-95%) to afford N-(1-((1-(4-chlorobenzyl)-1H-pyrazol-4-yl)methyl)azetidin-3-yl)-5-cyclopropylisoxazole-3-carboxamide as a white solid (70 mg, 8.8%). ESI-LCMS (m/z): 412 [M+H]$^+$; $^1$HNMR (400 MHz, CD$_3$OD) δ ppm: 7.64 (s, 1H), 7.50 (s, 1H), 7.37-7.33 (m, 2H), 7.20 (d, J=8.8 Hz, 2H), 6.37 (s, 1H), 5.32 (s, 2H), 4.61-4.58 (m, 1H), 3.70-3.66 (m, 2H), 3.61 (s, 2H), 3.22-3.18 (m, 2H), 2.19-2.15 (m, 1H), 1.18-1.13 (m, 2H), 1.00-0.96 (m, 2H).

Example 19

SMYD3 Biochemical Assay

General Materials

S-adenosylmethionine (SAM), S-adenosylhomocysteine (SAH), Tris, Tween20, dimethylsulfoxide (DMSO), bovine skin gelatin (BSG), and Tris(2-carboxyethyl)phosphine hydrochloride solution (TCEP) were purchased from Sigma-Aldrich at the highest level of purity possible. $^3$H-SAM was purchase from American Radiolabeled Chemicals with a specific activity of 80 Ci/mmol. 384-well opaque white OptiPlates and SPA beads (Perkin Elmer, catalog # RPNQ0013) were purchased from PerkinElmer.

Substrates

N-terminally GST-tagged MEKK2 (MAP3K2) protein corresponding to reference sequence AAF63496.3 was purchased from Life Technologies (catalog # PV4010). This protein was expressed in High Five insect cells and purified to >85% purity. Protein identity was confirmed by MS/MS analysis after proteolytic digestion. The protein sequence used was:

(SEQ ID No. 1)
MAPILGYWKIKGLVQPTRLLLEYLEEKYEEHLYERDEGDKWRNK

KFELGLEFPNLPYYIDGDVKLTQSMAIIRYIADKHNMLGGCPKERA

EISMLEGAVLDIRYGVSRIAYSKDFETLKVDFLSKLPEMLKMFEDR

LCHKTYLNGDHVTHPDFMLYDALDVVLYMDPMCLDAFPKLVCF

KKRIEAIPQIDKYLKSSKYIAWPLQGWQATFGGGDHPPKSDLVPRH

NQTSLYKKAGTMDDQQALNSIMQDLAVLHKASRPALSLQETRKA

KSSSPKKQNDVRVKFEHRGEKRILQFPRPVKLEDLRSKAKIAFGQS

MDLHYTNNELVIPLTTQDDLDKALELLDRSIHMKSLKILLVINGST

QATNLEPLPSLEDLDNTVFGAERKKRLSIIGPTSRDRSSPPPGYIPDE

LHQVARNGSFTSINSEGEFIPESMEQMLDPLSLSSPENSGSGSCPSL

DSPLDGESYPKSRMPRAQSYPDNHQEFSDYDNPIFEKFGKGGTYPR

RYHVSYHHQEYNDGRKTFPRARRTQGNQLTSPVSFSPTDHSLSTSS

GSSIFTPEYDDSRIRRRGSDIDNPTLTVMDISPPSRSPRAPTNWRLG

KLLGQGAFGRVYLCYDVDTGRELAVKQVQFDPDSPETSKEVNAL

ECEIQLLKNLLHERIVQYYGCLRDPQEKTLSIFMEYMPGGSIKDQL

KAYGALTENVTRKYTRQILEGVHYLHSNMIVHRDIKGANILRDST

GNVKLGDFGASKRLQTICLSGTGMKSVTGTPYWMSPEVISGQGYG

RKADIWSVACTVVEMLTEKPPWAEFEAMAAIFKIATQPTNPKLPP

HVSDYTRDFLKRIFVEAKLRPSADELLRHMFVHYH..

Molecular Biology

Full-length human SMYD3 isoform 1 (BAB86333) was inserted into a modified pET21b plasmid containing a His6 tag and TEV and SUMO cleavage sites. Because two common variants of SMYD3 exist in the population, site directed mutagenesis was subsequently performed to change amino acid 13 from an asparagine to a lysine, resulting in plasmid pEPZ533. A lysine at position 13 conforms to the more commonly occurring sequence (NP_001161212).

Protein Expression

E. coli (BL21 codonplus RIL strain, Stratagene) were transformed with plasmid pEPZ553 by mixing competent cells and plasmid DNA and incubating on ice for 30 minutes followed by heat shock at 42° C. for 1 minute and cooling on ice for 2 minutes. Transformed cells were grown and selected on LB agar with 100 μg/mL ampicillin and 17 μg/mL chloramphenicol at 37° C. overnight. A single clone was used to inoculate 200 mL of LB medium with 100 μg/mL ampicillin and 17 μg/mL chloramphenicol and incubated at 37° C. on an orbital shaker at 180 rpm. Once in log growth, the culture was diluted 1:100 into 2 L of LB medium and grown until $OD_{600}$ was about 0.3 after which the culture was incubated at 15° C. and 160 rpm. Once $OD_{600}$ reached about 0.4, IPTG was added to a final concentration of 0.1 mM and the cells were grown overnight at 15° C. and 160 rpm. Cells were harvested by centrifugation at 8000 rpm, for 4 minutes at 4° C. and stored at −80° C. for purification.

Protein Purification

Expressed full-length human His-tagged SMYD3 protein was purified from cell paste by Nickel affinity chromatography after equilibration of the resin with Buffer A (25 mM Tris, 200 mM NaCl, 5% glycerol, 5 mM β-mercaptoethanol, pH7.8). The column was washed with Buffer B (Buffer A plus 20 mM imidazole) and His-tagged SMYD3 was eluted with Buffer C (Buffer A plus 300 mM imidazole). The His tag, TEV and SUMO cleavage sites were removed generating native SMYD3 by addition of ULP1 protein at a ratio of 1:200 (ULP1:SMYD3). Imidazole was removed by dialysis overnight in Buffer A. The dialyzed solution was applied to a second Nickel column and the native SMYD3 protein was collected from the column flow-through. The flow-through was dialyzed in Buffer D (25 mM Tris, 5% glycerol, 5 mM β-mercaptoethanol, 50 mM NaCl, pH7.8) and ULP1 was removed using a Q sepharose fast flow column. SMYD3 was eluted in Buffer A and further purified using an S200 size-exclusion column equilibrated with Buffer A. SMYD3 was concentrated to 2 mg/mL with a final purity of 89%.

Predicted Translation:

SMYD3 (Q9H7B4)
(SEQ ID No. 2)
MEPLKVEKFATAKRGNGLRAVTPLRPGELLFRSDPLAYTVCKGSR

GVVCDRCLLGKEKLMRCSQCRVAKYCSAKCQKKAWPDHKRECK

CLKSCKPRYPPDSVRLLGRVVFKLMDGAPSESEKLYSFYDLESNIN

KLTEDKKEGLRQLVMTFQHFMREEIQDASQLPPAFDLFEAFAKVIC

NSFTICNAEMQEVGVGLYPSISLLNHSCDPNCSIVFNGPHLLLRAV

RDIEVGEELTICYLDMLMTSEERRKQLRDQYCFECDCFRCQTQDK

DADMLTGDEQVWKEVQESLKKIEELKAHWKWEQVLAMCQAIISS

NSERLPDINIYQLKVLDCAMDACINLGLLEEALFYGTRTMEPYRIFF

PGSHPVRGVQVMKVGKLQLHQGMFPQAMKNLRLAFDIMRVTHG

REHSLIEDLILLLEECDANIRAS..

General Procedure for SMYD3 Enzyme Assays on MEKK2 Protein Substrate

The assays were all performed in a buffer consisting of 25 mM Tris-Cl pH 8.0, 1 mM TCEP, 0.005% BSG, and 0.005% Tween 20, prepared on the day of use. Compounds in 100% DMSO (1 ul) were spotted into a 384-well white opaque OptiPlate using a Bravo automated liquid handling platform outfitted with a 384-channel head (Agilent Technologies). DMSO (1 ul) was added to Columns 11, 12, 23, 24, rows A-H for the maximum signal control and 1 ul of SAH, a known product and inhibitor of SMYD3, was added to columns 11, 12, 23, 24, rows I-P for the minimum signal control. A cocktail (40 ul) containing the SMYD3 enzyme was added by Multidrop Combi (Thermo-Fisher). The compounds were allowed to incubate with SMYD3 for 30 min at room temperature, then a cocktail (10 ul) containing SAM and MEKK2 was added to initiate the reaction (final volume=51 ul). The final concentrations of the components were as follows: SMYD3 was 0.4 nM, $^3$H-SAM was 8 nM, MEKK2 was 12 nM, SAH in the minimum signal control wells was 1 mM, and the DMSO concentration was 2%. The assays were stopped by the addition of non-radiolabeled SAM (10 ul) to a final concentration of 100 uM, which dilutes the $^3$H-SAM to a level where its incorporation into MEKK2 is no longer detectable. Radiolabeled MEKK2 was detected using a scintillation proximity assay (SPA). 10 uL of a 10 mg/mL solution of SPA beads in 0.5 M citric acid was added and the plates centrifuged at 600 rpm for 1 min to precipitate the radiolabeled MEKK2 onto the SPA beads. The plates were then read in a PerkinElmer TopCount plate reader to measure the quantity of $^3$H-labeled MEKK2 as disintegrations per minute (dpm) or alternatively, referred to as counts per minute (cpm). % inhibition calculation $$\% \text{ ink} = 100 - \left( \frac{dpm_{cmpd} - dpm_{min}}{dpm_{max} - dpm_{min}} \right) \times 100$$

Where dpm=disintegrations per minute, cmpd=signal in assay well, and min and max are the respective minimum and maximum signal controls.

Four-parameter IC50 fit $$Y = \text{Bottom} + \frac{(\text{Top} - \text{Bottom})}{\left(1 + \left(\frac{X}{IC_{50}}\right)^{Hill\ Coefficient}\right)}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

SMYD3 biochemical assay data for representative Compounds of the Disclosure are presented in Table 1 in the column titled "SMYD3 Biochem $IC_{50}$ (µM)."

Example 20

SMYD3 Cell Assay

Trimethyl-MEKK2-In-Cell Western Assay

293T/17 adherent cells were purchased from ATCC (American Type Culture Collection), Manassas, Va., USA. MEM/Glutamax medium, Optimem Reduced Serum medium, penicillin-streptomycin, 0.05% trypsin and 1×D-PBS were purchased from Life Technologies, Grand Island, N.Y., USA. PBS-10× was purchased from Ambion, Life Technologies, Grand Island, N.Y., USA. PBS with Tween 20 (PBST (10×)) was purchased from KPL, Gaithersburg, Md., USA. Tet System FBS—approved FBS US Source was purchased from Clontech, Mountain View, Calif., USA. Odyssey blocking buffer, 800CW goat anti-rabbit IgG (H+L) antibody, 680CW Goat anti-mouse IgG (H+L) and Licor Odyssey infrared scanner were purchased from Licor Biosciences, Lincoln, Nebr., USA. Tri-methyl-Lysine [A260]-MEKK2 antibody, MEKK2 and SMYD3 plasmids were made at Epizyme. Anti-flag monoclonal mouse antibody was purchased from Sigma, St. Louis, Mo., USA. Methanol was purchased from VWR, Franklin, Mass., USA. 10% Tween 20 was purchased from KPL, Inc., Gaithersburg, Md., USA. Fugene was purchased from Promega, Madison, Wis., USA. The Biotek ELx405 was purchased from BioTek, Winooski, Vt., USA. The multidrop combi was purchased from Thermo Scientific, Waltham, Mass., USA.

293T/17 adherent cells were maintained in growth medium (MEM/Glutamax medium supplemented with 10% v/v Tet System FBS and cultured at 37° C. under 5% $CO_2$. Cell treatment, In Cell Western (ICW) for detection of trimethyl-lysine-MEKK2 and MEKK2.

293T/17 cells were seeded in assay medium at a concentration of 33,333 cells per $cm^2$ in 30 mL medium per T150 flask and incubated at 37° C. under 5% $CO_2$. Plasmids were prepared for delivery to cells by first mixing 1350 µL Opti-MEM with Fugene (81 µL) in a sterile Eppendorf and incubated for five minutes at room temperature (RT). MEKK2-flag (13.6 ug/T150) MEKK2 p3XFlag-CMV-14 with C-3XFlag and SMYD3 (0.151 ug/T150) SMYD3 p3XFlag-CMV-14 without C-3XFlag plasmids were aliquotted to a 1.7 mL sterile microfuge tube. The gene ID for MEKK2 and SMYD3 is NM_006609.3 and Q9H7B4, respectively. Entire volume of Opti-MEM/Fugene mixture was then added to a microfuge tube containing DNA plasmid, mixed and then incubated×15 minutes at RT. The medium on the 293T/17 cells was refreshed, and the DNA/Fugene complex is added aseptically to each flask, rocked gently, and incubated at 37 C for 5 hours. Medium was then removed, and cells were washed once with PBS in the flask. Trypsin 0.05% (3 mL) was added and cells incubated for three minutes. Room temperature MEM+10% Tet system FBS was added and cells were mixed gently, and counted using the Vi-cell. Cells were seeded at 100,000 cells/mL in 50 µL MEM/10% Tet FBS/Pen/Strep to a 384 well black/clear poly-D-lysine coated plate containing test agent diluted in DMSO. The final top concentration of test compound was 40 µM. The total concentration of DMSO did not exceed 0.2% (v/v). Plates were incubated×30 minutes at RT in low-airflow area, followed by incubation at 37° C. under 5% $CO_2$ for 24 hours. Medium was aspirated from all wells of assay plates prior to fixation and permeabilization with ice cold (−20° C.) methanol (90 µL/well) for ten minutes. Plates were rinsed with PBS three times on BioTek ELx405. PBS was removed with a final aspiration, and Odyssey blocking buffer (50 µL/well) was added to each well and incubated for one hour at RT. Primary antibody solution was prepared (anti-trimethyl-MEKK2 at 1:600 dilution plus mouse anti-flag antibody at 1:10,000 dilution in diluent (Odyssey Blocking buffer+0.1% Tween 20)) and 20 µL per well was dispensed using the Multidrop Combi. Assay plates were then sealed with foil, and incubated overnight at 4° C. Plates were washed five times with PBS-Tween (1×) on Biotek ELx405 and blotted on paper towel to remove excess reagent. Detection antibody solution (IRDye 800 CW goat anti-rabbit IgG diluted 1:400 in diluent (Odyssey Blocking buffer+0.1% Tween 20), plus IRDye 680CW goat anti-mouse IgG at 1:500 in diluent (Odyssey Blocking buffer+ 0.1% Tween 20) was added (20 µL/well) and incubated in dark for one hour at RT. Plates were then washed four times with PBS-T (1×) on ELx405. A final rinse with water was performed (115 µL/well×three washes on the ELx405). Plates were then centrifuged upside down, on paper towel, at 200×g to remove excess reagent. Plates were left to dry in dark for one hour. The Odyssey Imager was used to measure the integrated intensity of 700 and 800 wavelengths at resolution of 84 µm, medium quality, focus offset 4.0, 700 channel intensity=3.5 to measure the MEKK2-flag signal, 800 channel intensity=5 to measure the Trimethyl-MEKK2 signal of each well.

Calculations:

First, the ratio for each well was determined by:

$$\left( \frac{\text{Trimethyl } MEKK2 \text{ 800 mm value}}{\text{flag tagged } MEKK2 \text{ 700 mm value}} \right)$$

Each plate included fourteen control wells of DMSO only treatment (Minimum Inhibition) as well as fourteen control wells for maximum inhibition (Background). The average of the ratio values for each control type was calculated and used to determine the percent inhibition for each test well in the plate. Reference compound was serially diluted two-fold in DMSO for a total of nine test concentrations, beginning at 40 μM. Percent inhibition was calculated (below).

$$\text{Percent Inhibition} = 100 - \left( \left( \frac{\text{(Individual Test Sample Ratio)} - \text{(Background Avg Ratio)}}{\text{(Minimum Inhibition Ratio)} - \text{(Background Average Ratio)}} \right) * 100 \right)$$

Non-linear regression curves were generated to calculate the $IC_{50}$ and dose-response relationship using triplicate wells per concentration of compound.

SMYD3 cell assay data for representative Compounds of the Disclosure are presented in Table 1 in the column titled "SMYD3 Cell $IC_{50}$ (μM)."

Example 21

SMYD2 Biochemical Assay

General Materials

S-adenosylmethionine (SAM), S-adenosylhomocysteine (SAH), bicine, Tween20, dimethylsulfoxide (DMSO), bovine skin gelatin (BSG), and Tris(2-carboxyethyl)phosphine hydrochloride (TCEP) were purchased from Sigma-Aldrich at the highest level of purity possible. $^3$H-SAM was purchase from American Radiolabeled Chemicals with a specific activity of 80 Ci/mmol. 384-well streptavidin Flashplates were purchased from PerkinElmer.

Substrates

Peptide was synthesized with a N-terminal linker-affinity tag motif and a C-terminal amide cap by 21$^{st}$ Century Biochemicals. The peptide was high high-performance liquid chromatography (HPLC) purified to greater than 95% purity and confirmed by liquid chromatography mass spectrometry (LC-MS). The sequence was ARTKQTARKSTG-GKAPRKQLATKAARKSA(K-Biot)-amide. (SEQ ID No: 3)

Production of Recombinant SMYD2 Enzymes for Biochemical Enzyme Activity Assays

Full length SMYD2 (NP_064582.2) was cloned into a pFastbac-Htb-lic vector with an N-terminal His6 tag and FLAG tag, preceded by a TEV protease cleavage site. The protein was expressed in Sf9 insect cells. Cells were resuspended in lysis buffer (25 mM HEPES-NaOH, pH 7.5, 200 mM NaCl, 5% glycerol, and 5 mM β-ME) and lysed by sonication. The protein was purified by Ni-NTA (Qiagen), followed by TEV cleavage to remove the His6 tag, subtractive Ni-NTA (Qiagen), and gel filtration chromatography using an S200 column (GE Healthcare). Purified protein was stored in 20 mM Tris-HCl, pH 8.0, 100 mM NaCl, and 1 mM TCEP.

General Procedure for SMYD2 Enzyme Assays on Peptide Substrates

The assays were all performed in a buffer consisting of 20 mM Bicine (pH=7.6), 1 mM TCEP, 0.005% Bovine Skin Gelatin, and 0.002% Tween20, prepared on the day of use. Compounds in 100% DMSO (1 ul) were spotted into a polypropylene 384-well V-bottom plates (Greiner) using a Platemate Plus outfitted with a 384-channel head (Thermo Scientific). DMSO (1 ul) was added to Columns 11, 12, 23, 24, rows A-H for the maximum signal control and 1 ul of SAH, a known product and inhibitor of SMYD2, was added to columns 11, 12, 23, 24, rows I-P for the minimum signal control. A cocktail (40 ul) containing the SMYD2 enzyme was added by Multidrop Combi (Thermo-Fisher). The compounds were allowed to incubate with SMYD2 for 30 min at room temperature, then a cocktail (10 ul) containing $^3$H-SAM and peptide was added to initiate the reaction (final volume=51 ul). The final concentrations of the components were as follows: SMYD2 was 1.5 nM, $^3$H-SAM was 10 nM, and peptide was 60 nM, SAH in the minimum signal control wells was 1000 uM, and the DMSO concentration was 2%. The assays were stopped by the addition of non-radioactive SAM (10 ul) to a final concentration of 600 uM, which dilutes the $^3$H-SAM to a level where its incorporation into the peptide substrate is no longer detectable. 50 ul of the reaction in the 384-well polypropylene plate was then transferred to a 384-well Flashplate and the biotinylated peptides were allowed to bind to the streptavidin surface for at least 1 hour before being washed three times with 0.1% Tween20 in a Biotek ELx405 plate washer. The plates were then read in a PerkinElmer TopCount plate reader to measure the quantity of $^3$H-labeled peptide bound to the Flashplate surface, measured as disintegrations per minute (dpm) or alternatively, referred to as counts per minute (cpm).

% Inhibition Calculation $$\% \text{ ink} = 100 - \left( \frac{dpm_{cmpd} - dpm_{min}}{dpm_{max} - dpm_{min}} \right) \times 100$$

Where dpm=disintegrations per minute, cmpd=signal in assay well, and min and max are the respective minimum and maximum signal controls.

Four-Parameter IC50 Fit $$\% \text{ inhibition} = \text{Bottom} + \frac{\text{Top} - \text{Bottom}}{(1 + (IC_{50}/[I])^{Hill\ Coefficient})}$$

Where top and bottom are the normally allowed to float, but may be fixed at 100 or 0 respectively in a 3-parameter fit. The Hill Coefficient normally allowed to float but may also be fixed at 1 in a 3-parameter fit. I is the compound concentration.

SMYD2 biochemical assay data for representative Compounds of the Disclosure are presented in Tables 2 and 3 in the column titled "SMYD2 Biochem $IC_{50}$ (μM)."

Having now fully described this invention, it will be understood by those of ordinary skill in the art that the same can be performed within a wide and equivalent range of conditions, formulations, and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A compound having Formula I:

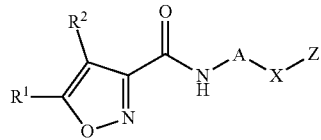

I or a pharmaceutically acceptable salt or hydrate thereof, wherein:

$R^1$ is selected from the group consisting of $C_{1-6}$ alkyl, $C_{1-4}$ alkenyl, $C_{1-4}$ haloalkyl, $C_{3-6}$ cycloalkyl, and hydroxyalkyl;

$R^2$ is selected from the group consisting of hydrogen, halo, and carboxamido;

A is optionally substituted 4- to 14-membered heterocyclenyl;

with the provisos:
a) when $R^1$ is ethyl, n-propyl, isopropyl, isobutyl, or cyclopropyl; and $R^2$ is hydrogen, then A is not optionally substituted, optionally bridged piperidinenyl; and b) when $R^1$ is $C_{1-6}$ alkyl or $C_{3-6}$ cycloalkyl; and $R^2$ is hydrogen, then A is not optionally substituted pyrrolidinenyl;

X is selected from the group consisting of —S(=O)$_2$—, —S(=O)$_2$N(R$^7$)—, —N(R$^7$)S(=O)$_2$—, —S(=O)$_2$C(R$^8$)(H)—, —C(=O)—, —C(=O)N(R$^7$)—, —N(R$^7$)C(=O)—, —C(=O)O—, —OC(=O)—, —C(=O)C(R$^8$)(H)N(R$^7$)—, —N(R$^7$)C(=O)C(R$^8$)(H)—, —C(R$^8$)(H)C(=O)N(R$^7$)—, —C(R$^8$)(H)N(R$^7$)C(=O)—, and —C(=O)C(R$^8$)(H)—; or X is absent;

Z is selected from the group consisting of hydrogen, optionally substituted $C_{1-6}$ alkyl, fluoroalkyl, hydroxyalkyl, amino, alkylamino, dialkylamino, heterocycloamino, (amino)alkyl, (alkylamino)alkyl, (dialkylamino)alkyl, (cycloalkylamino)alkyl, (heterocyclo)alkyl, (cycloalkyl)alkyl, (amino)(hydroxy)alkyl, (amino)(aryl)alkyl, (amino)(heteroaryl)alkyl (hydroxy)(aryl)alkyl, (aralkylamino)alkyl, (hydroxyalkylamino)alkyl, alkoxyalkyl, optionally substituted $C_{6-14}$ aryl, optionally substituted 4- to 14-membered heterocyclo, optionally substituted 5- to 14-membered heteroaryl optionally substituted $C_{3-12}$ cycloalkyl, aralkyl, and (heteroaryl)alkyl;

wherein —X—Z is attached to any available carbon or nitrogen atom of A;

R[7] is selected from the group consisting of hydrogen and C$_{1-4}$ alkyl; and

R[8] is selected from the group consisting of hydrogen, C$_{1-4}$ alkyl, hydroxy, amino, alkylamino, dialkylamino, cycloalkylamino, (amino)alkyl, (alkylamino)alkyl, (dialkylamino)alkyl, and hydroxyalkyl.

2. The compound of claim 1, or a pharmaceutically acceptable salt or hydrate thereof, having Formula VI:

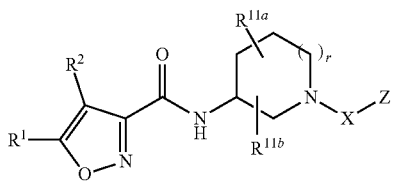

VI wherein:

R$^{11a}$ and R$^{11b}$ are each independently selected from the group consisting of hydrogen, C$_{1-4}$ alkyl, and alkoxycarbonyl;

X is selected from the group consisting of —C(=O)—, —S(=O)$_2$—, and —C(=O)C(R$^8$)(H)—;

Z is selected from the group consisting of (amino)alkyl, (alkylamino)alkyl, (dialkylamino)alkyl, (amino)(aryl)alkyl, (aralkylamino)alkyl, (heterocyclo)alkyl, optionally substituted C$_{3-12}$ cycloalkyl, and aralkyl; and r is 0 or 1.

3. The compound of claim 1, or a pharmaceutically acceptable salt or hydrate thereof, having Formula XVI:

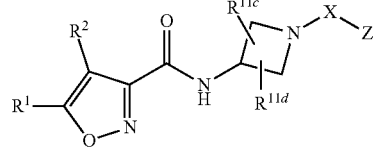

XVI wherein:

R$^{11c}$ and R$^{11d}$ are each independently selected from the group consisting of hydrogen and C$_{1-4}$ alkyl; and X is selected from the group consisting of —C(=O)— and —S(=O)$_2$; or X is absent.

4. The compound of claim 3, or a pharmaceutically acceptable salt or hydrate thereof, wherein:

R$^{11c}$ and R$^{11d}$ are hydrogen;

X is absent;

Z is selected from the group consisting of hydrogen, optionally substituted C$_{1-6}$ alkyl, fluoroalkyl, hydroxyalkyl, (amino)alkyl, (alkylamino)alkyl, (dialkylamino)alkyl, (heterocyclo)alkyl, (cycloalkyl)alkyl, (hydroxy)(aryl)alkyl, alkoxyalkyl, optionally substituted C$_{6-14}$ aryl, optionally substituted 4- to 14-membered heterocyclo, optionally substituted 5- to 14-membered heteroaryl, optionally substituted C$_{3-12}$ cycloalkyl, aralkyl, and (heteroaryl)alkyl; and R$^2$ is hydrogen.

5. The compound of claim 1, or a pharmaceutically acceptable salt or hydrate thereof, having Formula XVII:

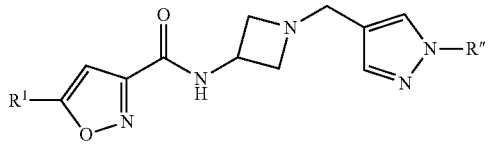

XVII wherein R'' is selected from the group consisting of aralkyl and (heteroaryl)alkyl.

6. The compound of claim 1, or a pharmaceutically acceptable salt or hydrate thereof, wherein R$^1$ is selected from the group consisting of C$_{1-4}$ alkyl and C$_{3-6}$ cycloalkyl.

7. The compound of claim 6, or a pharmaceutically acceptable salt or hydrate thereof, wherein R$^1$ is cyclopropyl.

8. The compound of claim 1, or a pharmaceutically acceptable salt or hydrate thereof, selected from the group consisting of:

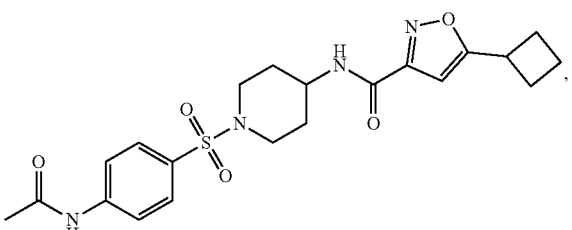

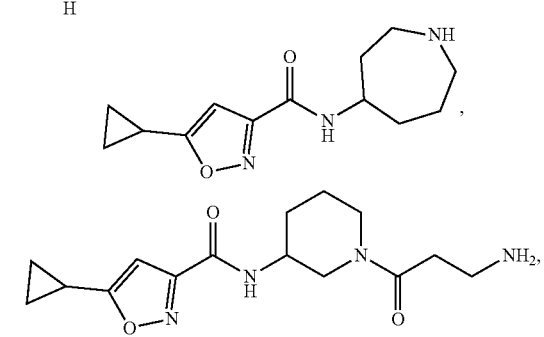

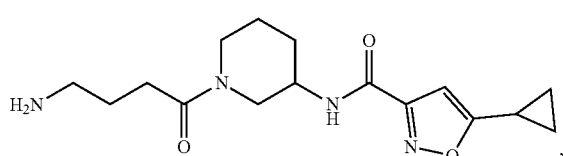

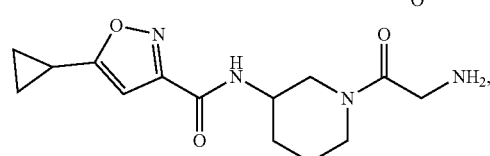

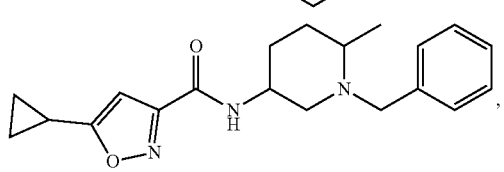

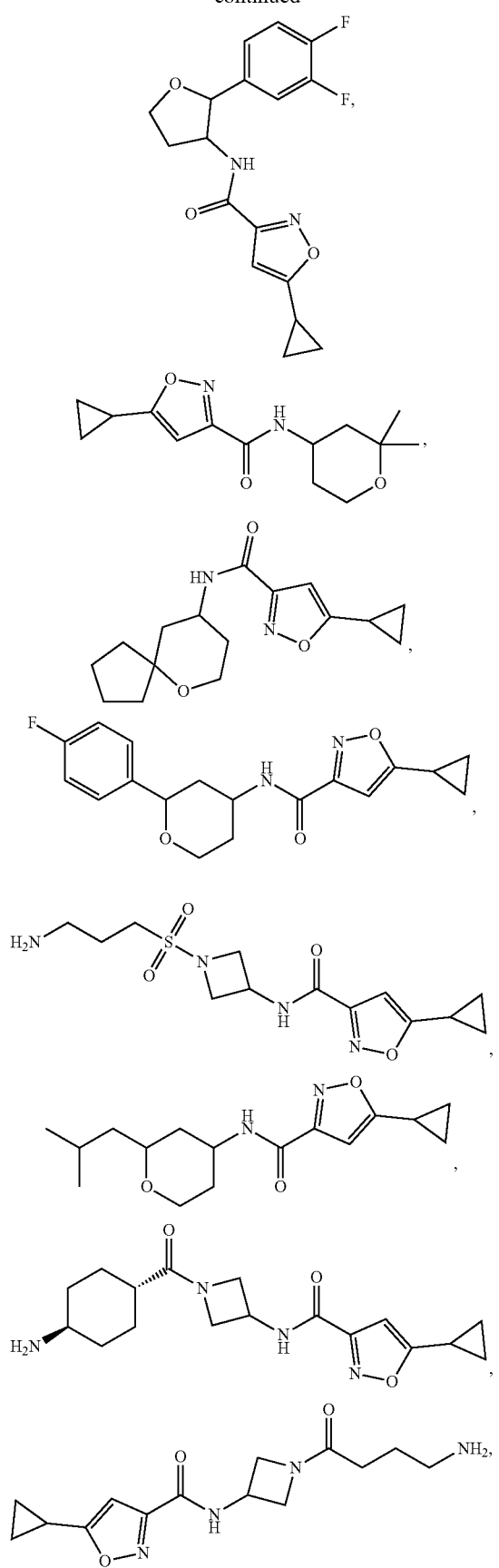
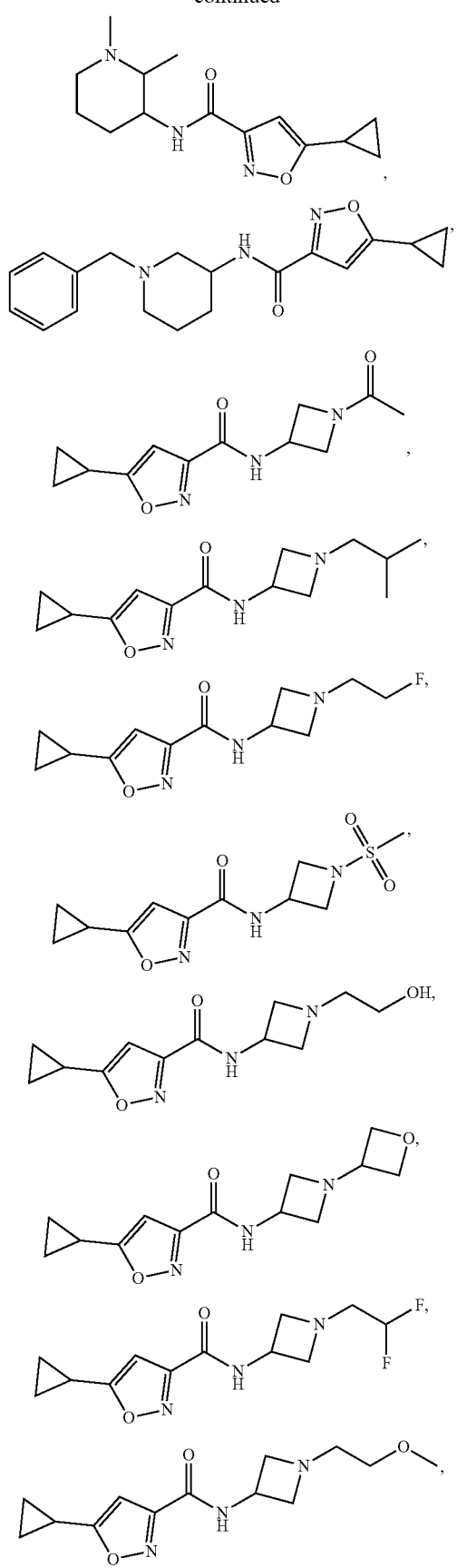

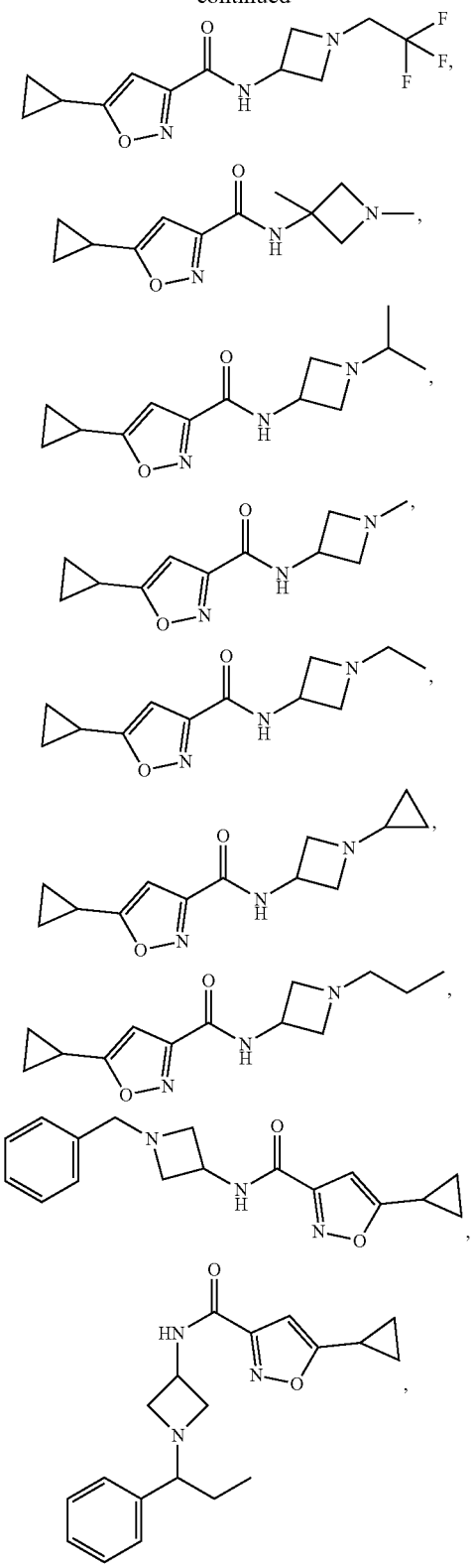
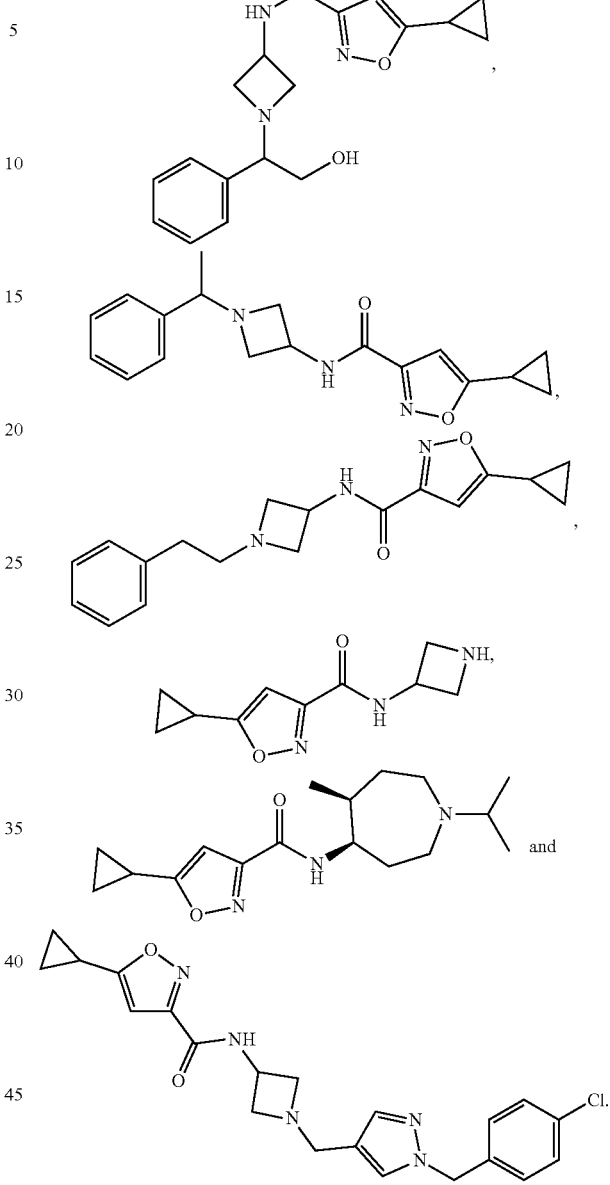

9. A pharmaceutical composition comprising the compound of claim 1, or a pharmaceutically acceptable salt or hydrate thereof, and a pharmaceutically acceptable carrier.

10. A method of treating a patient comprising administering to the patient a therapeutically effective amount of the compound of claim 1, or a pharmaceutically acceptable salt or hydrate thereof, wherein the patient has breast cancer, bladder cancer, cervical cancer, colon cancer, kidney cancer, liver cancer, lung cancer, head and neck cancer, skin cancer, pancreatic cancer, ovarian cancer, esophageal cancer, prostate cancer, or leukemia.

* * * * *

SEQUENCE LISTING

<160> NUMBER OF SEQ ID NOS: 3

<210> SEQ ID NO 1
<211> LENGTH: 855
<212> TYPE: PRT
<213> ORGANISM: Artificial Sequence
<220> FEATURE:
<223> OTHER INFORMATION: synthesized protein

<400> SEQUENCE: 1

```
Met Ala Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Val Pro Arg
    210                 215                 220

His Asn Gln Thr Ser Leu Tyr Lys Lys Ala Gly Thr Met Asp Asp Gln
225                 230                 235                 240

Gln Ala Leu Asn Ser Ile Met Gln Asp Leu Ala Val Leu His Lys Ala
                245                 250                 255

Ser Arg Pro Ala Leu Ser Leu Gln Glu Thr Arg Lys Ala Lys Ser Ser
            260                 265                 270

Ser Pro Lys Lys Gln Asn Asp Val Arg Val Lys Phe Glu His Arg Gly
        275                 280                 285

Glu Lys Arg Ile Leu Gln Phe Pro Arg Pro Val Lys Leu Glu Asp Leu
    290                 295                 300

Arg Ser Lys Ala Lys Ile Ala Phe Gly Gln Ser Met Asp Leu His Tyr
305                 310                 315                 320

Thr Asn Asn Glu Leu Val Ile Pro Leu Thr Thr Gln Asp Asp Leu Asp
                325                 330                 335

Lys Ala Leu Glu Leu Leu Asp Arg Ser Ile His Met Lys Ser Leu Lys
            340                 345                 350

Ile Leu Leu Val Ile Asn Gly Ser Thr Gln Ala Thr Asn Leu Glu Pro
```

```
              355                 360                 365
Leu Pro Ser Leu Glu Asp Leu Asp Asn Thr Val Phe Gly Ala Glu Arg
370                 375                 380
Lys Lys Arg Leu Ser Ile Ile Gly Pro Thr Ser Arg Asp Arg Ser Ser
385                 390                 395                 400
Pro Pro Pro Gly Tyr Ile Pro Asp Glu Leu His Gln Val Ala Arg Asn
                    405                 410                 415
Gly Ser Phe Thr Ser Ile Asn Ser Glu Gly Glu Phe Ile Pro Glu Ser
                    420                 425                 430
Met Glu Gln Met Leu Asp Pro Leu Ser Leu Ser Ser Pro Glu Asn Ser
                435                 440                 445
Gly Ser Gly Ser Cys Pro Ser Leu Asp Ser Pro Leu Asp Gly Glu Ser
            450                 455                 460
Tyr Pro Lys Ser Arg Met Pro Arg Ala Gln Ser Tyr Pro Asp Asn His
465                 470                 475                 480
Gln Glu Phe Ser Asp Tyr Asp Asn Pro Ile Phe Glu Lys Phe Gly Lys
                    485                 490                 495
Gly Gly Thr Tyr Pro Arg Arg Tyr His Val Ser Tyr His His Gln Glu
                500                 505                 510
Tyr Asn Asp Gly Arg Lys Thr Phe Pro Arg Ala Arg Thr Gln Gly
            515                 520                 525
Asn Gln Leu Thr Ser Pro Val Ser Phe Ser Pro Thr Asp His Ser Leu
530                 535                 540
Ser Thr Ser Ser Gly Ser Ser Ile Phe Thr Pro Glu Tyr Asp Asp Ser
545                 550                 555                 560
Arg Ile Arg Arg Arg Gly Ser Asp Ile Asp Asn Pro Thr Leu Thr Val
                565                 570                 575
Met Asp Ile Ser Pro Pro Ser Arg Ser Pro Arg Ala Pro Thr Asn Trp
            580                 585                 590
Arg Leu Gly Lys Leu Leu Gly Gln Gly Ala Phe Gly Arg Val Tyr Leu
            595                 600                 605
Cys Tyr Asp Val Asp Thr Gly Arg Glu Leu Ala Val Lys Gln Val Gln
        610                 615                 620
Phe Asp Pro Asp Ser Pro Glu Thr Ser Lys Glu Val Asn Ala Leu Glu
625                 630                 635                 640
Cys Glu Ile Gln Leu Leu Lys Asn Leu His Glu Arg Ile Val Gln
                645                 650                 655
Tyr Tyr Gly Cys Leu Arg Asp Pro Gln Glu Lys Thr Leu Ser Ile Phe
                660                 665                 670
Met Glu Tyr Met Pro Gly Gly Ser Ile Lys Asp Gln Leu Lys Ala Tyr
            675                 680                 685
Gly Ala Leu Thr Glu Asn Val Thr Arg Lys Tyr Thr Arg Gln Ile Leu
            690                 695                 700
Glu Gly Val His Tyr Leu His Ser Asn Met Ile Val His Arg Asp Ile
705                 710                 715                 720
Lys Gly Ala Asn Ile Leu Arg Asp Ser Thr Gly Asn Val Lys Leu Gly
                    725                 730                 735
Asp Phe Gly Ala Ser Lys Arg Leu Gln Thr Ile Cys Leu Ser Gly Thr
                740                 745                 750
Gly Met Lys Ser Val Thr Gly Thr Pro Tyr Trp Met Ser Pro Glu Val
            755                 760                 765
Ile Ser Gly Gln Gly Tyr Gly Arg Lys Ala Asp Ile Trp Ser Val Ala
            770                 775                 780
```

```
Cys Thr Val Val Glu Met Leu Thr Glu Lys Pro Pro Trp Ala Glu Phe
785                 790                 795                 800

Glu Ala Met Ala Ala Ile Phe Lys Ile Ala Thr Gln Pro Thr Asn Pro
            805                 810                 815

Lys Leu Pro Pro His Val Ser Asp Tyr Thr Arg Asp Phe Leu Lys Arg
        820                 825                 830

Ile Phe Val Glu Ala Lys Leu Arg Pro Ser Ala Asp Glu Leu Leu Arg
    835                 840                 845

His Met Phe Val His Tyr His
    850                 855

<210> SEQ ID NO 2
<211> LENGTH: 428
<212> TYPE: PRT
<213> ORGANISM: Artificial Sequence
<220> FEATURE:
<223> OTHER INFORMATION: synthesized protein

<400> SEQUENCE: 2

Met Glu Pro Leu Lys Val Glu Lys Phe Ala Thr Ala Lys Arg Gly Asn
1               5                   10                  15

Gly Leu Arg Ala Val Thr Pro Leu Arg Pro Gly Glu Leu Leu Phe Arg
            20                  25                  30

Ser Asp Pro Leu Ala Tyr Thr Val Cys Lys Gly Ser Arg Gly Val Val
        35                  40                  45

Cys Asp Arg Cys Leu Leu Gly Lys Glu Lys Leu Met Arg Cys Ser Gln
    50                  55                  60

Cys Arg Val Ala Lys Tyr Cys Ser Ala Lys Cys Gln Lys Lys Ala Trp
65                  70                  75                  80

Pro Asp His Lys Arg Glu Cys Lys Cys Leu Lys Ser Cys Lys Pro Arg
                85                  90                  95

Tyr Pro Pro Asp Ser Val Arg Leu Leu Gly Arg Val Val Phe Lys Leu
            100                 105                 110

Met Asp Gly Ala Pro Ser Glu Ser Glu Lys Leu Tyr Ser Phe Tyr Asp
        115                 120                 125

Leu Glu Ser Asn Ile Asn Lys Leu Thr Glu Asp Lys Lys Glu Gly Leu
    130                 135                 140

Arg Gln Leu Val Met Thr Phe Gln His Phe Met Arg Glu Glu Ile Gln
145                 150                 155                 160

Asp Ala Ser Gln Leu Pro Pro Ala Phe Asp Leu Phe Glu Ala Phe Ala
                165                 170                 175

Lys Val Ile Cys Asn Ser Phe Thr Ile Cys Asn Ala Glu Met Gln Glu
            180                 185                 190

Val Gly Val Gly Leu Tyr Pro Ser Ile Ser Leu Leu Asn His Ser Cys
        195                 200                 205

Asp Pro Asn Cys Ser Ile Val Phe Asn Gly Pro His Leu Leu Leu Arg
    210                 215                 220

Ala Val Arg Asp Ile Glu Val Gly Glu Glu Leu Thr Ile Cys Tyr Leu
225                 230                 235                 240

Asp Met Leu Met Thr Ser Glu Glu Arg Arg Lys Gln Leu Arg Asp Gln
                245                 250                 255

Tyr Cys Phe Glu Cys Asp Cys Phe Arg Cys Gln Thr Gln Asp Lys Asp
            260                 265                 270

Ala Asp Met Leu Thr Gly Asp Glu Gln Val Trp Lys Glu Val Gln Glu
        275                 280                 285
```

```
Ser Leu Lys Lys Ile Glu Glu Leu Lys Ala His Trp Lys Trp Glu Gln
    290             295                 300

Val Leu Ala Met Cys Gln Ala Ile Ile Ser Ser Asn Ser Glu Arg Leu
305             310                 315

Pro Asp Ile Asn Ile Tyr Gln Leu Lys Val Leu Asp Cys Ala Met Asp
                325                 330                 335

Ala Cys Ile Asn Leu Gly Leu Leu Glu Glu Ala Leu Phe Tyr Gly Thr
                340                 345                 350

Arg Thr Met Glu Pro Tyr Arg Ile Phe Phe Pro Gly Ser His Pro Val
            355                 360                 365

Arg Gly Val Gln Val Met Lys Val Gly Lys Leu Gln Leu His Gln Gly
    370                 375                 380

Met Phe Pro Gln Ala Met Lys Asn Leu Arg Leu Ala Phe Asp Ile Met
385             390                 395                 400

Arg Val Thr His Gly Arg Glu His Ser Leu Ile Glu Asp Leu Ile Leu
                405                 410                 415

Leu Leu Glu Glu Cys Asp Ala Asn Ile Arg Ala Ser
            420                 425

<210> SEQ ID NO 3
<211> LENGTH: 29
<212> TYPE: PRT
<213> ORGANISM: Artificial Sequence
<220> FEATURE:
<223> OTHER INFORMATION: synthesized protein
<220> FEATURE:
<221> NAME/KEY: MISC_FEATURE
<223> OTHER INFORMATION: C-terminal amide cap

<400> SEQUENCE: 3

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala
            20                  25
```